US012661132B2

(12) United States Patent

Majors et al.

(10) Patent No.: US 12,661,132 B2

(45) Date of Patent: Jun. 23, 2026

(54) IMPLANT GUIDES, DEVICES, SYSTEMS, AND METHODS OF USE

(71) Applicant: Paragon 28, Inc., Englewood, CO (US)

(72) Inventors: Benjamin Majors, Englewood, CO (US); Thomas R. Williams, Bon Aqua, TN (US); Peter Andrew Mladinich, Parker, CO (US); Garrett Jeffrey Lipker, Arvada, CO (US); Kenneth Allan Roggow, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 17/654,731

(22) Filed: Mar. 14, 2022

(65) Prior Publication Data

US 2022/0192687 A1     Jun. 23, 2022

Related U.S. Application Data

(63) Continuation of application No. PCT/US2020/049007, filed on Sep. 2, 2020.

(60) Provisional application No. 62/899,520, filed on Sep. 12, 2019, provisional application No. 62/961,896, filed on Jan. 16, 2020.

(51) Int. Cl.
*A61B 17/17* (2006.01)
*A61B 17/72* (2006.01)

(52) U.S. Cl.
CPC ...... *A61B 17/1775* (2016.11); *A61B 17/1717* (2013.01); *A61B 17/1725* (2013.01); *A61B 17/7216* (2013.01); *A61B 17/7241* (2013.01); *A61B 17/7291* (2013.01)

(58) Field of Classification Search
CPC ............ A61B 17/1775; A61B 17/1717; A61B 17/1725
See application file for complete search history.

(56) References Cited

U.S. PATENT DOCUMENTS

| | | | |
|---|---|---|---|
| 8,491,583 B2 | 7/2013 | Gall | |
| 9,445,850 B2 | 9/2016 | Kinmon | |
| 10,034,742 B2 | 7/2018 | Diduch | |
| 10,076,374 B2 | 9/2018 | Diduch | |
| 2009/0099571 A1 | 4/2009 | Cresina | |
| 2009/0149861 A1* | 6/2009 | Brodsky | A61B 17/72 |
| | | | 606/62 |

(Continued)

FOREIGN PATENT DOCUMENTS

| | | |
|---|---|---|
| JP | 2016504962 | 2/2016 |
| JP | 2017515554 | 6/2017 |
| WO | 2015164689 | 10/2015 |

OTHER PUBLICATIONS

Didomenico et al., "Intramedullary Nail Fixation for Tibiotalocalcaneal Arthrodesis," International Advances in Foot and Ankle Surgery. Springer, London, pp. 453-465, 2012.

(Continued)

*Primary Examiner* — Tessa M Matthews

(74) *Attorney, Agent, or Firm* — Heslin Rothenberg Farley & Mesiti P.C.; Jacquelyn A. Graff, Esq.

(57) ABSTRACT

Implant guides, devices, systems and methods for implants to correct bone deformities and fractures in the lower extremity are disclosed. Specifically, implant guides, devices, systems and methods used for implants to correct bone deformities and/or fractures in the foot and ankle are disclosed.

18 Claims, 101 Drawing Sheets

(56) References Cited

U.S. PATENT DOCUMENTS

| | | | | |
|---|---|---|---|---|
| 2011/0245885 A1* | 10/2011 | Powell | A61B 17/1725 606/86 R | |
| 2012/0109217 A1* | 5/2012 | Perineau | A61B 17/7291 606/301 | |
| 2013/0046311 A1 | 2/2013 | Blake | | |
| 2013/0085502 A1 | 4/2013 | Harrold | | |
| 2013/0116693 A1 | 5/2013 | Nelson | | |
| 2014/0114312 A1 | 4/2014 | Krause | | |
| 2014/0214101 A1* | 7/2014 | Roethlisberger | A61B 17/1725 606/86 R | |
| 2015/0057663 A1 | 2/2015 | Kinmon | | |
| 2015/0305791 A1* | 10/2015 | Purohit | A61B 17/1707 606/96 | |
| 2017/0189085 A1 | 7/2017 | Krause | | |
| 2017/0290656 A1 | 10/2017 | Piccirillo et al. | | |
| 2017/0296241 A1 | 10/2017 | Garlock et al. | | |
| 2018/0071105 A1* | 3/2018 | Orbay | A61B 17/8057 | |
| 2018/0242988 A1 | 8/2018 | Dacosta | | |
| 2018/0263669 A1 | 9/2018 | Peterson | | |
| 2022/0378408 A1* | 12/2022 | Thommen | A61B 1/00094 | |

OTHER PUBLICATIONS

International Search Report and Written Opinion of the International Searching Authority for PCT/US2020/049007, Dec. 2, 2020, 10 pages.

International Preliminary Report on Patentability for International Application No. PCT/US2020/049007 dated Mar. 15, 2022, 8 pages, International Bureau of WIPO.

Partial Supplementary European search report for European Application No. 20863238.0, Sep. 9, 2023, 14 pages.

* cited by examiner

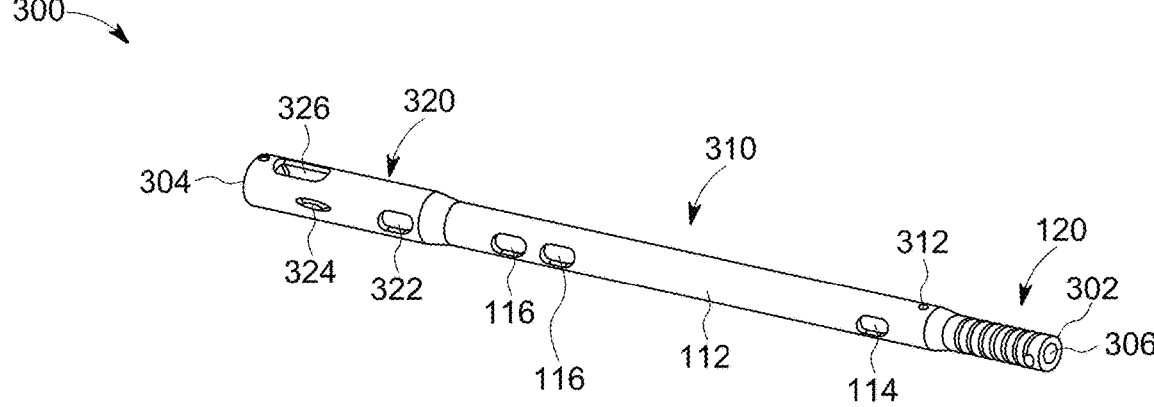
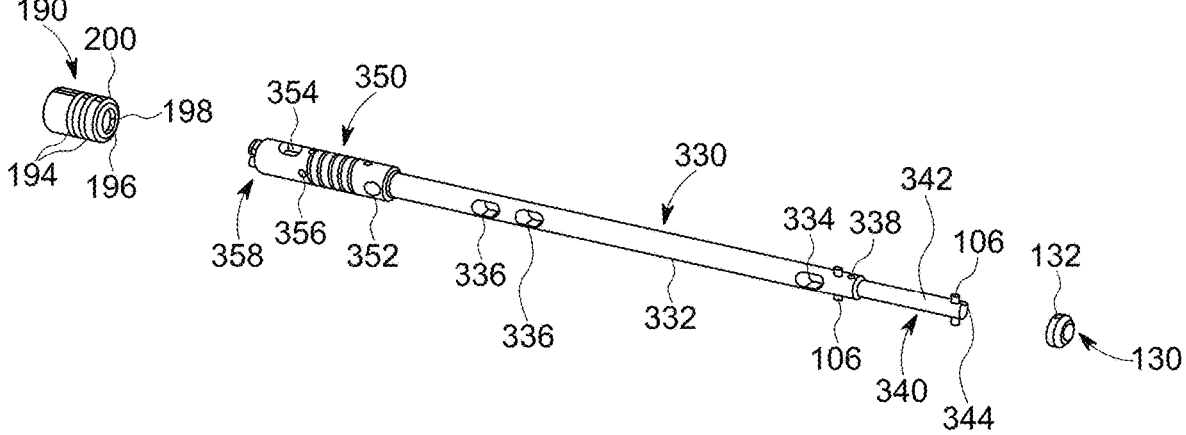
FIG. 10

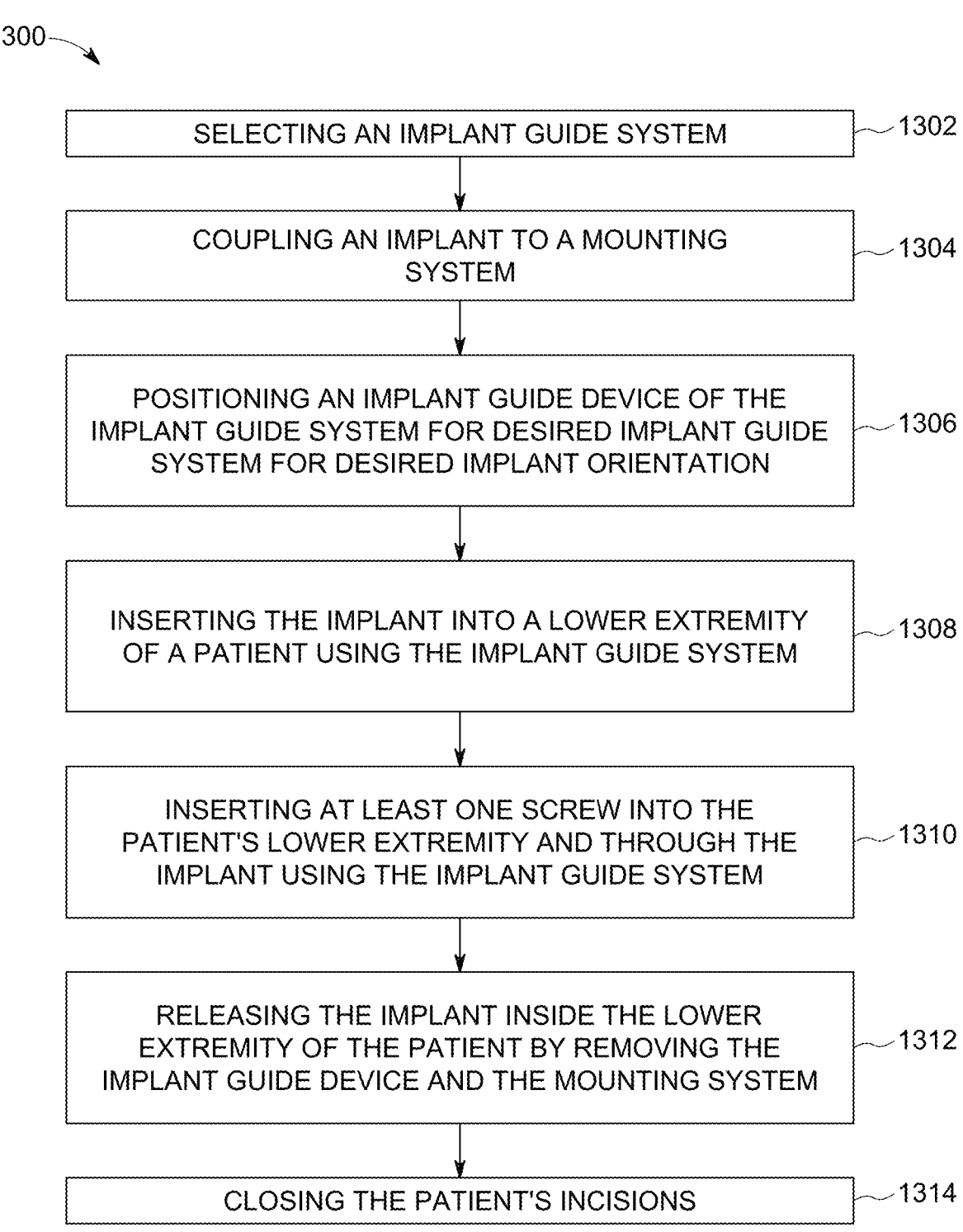

1300

| SELECTING AN IMPLANT GUIDE SYSTEM | 1302 |

| COUPLING AN IMPLANT TO A MOUNTING SYSTEM | 1304 |

| POSITIONING AN IMPLANT GUIDE DEVICE OF THE IMPLANT GUIDE SYSTEM FOR DESIRED IMPLANT GUIDE SYSTEM FOR DESIRED IMPLANT ORIENTATION | 1306 |

| INSERTING THE IMPLANT INTO A LOWER EXTREMITY OF A PATIENT USING THE IMPLANT GUIDE SYSTEM | 1308 |

| INSERTING AT LEAST ONE SCREW INTO THE PATIENT'S LOWER EXTREMITY AND THROUGH THE IMPLANT USING THE IMPLANT GUIDE SYSTEM | 1310 |

| RELEASING THE IMPLANT INSIDE THE LOWER EXTREMITY OF THE PATIENT BY REMOVING THE IMPLANT GUIDE DEVICE AND THE MOUNTING SYSTEM | 1312 |

| CLOSING THE PATIENT'S INCISIONS | 1314 |

POSITION PATIENT'S LOWER EXTREMITY — 1350

EXPOSE TIBIOTALAR JOINT — 1352

EXPOSE SUBTALAR JOINT — 1354

PREPARATION OF THE ANKLE JOINT — 1356

TEMPORARILY FIXATE THE ANKLE — 1358

FORM A CANAL IN THE PATIENT'S LOWER EXTREMITY — 1360

INSERT THE IMPLANT — 1362

INSERT THE TIBIA SCREW — 1364

INSERT THE CALCANEAL SCREW — 1366

INSERT THE TALOCALCANEAL SCREW — 1368

INSERT THE TENSIONING SCREW — 1370

1400

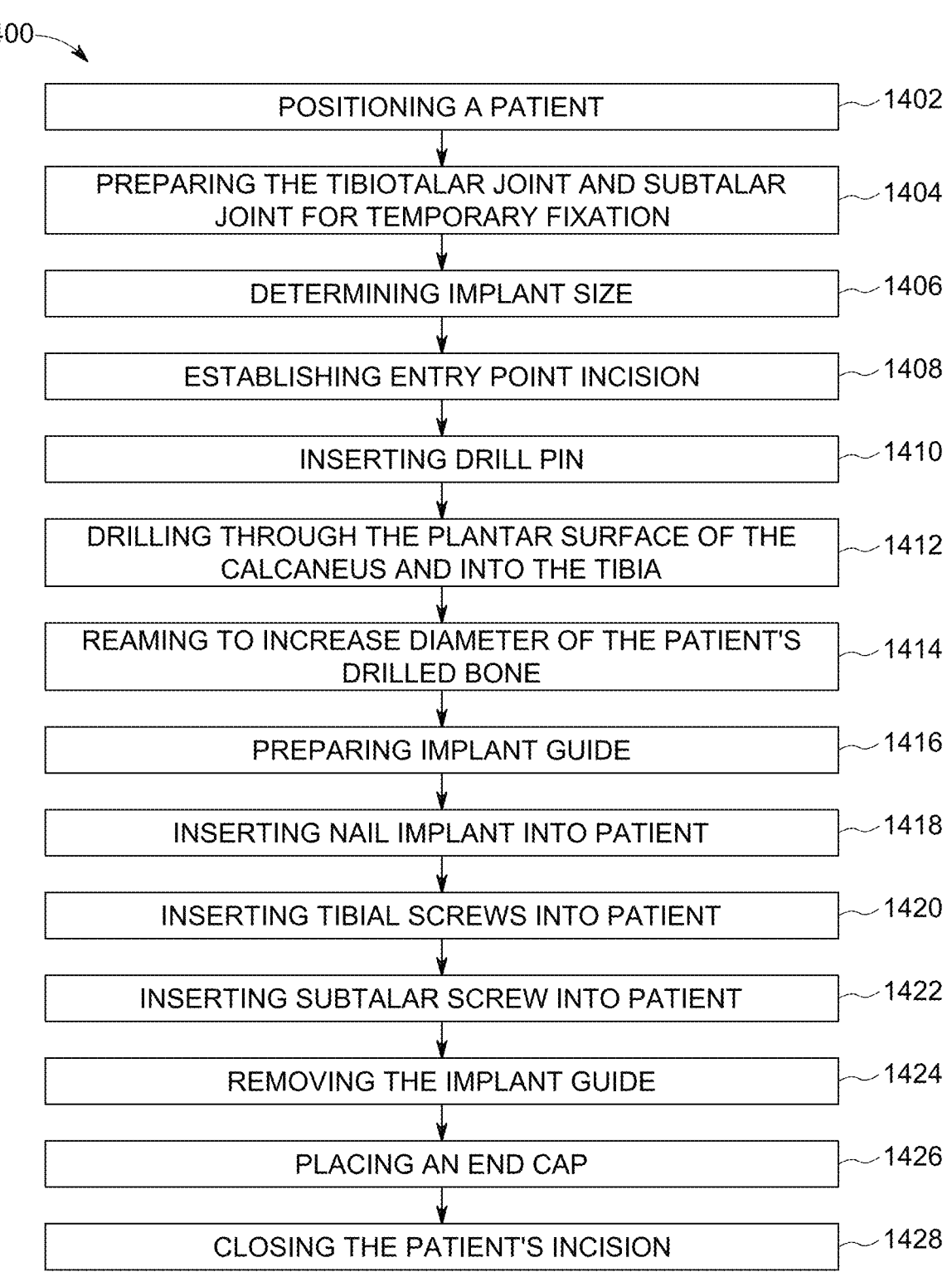

| | |
|---|---|
| POSITIONING A PATIENT | 1402 |
| PREPARING THE TIBIOTALAR JOINT AND SUBTALAR JOINT FOR TEMPORARY FIXATION | 1404 |
| DETERMINING IMPLANT SIZE | 1406 |
| ESTABLISHING ENTRY POINT INCISION | 1408 |
| INSERTING DRILL PIN | 1410 |
| DRILLING THROUGH THE PLANTAR SURFACE OF THE CALCANEUS AND INTO THE TIBIA | 1412 |
| REAMING TO INCREASE DIAMETER OF THE PATIENT'S DRILLED BONE | 1414 |
| PREPARING IMPLANT GUIDE | 1416 |
| INSERTING NAIL IMPLANT INTO PATIENT | 1418 |
| INSERTING TIBIAL SCREWS INTO PATIENT | 1420 |
| INSERTING SUBTALAR SCREW INTO PATIENT | 1422 |
| REMOVING THE IMPLANT GUIDE | 1424 |
| PLACING AN END CAP | 1426 |
| CLOSING THE PATIENT'S INCISION | 1428 |

FIG. 77

IMPLANT GUIDES, DEVICES, SYSTEMS, AND METHODS OF USE

CROSS REFERENCE TO RELATED APPLICATIONS

This application is a continuation of PCT Application No. PCT/US2020/049007 filed Sep. 2, 2020, and entitled "Implant Guides, Devices, Systems, and Methods of Use," which claims priority benefit under 35 U.S.C. § 119(e) of U.S. Provisional Patent Application No. 62/899,520 filed Sep. 12, 2019, and entitled "Implant Guides, Devices, Systems, and Methods of Use," and U.S. Provisional Patent Application No. 62/961,896 filed Jan. 16, 2020, and entitled "Implant Guides, Devices, Systems, and Methods of Use," the disclosure of which are incorporated herein by reference in their entireties.

FIELD OF THE INVENTION

The present invention relates generally to general surgery, podiatric, and orthopaedic implants used for correcting bone deformities. More specifically, but not exclusively, the present invention relates to implant guides, devices, systems and methods for implants to correct bone deformities.

BACKGROUND OF THE INVENTION

Commonly, a fusion of the tibia-talus-calcaneus (TTC) complex is required due to pathology, trauma or failed previous operations. The currently available options for fusing the three bones together include intramedullary (IM) nails, crossing screws or plating. The currently available implants cross two joints: the tibiotalar or ankle joint and the talocalcaneal or subtalar joint. During the use of the currently available implants there is a period of resorption that occurs causing a gaping between joint surfaces. This gaping can lead to a failed fusion (nonunion) and ultimately device failure. Thus, new implant guides, devices, systems and methods for implants are needed to ensure that gaping is prevented or minimized, and bony opposition is maintained during the healing process.

SUMMARY OF THE INVENTION

Aspects of the present invention provide implant guides, devices, systems and methods for correcting bone deformities in the foot and ankle.

In one aspect, provided herein is an implant guide device. The implant guide device includes a base, a first arm coupled to a first end of the base, a second arm coupled to a second end of the base, and a targeting arm hingedly coupled to at least one of the first arm and the second arm.

In another aspect, provided herein is an implant guide system. The implant guide system includes an implant guide device. The implant guide device of the implant guide system includes a base, a first arm coupled to a first end of the base, a second arm coupled to a second end of the base, and a targeting arm hingedly coupled to at least one of the first arm and the second arm. Further, the implant guide system includes a mounting system traversing an aperture of the base. Still further, the implant guide system includes an implant coupled to the mounting system.

Also provided herein is a surgical method. The surgical method includes selecting an implant guide system, coupling an implant to a mounting system of the implant guide system, and positioning an implant guide device of the implant guide system for desired implant orientation. The surgical method also includes inserting the implant into a lower extremity of a patient using the implant guide system, and inserting at least one fastener into the patient's lower extremity and through the implant using the implant guide system. Further, the surgical method includes releasing the implant inside the lower extremity of the patient by removing the implant guide device and the mounting system and closing the patient's incisions.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 10 is an exploded, perspective view of the implant and the implant engaging portion of the mounting system of FIG. 3, in accordance with an aspect of the present disclosure;

FIG. 75 depicts a first surgical method, in accordance with aspects of the present disclosure;

FIG. 77 depicts a third surgical method, in accordance with an aspect of the present disclosure;

DETAILED DESCRIPTION FOR CARRYING OUT THE INVENTION

Figure 1:
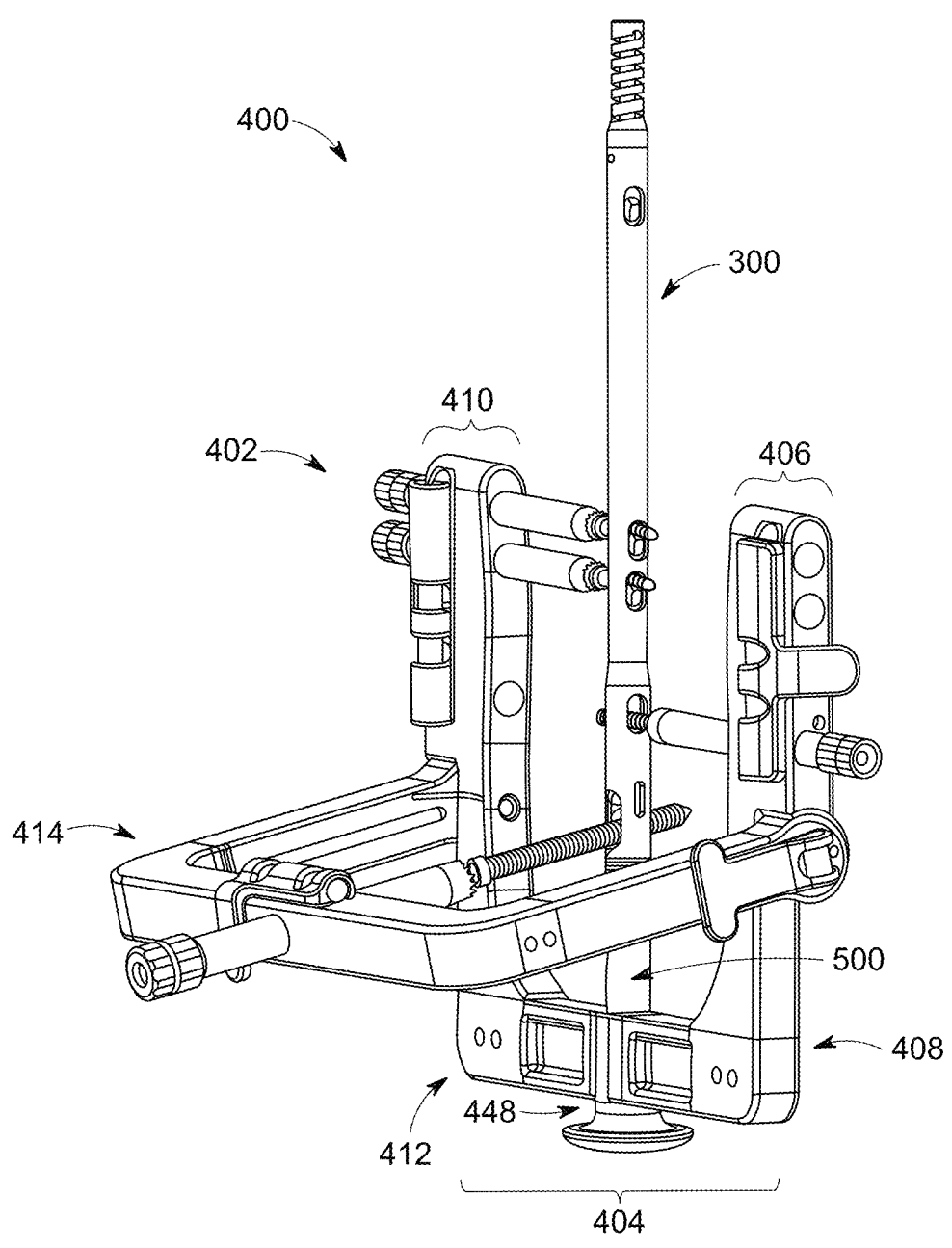
FIG. 1 is a perspective view of an implant guide system, in accordance with an aspect of the present disclosure.

Generally stated, disclosed herein are implant guides, devices, and systems for use in inserting implants into patients, where the implants are configured to correct bone deformities. Further, methods for using the implant guides, devices, and systems are discussed.

In this detailed description and the following claims, the words proximal, distal, anterior or plantar, posterior or dorsal, medial, lateral, superior and inferior are defined by their standard usage for indicating a particular part or portion of a patient's body, a bone, a device, or an implant according to the relative disposition of the patient or directional terms of reference. For example, "proximal" means a particular part or portion of a patient's extremity, a bone, a device or implant nearest the torso, while "distal" indicates the portion of the patient's extremity, bone, device or implant farthest from the torso. As for directional terms, "anterior" is a direction towards the front side of the body, bone, device, or implant, "posterior" means a direction towards the back side of the body, bone, device, or implant, "medial" means towards the midline of the body, "lateral" is a direction towards the sides or away from the midline of the body, "superior" means a direction above and "inferior" means a direction below another object or structure. Further, specifically in regard to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Fusion of the tibia-talus-calcaneus (TTC) complex due to pathology, trauma, or failed previous operations, may include insertion of an implant (i.e. intramedullary (IM) nails) as well as one or more bone screws or bone fasteners, where fasteners referred to herein are to include screws, pins, fixation members, and the like thereof. IM nails may be configured to provide, for instance, continuous compression across both the tibiotalar or ankle joint and the talocalcaneal or subtalar joint. Providing continuous compression at the ankle joint or subtalar joint may ensure that bony apposition is maintained throughout the fusion process. According to one embodiment, an IM nail may allow for different compressive loads for each of the respective joints. The IM nail may include an internal spring for providing compression to the subtalar joint, and an external spring for providing compression to the ankle joint. Providing independent compression to each of the respective joints may prevent joint gaping during the fusion process. For instance, the internal spring of the IM nail may be configured or sized and shaped to provide optimal compression between the talus and calcaneus, and the external spring may be configured or sized and shaped to provide optimal compression between the talus and tibia. The compression may be dynamic to allow for continual compression of the joint surfaces during bone resorption or bone remodeling.

Aspects of the present disclosure provide implant guides, devices, systems, and methods for use in inserting an implant for fusion of the TTC complex. For instance, an implant guide system is described herein that is configured to provide optimal positioning of an implant during a surgical procedure. In particular, disclosed herein are implant guides, devices, systems, and methods that can be advantageous for reducing surgical time, reducing the number of operators or assistants needed during surgery, streamlining surgical techniques, providing predictability and reliability when inserting bone screws or bone fasteners into a patient, reducing the likelihood of set-up errors, and reducing the likelihood of misplacement of the implant and bone screws, thereby facilitating a more rigid configuration of the inserted implant.

Referring now to FIG. 1, an embodiment of an implant guide system 400 is shown. The implant guide system 400 includes an implant guide device 402. The implant guide device 402 includes a base 404, a first arm 406 coupled to a first end 408 of the base 404, and a second arm 410 coupled to a second end 412 of the base 404. The implant guide device 402 also includes a targeting arm 414 hingedly coupled to at least one of the first arm 406 and the second arm 410. The implant guide system 400 also includes a mounting system 500 traversing an aperture 448 of the base 404. Further, the implant guide system 400 includes an implant 300 coupled to the mounting system 500. The aperture 448 may be, for example, configured or sized and shaped to receive the implant 300, and further receive a portion of the mounting system 500. The implant 300 may be of the type described in greater detail in U.S. Provisional Application No. 62/812,247, entitled Implants, Systems and Methods of Use, which is hereby incorporated by reference in its entirety.

Figure 2:
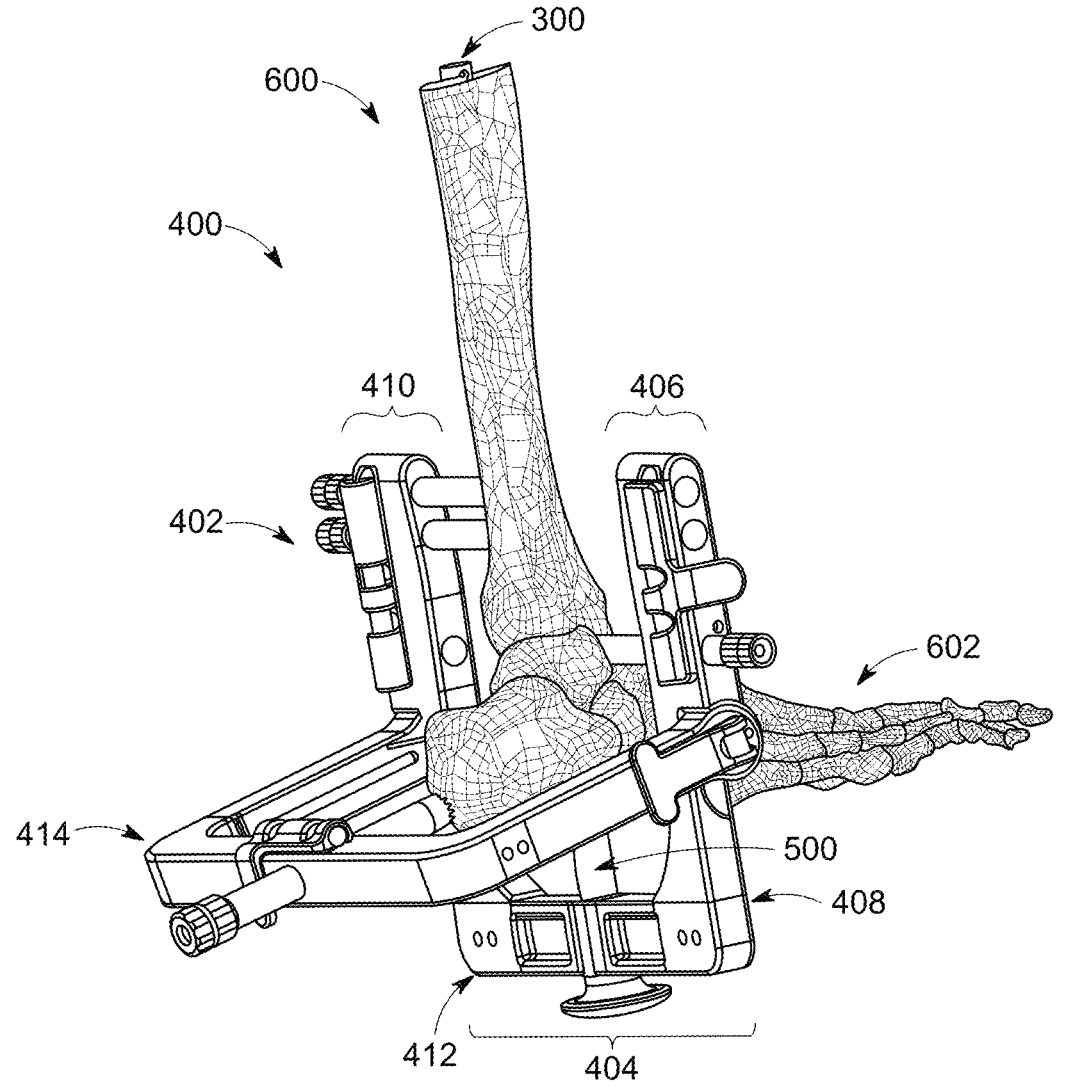
FIG. 2 is a perspective view of the implant guide system of FIG. 1, in which an implant is inserted into a patient's lower extremity, in accordance with an aspect of the present disclosure.
Figure 3:
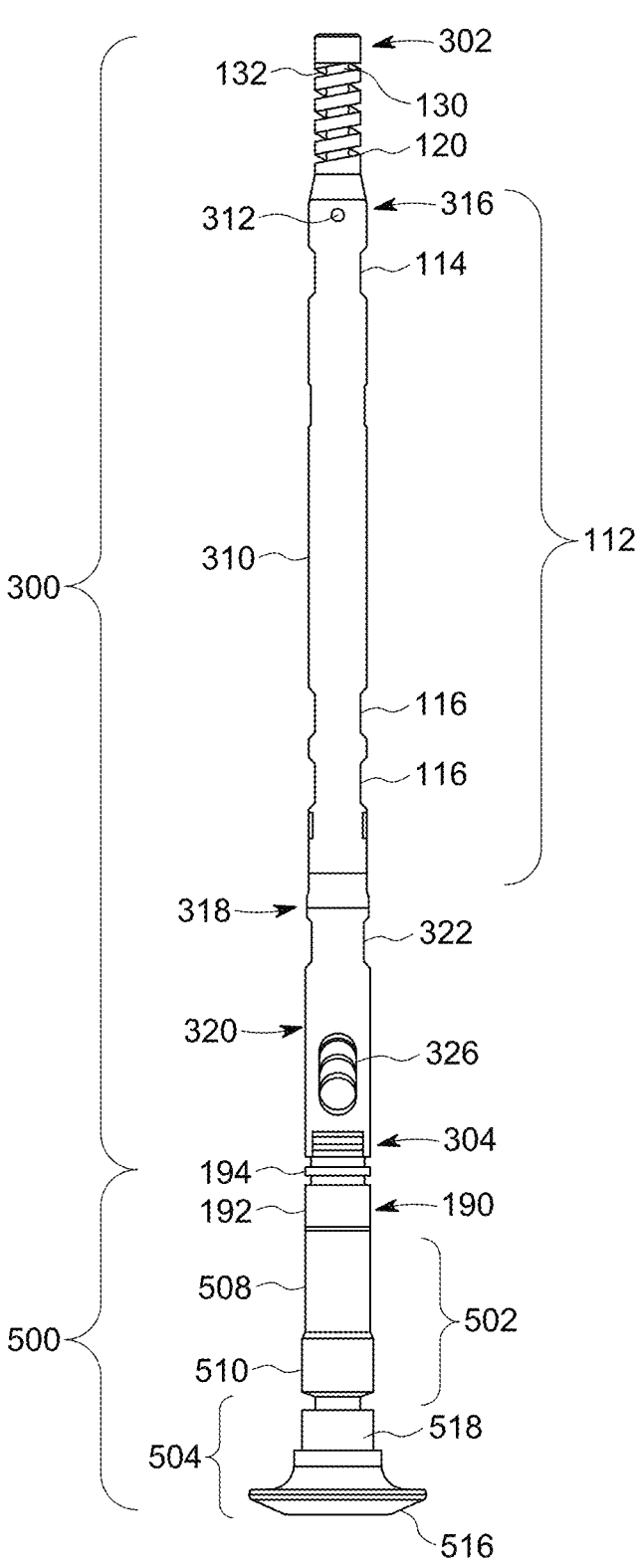
FIG. 3 is a first side view of an implant and mounting system of the implant guide system of FIG. 1, in accordance with an aspect of the present disclosure.
Figure 4:
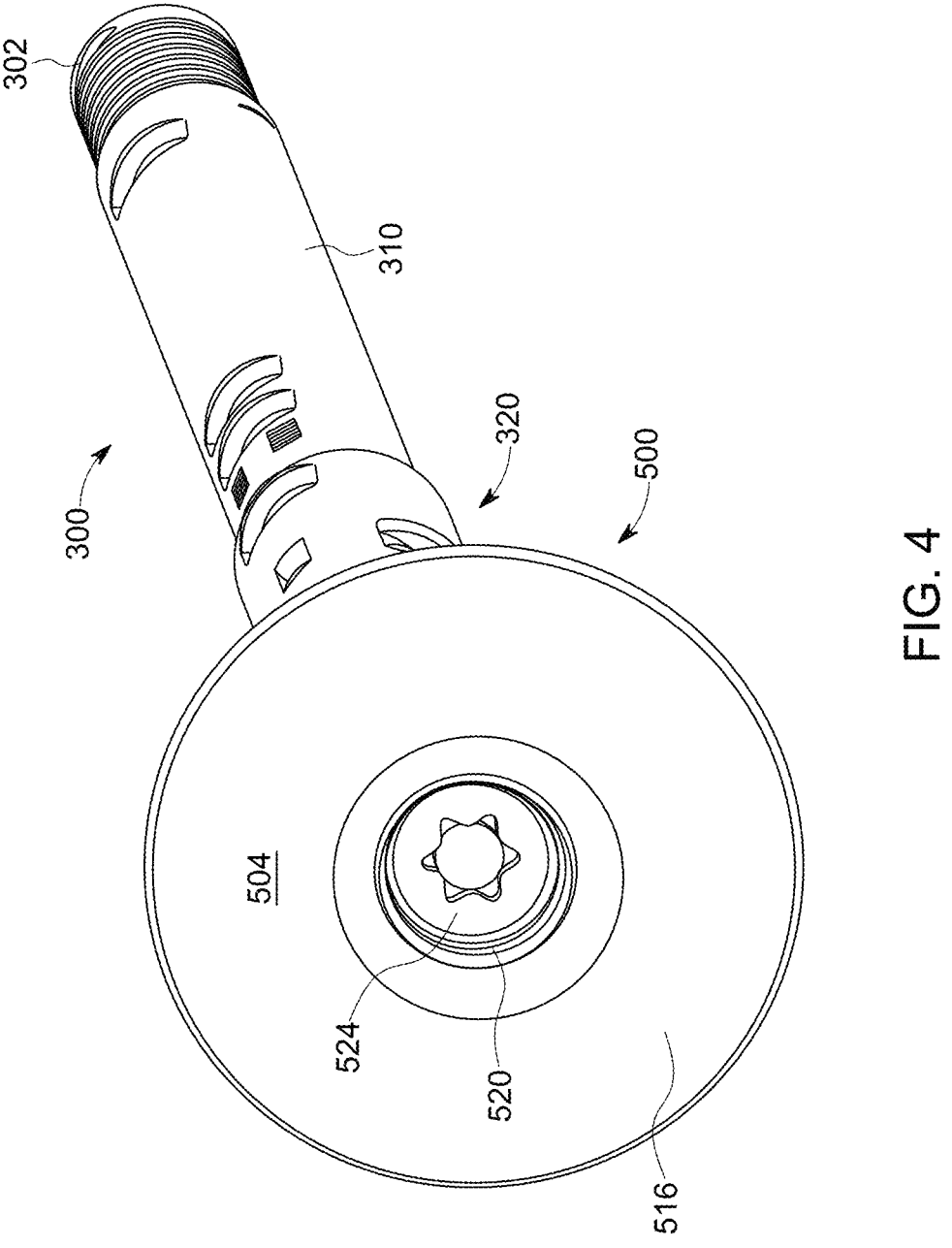
FIG. 4 is a first end perspective view of the implant and mounting system of FIG. 3, in accordance with an aspect of the present disclosure.
Figure 5:
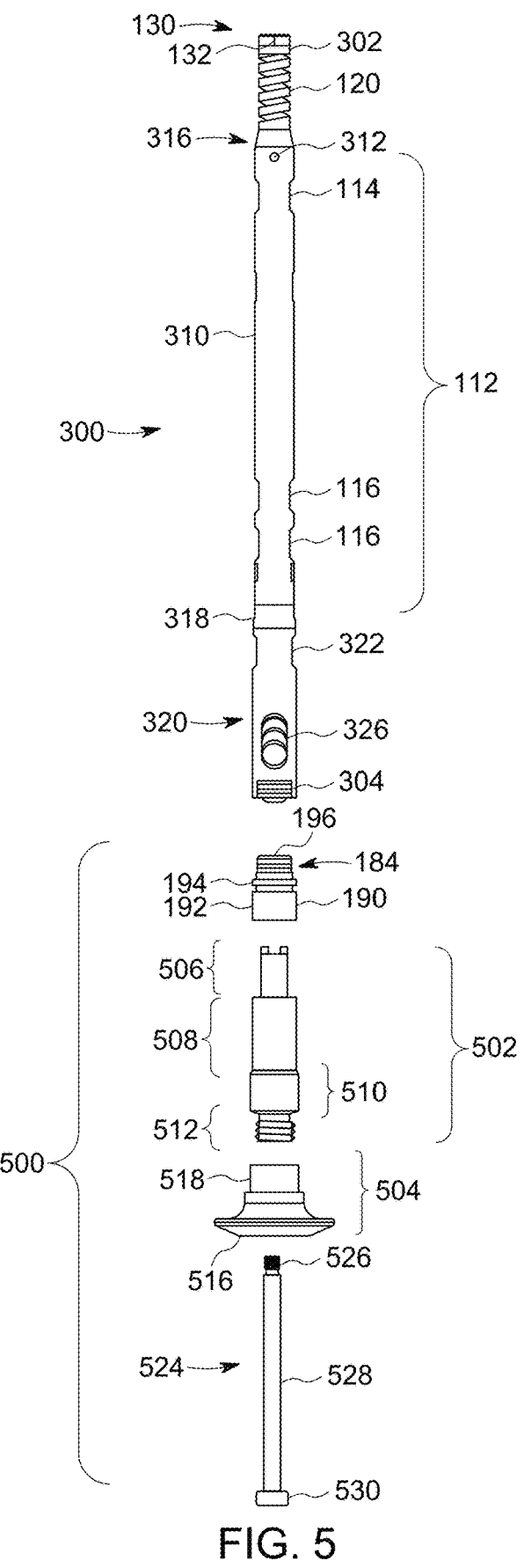
FIG. 5 is an exploded, first side view of the implant and mounting system of FIG. 3, in accordance with an aspect of the present disclosure.
Figure 6:
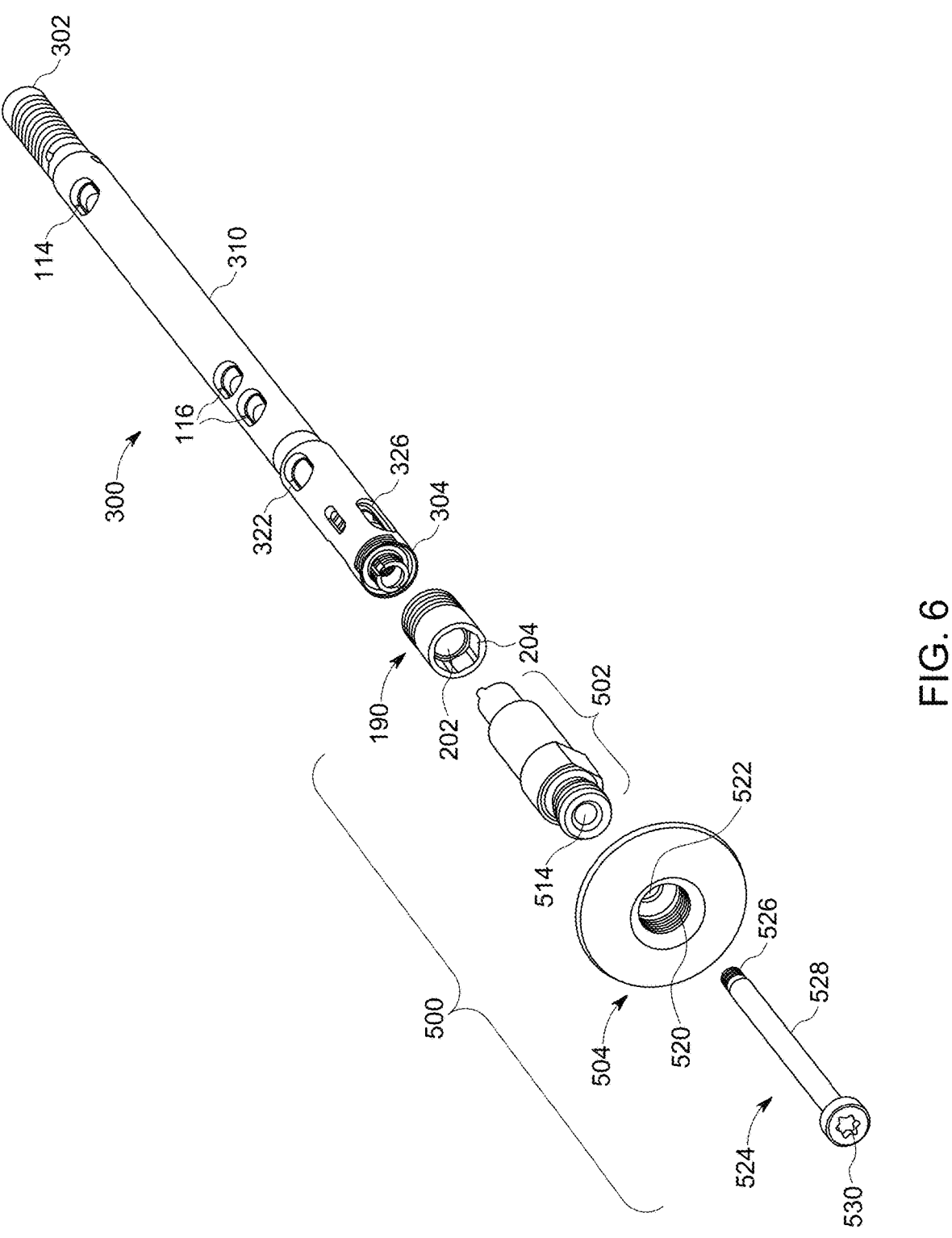
FIG. 6 is an exploded, first end perspective view of the implant and mounting system of FIG. 3, in accordance with an aspect of the present disclosure.
Figure 7:
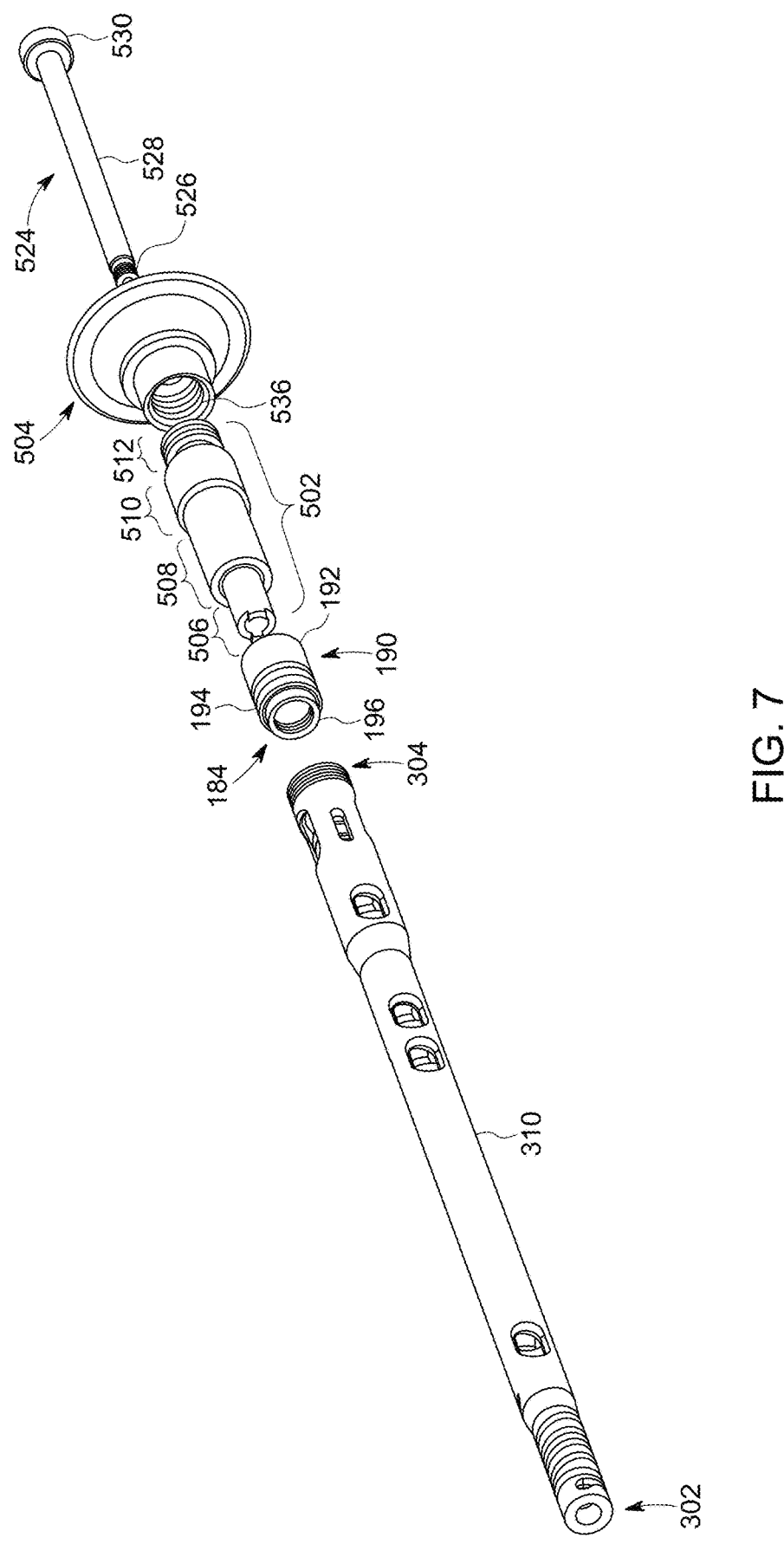
FIG. 7 is an exploded, second end perspective view of the implant and mounting system of FIG. 3, in accordance with an aspect of the present disclosure.

FIG. 2 is a perspective view of the implant guide system of FIG. 1, in which an implant 300 is inserted into a patient's lower extremity 600, in accordance with an aspect of the present disclosure. For insertion of the implant 300, the base 404 of the implant guide device 402 may be positioned, for example, inferior to the plantar portion of a foot 602 of the patient's lower extremity 600, with the first arm 406 of the implant guide device 402 positioned on the medial side of the patient's lower extremity 600 and the second arm 410 of the implant guide device 402 positioned on the lateral side of the patient's lower extremity 600. Further, the targeting arm 414 may be positioned towards the posterior portion of the patient's foot 602.

Referring now to FIGS. 3-7, the implant 300 and a mounting system 500 of the implant guide system 400 are shown. The implant 300, according to various embodiments, may include a nail system or IM nail (e.g., dual spring dynamic nail). The implant 300 includes a first or proximal end 302 and a second or distal end 304, with the second end 304 being configured to couple to the mounting system 500.

With continued reference to FIGS. 3-7, the implant 300 may include a first member or outer sheath 310, and a coupling member 130 at the first or proximal end 302. The coupling member 130 may include an anti-rotation pin opening 132 for maintaining the coupling member's 130 composition. The first member or outer sheath 310 may include a body portion 112.

With continued reference to FIGS. 3-7, the body portion 112 may include a first or proximal portion 316 coupled to a first deformable member 120 (e.g., an external spring) and a second or distal portion 318 coupled to a distal end portion 320 of the outer sheath 310. The body portion 112 may also include an anti-rotation pin opening 312 for assisting in maintaining composition of the implant 300. The body portion 112 may further include one or more holes 114, 116 traversing the implant 300 and perpendicular to the longitudinal axis of the body portion 112 of the implant 300. The at least one hole 114, of the one or more holes 114, 116 may be located, for example, at the first or proximal portion 316 of the body portion 112, and at least one hole 116 of the one or more holes 114, 116 may be located, for example, at the second or distal portion 318 of the body portion 112. The one or more holes 114, 116 may be, for example, sized and shaped or configured to receive a bone screw or bone fastener to be, for example, inserted into a tibia bone of a patient.

Also shown in FIGS. 3-7, the distal end portion 320 of the first member or outer sheath 310 may further include one or more holes 322, 326 that traverse and are perpendicular to the longitudinal axis of the implant 300. The one or more holes 322, 326 of the distal end portion 320 may be, for example, sized and shaped or configured to receive a bone screw or bone fastener to be, for example, inserted into a talus or a calcaneus bone of a patient. For instance, when the implant 300 is inserted into a patient's lower extremity, a first hole 326 may be configured to extend from an anterior portion of the implant 300 to a posterior portion of the implant 300, whereas a second hole 322 may be configured to extend from a lateral portion of the implant 300 to a medial portion of the implant 300. The one or more holes 114, 116, 322, 326 may be, for example, elongated, round, circular, oval, or the like.

As shown in FIGS. 3-7, the mounting system 500 may include the implant engaging portion 190 configured or sized and shaped to couple to the second end 304 of the implant 300, a mounting screw spacer 502 and a strike plate 504. The implant engaging portion 190 may include a body portion 192 with at least one groove 194 inset into an exterior surface of the body portion 192. The implant engaging portion 190 may also include a coupling protrusion 196 extending away from a first or end 184 of the body portion 192. The coupling protrusion 196 may include a threaded portion 200 surrounding the circumference of the exterior surface of the coupling protrusion 196 for insertion into the distal end 304 of the outer sheath 310. The implant engaging portion 190 may also include a through hole 202 with a tool engagement opening or drive opening 204 to receive a tool for removing pre-loaded compression from the implant 300. The implant engaging portion 190 may be configured or sized and shaped to hold, for example, the first deformable member 120 of the implant 300 in compression. Placing the implant 300 in compression allows for the implant 300 to be inserted into a patient in a "pre-loaded" position. The "pre-loaded" position includes compression of the first deformable member 120.

Figure 11:
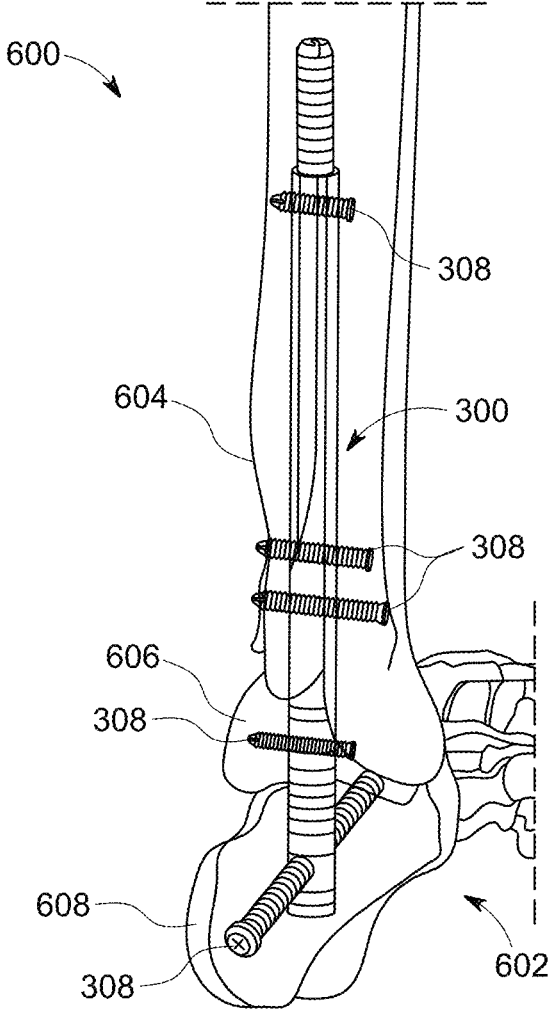
FIG. 11 is a perspective view of the implant of FIG. 9 inserted into a patient's lower extremity, in accordance with an aspect of the present disclosure.

With continued reference to FIGS. 3-7, the mounting system 500 may facilitate aligning the implant 300 relative to the implant guide device 402, as shown in FIG. 1. For example, using the implant guide device 402 to engage one or more accessories facilitates insertion of one or more bone screws 308, as shown in FIG. 11, through the fastener holes 114, 116, 322 and into the patient's lower extremity 600, as shown in FIG. 2. Using the mounting system 500 to properly align the implant 300 relative to the implant guide device 402 ensures that inserting the one or more bone screws 308 via the implant guide device 402 will predictably engage fastener holes 114, 116, 322 while simultaneously avoiding hitting and/or damaging the implant 300 during insertion of the one or more bone screws 308. Insertion of the one or more bone screws 308 may provide additional fixation and stability of the implant 300 once inserted into the patient's lower extremity 600, as shown in FIG. 2).

Still referring to FIGS. 3-7, the mounting screw spacer 502 of the mounting system 500 may include an insertion portion 506, a screw spacing portion 508, a base engaging portion 510, and a strike plate attachment portion 512. As shown in FIG. 1, the base engaging portion 510 may be configured to traverse an aperture 448 of the base 404 of the implant guide device 402. The strike plate attachment portion 512 may include a threaded portion surrounding the circumference of the exterior surface of the strike plate attachment portion 512.

Further referencing FIGS. 3-7, the strike plate 504 of the mounting system 500 may include a striking portion 516, an attachment portion 518, a first threaded cavity 520, a second threaded cavity 536, and a strike plate aperture 522 traversing both the first threaded cavity 520 and the second threaded cavity. The first threaded cavity 520 may be located within the striking portion 516 of the strike plate 504 and the second threaded cavity 536 may be located within the attachment portion 518 of the strike plate 504. The first threaded cavity 520 may include threads for engaging an attachment. For example, the first threaded cavity 520 may engage a slap hammer attachment for lowering the implant 300 distally based on the implant 300 being over-inserted into the patient's lower extremity. For example, lowering the implant 300 distally may facilitate controlling the location of the implant 300 without striking the mounting system 500 (e.g., hitting the mounting system 500 with a mallet to lower the implant 300). The second threaded cavity 536 includes threads for engaging the strike plate attachment portion 512 of the mounting screw spacer 502. The second threaded cavity 536 may be configured or sized and shaped such that the strike plate 504 may be removed (e.g., during a surgical procedure) while the remainder of the mounting system 500 and implant 300 are engaged with the patient's lower extremity and/or the implant guide device 402, as shown in FIGS. 1-2. The strike plate 504 may include an enlarged configuration, for example, to provide a large surface area to be hit with a mallet during insertion of the implant 300. For instance, removeable strike plate 504 enables the strike plate to be replaced (e.g., based on the strike plate 504 becoming damaged and/or destroyed due to one or more hard hits with the mallet during insertion) without having to disassemble or disrupt any other feature or aspect of the mounting system 500.

With continued reference to FIGS. 3-7, the mounting system 500 may also include a mounting screw 524 including a threaded portion 526, a shaft 528, and a head 530. Further, the mounting screw spacer 502 may include a through hole 514 through which the mounting screw 524 may be inserted. For instance, the mounting screw 524 may be inserted through a strike plate aperture 522 of the strike plate 504, the through hole 514 of the mounting screw spacer 502, as well as the through hole 202 of the implant engaging portion 190 such that the shaft 528 of the mounting screw 524 traverses the strike plate 504 and mounting screw spacer 502 of the mounting system 500. The threaded portion 526 of the mounting screw 524 may be configured or sized and shaped to be inserted into the second or distal end 304 of the implant 300. Once the mounting screw 524 is inserted, the head 530 of the mounting screw 524 may be located, for example, within the first threaded cavity 520 of the strike plate 504.

Figure 8:
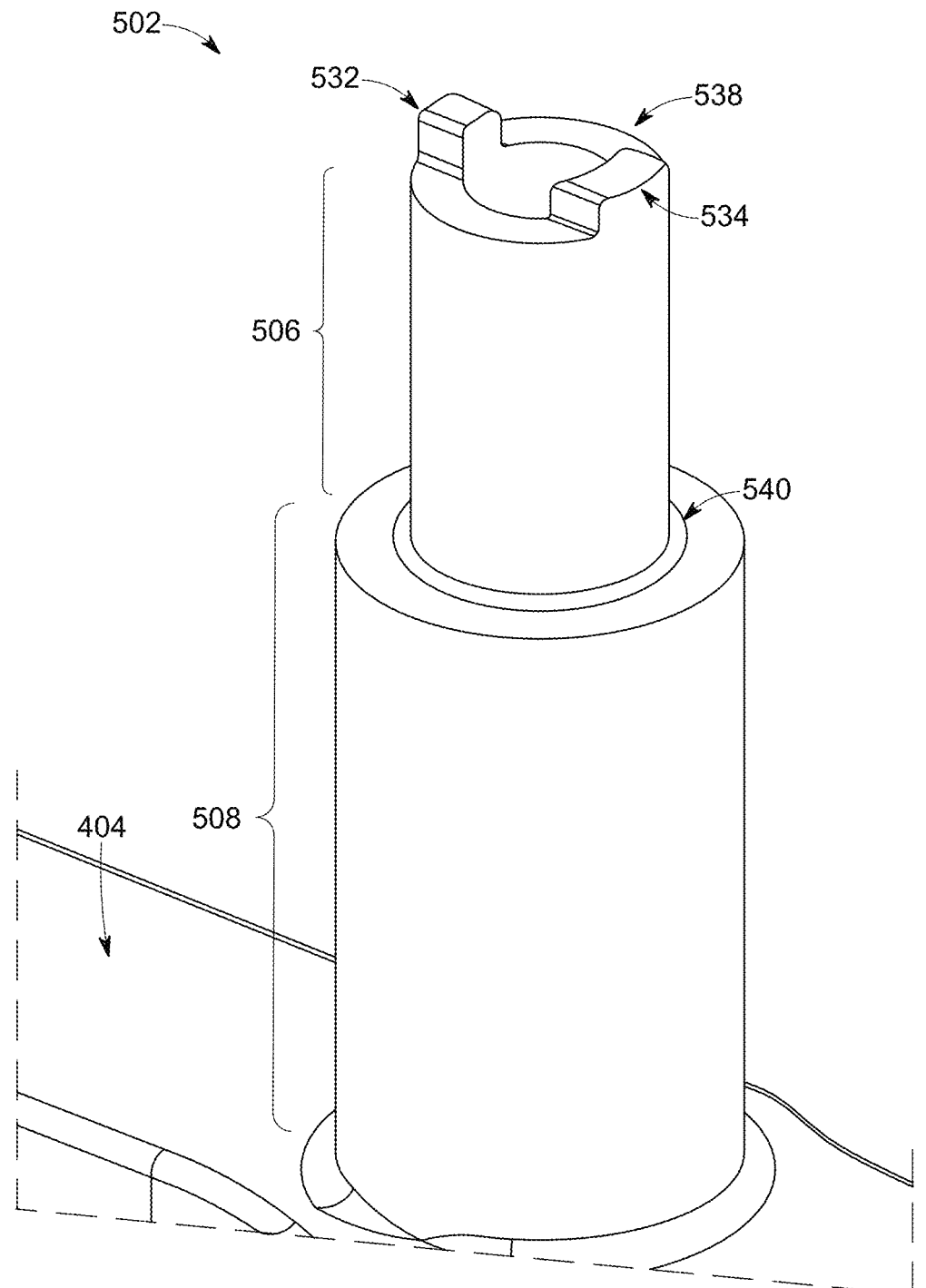
FIG. 8 is a perspective view of a mounting screw spacer of the mounting system of FIG. 3, in accordance with an aspect of the present disclosure.

Referring now to FIG. 8, a mounting screw spacer 502 of the mounting system 500 is shown. The insertion portion 506 of the mounting screw spacer 502 may include one or more alignment tabs 532, 534 for engaging the insertion portion 506 with the tool engagement opening 204 of the implant engaging portion, as shown in FIGS. 3-7. For example, a first alignment tab 532 may be configured or sized and shaped to dovetail with a corresponding recess of the tool engagement opening 204 and a second alignment tab 534 may be configured to interlock with a corresponding notch of the tool engagement opening 204 that is distinct from the recess corresponding to first alignment tab 532. For example, the one or more alignment tabs 532, 534 may be located on a first end 538 of the insertion portion 506, and a second end 540 of the insertion portion 506 is coupled to the screw spacing portion 508 of the mounting screw spacer 502. Each of the one or more alignment tabs 532, 534 may include one or more engaging portions of varying size, shape, positioning, or angle. For instance, as shown in FIG. 10, the first alignment tab 532 may be a narrow protrusion extending outward along the longitudinal axis of the mounting screw spacer 502, whereas the second alignment tab 534 may include a relatively wider protrusion extending outward along the longitudinal axis of the mounting screw spacer 502. Further, the first alignment tab 532 may include, for example, a convex engaging surface, whereas the second alignment tab 534 may include, for example, a concave engaging surface. The one or more alignment tabs 532, 534 may be configured or sized and shaped to prevent rotation of the mounting system 500 relative to the implant 300 while simultaneously aligning the mounting screw spacer 502 within the tool engagement opening 204 of the implant engaging portion. The one or more alignment tabs 532, 534 may facilitate attaching the mounting system 500 to several implant designs (e.g., a single spring dynamic nail, dual spring dynamic nail, etc.), according to various embodiments, such that the implant guide device 402, as shown in FIGS. 1-2, may facilitate inserting the several implant designs into the patient's lower extremity 600.

Figure 9:
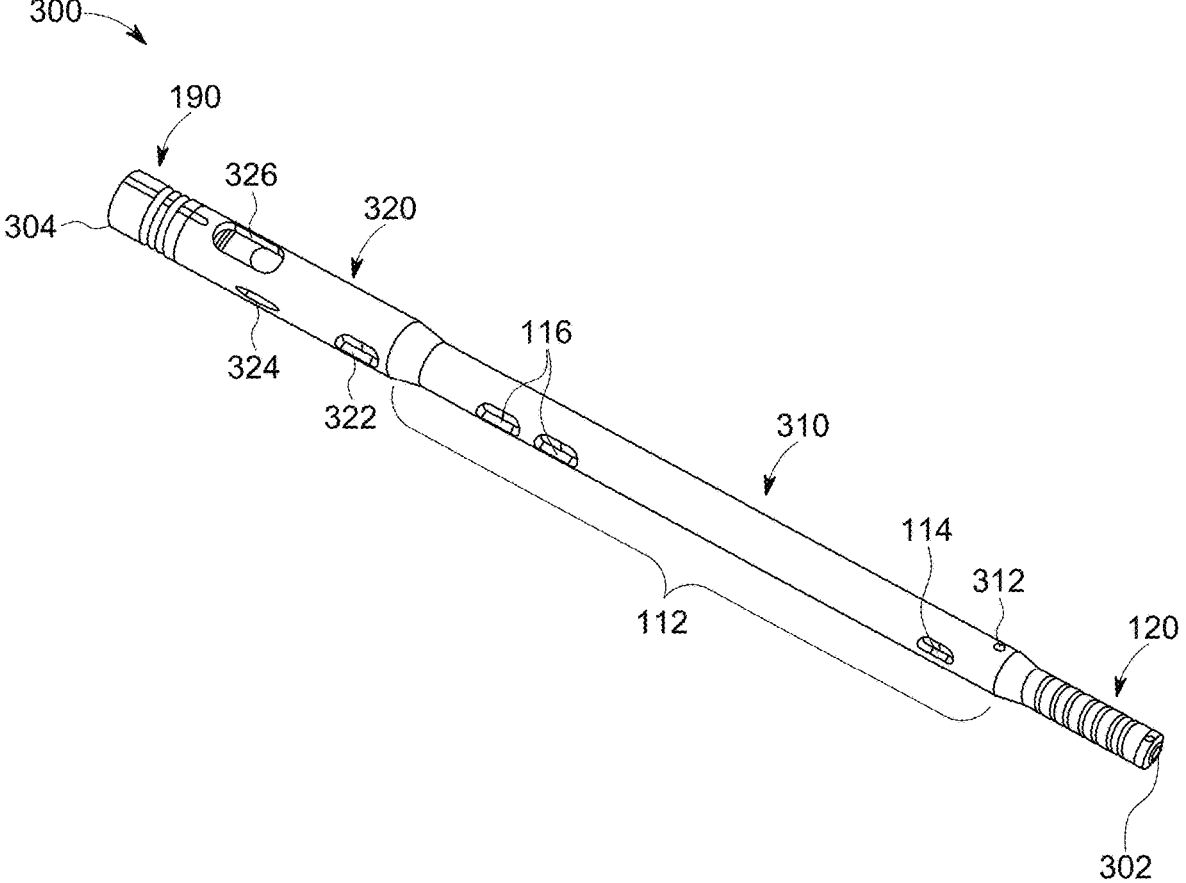
FIG. 9 is a first end perspective view of the implant and the implant engaging portion of the mounting system of FIG. 3, in accordance with an aspect of the present disclosure.

Referring now to FIGS. 9-10, the implant 300 as well as the implant engaging portion 190 of the mounting system, as shown in FIGS. 3-7, are shown. The implant 300 may include a through hole 306 extending through the first member 310 along a longitudinal axis. The implant 300 may also include a second member or inner rod 330, where the coupling member 130 is configured or sized and shaped to secure the first member or outer sheath 310 to the second member or inner rod 330 at the proximal end 302. Further, the implant engaging portion 190 may be configured or sized and shaped to secure the first member or outer sheath 310 to the second member or inner rod 330 at the distal end 304.

Further, as shown in FIGS. 9-10, the second member or inner rod 330 includes a shaft or body portion 332 with an inner rod clip 340 coupled to and extending away from a first end of the second member 330. The body portion 332 of the second member 330 may also include a first or proximate through hole or fastener hole 334 for receiving a bone screw or bone fastener to be inserted in a bone of patient's lower extremity. The through hole 334 may be positioned, for example, near the inner rod clip 340. The through hole 334 may be positioned to align with the through hole 114 of the first member 310 when assembled. The second member 330 may further include at least one fastener hole 336 positioned near a second deformable member (i.e., internal spring) 350.

The at least one fastener hole 336 may be positioned to align with the at least one hole 116 of the first member 310 when assembled.

With continued reference to FIGS. 9-10, the distal end portion 320 of the first member or outer sheath 310 may also include an anti-rotation pin opening 324 for assisting in maintaining composition of the implant 300. The second member 330 may also include at least one anti-rotation pin opening 338 positioned to align with anti-rotation pin opening 312 of the first member 310 to allow an anti-rotation pin 106 to be inserted through pin opening 312 and pin opening 338 to secure the first member 310 to the second member 330. The second member or inner rod 330 may also include an anti-rotation pin opening 344 extending through the inner rod clip 340. The second member 330 may further include an anti-rotation pin opening 356 for assisting in maintaining composition of the second deformable member 350. Each anti-rotation pin opening 312, 324, 338, 344, 356 may be, for example, sized and shaped or configured to receive an anti-rotation pin 106.

Still referencing FIGS. 9-10, the inner rod clip 340 of the second member 330 may include a base portion 342 coupled to and extending away from the body portion 332. When assembled, the base portion 342 is positioned within the through hole 306 of the first member 310 and surrounded by the deformable member 120. The second deformable member 350 may be cut into or integral with the inner rod 330. The second deformable member 350 may include, for example, a helical-cut, machined spring. The spring 350 may include a first through hole or fastener hole 352 extending through the spring 350 from one side to the other side, and a second through hole or fastener hole 354 extending through the spring 350 from the one side to the other side. The spring 350 may further include a coupling portion 358 positioned on the distal end of the second member 330. The coupling portion 358 may include an opening 360 with internal threads positioned on an interior surface of the opening 360 for receiving the threaded portion 526 of the mounting screw 524. According to various embodiments, the coupling portion 358 may include one or more alignment recesses for engaging corresponding alignment protrusions in the implant engaging portion 190. The coupling portion 358 may also include external threads surrounding the circumference of the coupling portion 358 for insertion into an interior threaded portion 198 of the implant engaging portion 190.

FIG. 11 shows the implant 300 inserted into a patient's lower extremity 600. The implant 300 is configured or sized and shaped to traverse through the longitudinal axis of the patient's tibia 604 as well as the patient's talus 606 and calcaneus 608. The implant 300 may be secured to each bone 604, 606, 608 of the patient's lower extremity 600 using a plurality of bone screws 308 inserted through one or more through holes 114, 116, 322, 326, 334, 336, 352, 354 of the implant 300. For instance, one or more bone screws 308 may be inserted perpendicular to the longitudinal axis of both the patient's tibia 604 and the implant 300. Further, one or more bone screws 308 may be configured or sized and shaped to traverse a portion of the patient's talus 606 as well as one or more through holes 114, 116, 322, 326, 334, 336, 352, 354 of the implant 300. As shown in FIG. 11, the implant 300 may be secured to the calcaneus 608 using a bone screw 308 extending through a posterior portion of the calcaneus 608 and through a through hole of the implant 300.

Figure 12:
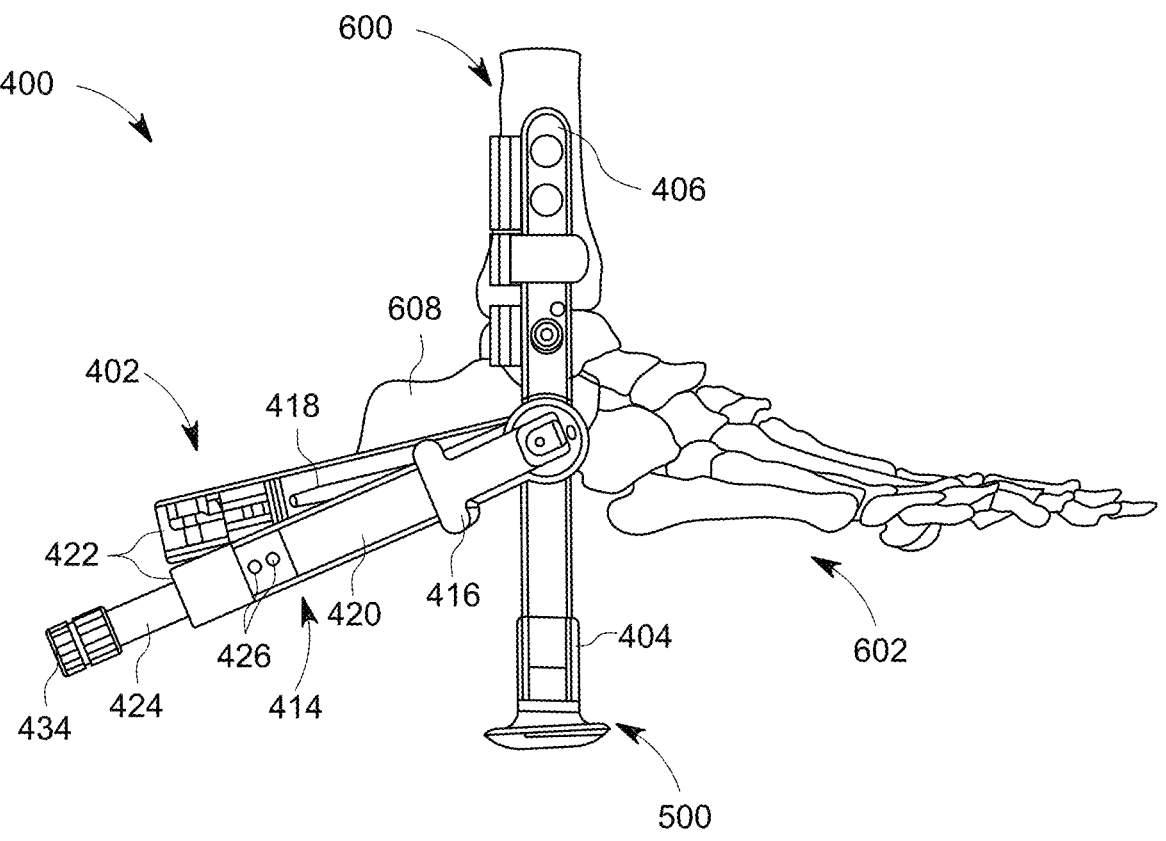
FIG. 12 is a side, first position view of the implant guide system of FIG. 1 in relation to a patient's lower extremity, in accordance with an aspect of the present disclosure.
Figure 13:
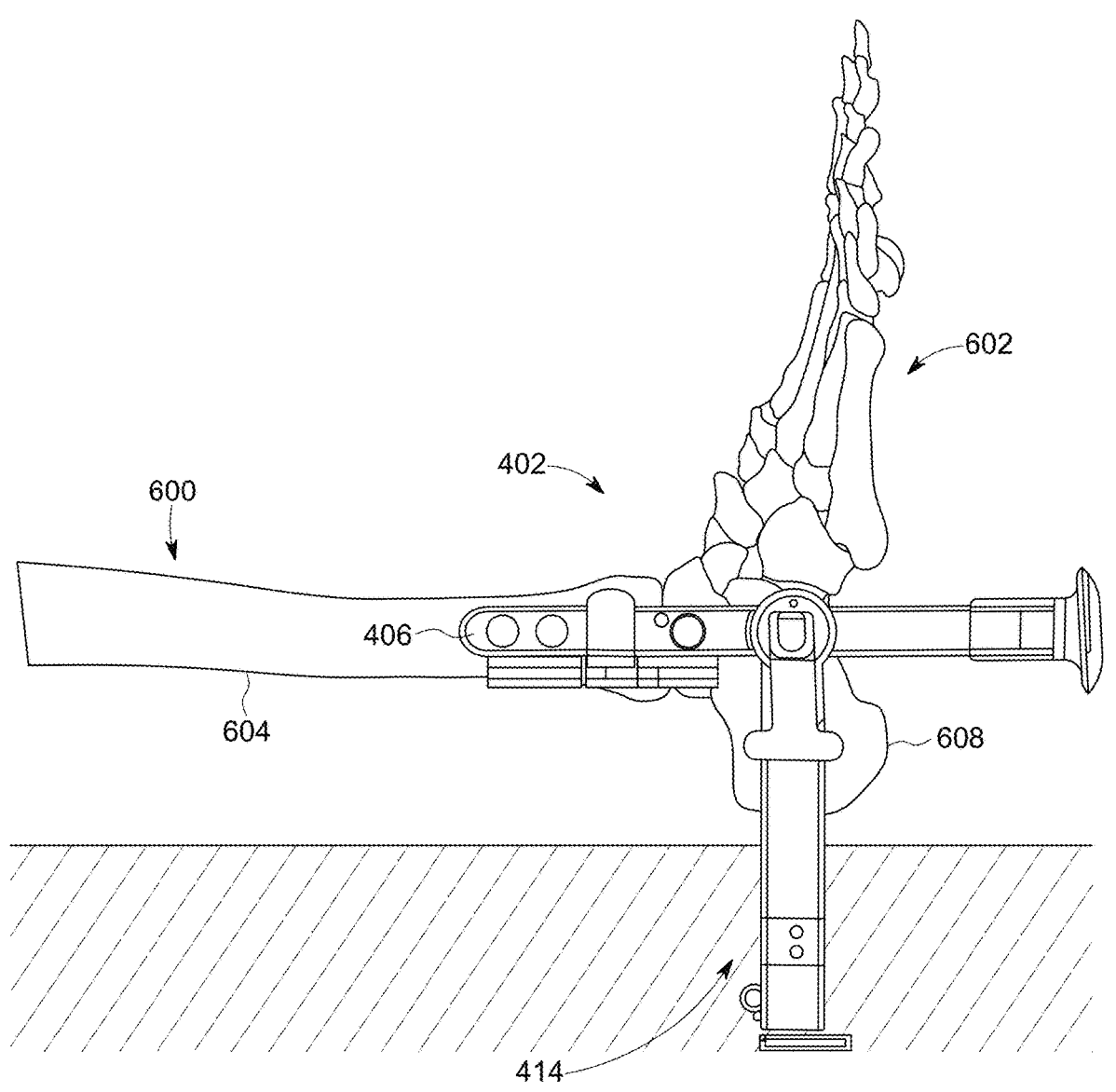
FIG. 13 is a side, second position view of the implant guide system of FIG. 1 in relation to a patient's lower extremity, in accordance with an aspect of the present disclosure.

FIGS. 12-13 show the implant guide system 400 coupled to a patient's lower extremity 600. As shown in FIG. 12, the targeting arm 414 of the implant guide device 402 may be hingedly coupled to at least one of the first arm 406 and the second arm 408, as shown in FIGS. 1-2. The targeting arm 414 may be, for example, coupled to the first arm 406 via a targeting arm lock 416. The targeting arm lock 416 may include a hinged lever for fixing a position of the targeting arm 414.

With continued reference to FIGS. 12-13, the targeting arm 414 may be positioned, for example, at approximately a 90° angle relative to a longitudinal axis of the first arm 406 in order to insert a bone screw 308 into a posterior portion of the calcaneus 608. In order to obtain a more optimal angle for inserting the bone screw into the posterior portion of the calcaneus 608, it may be desirous to modify the trajectory of the bone screw 308 (e.g., ±5° in either direction) to provide an optimal entry point for the bone screw 308. The targeting arm lock 416 may be loosened, for example, by extending the hinged lever away from the first arm 406 of the implant guide device 402. This loosening may allow the targeting arm 414 to be repositioned in order to modify the entry point of the bone screw 308. Once the targeting arm 414 is positioned at a desired angle relative to the longitudinal axis of the first arm 406, the targeting arm lock 416 may be retracted toward the first arm 406 of the implant guide device 402. The targeting arm 414 may be configured or sized and shaped such that an adjustment of the trajectory of the bone screw 308 by ±5° in either direction may modify the entry point of the bone screw 308 into the calcaneus 608 but still enable the bone screw 308 to insert through a hole 326 of the distal end portion 320 of the implant 300. Advantageously, altering the trajectory of the bone screw 308 (e.g., at an angle of ±5° in either direction) for insertion into the posterior portion of the calcaneus 608 enables multiple bone screws 308 to be inserted into the calcaneus 608 (e.g., insert/throw parallel screws into the calcaneus 608).

Further referencing FIGS. 12-13, the targeting arm 414 may include one or more inlays 418 (e.g., a metal rod) embedded in a crevice within a side support portion 420 of the targeting arm 414. The one or more inlays 418 may be configured or sized and shaped to provide a visual for aligning a bone screw 308 to be inserted into the calcaneus 608. For example, the one or more inlays 418 may be positioned longitudinally within the side support portion 420 in a manner corresponding to the trajectory of an accessory to be inserted into a patient's calcaneus 608. For instance, the one or more inlays 418 may be configured or sized and shaped such that insertion of a screw 308 via a screw guide 424 will enable the screw 308 to align parallel to the one or more inlays 418 such that the inlay 418 provides a visual representation of an insertion point of the screw 308 via the screw guide 424 into the calcaneus 608. As shown, each side support portion 420 may include, for example, an inlay 418. For instance, based on the implant guide device 402 including a targeting arm 414 with two side support portions 420, one side support portion 420 coupled to the first arm 406 and another side support portion 420 coupled to the second arm 410. Each side support portion 420 may include, for example, an inlay 418 for providing a visual trajectory of the accessory to be inserted. The inlay 418 of the side support portion 420 that is coupled to the first arm 406 may be configured or sized and shaped to provide, for instance, a lateral view of the trajectory of the accessory to be inserted, whereas the inlay 418 of the side support portion 420 that is coupled to the second arm 410 may be configured or sized and shaped to provide, for instance, a medial view of the trajectory of the accessory to be inserted. Absent the one or more inlays 418, fluoroscopy may show the entry point in the calcaneus 608 and/or the fastener hole 326 of the implant 300, but typically a surgeon must mentally visualize alignment and/or the trajectory of the accessory to be inserted. Advantageously, the one or more inlays 418 may assist the surgeon by facilitating visualization of the trajectory of the accessory to be inserted.

Still referencing FIGS. 12-13, the targeting arm 414 may also include an accessory engagement portion 422 coupled to the side support portion 420 via, for instance, one or more stabilizing pins 426. The accessory engagement portion 422 may be configured or sized and shaped to engage the screw guide 424 for insertion of the bone screw into the calcaneus 608. For instance, the screw guide 424 may traverse a hollow conduit of the accessory engagement portion 422. The screw guide 424 may, for example, be configured or sized and shaped to engage with a drill guide 434 used to facilitate drilling a bone screw 308 into a bone of the patient.

Further referring to FIGS. 12-13, the targeting arm 414 may also be configured or sized and shaped to provide elevated support to the patient's lower extremity 600. As shown in FIG. 13, a patient's lower extremity 600 is positioned in a supine position with the first arm 406 of the implant guide device 402 parallel to the patient's tibia 604, when the foot 602 is pointing in an upwards position. Further, the targeting arm 414 is positioned perpendicular and inferior to the first arm 406 of the implant guide device 402 as well as the patient's tibia 604, while resting on a horizontal surface (e.g., an operating table) such that the patient's foot 602 is elevated above the horizontal surface. Based on the targeting arm 414 being positioned as shown in FIG. 13, the targeting arm 414 may independently bolster the implant guide device 402 and the patient's lower extremity 600 during, for instance, a surgical operation. Advantageously, using the targeting arm 414 to prop (i.e., provide kickstand functionality) the patient's lower extremity 600 and the implant guide device 402 above a horizontal surface may, for instance, eliminate the need for an assistant to prop or hold the patient's lower extremity 600 above an operating table during insertion of bone screws 308 to facilitate access to the patient's lower extremity 600 during a surgical procedure.

Figure 14:
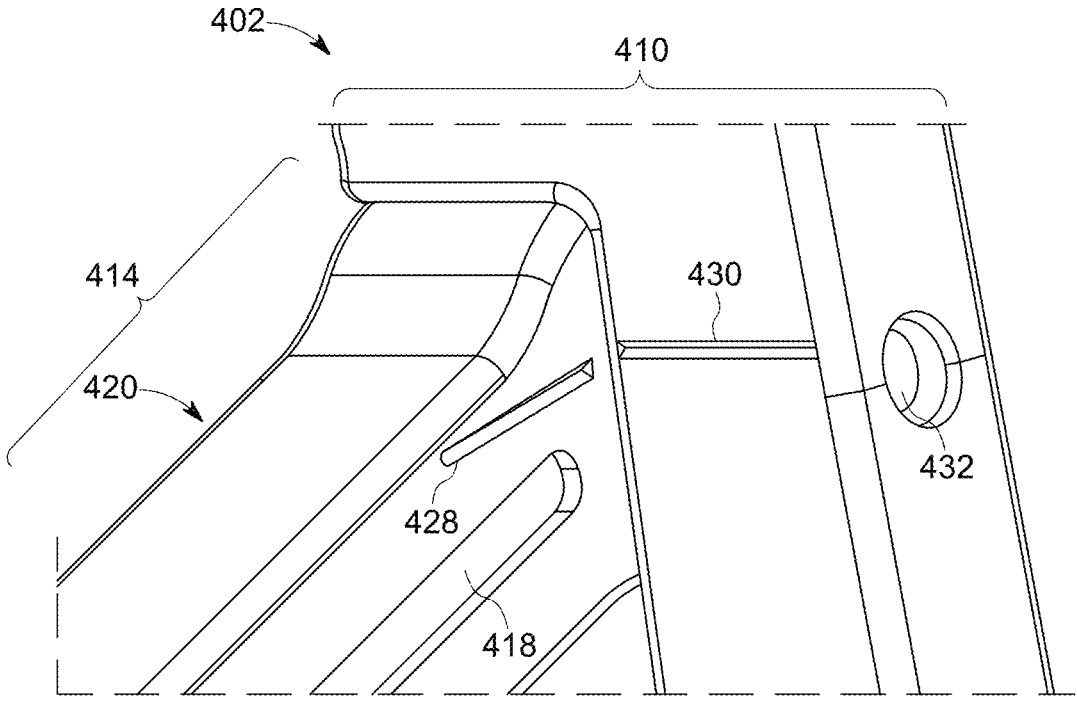
FIG. 14 is a perspective view of a portion of an implant guide device of the implant guide system of FIG. 1, in accordance with an aspect of the present disclosure.
Figure 15:
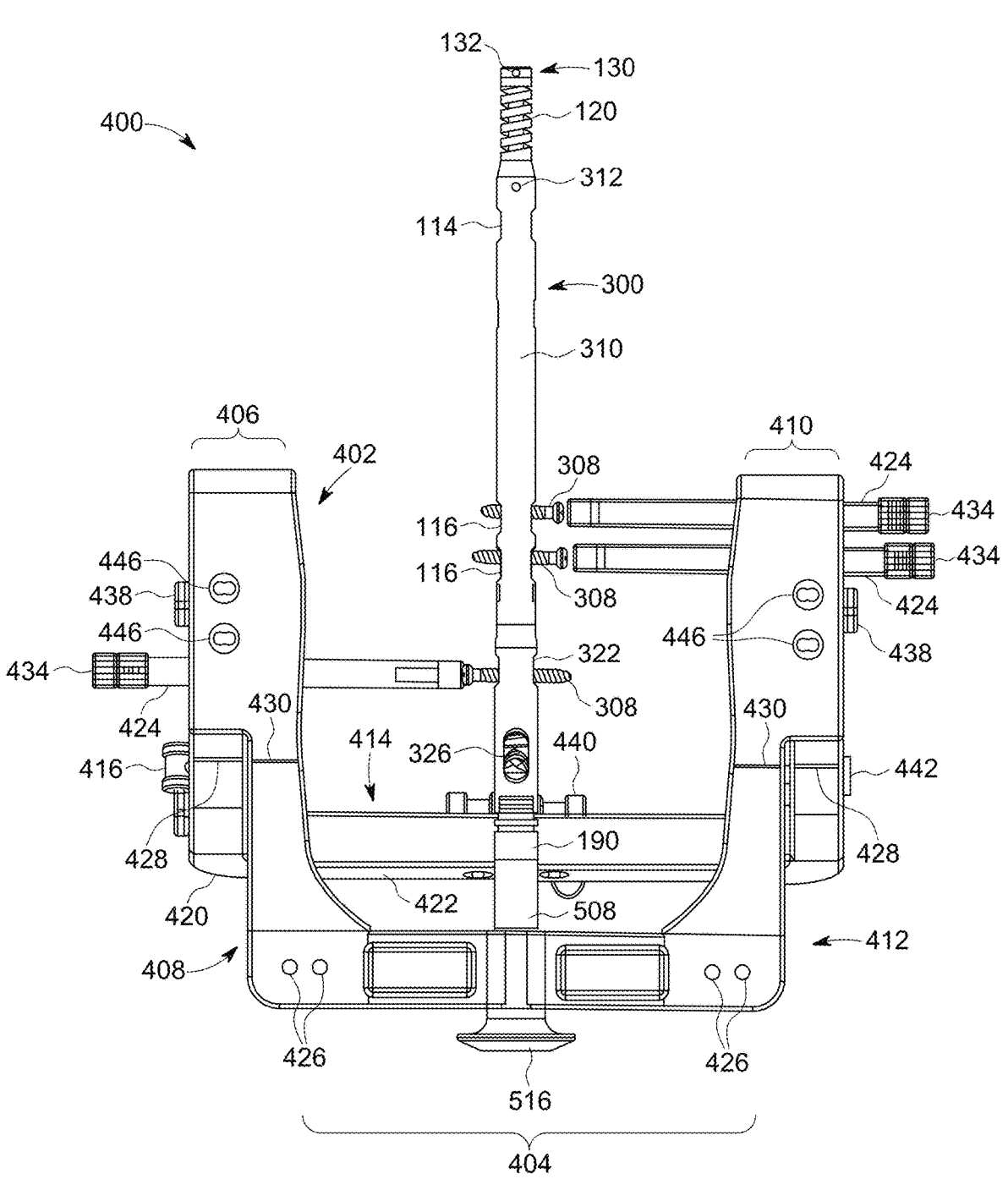
FIG. 15 is a top view of the implant guide system of FIG. 1, in accordance with an aspect of the present disclosure.
Figure 16:
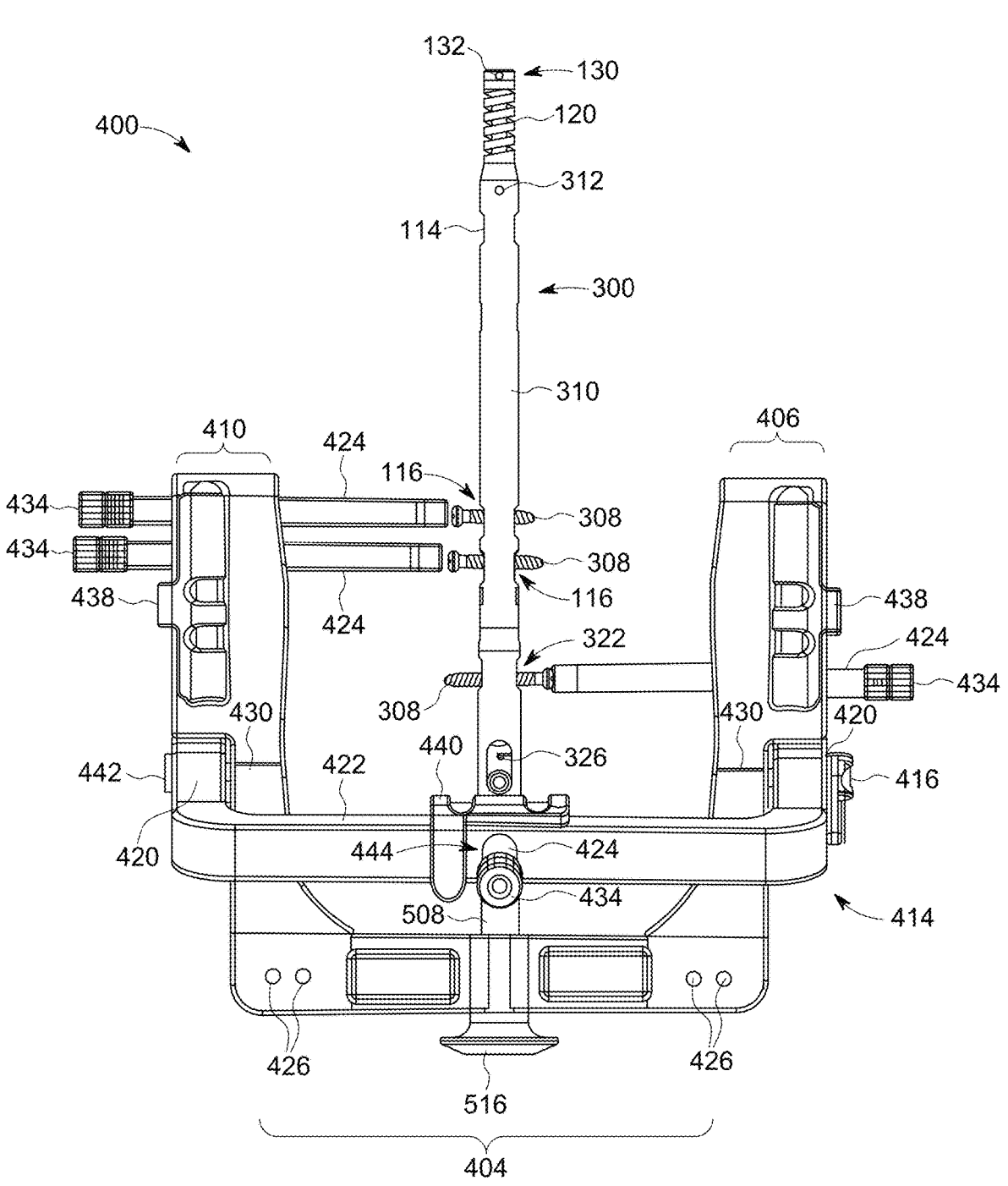
FIG. 16 is a bottom view of the implant guide system of FIG. 1, in accordance with an aspect of the present disclosure.
Figure 17:
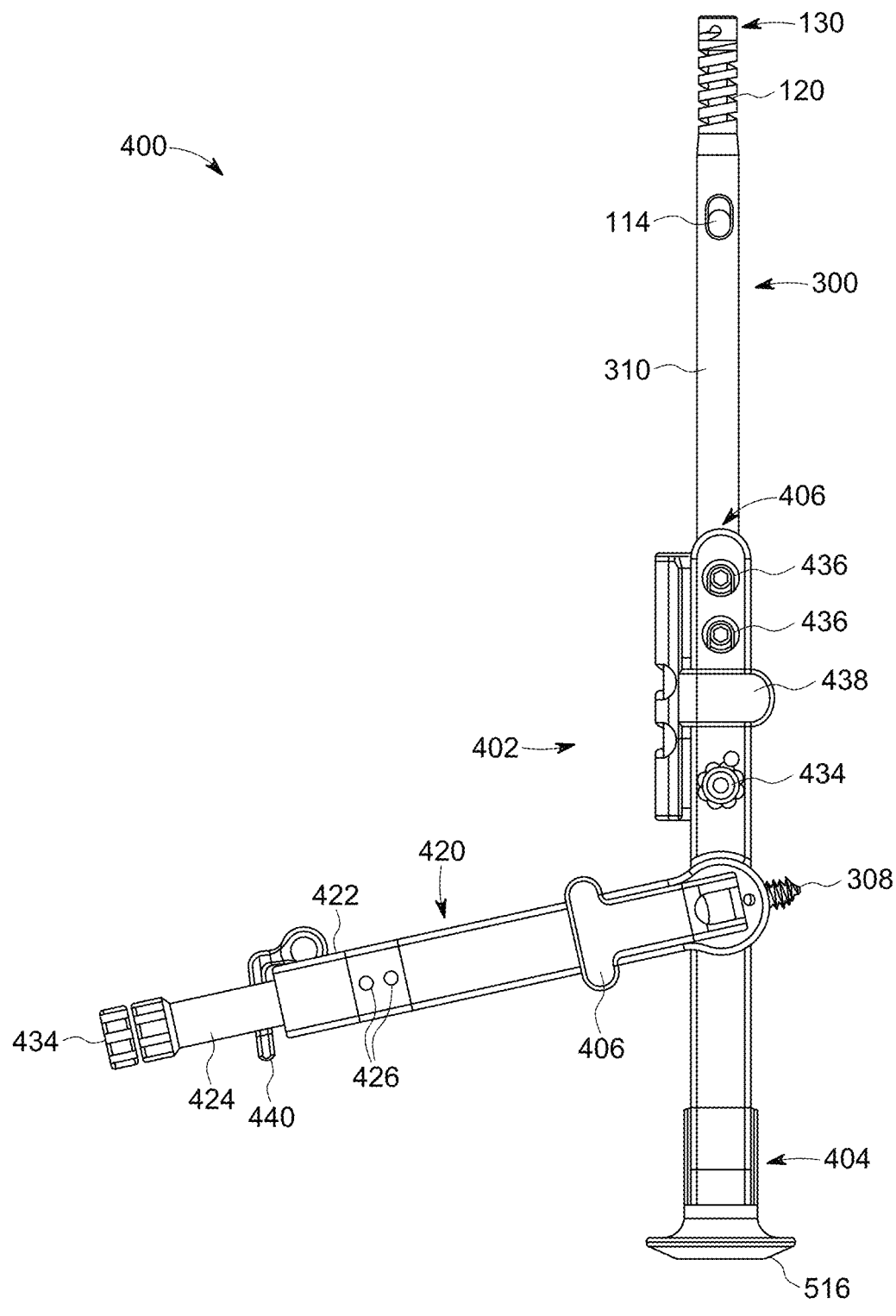
FIG. 17 is a first side view of the implant guide system of FIG. 1, in accordance with an aspect of the present disclosure.
Figure 18:
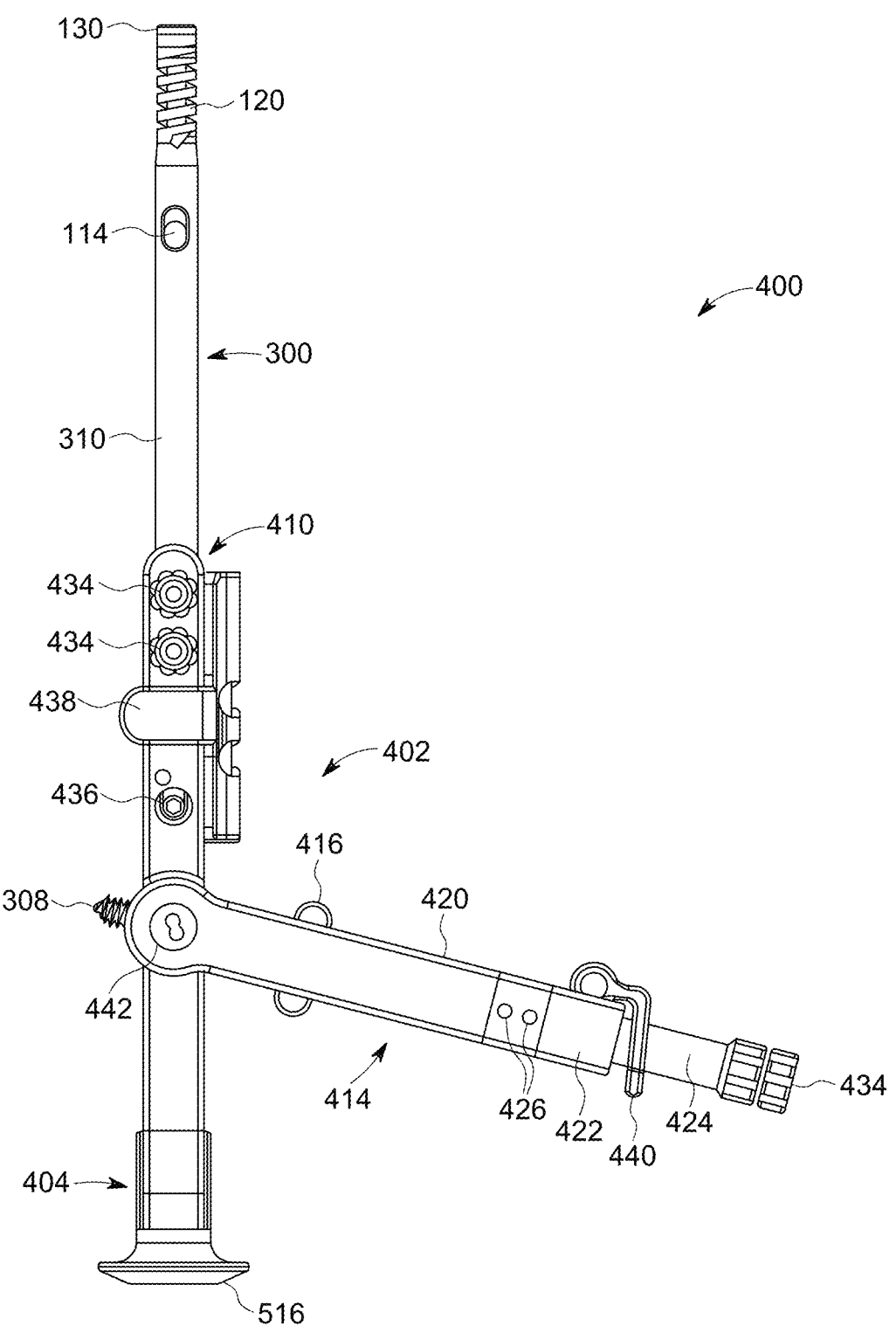
FIG. 18 is a second side view of the implant guide system of FIG. 1, in accordance with an aspect of the present disclosure.
Figure 19:
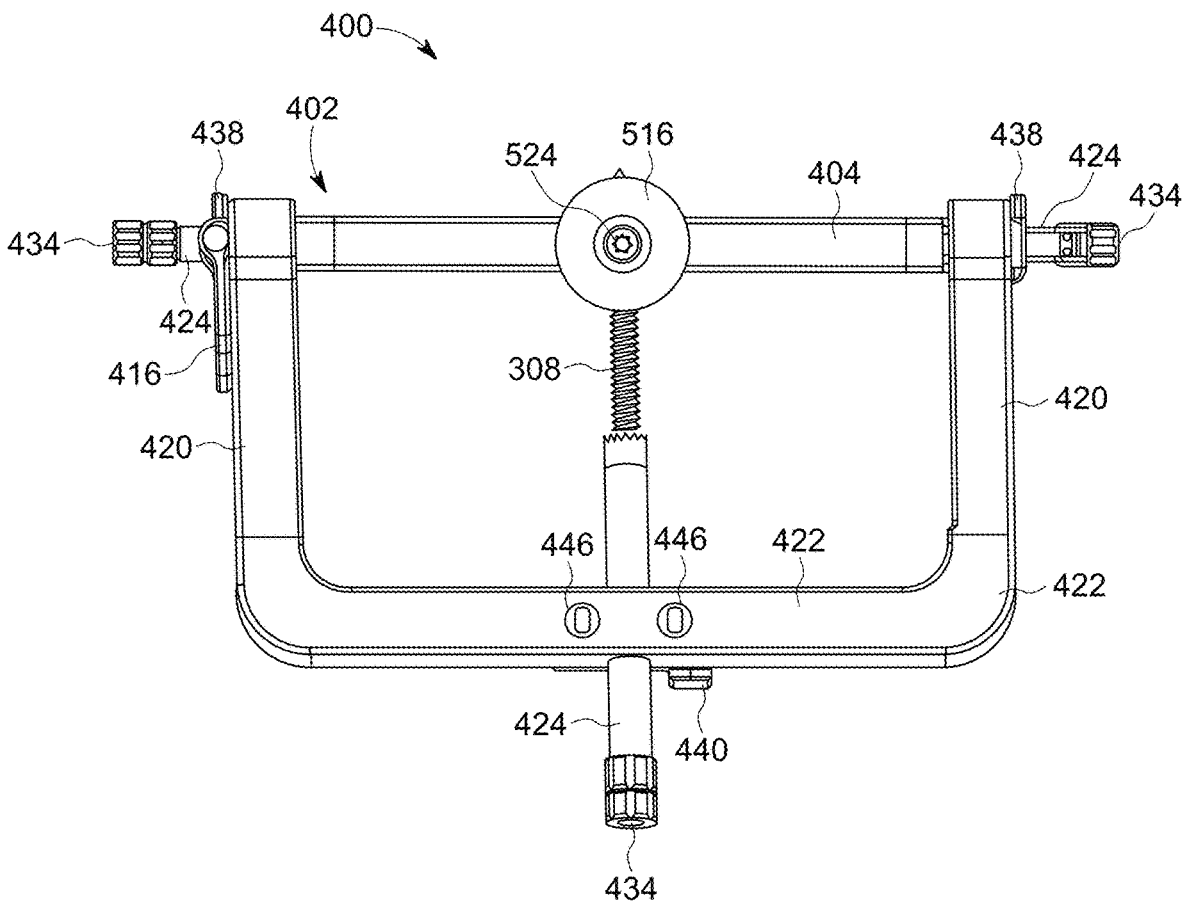
FIG. 19 is a first end view of the implant guide system of FIG. 1, in accordance with an aspect of the present disclosure.
Figure 20:
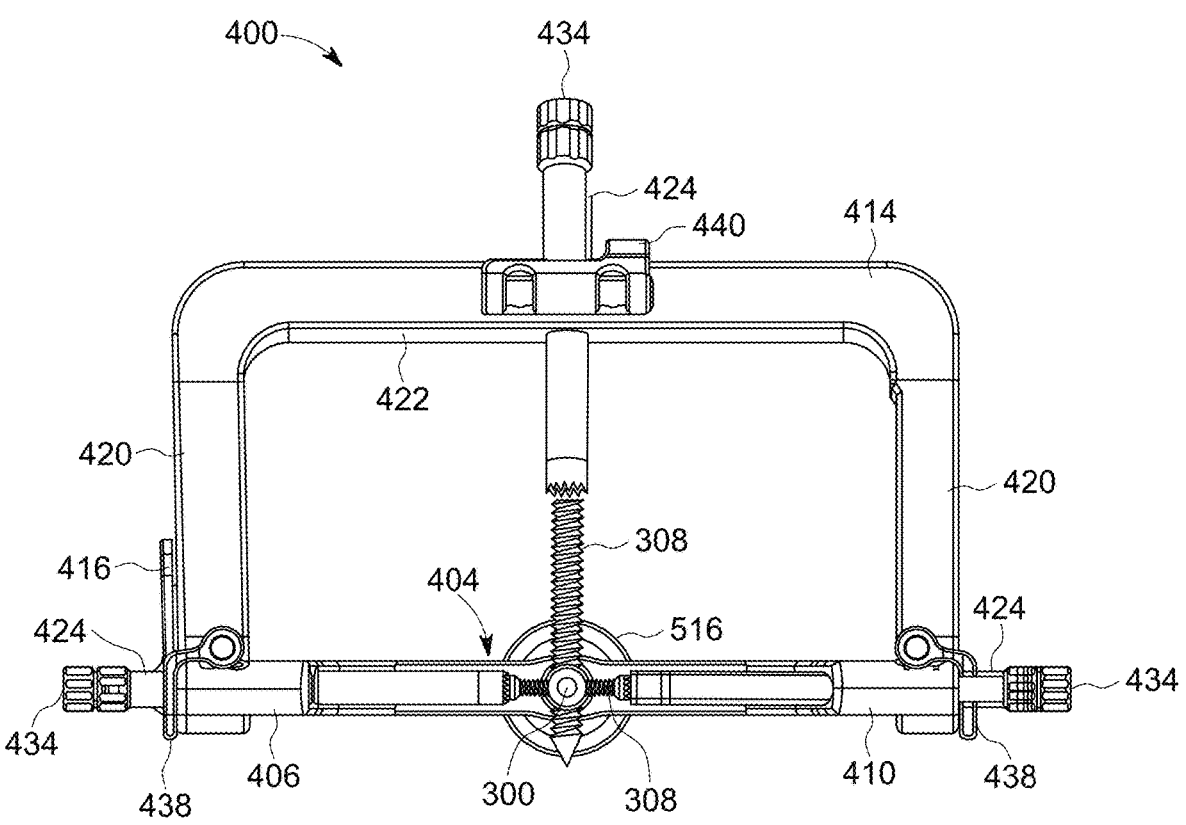
FIG. 20 is a second end view of the implant guide system of FIG. 1, in accordance with an aspect of the present disclosure.
Figure 21:
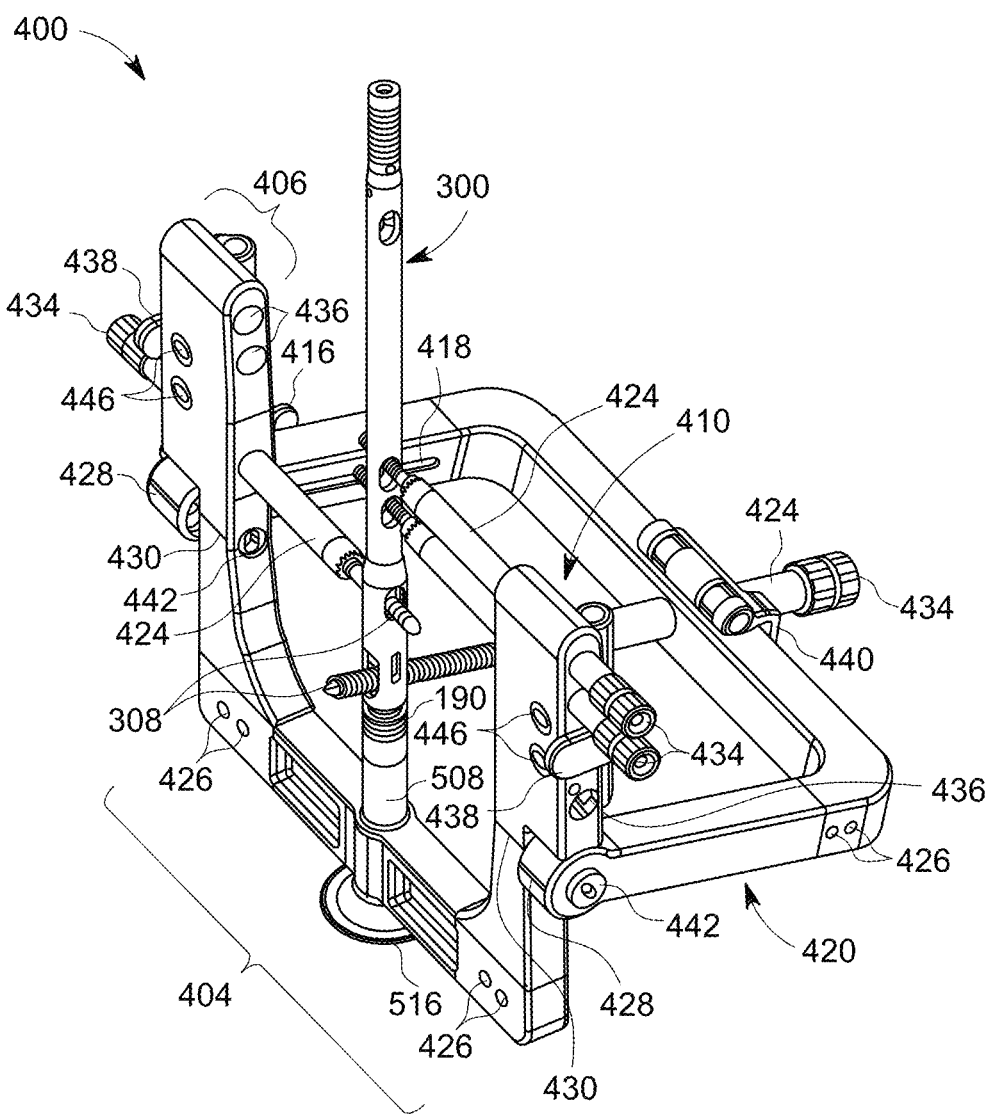
FIG. 21 is a first perspective view of the implant guide system of FIG. 1, in accordance with an aspect of the present disclosure.
Figure 22:
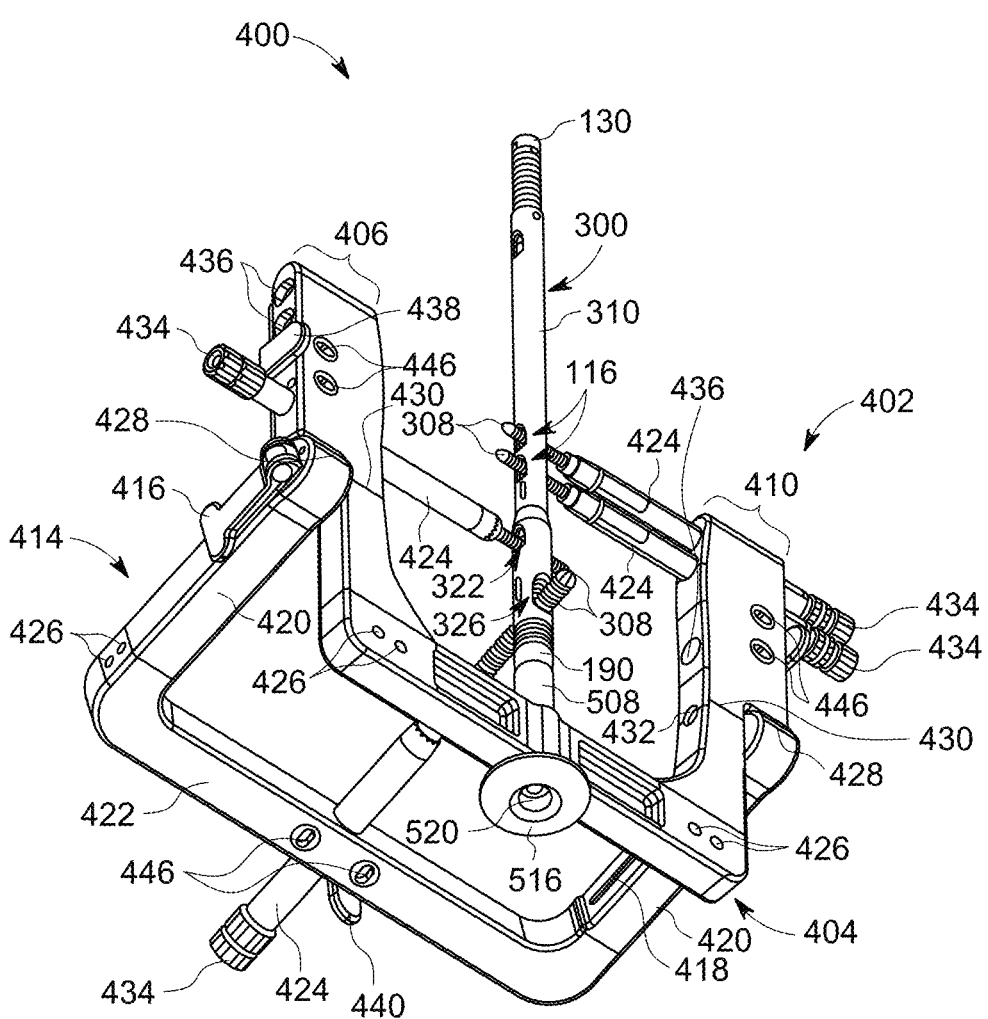
FIG. 22 is a second perspective view of the implant guide system of FIG. 1, in accordance with an aspect of the present disclosure.

FIG. 14 shows a portion of the implant guide device 402 of the implant guide system 400. The implant guide device 402 may include, for example, one or more side support orientation markings 428 of the side support portion 420 of the targeting arm 414 of the implant guide device 402. Further, the implant guide device 402 may also include one or more arm orientation markings 430 for aligning the targeting arm to at least one of the first arm 406 and the second arm 410. The one or more side support orientation markings 428 may also be located, for example, at other locations on the side support portion 420 of the targeting arm 414 such that the one or more side support orientation markings 428 may be viewable when viewing the targeting arm 414 at, for example, a medial view, a lateral view, an anterior view, a posterior view, or another viewing trajectory. The one or more side support orientation markings 428 may facilitate aligning the targeting arm 414 relative to at least one of the first arm 406 and the second arm 410 at any desirable angle (e.g. a nominal calcaneus angle).

Also shown in FIG. 14 is a pivot hole 432 through which a pin may be inserted for coupling the targeting arm 414 to at least one of the first arm 406 and the second arm 410. Pivoting the targeting arm 414 about the pivot hole 432 facilitates adjusting the trajectory of an accessory for insertion.

Referring now to FIGS. 15-22, the implant guide system 400 is shown. The implant guide device 402 may be configured or sized and shaped to engage a plurality of accessories. For instance, the first arm 406 and the second arm 410 may be configured or sized and shaped to secure one or more screw guides 424 for inserting a bone screw 308 into a lower extremity of a patient. For instance, the implant guide device 402 may include a plurality of through holes 436, through which each screw guide 424 may be configured or sized and shaped to be inserted. The through holes 436 may be configured or sized and shaped to align with, for instance, fastener holes 116 of the implant 300 to facilitate inserting bone screws 308 into fastener holes 116 of the implant 300 as well as into the lower extremity. In particular, one or more through holes 436 may be positioned at a proximal portion of at least one of the first arm 406 and the second arm 410 of the implant guide device 402 to align with fastener holes 116 for inserting bone screws 308 into the tibia of the patient. Further, one or more through holes 436 may be positioned at a distal portion of the at least one of the first arm 406 and the second arm 410 to align with fastener hole 322 for inserting a bone screw 308 into the talus of the patient.

With continued reference to FIGS. 15-22, the through holes 436 may also be associated with and configured or sized and shaped to engage with one or more locks 438 (e.g., cam locks) for securing the plurality of accessories. For instance, the one or more locks 438 may be hingedly connected to at least one of the first arm 406 and the second arm 410. The locks 438 may engage with through holes 436 by pivoting the one or more locks 438 to extend away from the at least one of the first arm 406 and the second arm 410. The pivoting of the locks 438 loosens an accessory traversing the through hole 436 or pivoting the one or more locks 438 to retract towards the at least one of the first arm 406 and the second arm 410 to fasten an accessory traversing the through hole 436 into a desired position. The targeting arm 414 may also include a targeting arm through hole 444 configured or sized and shaped to engage a targeting arm lock 440 (e.g., cam lock) for securing an accessory. For example, the targeting arm lock 440 may be hingedly connected to the targeting arm 414 such that extending the targeting arm lock 440 away from the targeting arm 414 loosens an accessory traversing the through hole 444. In addition, retracting the targeting arm lock 440 toward the targeting arm 414 affixes an accessory traversing the targeting arm through hole 444. The implant guide device 402 may also include a plurality of fasteners 446 for fastening the locks 438 to at least one of the first arm 406 and the second arm 410 as well as fastening the targeting arm lock 440 to the targeting arm 414.

Still referencing FIGS. 15-22, the implant guide device 402 may include one or more targeting arm support pins 442 about which the targeting arm 414 may pivot relative to at least one of the first arm 406 and the second arm 410. The targeting arm 414 may be configured or sized and shaped to pivot relative to the at least one of the first arm 406 and the second arm 410 for aligning the screw guide 424 for insertion of a bone screw 308 into the lower extremity of the patient. The one or more targeting arm support pins 442 may be configured or sized and shaped to traverse a pivot hole 432 of at least one of the first arm 406 and the second arm 410. As shown, for example, in FIG. 15, one or more side support orientation markings 428 as well as one or more arm orientation markings 430 may be configured or sized and shaped to be visible when viewing the implant guide device 402 from an anterior view to facilitate aligning the targeting arm 414.

Figure 23:
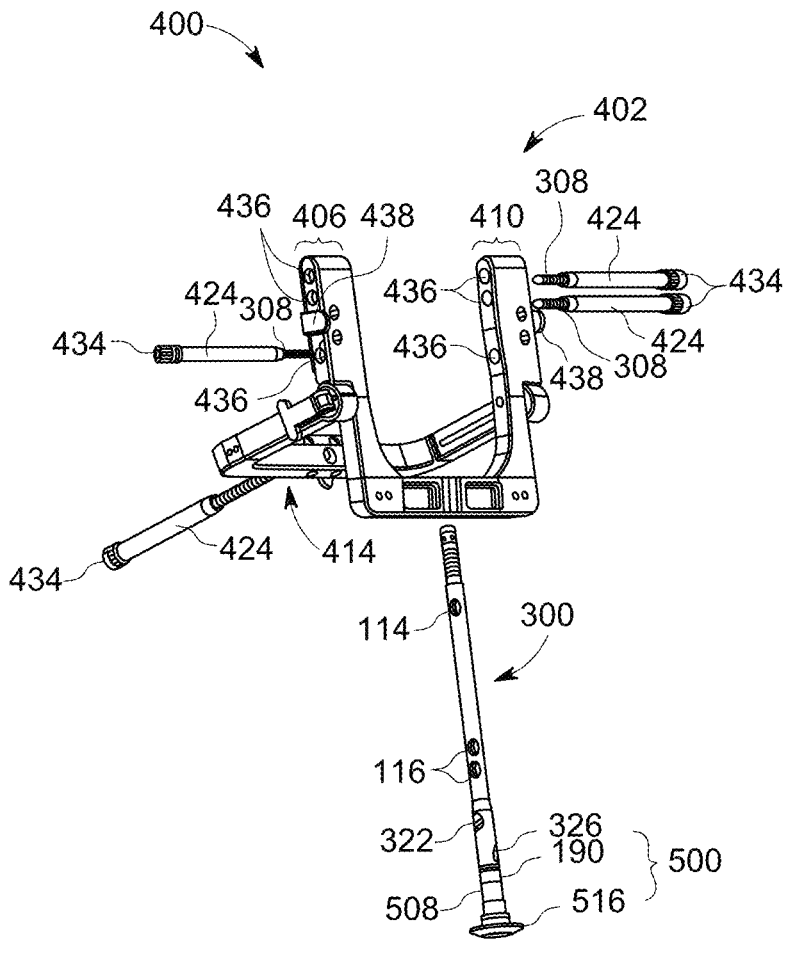
FIG. 23 is a partially exploded, perspective view of the implant guide system of FIG. 1, with the implant guide device detached from the implant and accessories, in accordance with an aspect of the present disclosure.
Figure 24:
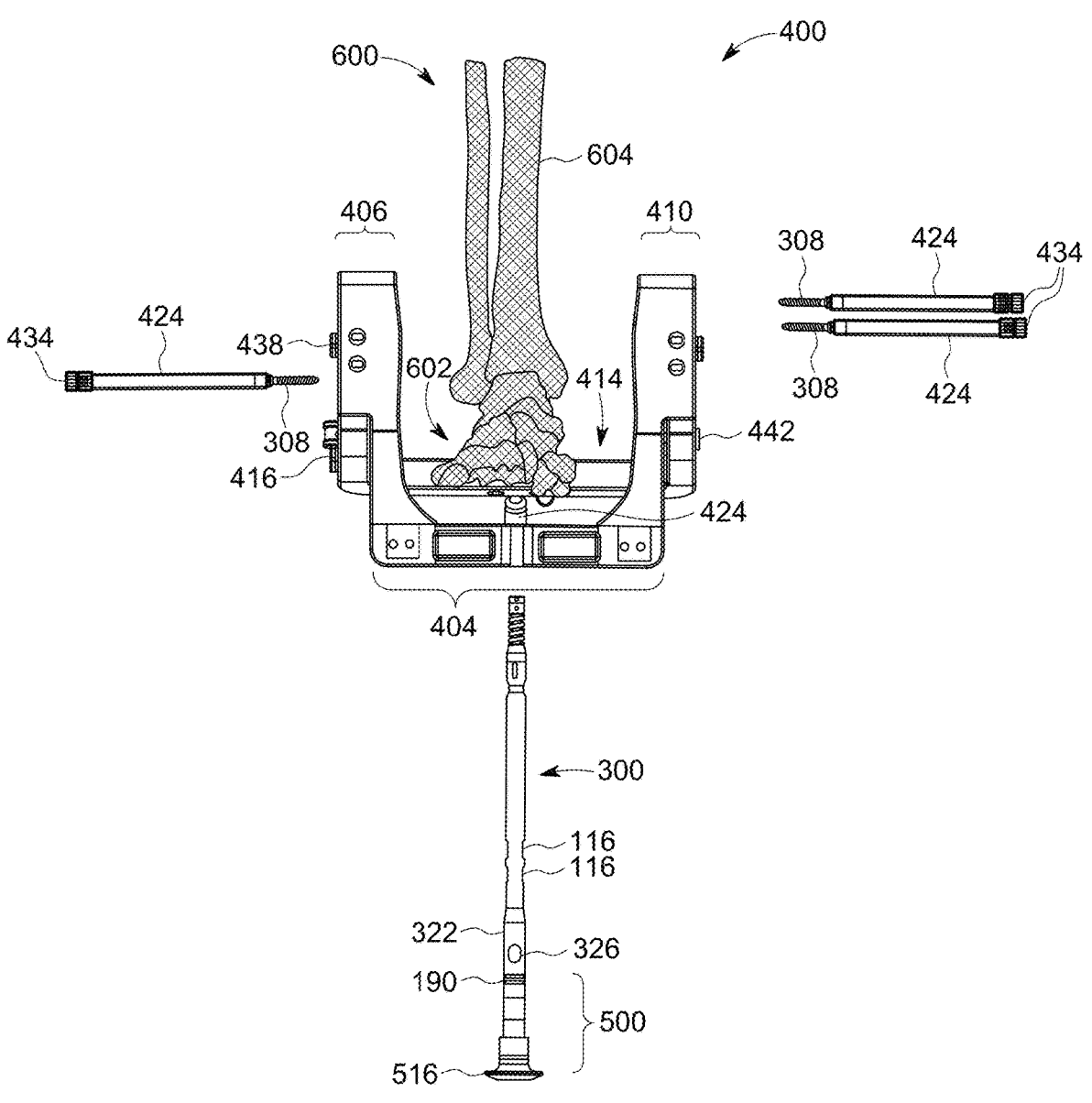
FIG. 24 is a partially exploded, top view of the implant guide system of FIG. 1 in relation to a patient's lower extremity, in accordance with an aspect of the present disclosure.
Figure 25:
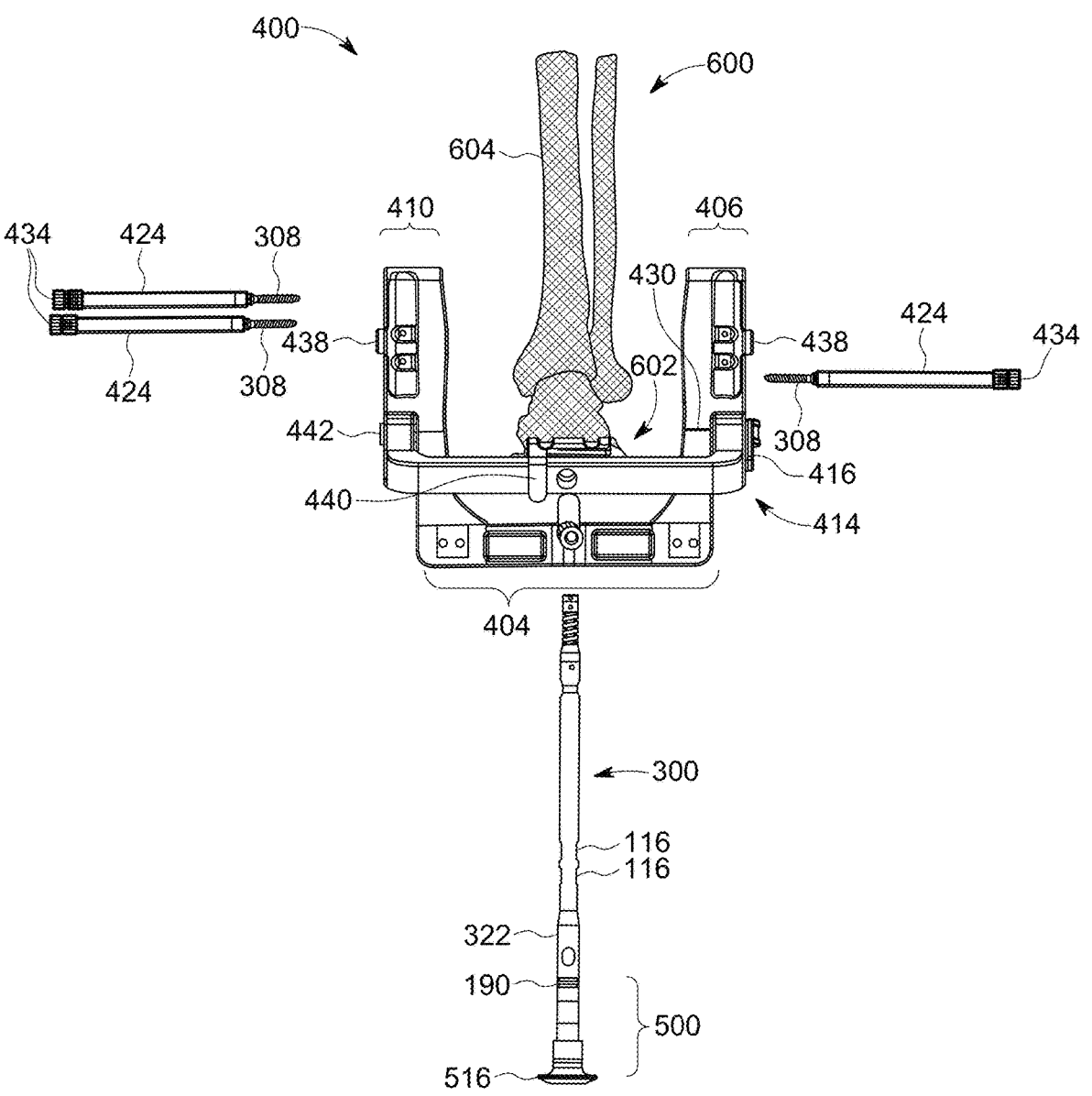
FIG. 25 is a partially exploded, bottom view of the implant guide system of FIG. 1 in relation to a patient's lower extremity, in accordance with an aspect of the present disclosure.
Figure 26:
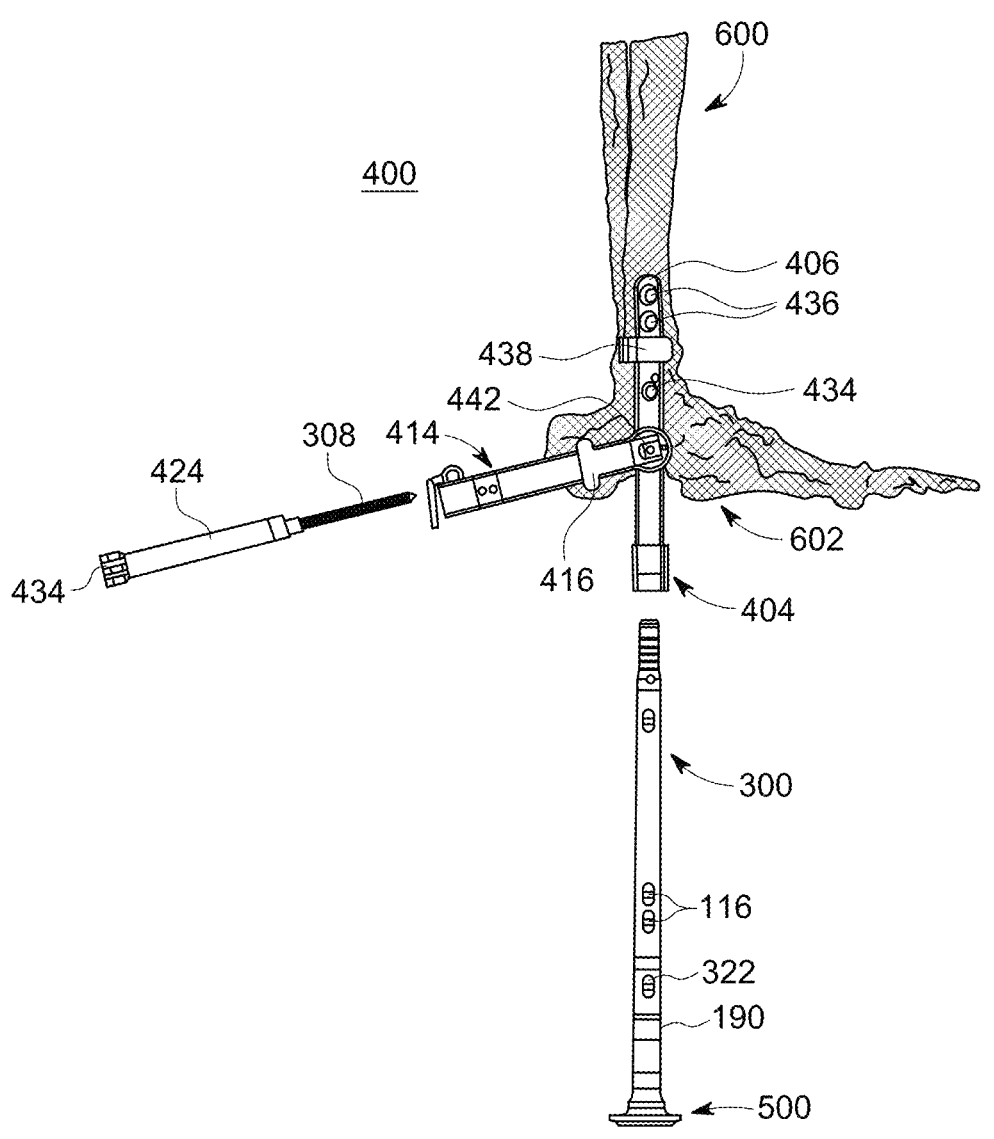
FIG. 26 is a partially exploded, first side view of the implant guide system of FIG. 1 in relation to a patient's lower extremity, in accordance with an aspect of the present disclosure.
Figure 27:
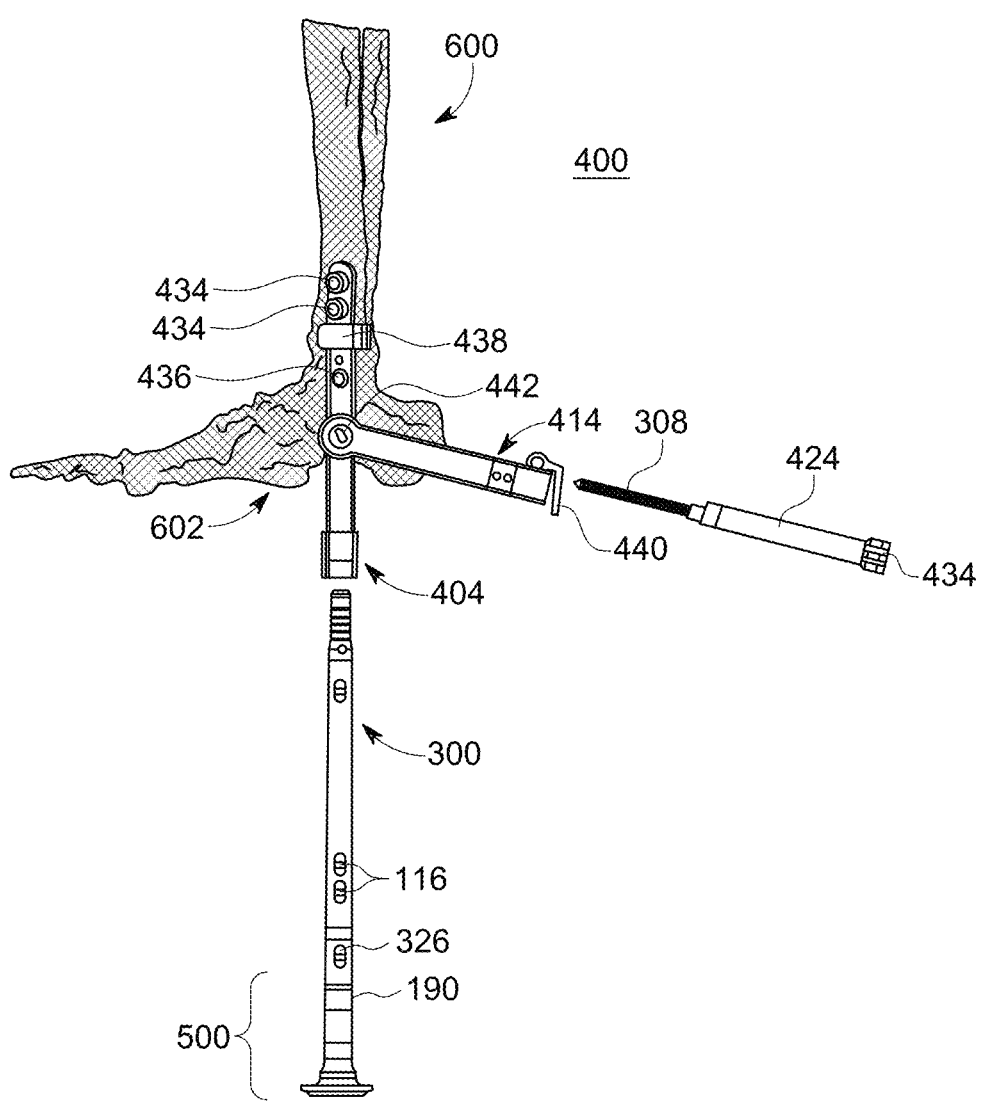
FIG. 27 is a partially exploded, second side view of the implant guide system of FIG. 1 in relation to a patient's lower extremity, in accordance with an aspect of the present disclosure.
Figure 28:
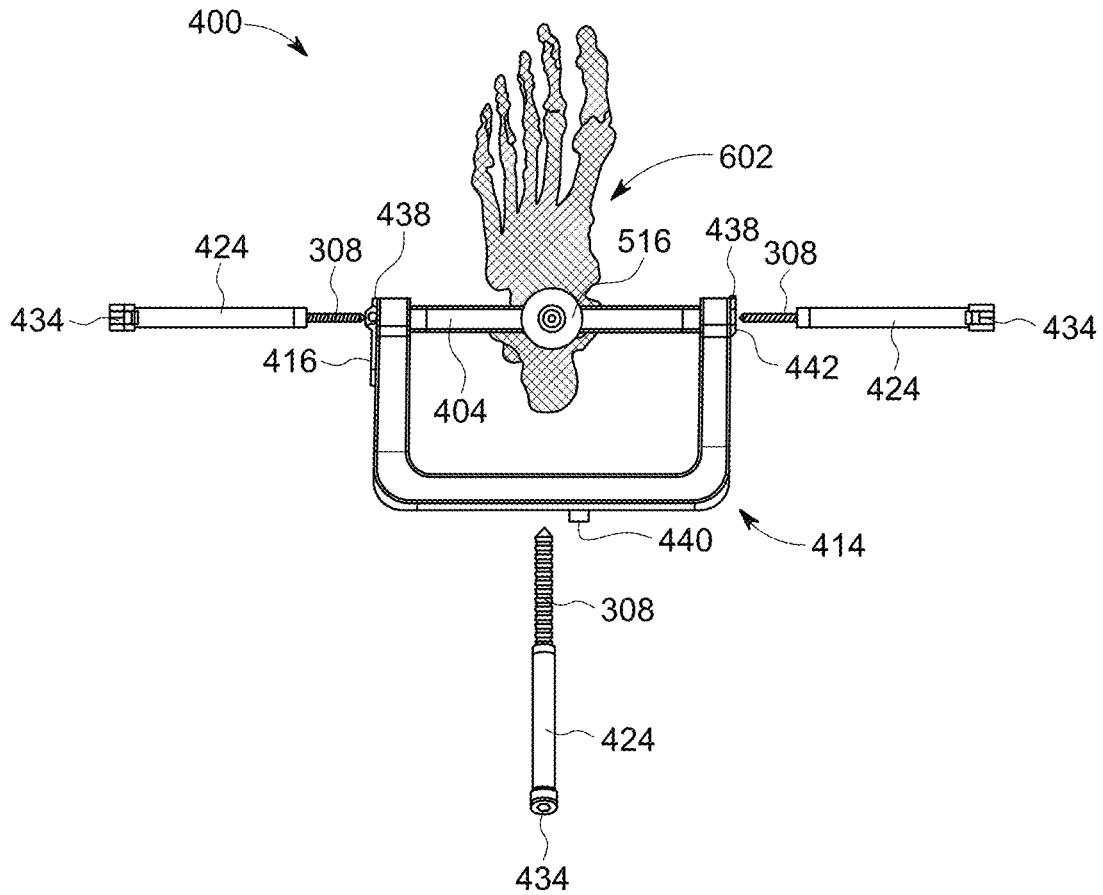
FIG. 28 is a partially exploded, first end view of the implant guide system of FIG. 1 in relation to a patient's lower extremity, in accordance with an aspect of the present disclosure.
Figure 29:
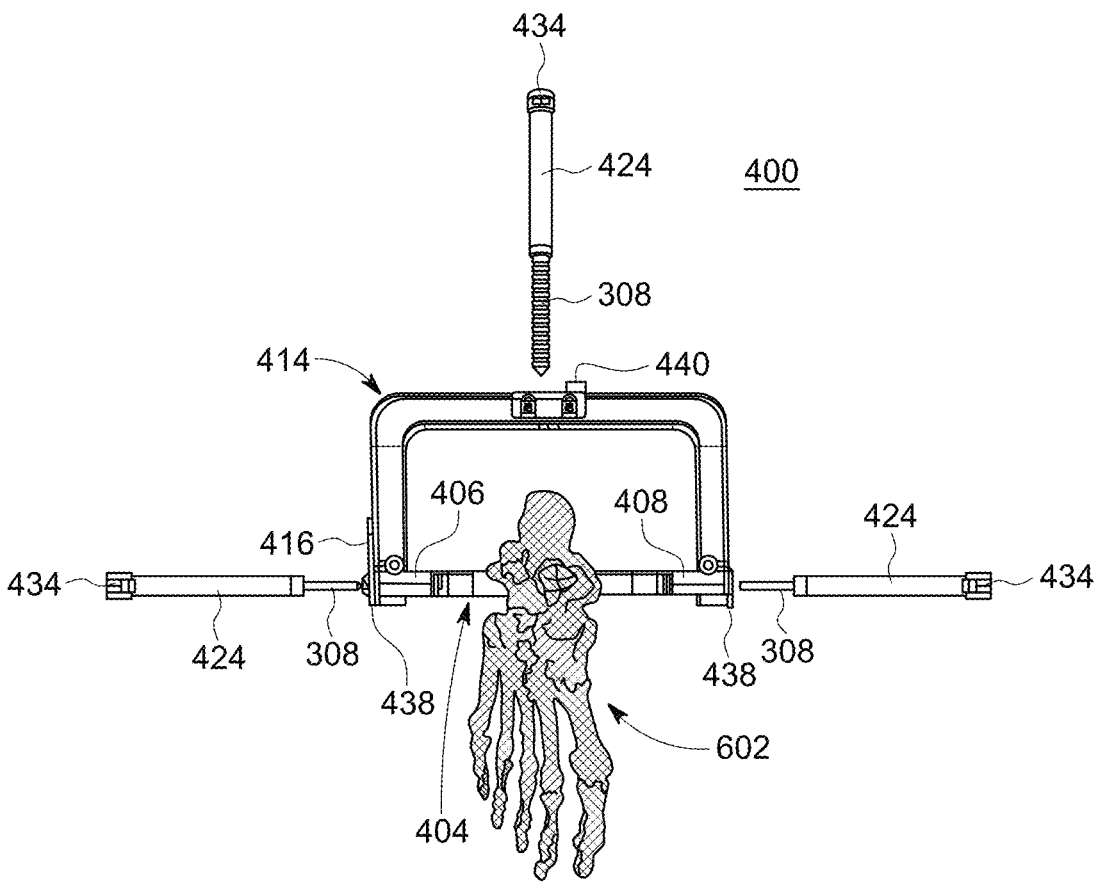
FIG. 29 is a partially exploded, second end view of the implant guide system of FIG. 1 in relation to a patient's lower extremity, in accordance with an aspect of the present disclosure.
Figure 30:
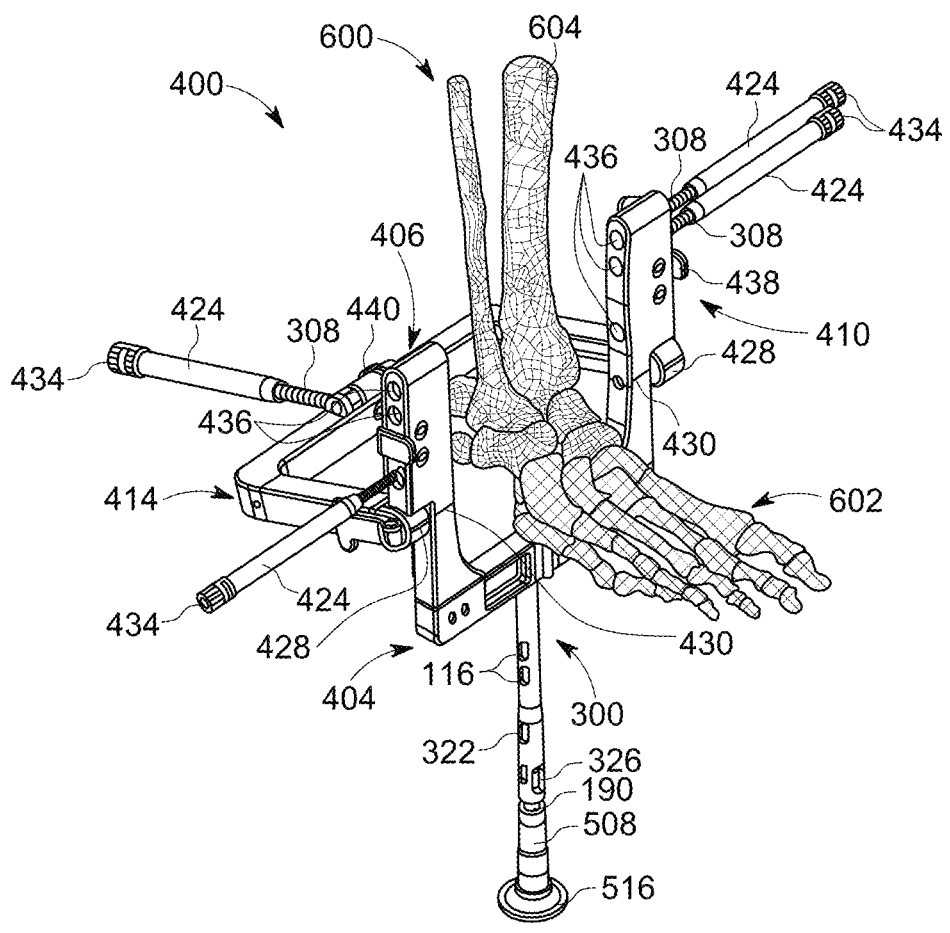
FIG. 30 is a partially exploded, first perspective view of the implant guide system of FIG. 1 in relation to a patient's lower extremity, in accordance with an aspect of the present disclosure.
Figure 31:
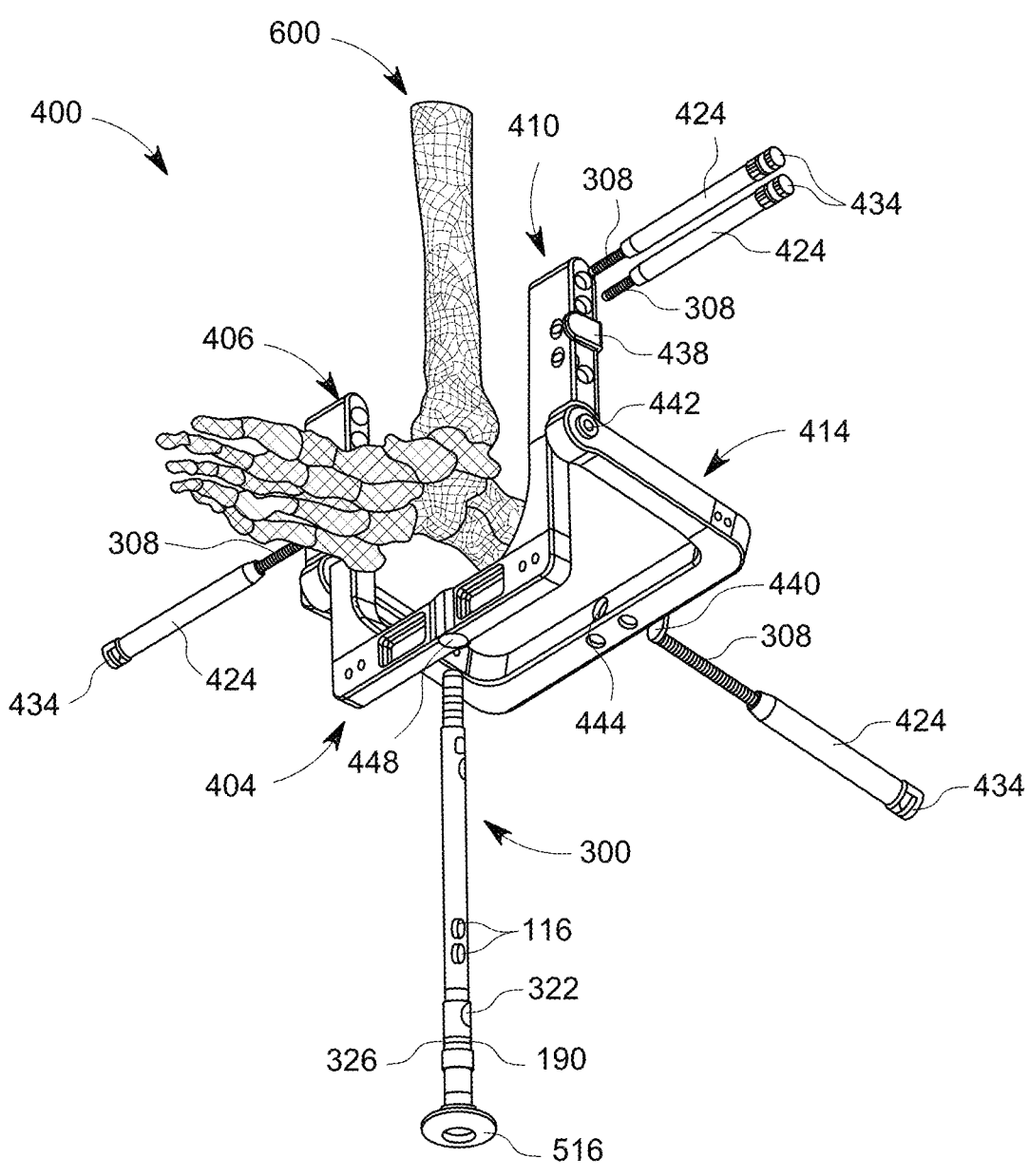
FIG. 31 is a partially exploded, second perspective view of the implant guide system of FIG. 1 in relation to a patient's lower extremity, in accordance with an aspect of the present disclosure.

FIG. 23 shows the implant guide system 400 with the implant guide device 402 detached from the implant 300 and accessories. The accessories may include, for example, one or more screw guides 424. Each screw guide 424 may be configured or sized and shaped to engage a drill guide 434 during insertion of a bone screw 308 into the patient.

Referring now to FIGS. 24-31 the implant guide system 400 is shown, in relation to a patient's lower extremity 600. The bone screws 308 may be thrown or inserted into the patient's lower extremity 600 from a medial side and/or a distal side of the implant guide device 402. Based on the targeting arm 414 being hingedly coupled to at least one of the first arm 406 and the second arm 410, the targeting arm 414 can be positioned on an anterior side and/or a posterior side of the implant guide device 402.

Advantageously, based on the targeting arm 414 being hingedly coupled to at least one of the first arm 406 and the second arm 410, the implant guide device 402 is reversible such that the implant guide device 402 maintains functionality regardless of whether the first arm 406 or the second arm 410 are positioned medially to the patient's lower extremity 600, or whether the first arm 406 or the second arm 410 are positioned laterally to the patient's lower extremity 600. The reversible aspect of the implant guide device 402, in part, enables the implant guide device 402 to be ambidextrous.

Figure 32:
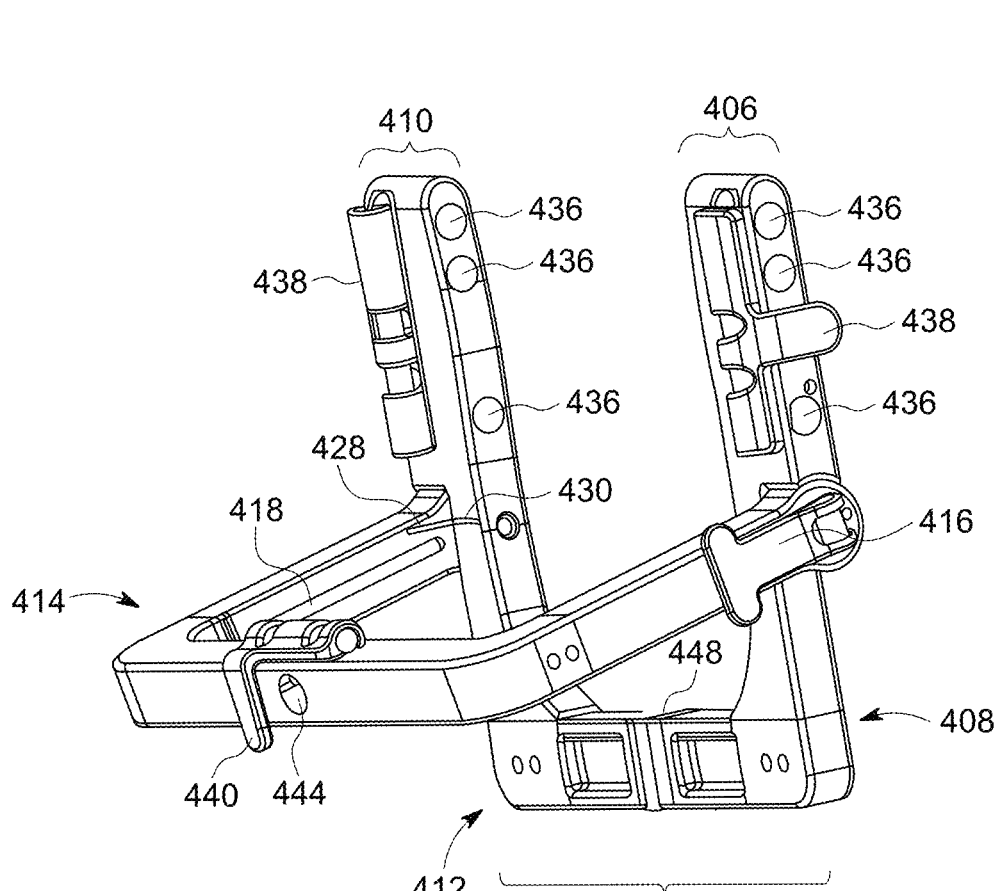
FIG. 32 is a perspective view of an implant guide device of the implant guide system FIG. 1, in accordance with an aspect of the present disclosure.
Figure 33:
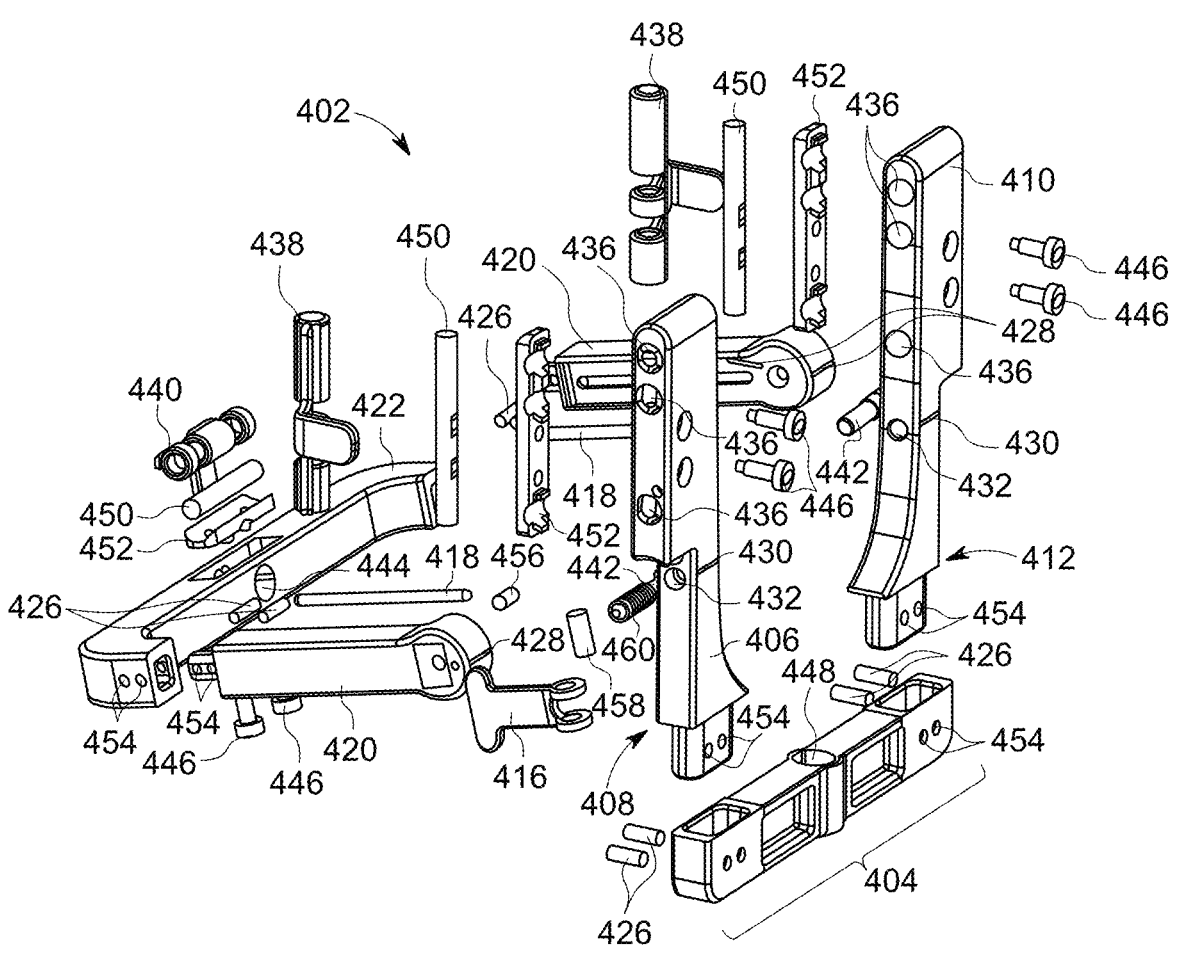
FIG. 33 is an exploded, first perspective view of the implant guide device of FIG. 32, in accordance with an aspect of the present disclosure.
Figure 34:
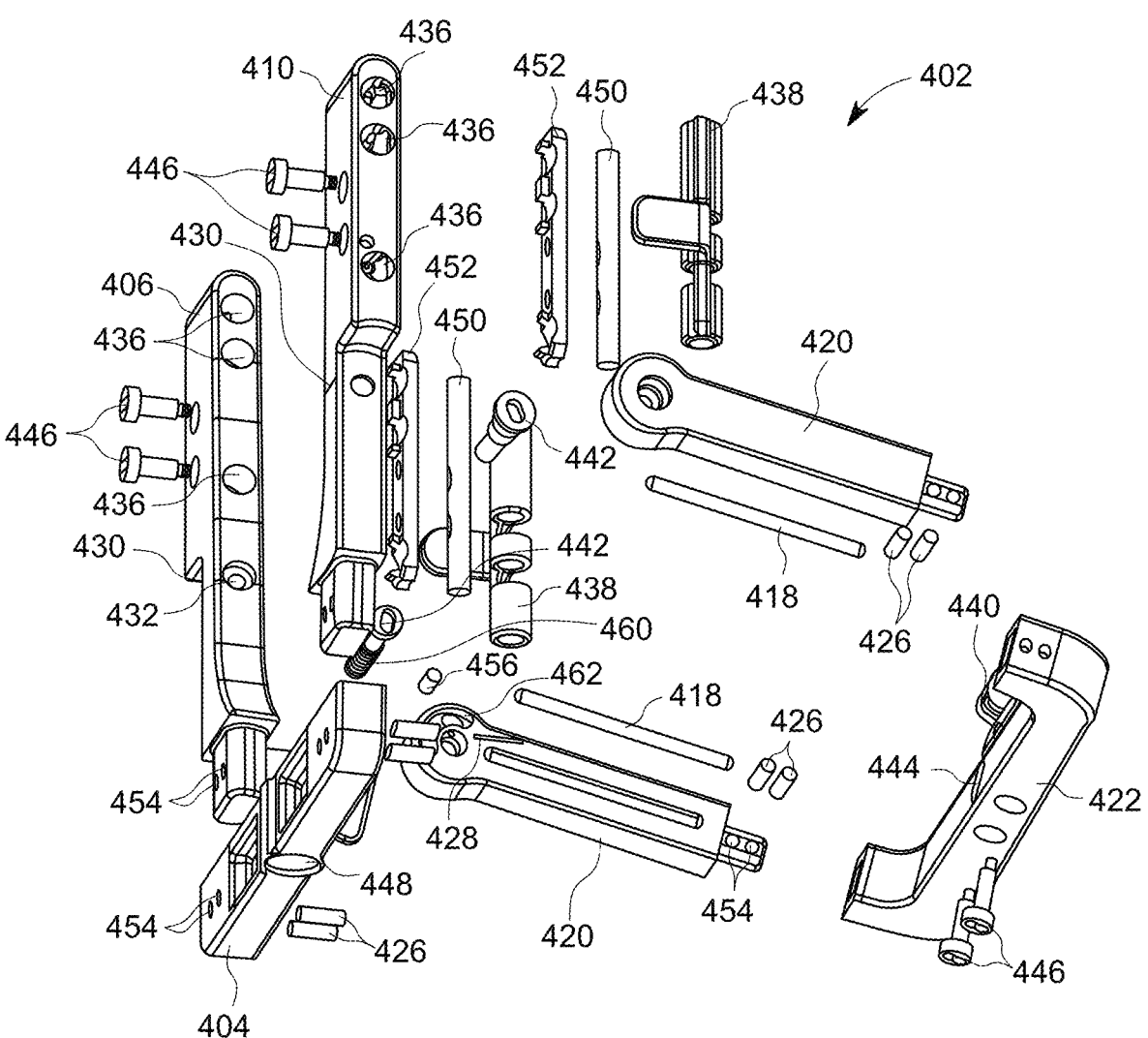
FIG. 34 is an exploded, second perspective view of the implant guide device of FIG. 32, in accordance with an aspect of the present disclosure.
Figure 35:
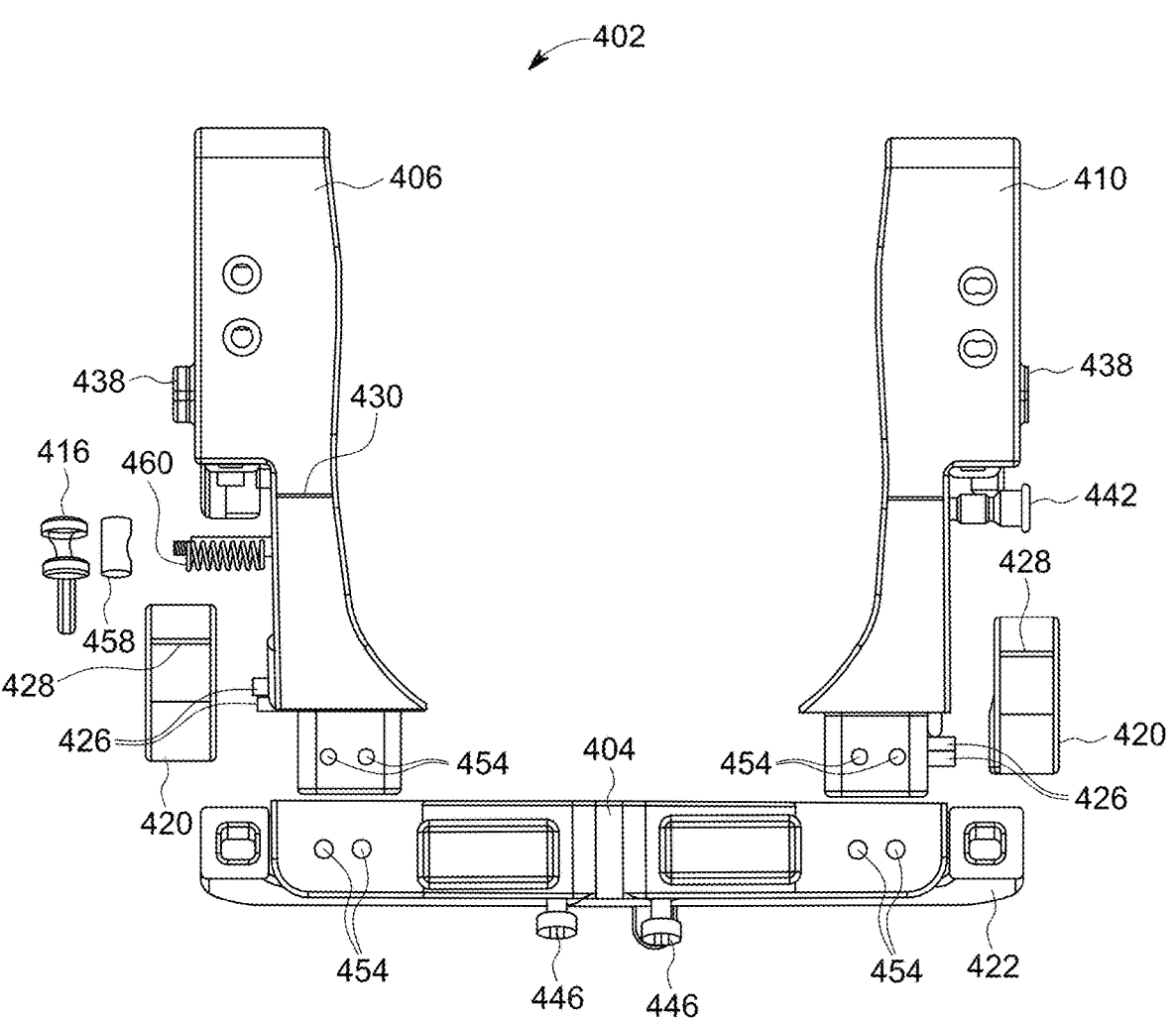
FIG. 35 is an exploded, top view of the implant guide device of FIG. 32, in accordance with an aspect of the present disclosure.
Figure 36:
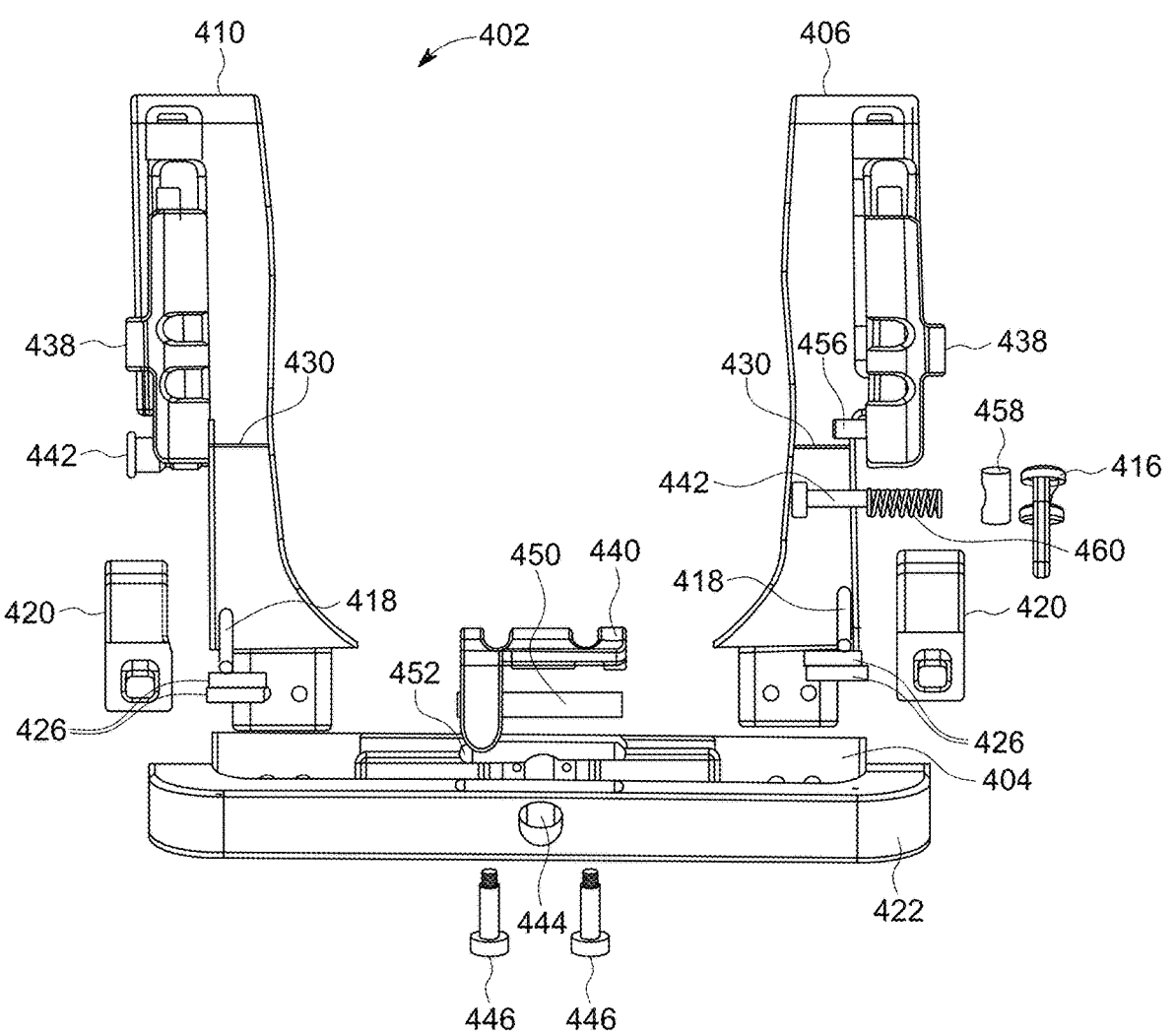
FIG. 36 is an exploded, bottom view of the implant guide device of FIG. 32, in accordance with an aspect of the present disclosure.
Figure 37:
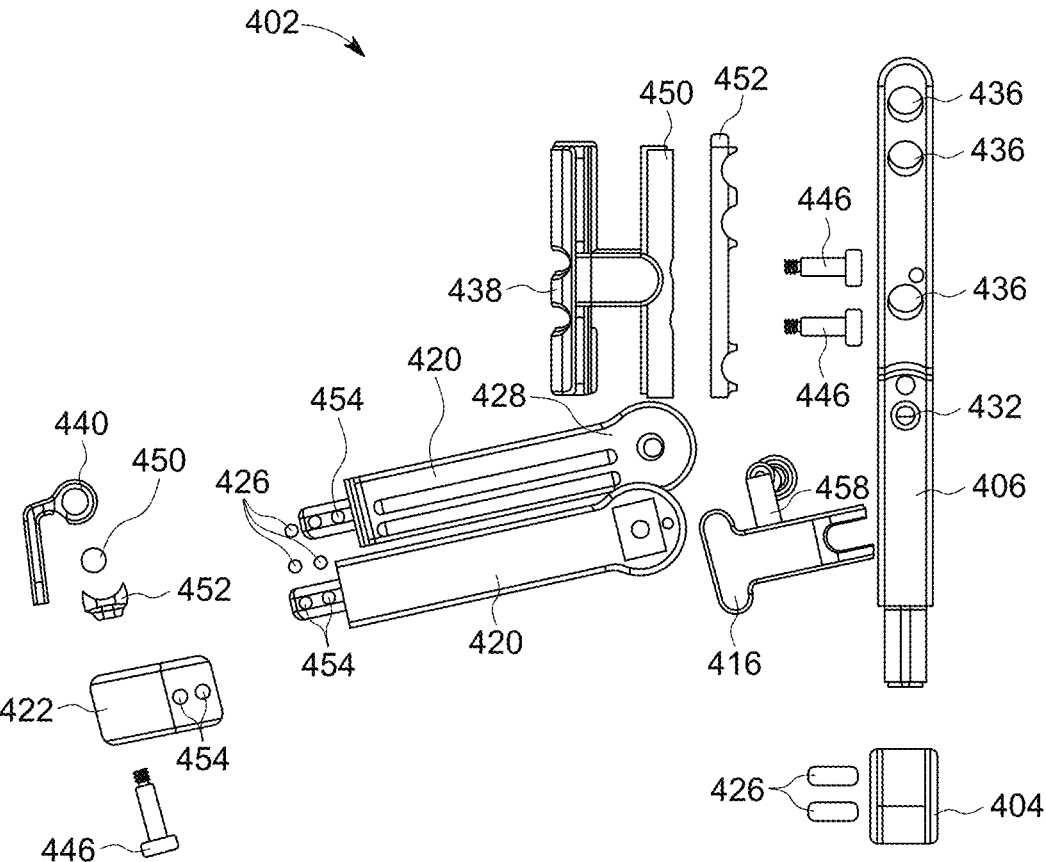
FIG. 37 is an exploded, first side view of the implant guide device of FIG. 32, in accordance with an aspect of the present disclosure.
Figure 38:
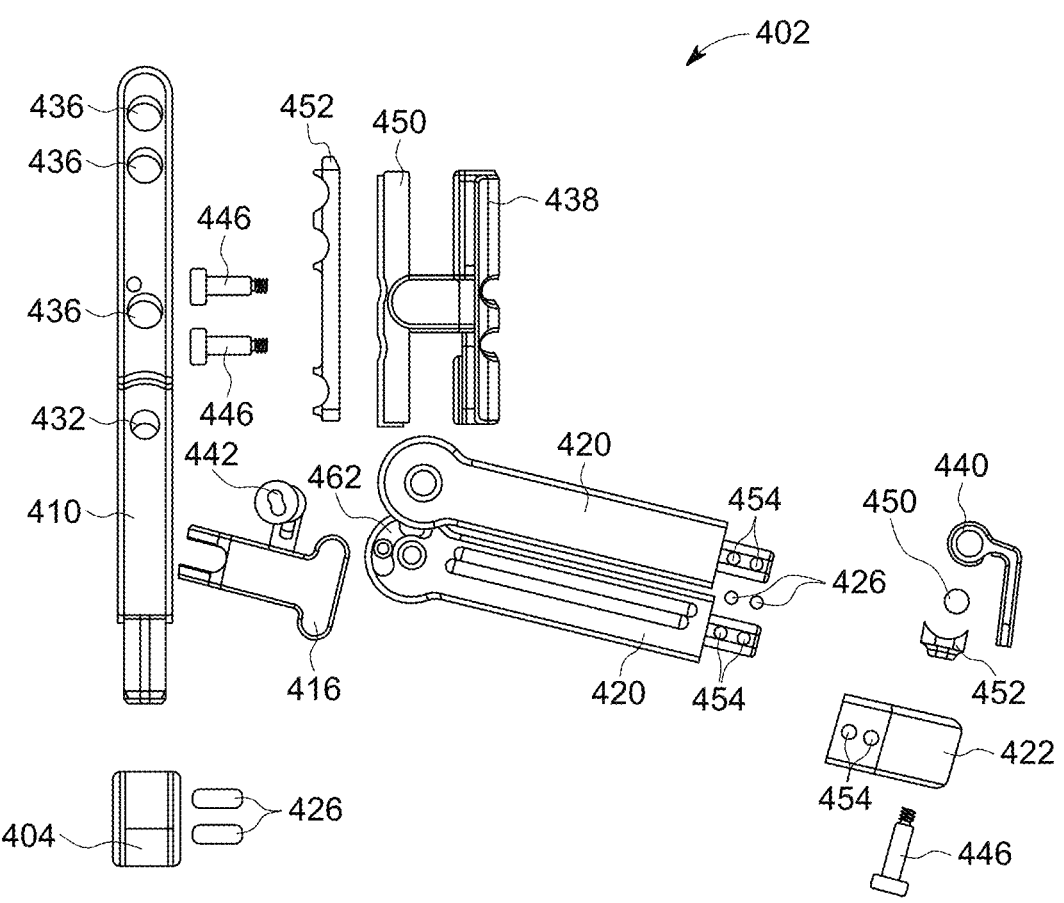
FIG. 38 is an exploded, second side view of the implant guide device of FIG. 32, in accordance with an aspect of the present disclosure.
Figure 39:
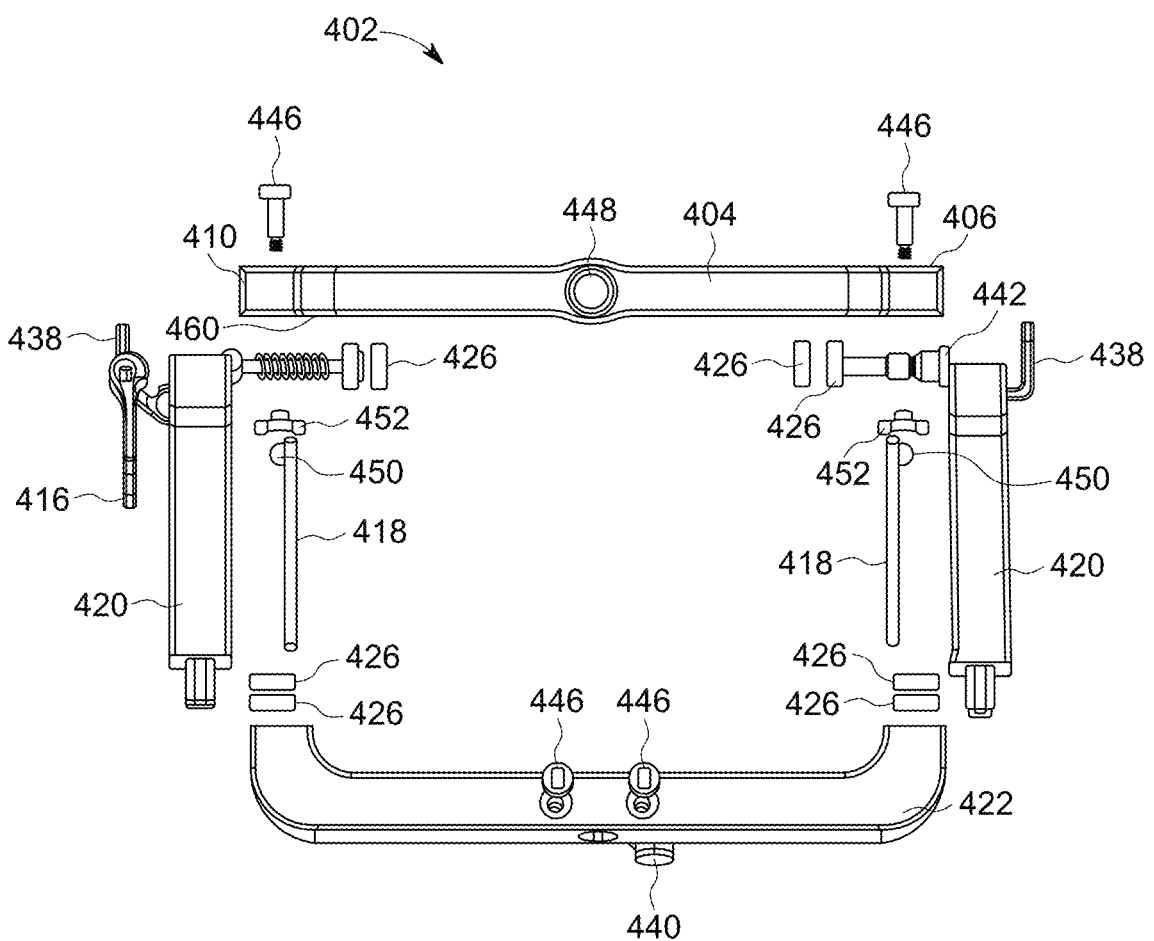
FIG. 39 is an exploded, first end view of the implant guide device of FIG. 32, in accordance with an aspect of the present disclosure.
Figure 40:
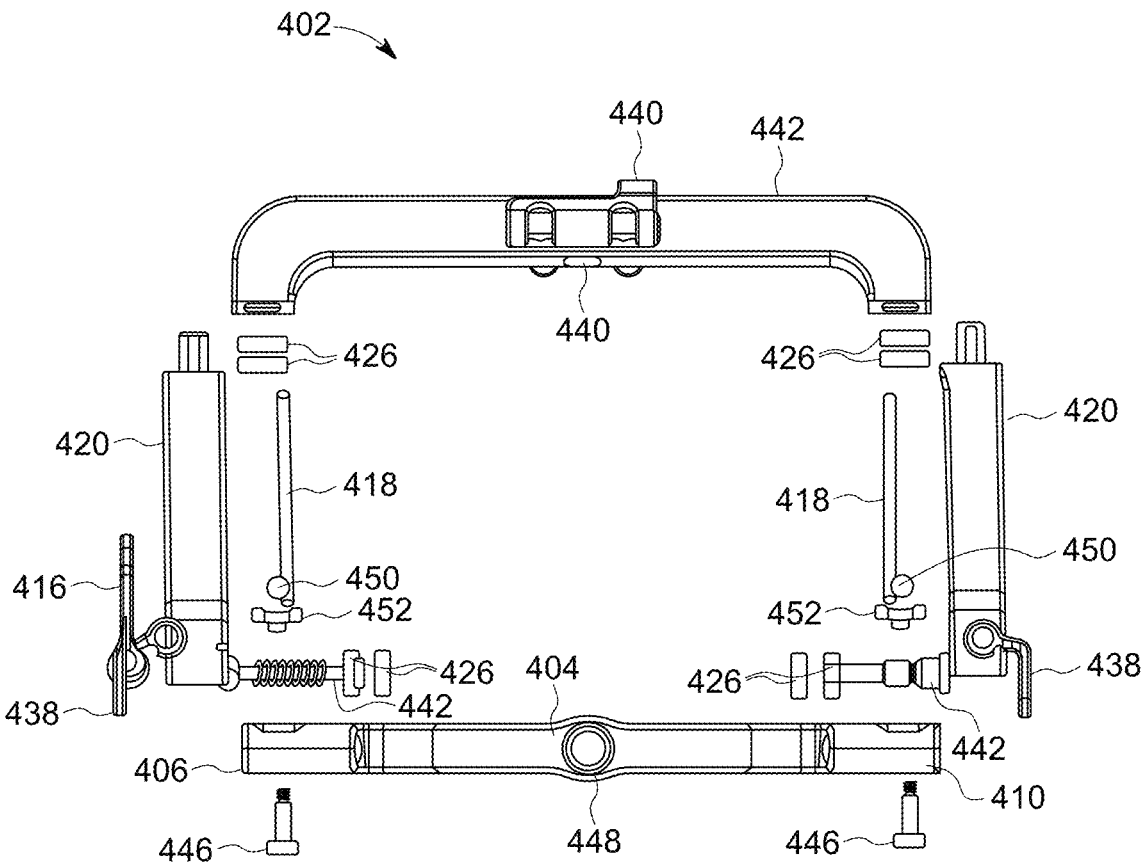
FIG. 40 is an exploded, second end view of the implant guide device of FIG. 32, in accordance with an aspect of the present disclosure.

Referring now to FIG. 32 the implant guide device 402 of the implant guide system is shown. The implant guide device 402 may be configured or sized and shaped to be substantially symmetrical to facilitate using the implant guide device 402 on the patient's left lower extremity as well as the patient's right lower extremity.

Referring now to FIGS. 33-40, exploded views of the implant guide device 402 are shown. The one or more locks 438 of the implant guide device 402 may be coupled to at least one of the first arm 406 and the second arm 410 via a locking pin 450, a locking pin support 452, and a plurality of fasteners 446. For instance, the one or more locks 438 may be configured or sized and shaped to pivot about the locking pin 450 when loosening and/or affixing an accessory within through holes 436. Similarly, targeting arm lock 440 may be configured or sized and shaped to engage a locking pin 450 and a locking pin support 452 when loosening and/or affixing an accessory through the targeting arm through hole 444.

With continued reference to FIGS. 33-40, the implant guide device 402 may include a plurality of stabilizing pin holes 454 for receiving stabilizing pins 426 when assembled. For instance, the first arm 406 may be coupled to the base 404 by inserting a portion of the first arm 406 that includes stabilizing pin holes 454 into a first end 408 of the base 404 and fixating the first arm 406 into the base 404 by embedding a stabilizing pin 426 into each stabilizing pin hole 454.

Further referencing FIGS. 33-40, the implant guide device 402 may include a hinge pin 456 for engaging a hinge pin conduit 462 of a side support portion 420. For instance, the hinge pin 456 may be partially inserted within the first arm 406 of the implant guide device 402 and partially inserted into the hinge pin conduit 462 of the side support portion 420 of the implant guide device 402. The hinge pin 456 may be configured or sized and shaped to limit rotation of the targeting arm 414. For example, the targeting arm 414 may only pivot a distance corresponding to a range the hinge pin

456 may travel within the hinge pin conduit 462. In particular, the targeting arm 414 may be configured or sized and shaped to only pivot between 90-180° relative to at least one of the first arm 406 and the second arm 410 based on the hinge pin 456 engaging the hinge pin conduit 462 to limit rotation of the targeting arm 414.

Still referencing FIGS. 33-40, the implant guide device 402 may also include a targeting arm lock pin 458 configured or sized and shaped to engage the targeting arm lock 416. For instance, the targeting lock 416 may be configured or sized and shaped to pivot about the targeting arm lock pin 458 when loosening the targeting arm 414 or affixing the targeting arm 414 into a desired position. The targeting arm lock pin 458 may also be configured or sized and shaped to engage a threaded portion of a targeting arm support pin 442. Further, the targeting arm support pin 442 may engage a spring 460 when rotating the targeting arm 414. Additionally, the spring 460 and the targeting arm support pin 442 may be configured or sized and shaped to traverse a pivot hole 432 of the first arm 406 of the implant guide device 402.

Figure 41:
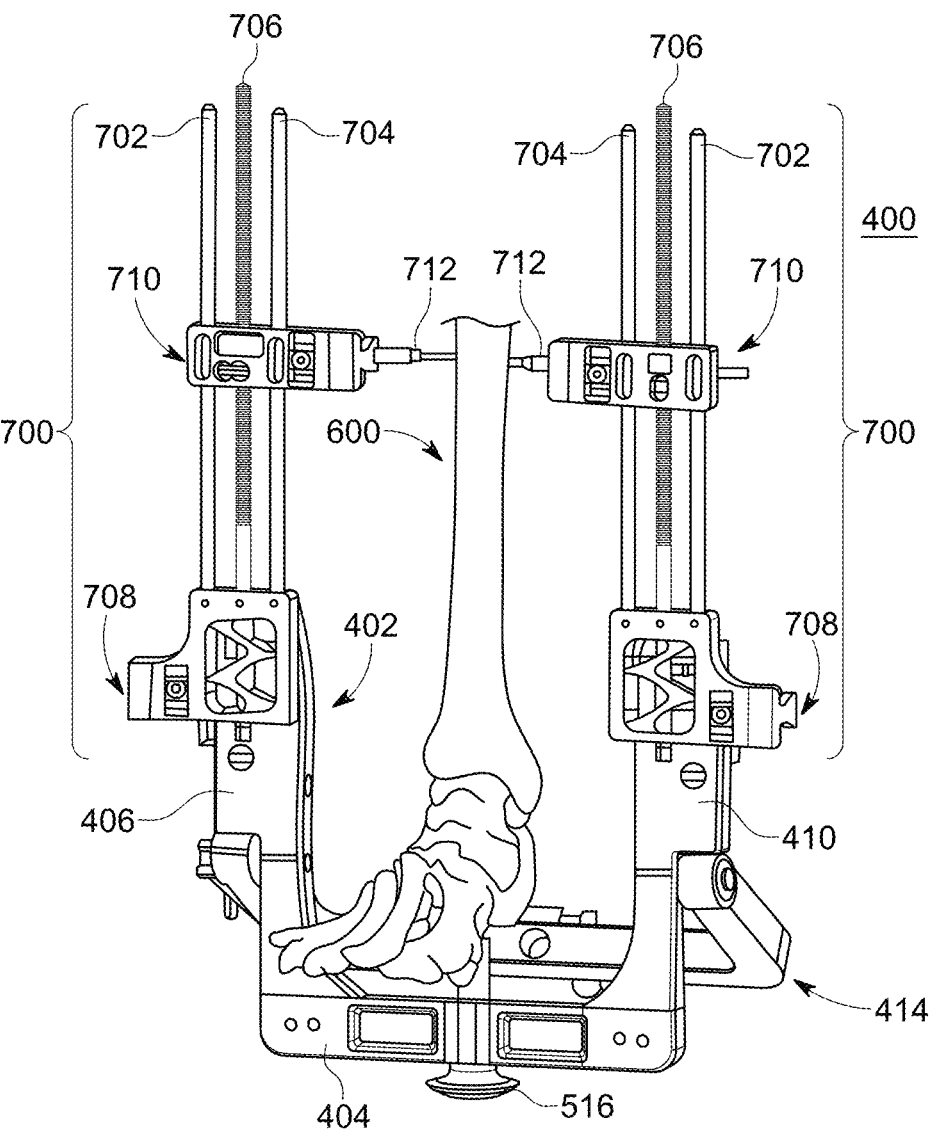
FIG. 41 is a perspective view of an implant guide system that includes an external compression attachment, in accordance with an aspect of the present disclosure.

Referring now to FIG. 41, an implant guide system 400 that includes, for example, an external compression attachment 700 is shown. The external compression attachment 700 may be configured or sized and shaped to provide external compression outside of and independent to the implant 300. In particular, the external compression attachment 700 may extend from at least one of the first arm 406 and the second arm 410 to provide compression at a proximal portion of the patient's lower extremity 600 relative to the implant guide device 402. The external compression attachment 700 may be configured or sized and shaped to engage one or more through holes of at least one of the first arm 406 and the second arm 410 for securing the external compression device 700 to the implant guide device 402.

With further reference to FIG. 41, the external compression attachment 700 may include one or more outer support rods 702 and one or more inner support rods 704 for supporting a compression portion 710 of the external compression attachment 700. The external compression attachment 700 may also be configured or sized and shaped to include a threaded rod 706, which may be configured or sized and shaped to engage the compression portion 710 for adjusting a location of the compression portion along the one or more outer support rods 702 and one or more inner support rods 704. The external compression attachment 700 may also be configured or sized and shaped to include an attachment portion 708 to engage one or more through holes of at least one of the first arm 406 and the second arm 410 of the implant guide device 402. The compression portion 710 may include a compression applicator 712 for applying compression to the patient's lower extremity 600.

Figure 42:
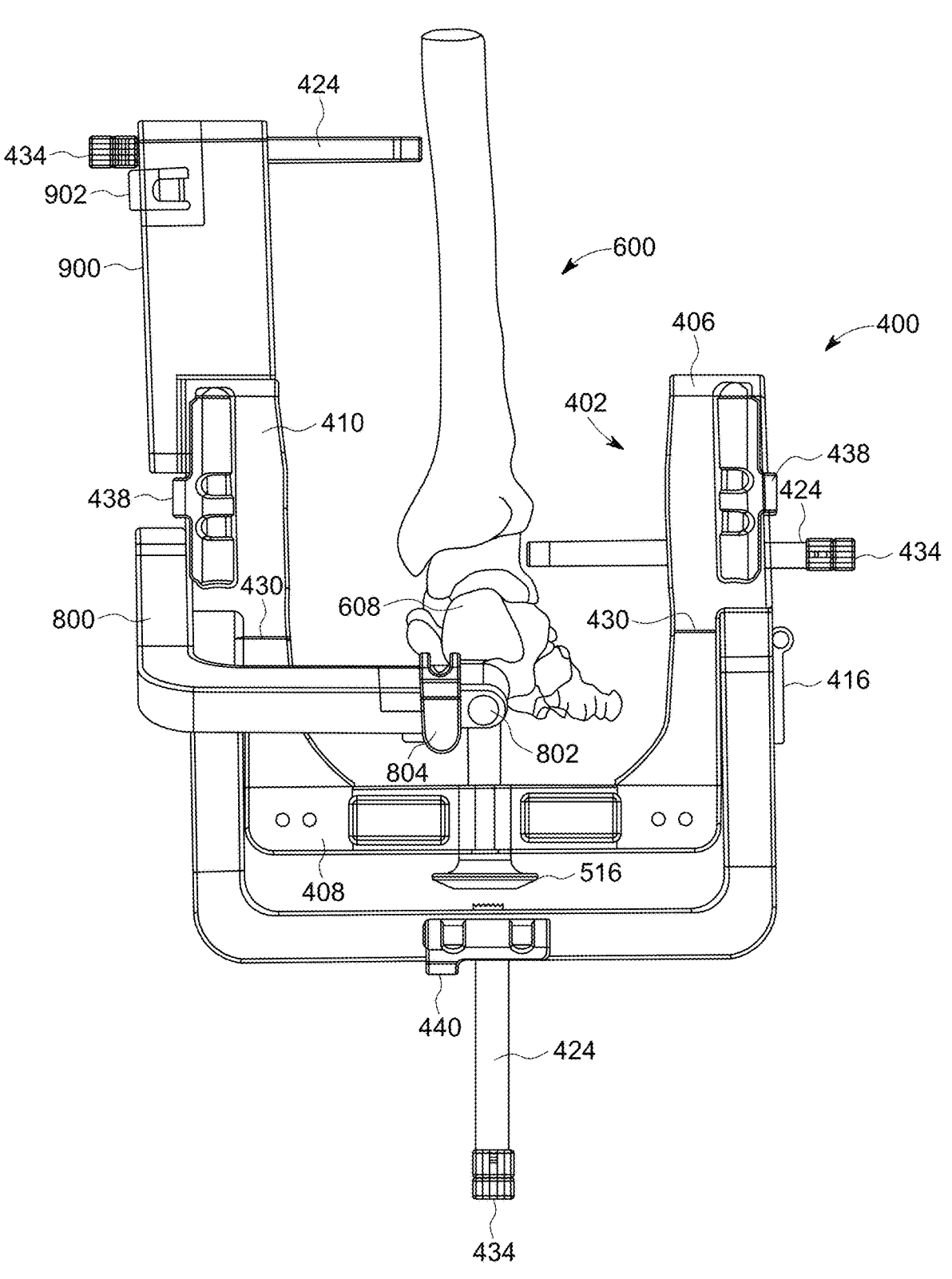
FIG. 42 is a perspective view of an implant guide system that includes a single-armed targeting accessory and an extension accessory, in accordance with an aspect of the present disclosure.

Referring now to FIG. 42, an implant guide system 400 that includes a single-armed targeting accessory 800 and an extension accessory 900 is shown. The single-armed targeting accessory 800 may, for example, be coupled to at least one of the first arm 406 and the second arm 410 of the implant guide device 402. For instance, the single-armed targeting accessory 800 may be coupled to the second arm 410, as shown in FIG. 42. The single-armed targeting accessory 800 may be coupled using a lock 438 to affix at least a portion of the single-armed targeting accessory 800 within a through hole 436 of the second arm 410. The single-armed targeting accessory 800 may be configured or sized and shaped to facilitate insertion of a bone screw 308 into a posterior portion of a patient's lower extremity. For instance, the single-armed targeting accessory 800 may include a targeting accessory through hole 802 for inserting an accessory (e.g., a screw guide 424 and/or a drill guide 434). In particular, the single-armed targeting accessory 800 may be configured or sized and shaped to facilitate insertion of a talocalcaneal bone screw. For instance, when using the single-armed targeting accessory 800, the targeting arm 414 may be swiveled to its lowest (i.e., most distal) position to make room for the single-armed targeting accessory 800 posterior to the calcaneus 608.

With continued reference to FIG. 42, the implant guide system 400 also includes an extension accessory 900. The extension accessory 900 may be configured or sized and spaced, to, for instance, extend at least one of the first arm 406 and the second arm 410 of the implant guide device 402. The extension accessory 900 may be coupled to at least one of the first arm 406 and the second arm 410 of the implant guide device 402 using, for instance, a lock 438 to affix at least a portion of the extension accessory 900 within a through hole 436. The extension accessory 900 may include, for example, an extension accessory fastener 902 for engaging an accessory. For instance, the extension accessory fastener 902 may be configured or sized and shaped to affix a screw guide 424 and a drill guide 434 for inserting a bone screw into a proximal portion of the patient's lower extremity 600.

Figure 43A:
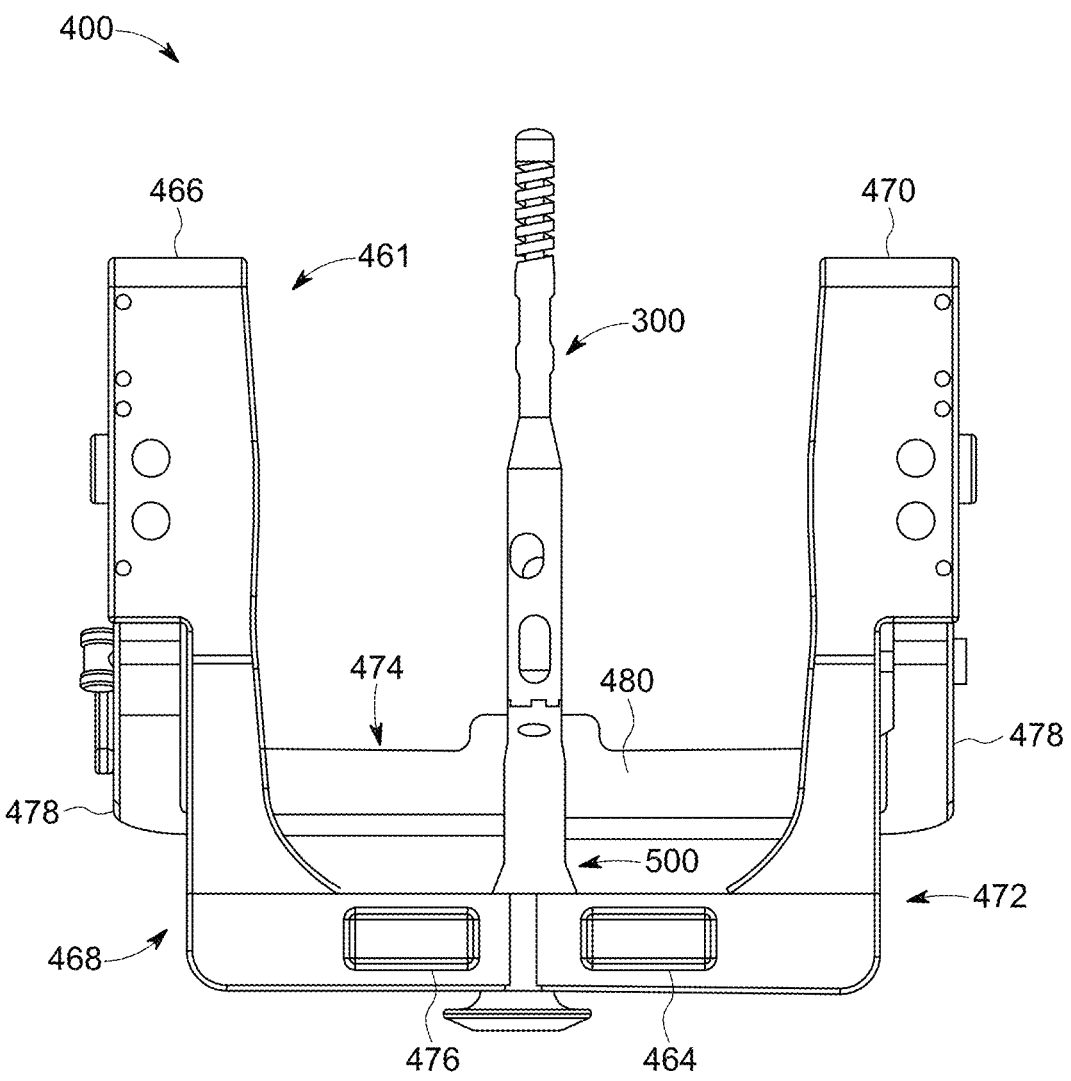
FIG. 43A is a top view of an implant guide system, in accordance with an aspect of the present disclosure.
Figure 43B:
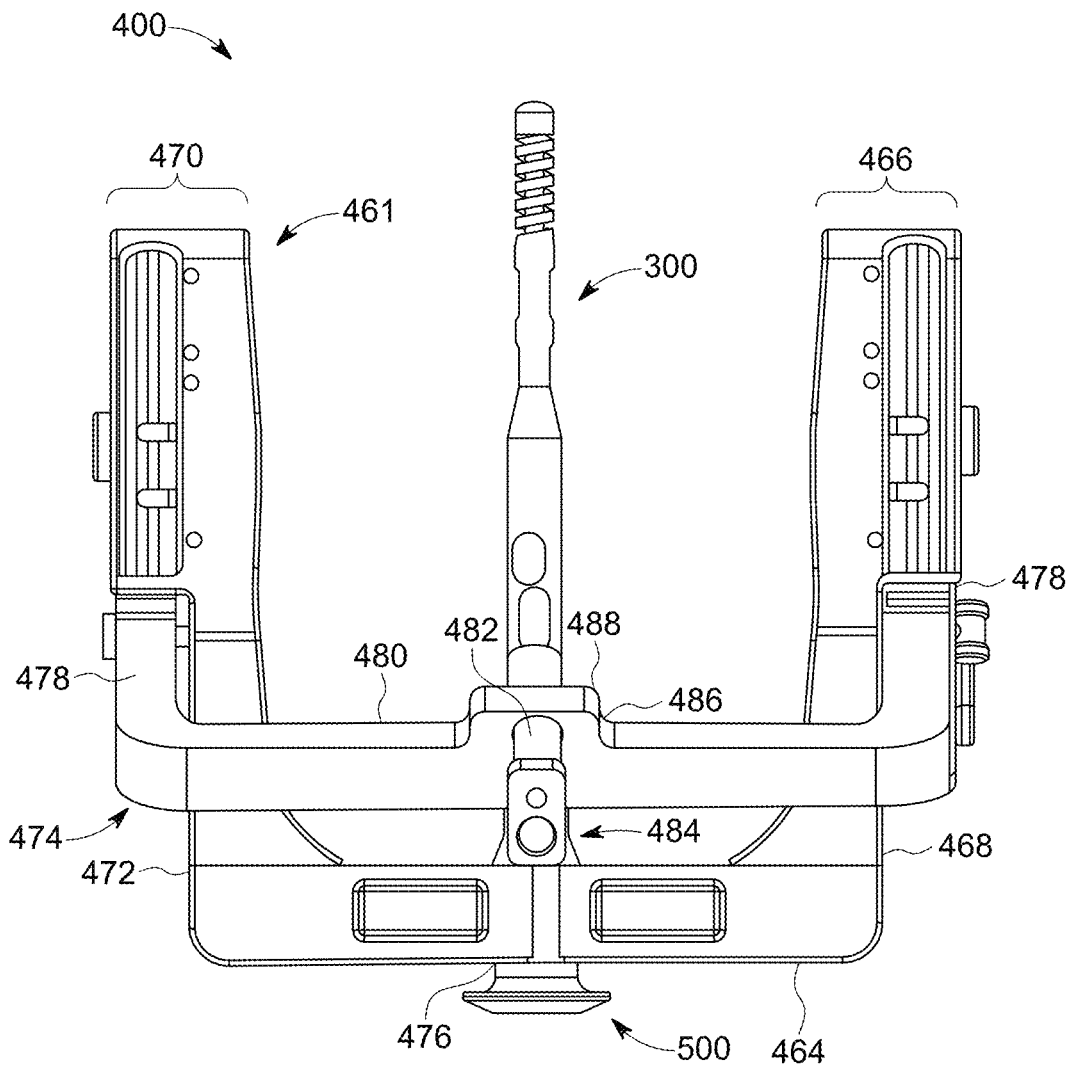
FIG. 43B is a bottom view of the implant guide system of FIG. 43A, in accordance with an aspect of the present disclosure.

FIGS. 43A-43B show another embodiment of the implant guide system 400. The implant guide system 400 includes, for example, an implant guide device 461. Some or all aspects of the implant guide device 461 may be the same or similar to implant guide device 402 as described above. In one embodiment, the implant guide device 461 includes a base 464 a first arm 466 coupled to a first end 468 of the base 464, and a second arm 470 coupled to a second end 472 of the base 464. The implant guide device 461 also includes a targeting arm 474 hingedly coupled to at least one of the first arm 466 and the second arm 470. The implant guide system 400 also includes a mounting system 500 traversing an aperture 476 of the base 464. Further, the implant guide system 400 includes an implant 300 coupled to the mounting system 500.

Still referencing FIGS. 43A-43B, the targeting arm 474 of the implant guide device 461 may include one or more side support portions 478 as well as an accessory engagement portion 480. The accessory engagement portion 480 may include a targeting arm through hole 482 configured or sized and shaped to engage a screw guide 484. Depending on the shape (e.g. circular, oblong, etc.) of a shaft 486 of the desired screw guide 484, the targeting arm through hole 482 may, for example, have various dimensions. For instance, for screw guides 484 that include a wider shaft 486, the accessory engagement portion 480 may include one or more protrusions 488 to accommodate targeting arm through holes 482 with larger dimensions. Various other embodiments of the targeting arm 474 are also contemplated herein.

Referring now to FIGS. 78-82, an alternate embodiment of the implant guide system 400 is shown including an implant guide device 1502. In some aspects, the implant guide device 1502 may include one or more components that are the same as and/or similar to the implant guide device 402 as shown and described previously. Additionally, the implant guide device 1502 may be implemented in conjunction with components of the implant guide system 400 as well as other implant guide systems. For example, the implant guide device 1502 may be configured to facilitate implantation of the implant 300 as shown and described previously and/or may be configured to facilitate implantation of other implants (some of which may be the same as and/or similar to the implant 300).

With continued reference to FIGS. 78-82, the implant guide device 1502 includes a base 1504, a first arm 1506 coupled to a first end 1508 of the base 1504, and a second arm 1510 coupled to a second end 1512 of the base 1504. The implant guide device 1502 is further shown to include one or more through holes 1536 disposed on both the first arm 1506 and the second arm 1508. In some aspects, the through holes 1536 may be arranged laterally (e.g., provide fluid communication through the first arm 1506/second arm 1510 in a medial-lateral direction). Additionally, the first arm 1506 and the second arm 1510 may include one or more retention mechanisms 1538 configured to retain and/or releasably couple drill guides (e.g., drill guide 434), screw guides (e.g., screw guide 424), or other components received within the through holes 1536. In some aspects, the retention mechanisms 1538 may be integral to the first arm 1506 and the second arm 1510. However, in some aspects the retention mechanisms 1538 may be coupled with the first arm 1506 and the second arm 1508 to form an assembly.

The retention mechanisms 1538 as shown in FIGS. 78-82 may be disposed within the first arm 1506 and the second arm 1510 of the implant guide device 1502 (e.g., housed within the first arm 1506 and the second arm 1510). The retention mechanisms 1538 may retain and/or releasably couple the components received by the through holes 1536 through a variety of means. In some aspects, the retention mechanisms 1538 may include one or more resilient members (e.g., springs, compression springs, coil springs, etc.) configured to apply one or more forces to components received by and positioned at least partially within the through holes 1536. For example, coil springs may be configured to apply a force to a component positioned at least partially within a through hole 1536 so as to frictionally retain said component in a desired position within the through hole 1536. In some aspects, a retention mechanism 1538 may be provided for and arranged adjacent (e.g., circumferentially around, etc.) to each of the through holes 1536 of both the first arm 1506 and the second arm 1510. In some aspects, a single retention mechanism 1538 may be configured to retain components in multiple through holes 1536 (e.g., a single coil spring is arranged circumferentially around two or more through holes 1536). Additionally, it should be noted that the retention mechanisms 1538 are configured to provide increased radiolucency. For example, the retention mechanisms 1538 (e.g., springs, coil springs, etc.) allow for increased visibility when imaging is performed intraoperatively as the retention mechanisms 1538 have a minimized radiopaque footprint (whereas other larger retention mechanisms may have larger radiopaque footprints and obstruct anatomical features when viewed through various medical imaging techniques).

Figure 44A:
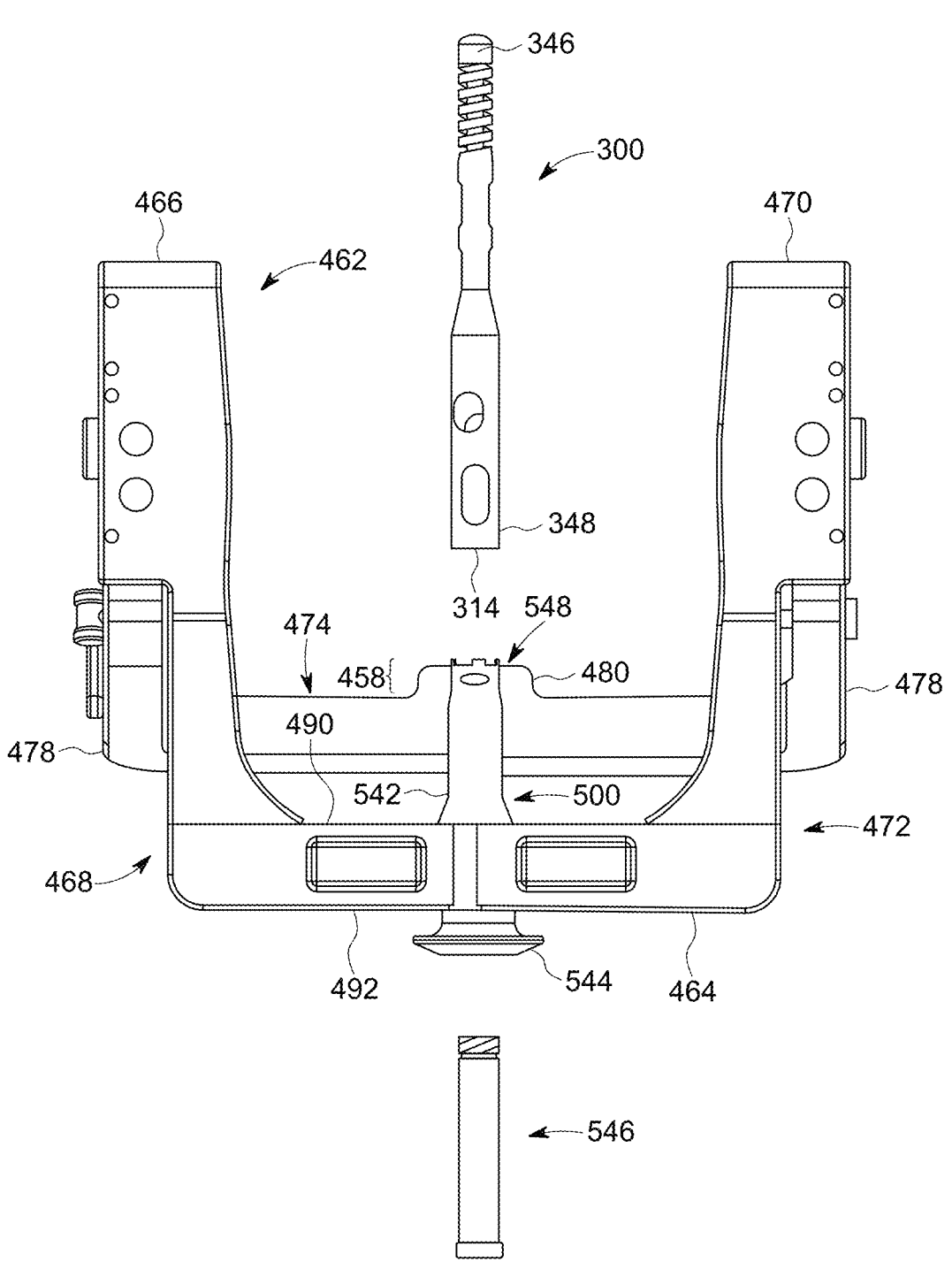
FIG. 44A is a partially exploded top view of the implant guide system of FIG. 43A, in accordance with an aspect of the present disclosure.
Figure 44B:
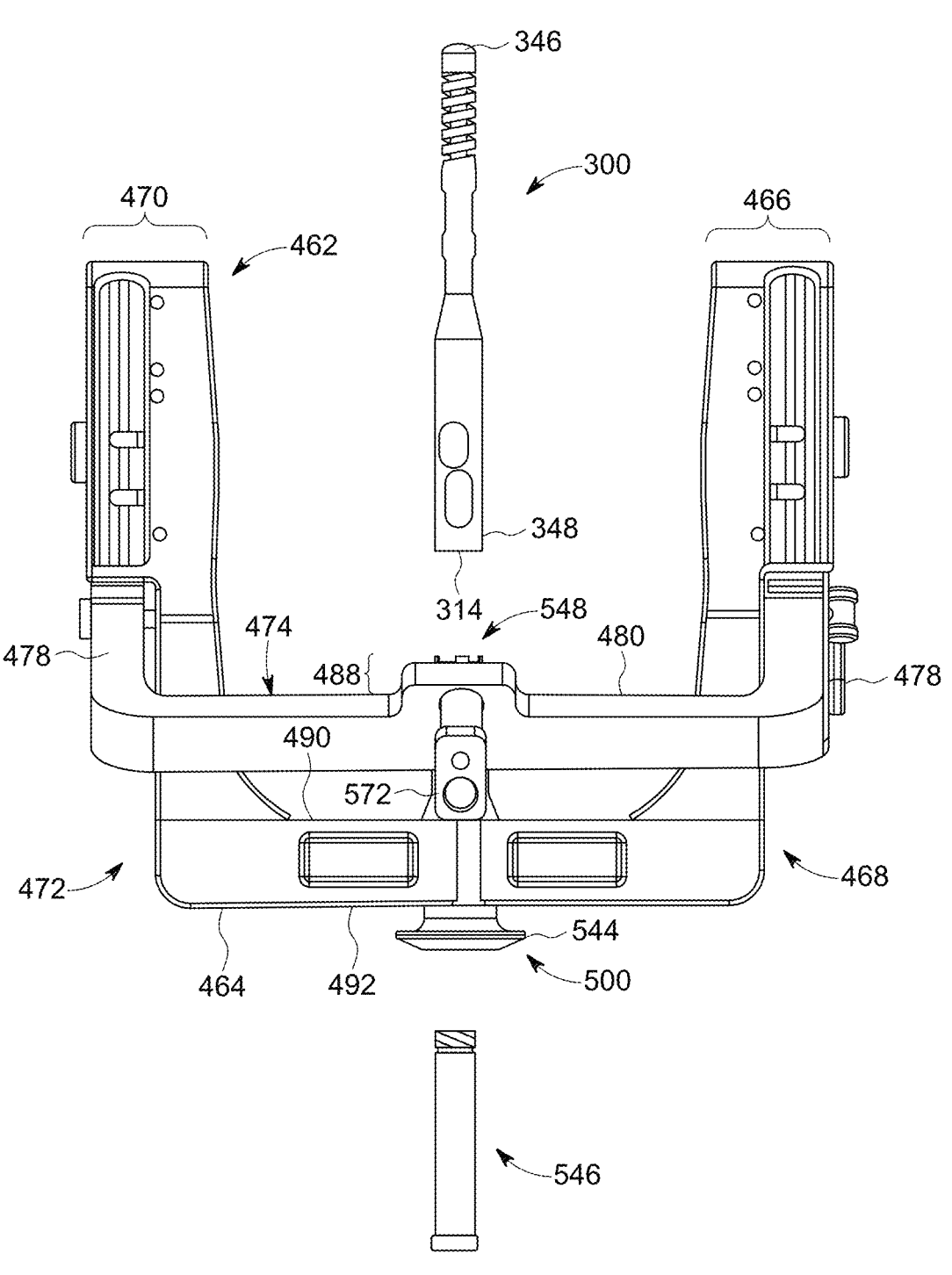
FIG. 44B is a partially exploded bottom view of the implant guide system of FIG. 43A, in accordance with an aspect of the present disclosure.

Referring now to FIGS. 44A-44B, the mounting system 500 may be at least partially affixed to the base 464 of the implant guide device 461 prior to coupling the implant 300 to the mounting system 500. For example, the mounting system 500 may include a mounting screw spacer 542 that is coupled to a first surface 490 (i.e., proximal surface) of the base 464, and a strike plate 544 coupled to a second surface 492 (i.e., distal surface) of the base 464, where the first surface 490 and second surface 492 are surfaces positioned opposite each other. The mounting screw 546 may, for example, then be inserted through the strike plate 544 and the implant 300 may be coupled to the mounting screw spacer 542 via at least one tab 550, 552. The at least one tab 550, 552 of the mounting screw spacer 542 may, for example, dovetail with at least one corresponding recess 314 of the implant 300. Further, the implant 300 may include a first end 346 and a second end 348, where the second end 348 includes at least one recess 314 into which the at least one tab 550, 552 of the mounting screw spacer 542 may dovetail. Advantageously, by having the mounting screw spacer 542 and the strike plate 544 coupled to the base 464, striking the strike plate 544 during insertion of the implant 300 may, for example, provide proper positioning of the implant guide device 461 for later insertion of the one or more bone fasteners 308 shown in FIG. 11 into a patient's lower extremity 600 as shown in FIG. 11.

Figure 45:
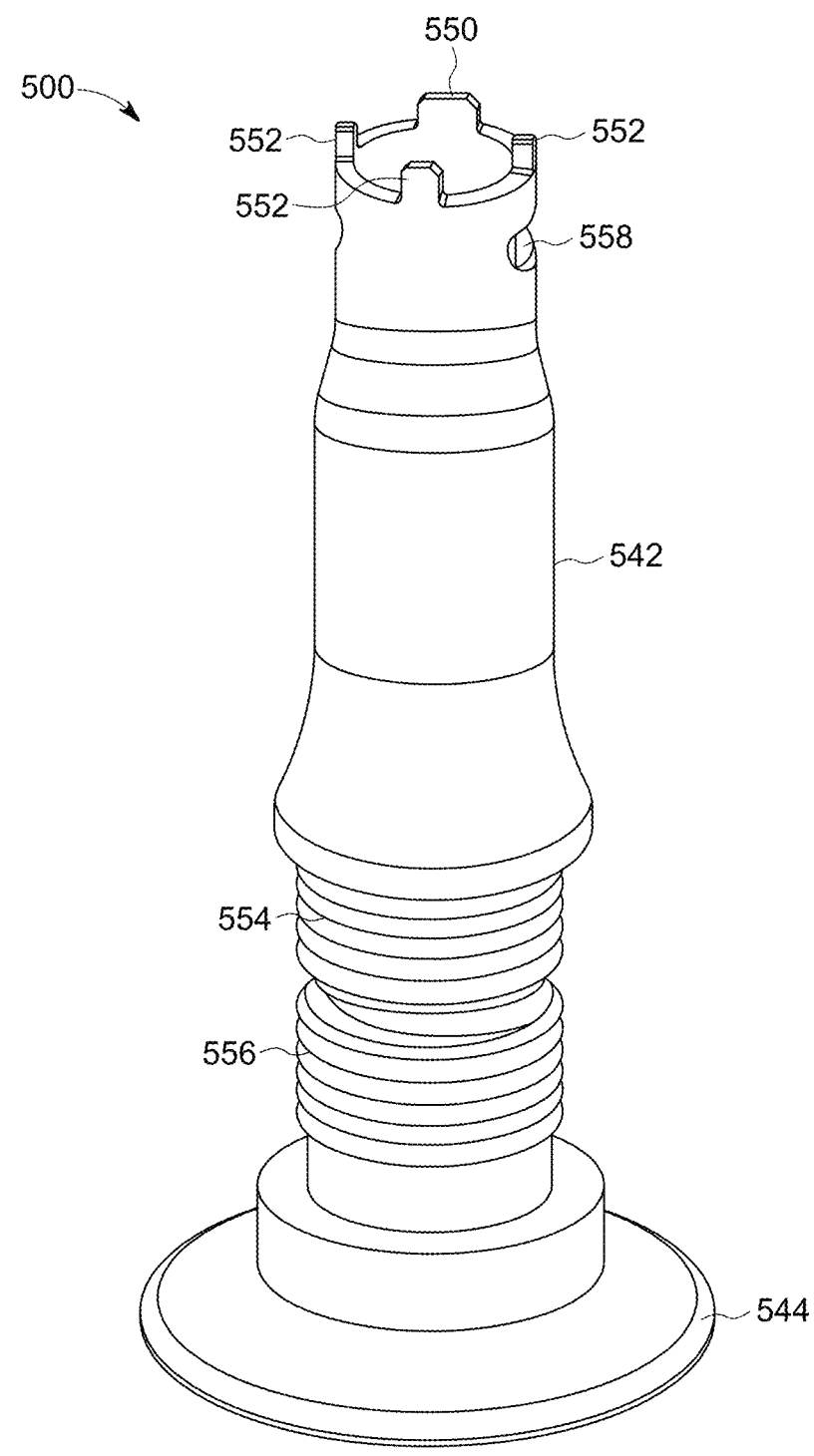
FIG. 45 is a perspective view of the mounting system of the implant guide system of FIG. 43A, in accordance with an aspect of the present disclosure.
Figure 46:
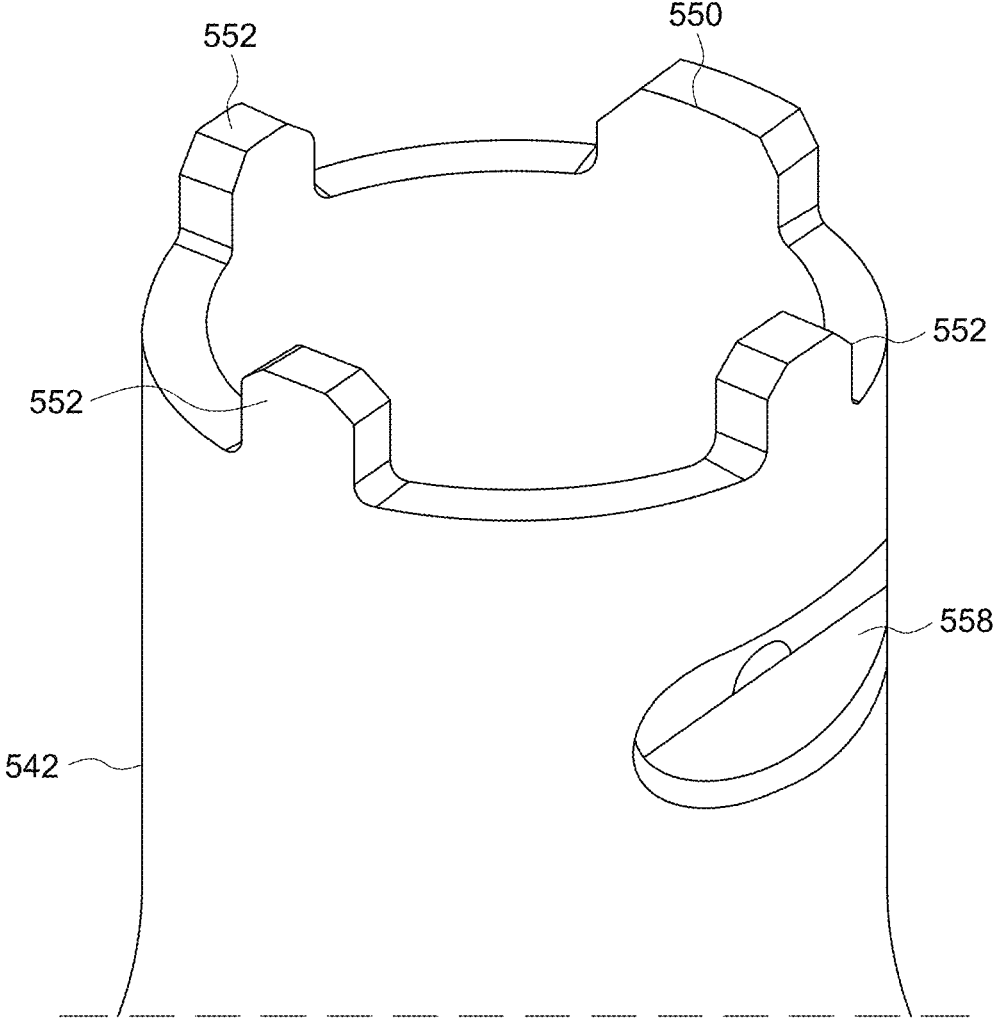
FIG. 46 is a magnified view of a mounting screw spacer of the mounting system of FIG. 45, in accordance with an aspect of the present disclosure.

As shown in FIGS. 45-46, the at least one tab 550, 552 of the mounting system 500 may include, for example, a plurality of tabs 550, 552. In one embodiment, the plurality of tabs 550, 552 may include, for example, a tab 550 having a larger width than other tabs 552 of the plurality of tabs 548. The tab 550 with a larger width may facilitate, for example, proper alignment of the implant 300 relative to the mounting system 500 (see FIGS. 44A-44B) so that the implant 300 may be aligned at only one predesignated orientation. The mounting screw spacer 542 may also include one or more laser markings 558 that may, for example, provide a visual indicator for aligning the mounting system 500 to provide appropriate implant 300 (see FIGS. 44A-44B) positioning. Further, the mounting screw spacer 542 may include a threaded portion 554 for attaching the mounting screw spacer 542 to the first surface 490 of the base 464 (see FIGS. 44A-44B). The mounting screw spacer 542 may, according to one embodiment, be separate from the strike plate 544 of the mounting system 500. For example, the threaded portion 544 may, for example, attach to the first surface 490 of the base 464 (see FIGS. 44A-44B). The strike plate 544 may also include a threaded portion 556 that attaches to the second surface 492 of the base 464 (see FIGS. 44A-44B). Thus, threaded portion 554 of the strike plate 544 may be separate and distinct from threaded portion 544 of the mounting screw spacer 542. Various other attachment mechanisms are also contemplated herein.

Figure 47A:
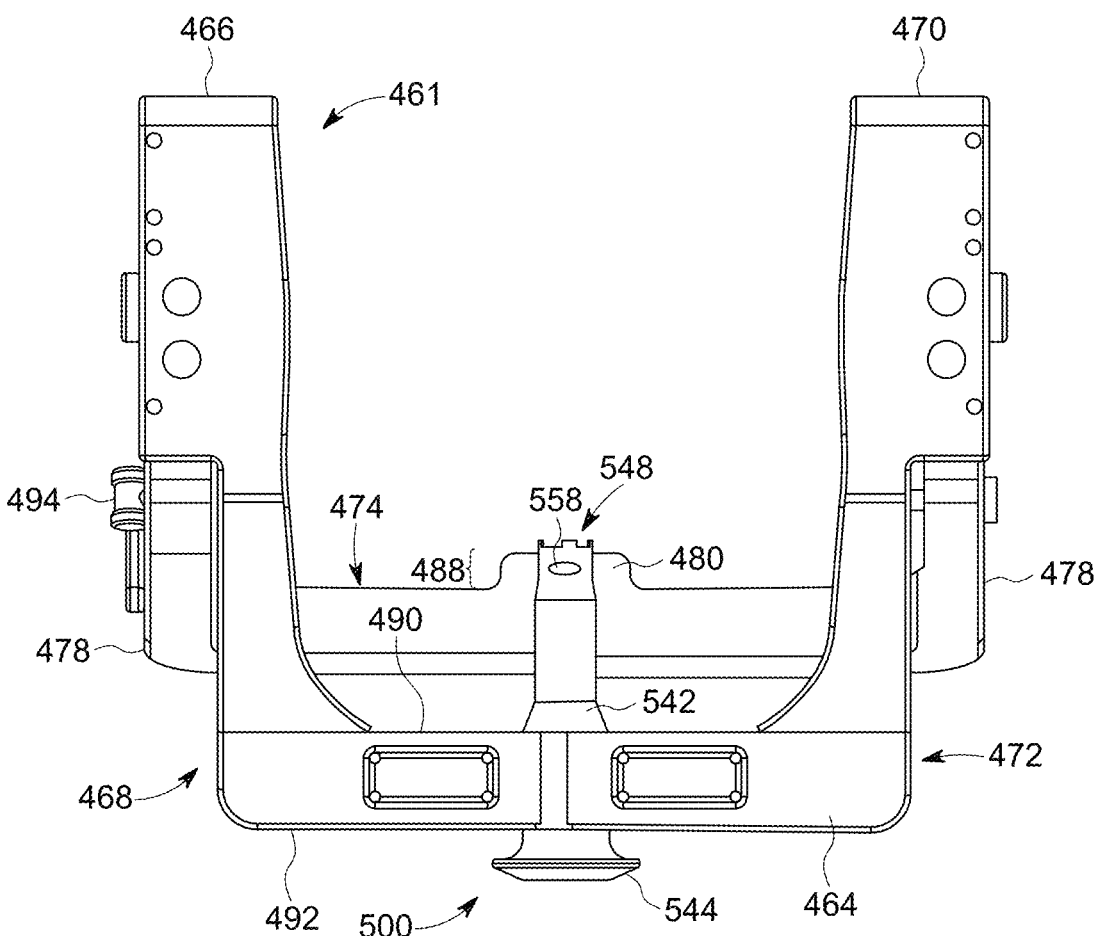
FIG. 47A is a top view of the mounting system and implant guide device of the implant guide system of FIG. 43A, in accordance with an aspect of the present disclosure.
Figure 47B:
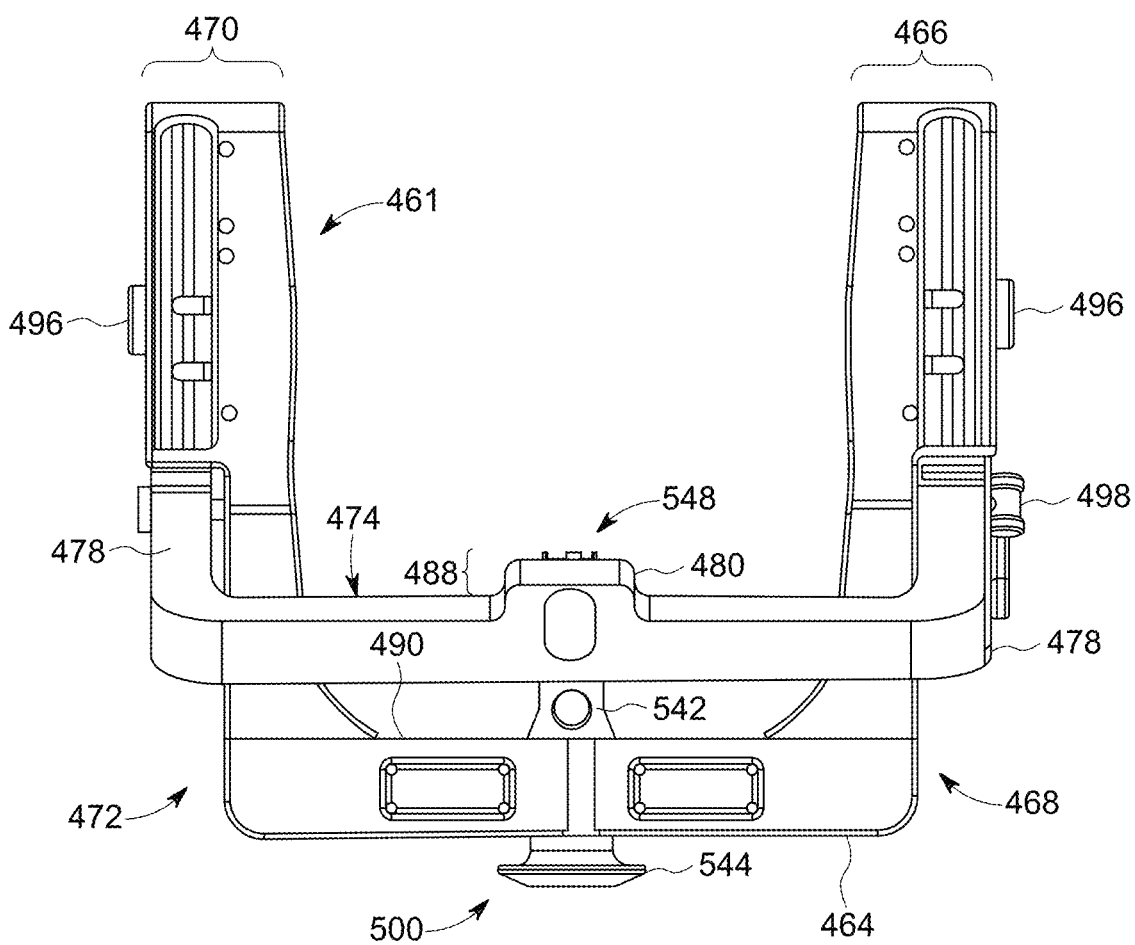
FIG. 47B is a bottom view of the mounting system and implant guide device of the implant guide system of FIG. 43A, in accordance with an aspect of the present disclosure.
Figure 48A:
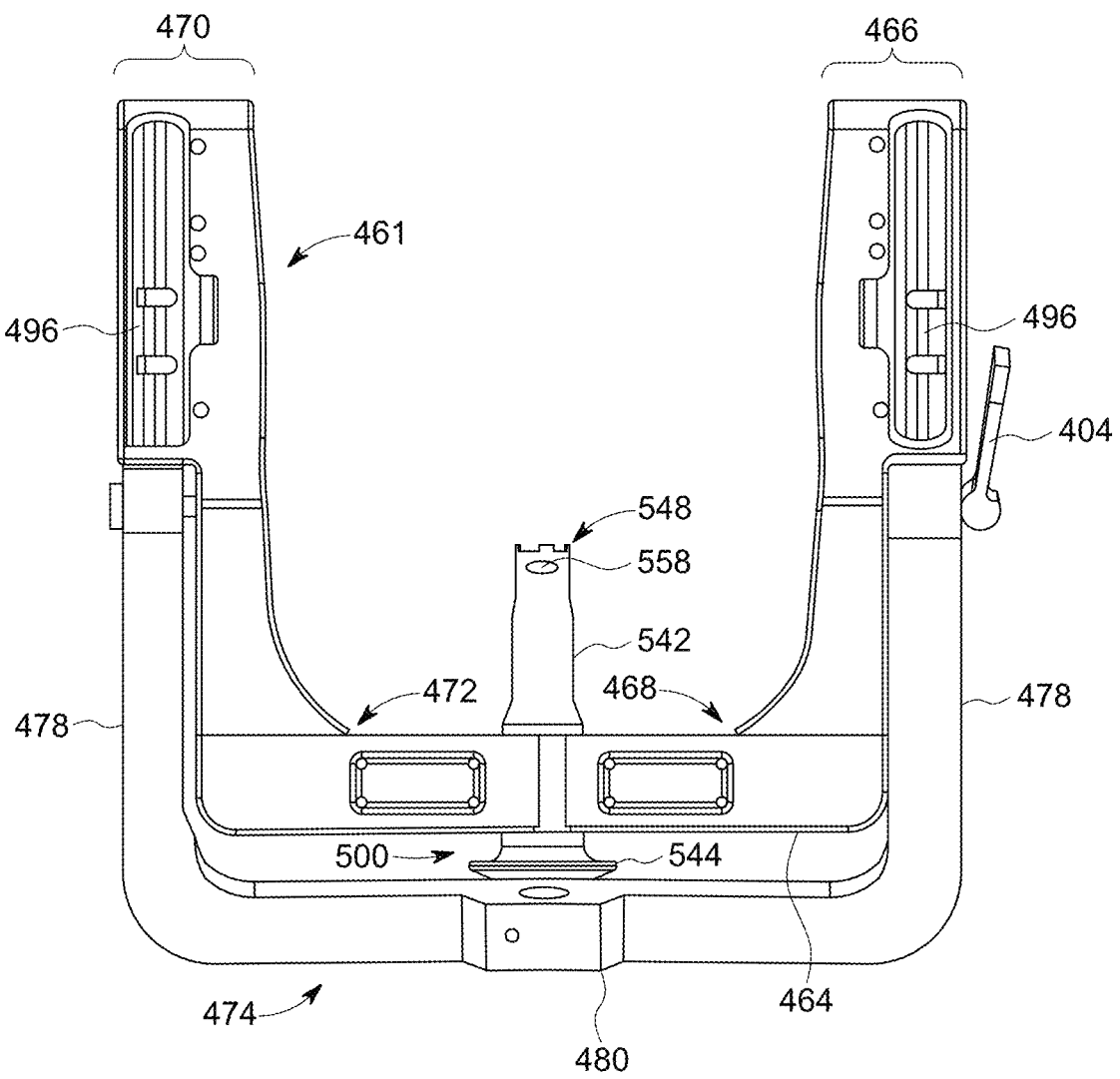
FIG. 48A is a bottom view of the mounting system and implant guide device of the implant guide system of FIG. 43A, in accordance with an aspect of the present disclosure.
Figure 48B:
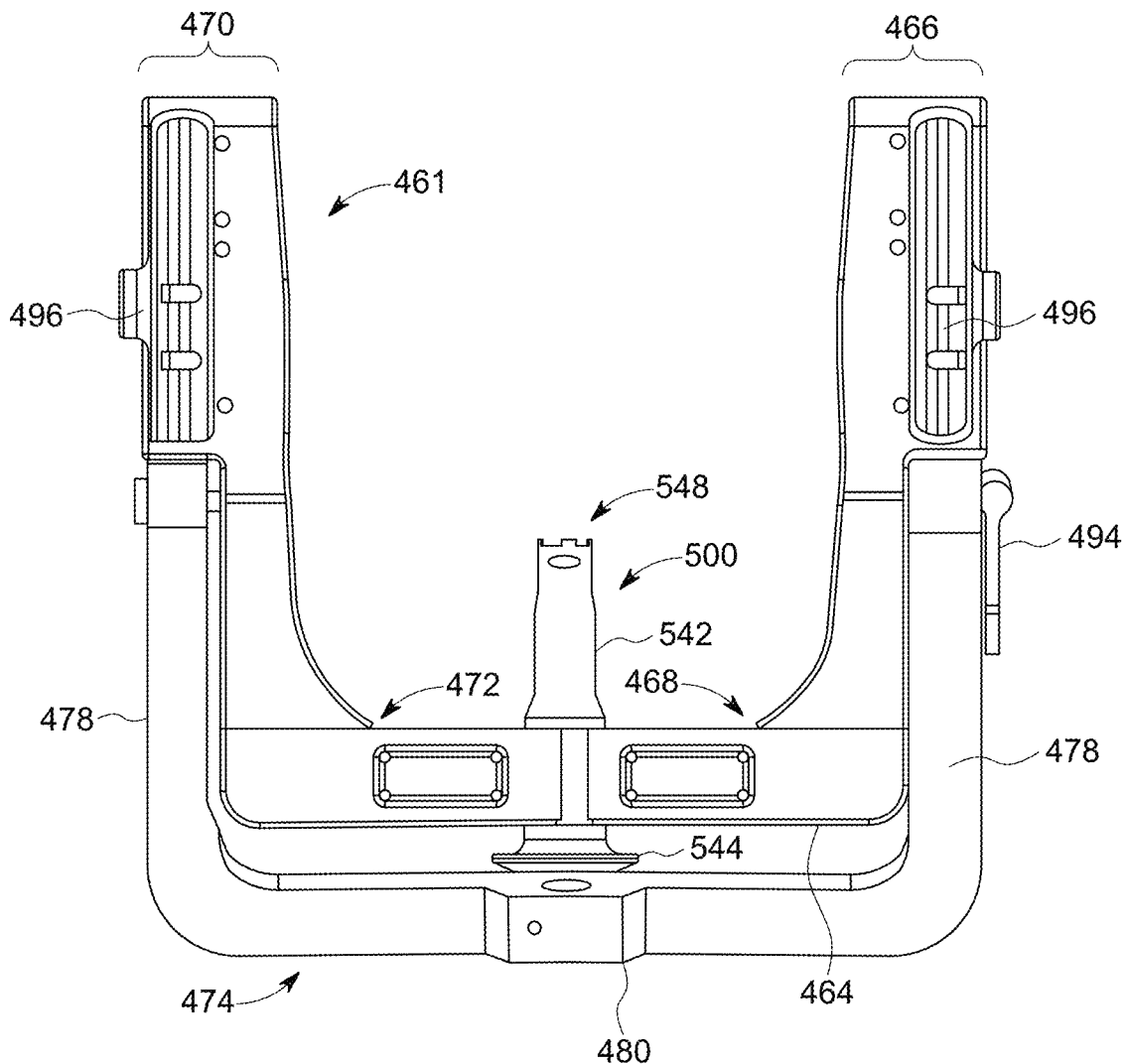
FIG. 48B is a bottom view of the mounting system and implant guide device of the implant guide system of FIG. 43A, in accordance with an aspect of the present disclosure.

Referring now to FIGS. 47A-48B, the targeting arm 474 of the implant guide device 461 may, according to one embodiment, rotate about at least one of the first arm 466 and the second arm 470. For example, the targeting arm 474 may rotate between approximately 90°-215°. For instance, the targeting arm 474 may be positioned at approximately 108° as shown in FIGS. 47A and 47B. A targeting arm lock 494 may be attached to the first arm 466, and the targeting arm lock 494 may facilitate rotation of the targeting arm 474 by functioning as a hinged lever for locking the position of the targeting arm 474. For instance, pressing the targeting arm lock 494 against the first arm 466 may lock the targeting arm 474 in place. Further, lifting the targeting arm lock 494, as shown in FIG. 48A, may allow for movement of the targeting arm 474 relative to the first arm 466 and the second arm 470. As shown in FIGS. 48A and 48B, the targeting arm 474 has been rotated from a position of approximately 108° shown in FIGS. 47A and 47B to a position of approximately 180°. Further, the implant guide device 461 may also include, according to one embodiment, one or more locks 496 positioned on at least one of the first arm 466 and the second arm 470 for locking an accessory (e.g., a screw guide, external compression attachment, extension accessory, etc. as described in greater detail above and which will not be described again here for brevity sake) into place that would be attached to at least one of the first arm 466 and the second arm 470. The targeting arm lock 494, as well as the one or more locks 496, may be rotated about a locking pin or targeting arm lock pin (see, e.g., FIGS. 33-40). For instance, the targeting arm lock 494 and the one or more locks 496 may rotate, for example, between 0°-200° about an axis. For example, the targeting arm lock 494 and the one or more locks 496 may be in a locked state when positioned at approximately 0°, as shown, for example, in FIG. 48B. Conversely, the targeting arm lock 494 and the one or more locks 496 may, for example, be opened when rotated approximately 180°-200°, as shown, for example, in FIG. 48A.

Figure 49B:
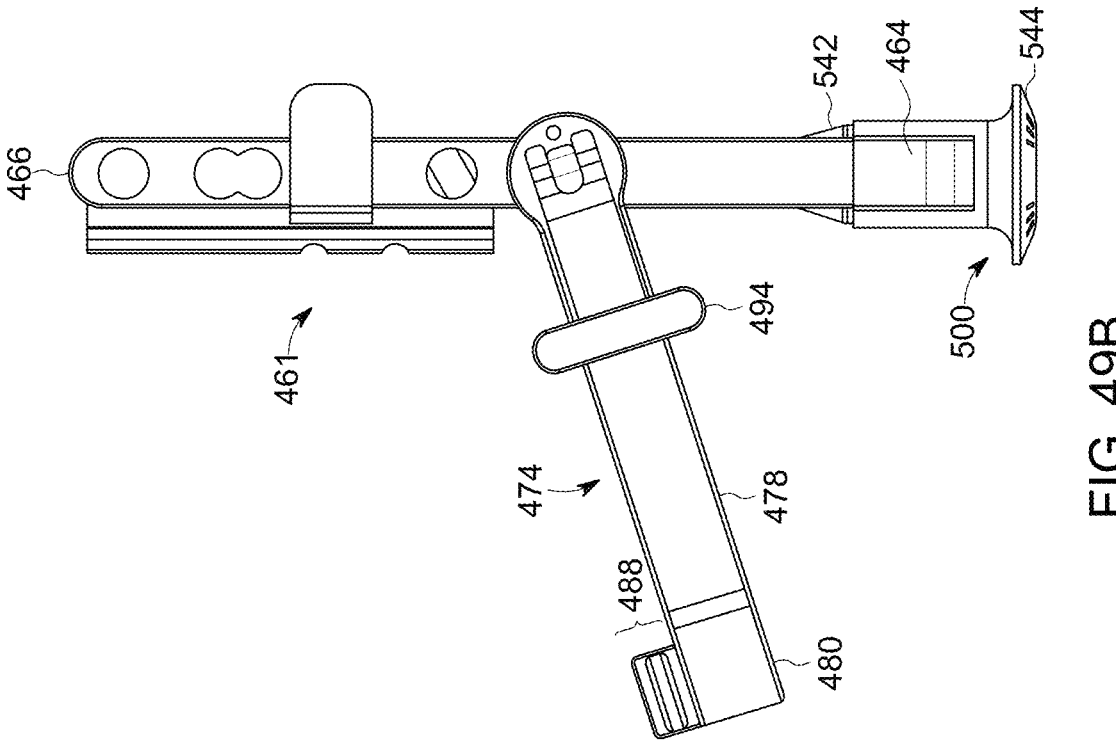
FIG. 49B is a side, second position view of the implant guide device and mounting system of the implant guide system of FIG. 43A, in accordance with an aspect of the present disclosure.
Figure 49A:
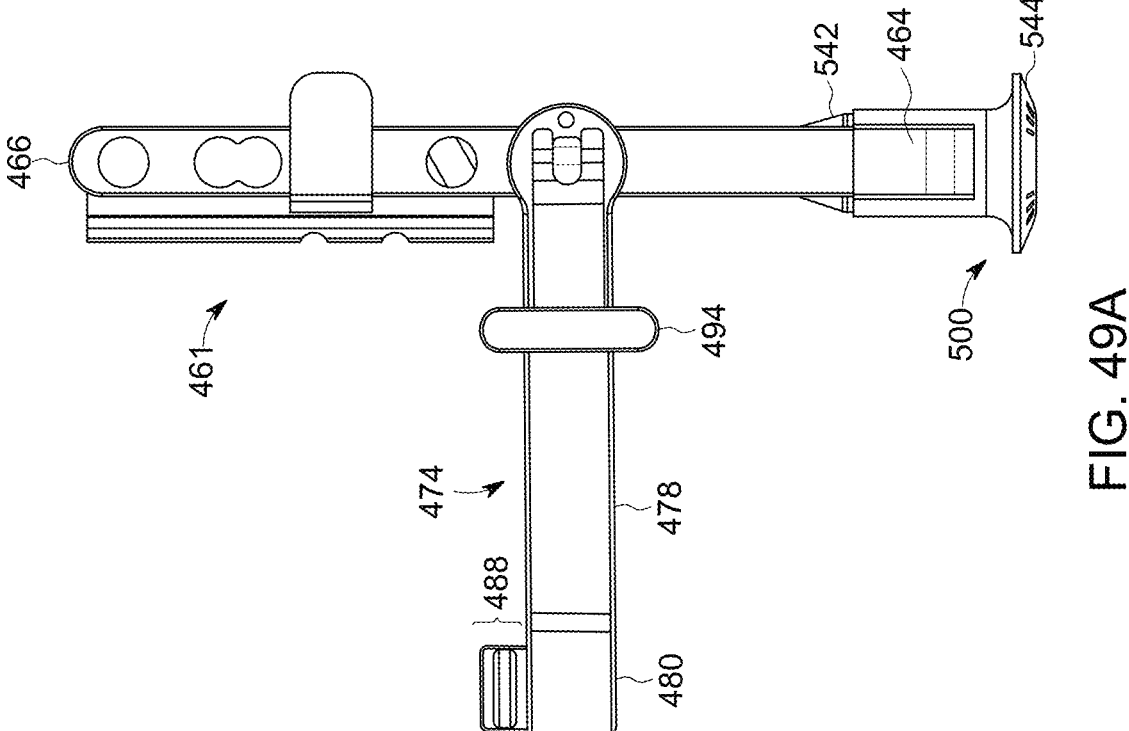
FIG. 49A is a side, first position view of the implant guide device and mounting system of the implant guide system of FIG. 43A, in accordance with an aspect of the present disclosure.
Figure 49D:
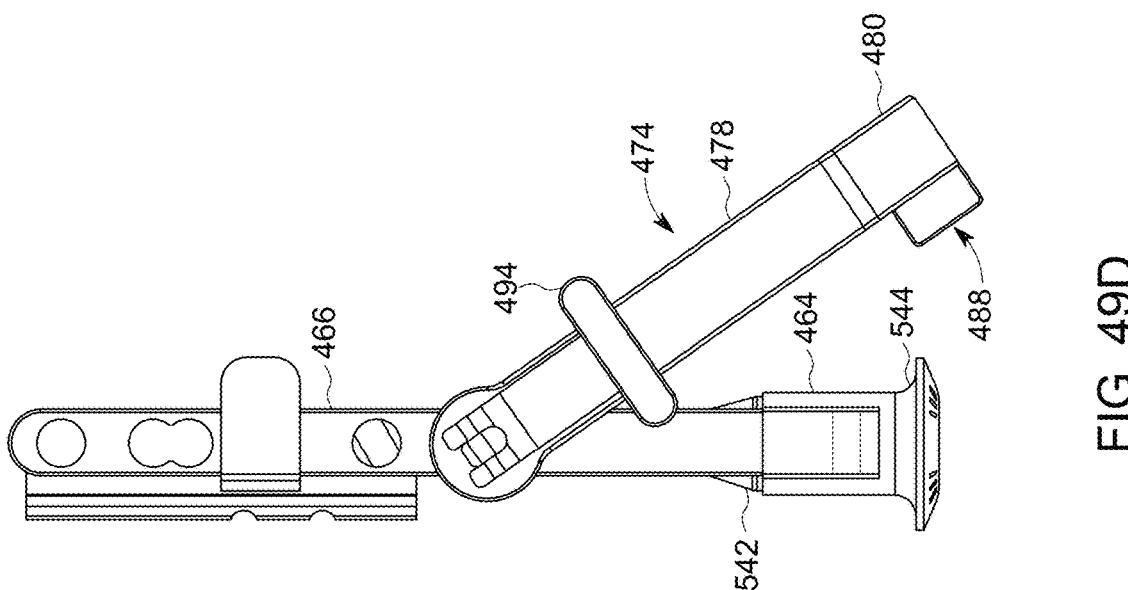
FIG. 49D is a side, fourth position view of the implant guide device and mounting system of the implant guide system of FIG. 43A, in accordance with an aspect of the present disclosure.
Figure 49C:
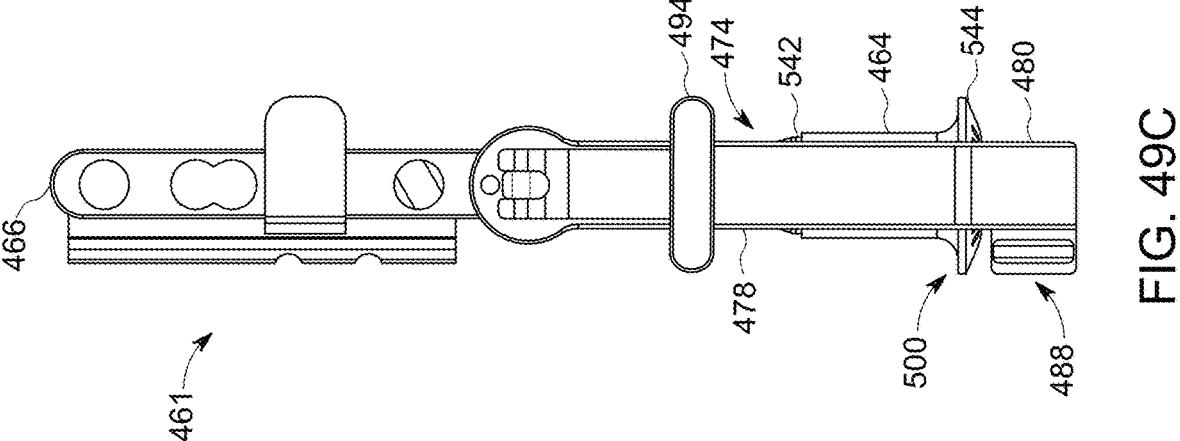
FIG. 49C is a side, third position view of the implant guide device and mounting system of the implant guide system of FIG. 43A, in accordance with an aspect of the present disclosure.
Figure 50:
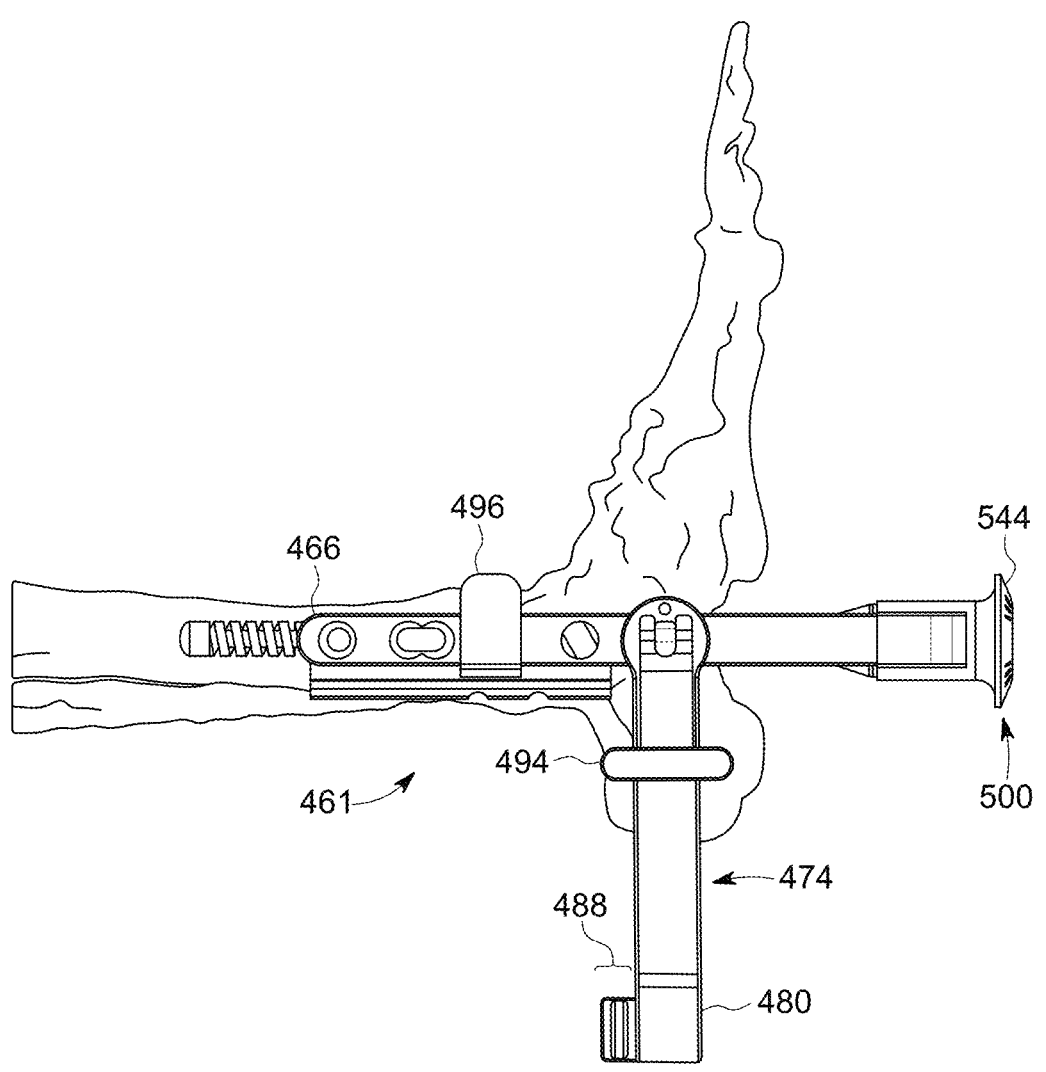
FIG. 50 is a side, first position view of the implant guide device and mounting system of the implant guide system of FIG. 43A in relation to the patient's lower extremity, in accordance with an aspect of the present disclosure.

Referring now to FIGS. 49A-50, other positions of the targeting arm 474 may also be possible in order to provide support to the implant guide device 461 and/or facilitate inserting one or more screws at a desired angle into a bone of the patient. For instance, a 90° positioning of the targeting arm 474, as shown in FIG. 49A, may prop up the implant guide device 461 during surgery to provide better access to, for example, the plantar portion of the patient's foot for inserting a nail implant, as shown in FIG. 50. A 108° positioning of the targeting arm 474, as shown in FIG. 49B, may be used, for example, when inserting a calcaneal screw into the posterior portion of the patient's calcaneus. A targeting arm 474 positioning of 180°, as shown in FIG. 49C, may be desirous for moving the targeting arm 474 out of the way of the surgical area to provide better access for insertion of, for example, a subtalar screw. Other targeting arm 474 positioning such as, for example the 215° positioning shown in FIG. 49D is also possible.

Figure 51:
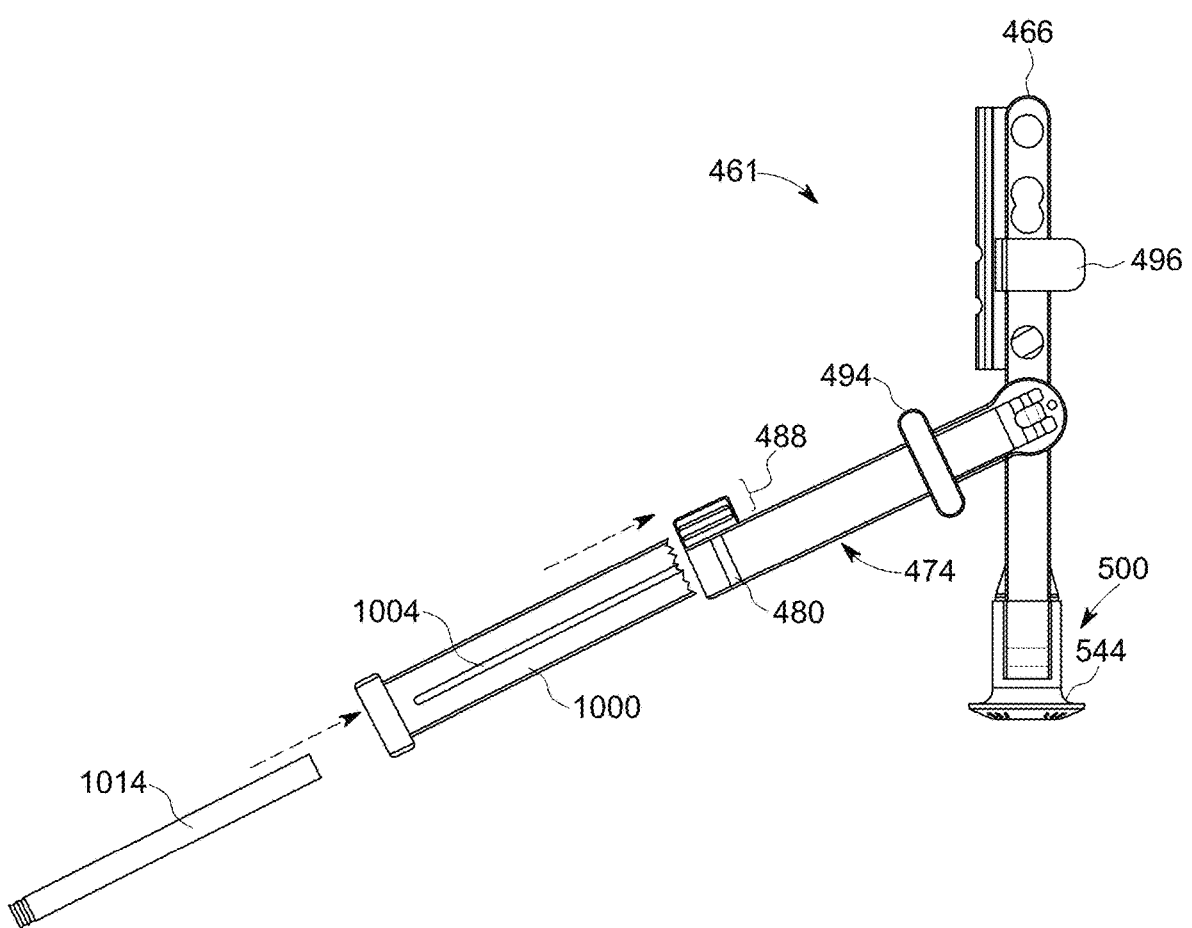
FIG. 51 is a side, second position view of the implant guide device, mounting system, and a calcaneal screw guide of the implant guide system of FIG. 43A, in accordance with an aspect of the present disclosure.
Figure 52:
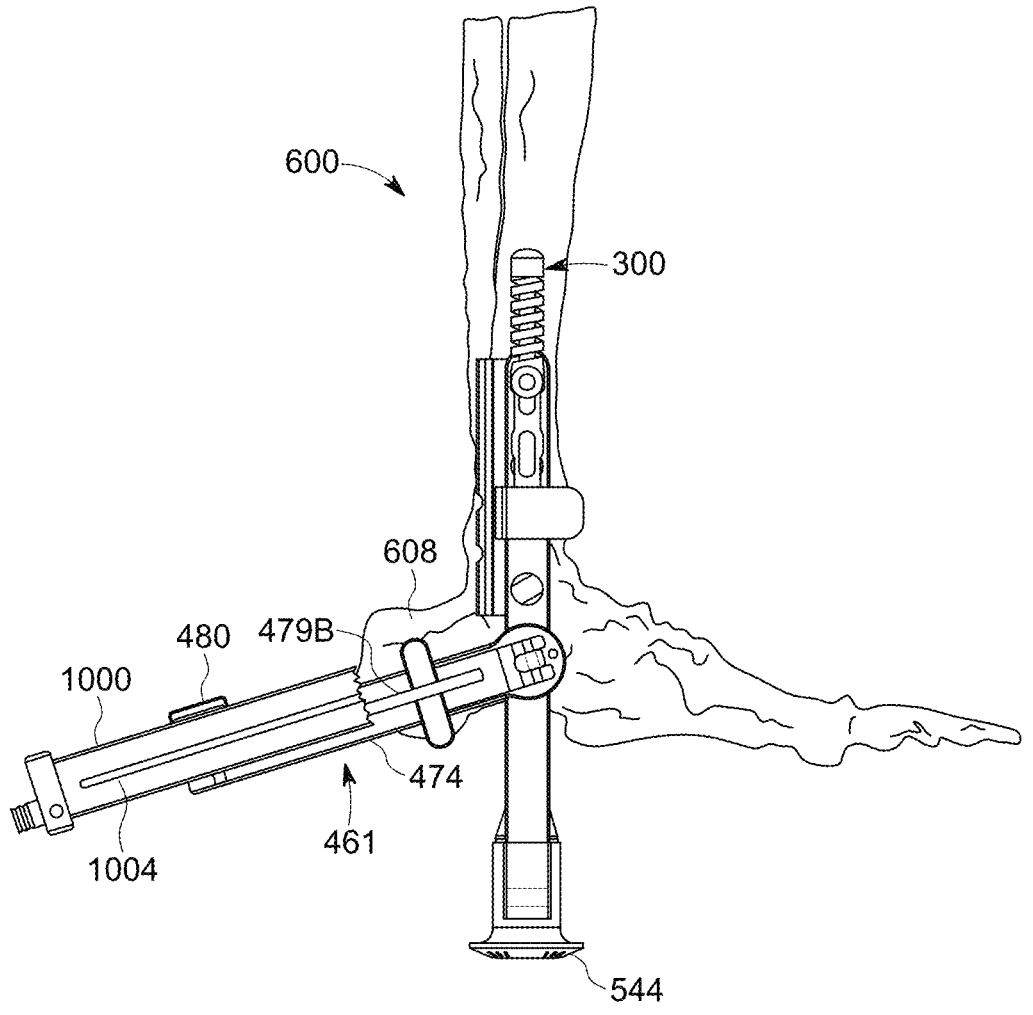
FIG. 52 is a side, second position view of the implant guide device, mounting system, and calcaneal screw guide of the implant guide system of FIG. 43A in relation to a patient's lower extremity, in accordance with an aspect of the present disclosure.
Figure 57A:
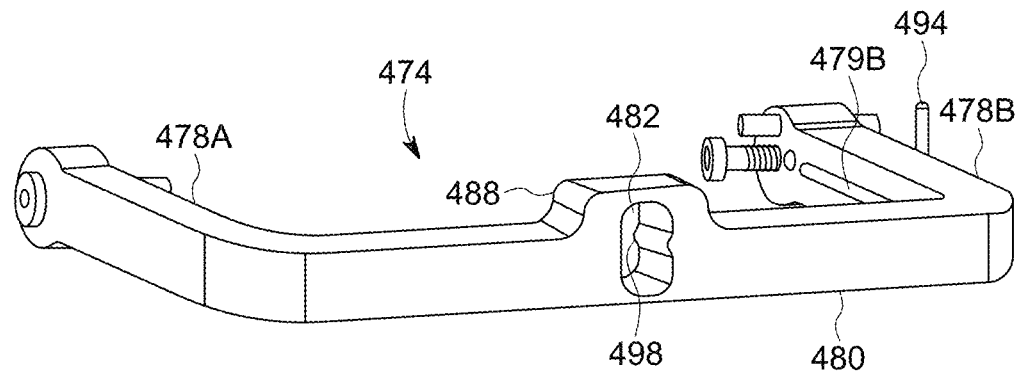
FIG. 57A is a perspective view of a targeting arm of the implant guide system of FIG. 43A, in accordance with an aspect of the present disclosure.
Figure 57B:
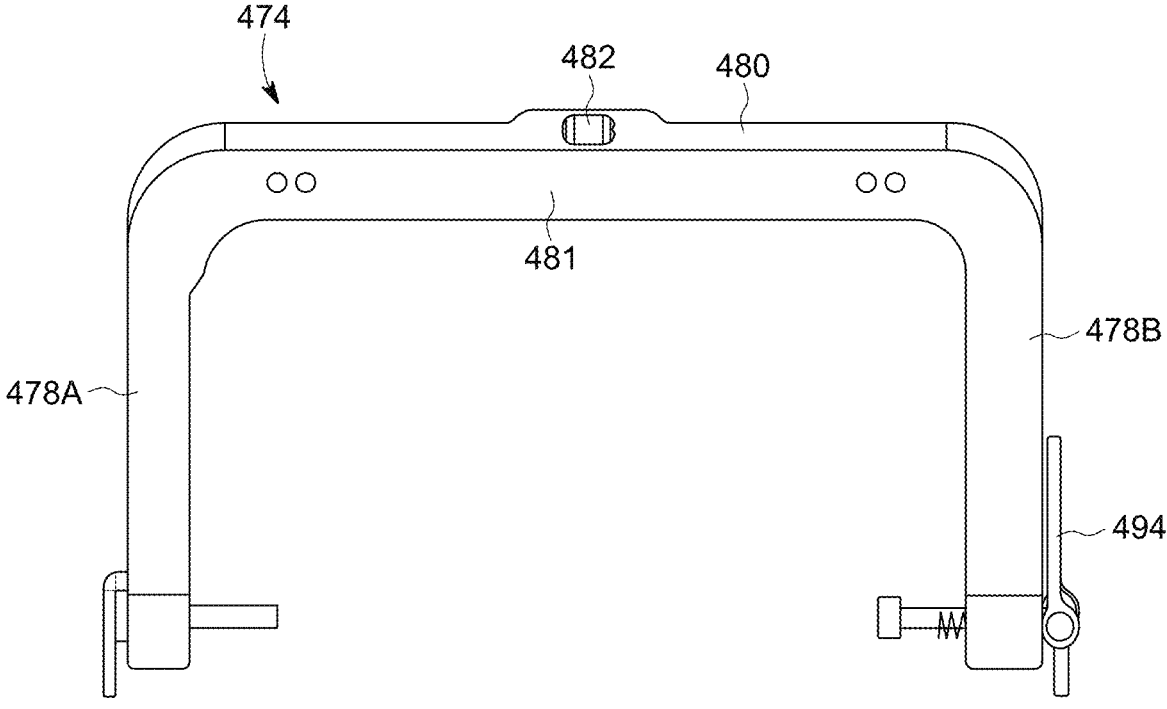
FIG. 57B is a first end view of a targeting arm of the implant guide system of FIG. 43A, in accordance with an aspect of the present disclosure.
Figure 57C:
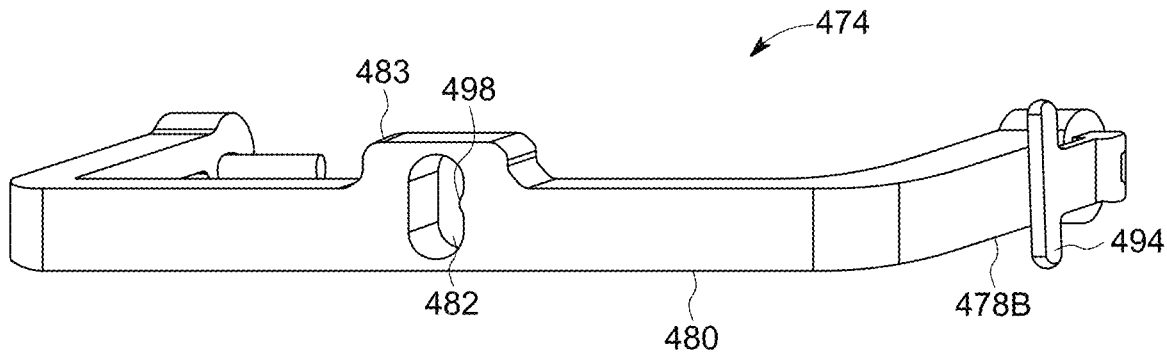
FIG. 57C is a perspective view of a targeting arm of the implant guide system of FIG. 43A, in accordance with an aspect of the present disclosure.
Figure 57D:
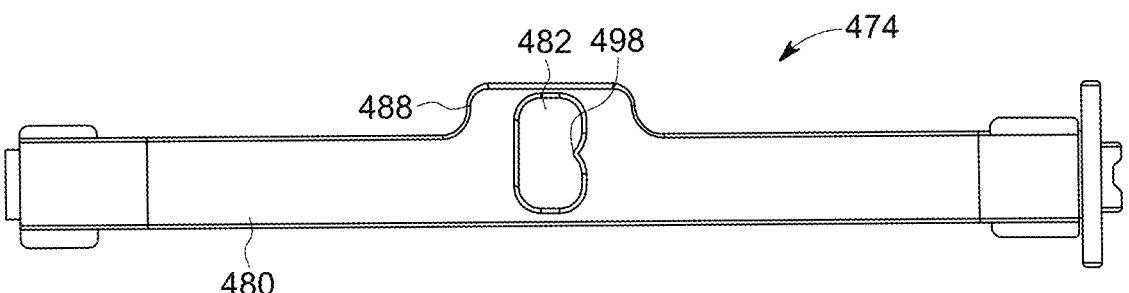
FIG. 57D is a bottom view of a targeting arm of the implant guide system of FIG. 43A, in accordance with an aspect of the present disclosure.

Referring now to FIG. 51, the targeting arm 474 of the implant guide device 461 may, for example, be used to insert a calcaneal screw 1002 (see FIG. 55) into the posterior portion of the patient's calcaneus 608 (see FIG. 52). For instance, for insertion of the calcaneal screw 1002 (see FIG. 55), it may be desired that the targeting arm 474 is, for example, positioned at approximately 108°. A calcaneal screw guide 1000 may be inserted through a targeting arm through hole 482 (see FIG. 57A) of the accessory engagement portion 480 of the targeting arm 474. A drill guide 1014 may be inserted through a drill guide aperture 1008 (see FIG. 54) of the calcaneal screw guide 1000 in preparation for inserting the calcaneal screw 1002 (see FIG. 55).

Figures 53A, 53B:
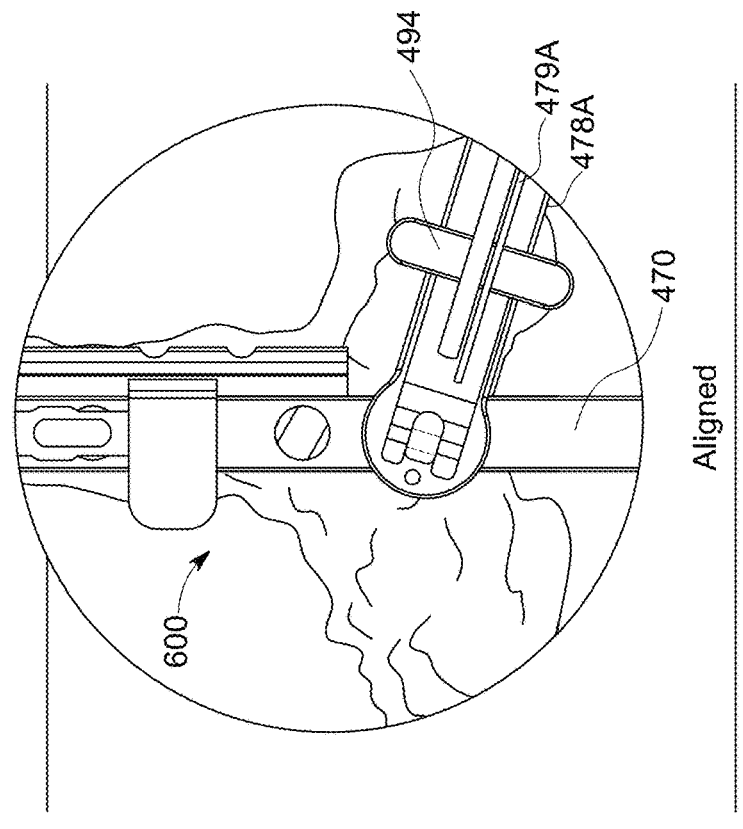
FIG. 53A is a lateral view the implant guide system of FIG. 43A in which the inlays of the targeting arm of the implant guide device are misaligned, in accordance with an aspect of the present disclosure.
FIG. 53B is a lateral view of the implant guide system of FIG. 43A in which the inlays of the targeting arm of the implant guide device are aligned, in accordance with an aspect of the present disclosure.
Figure 55:
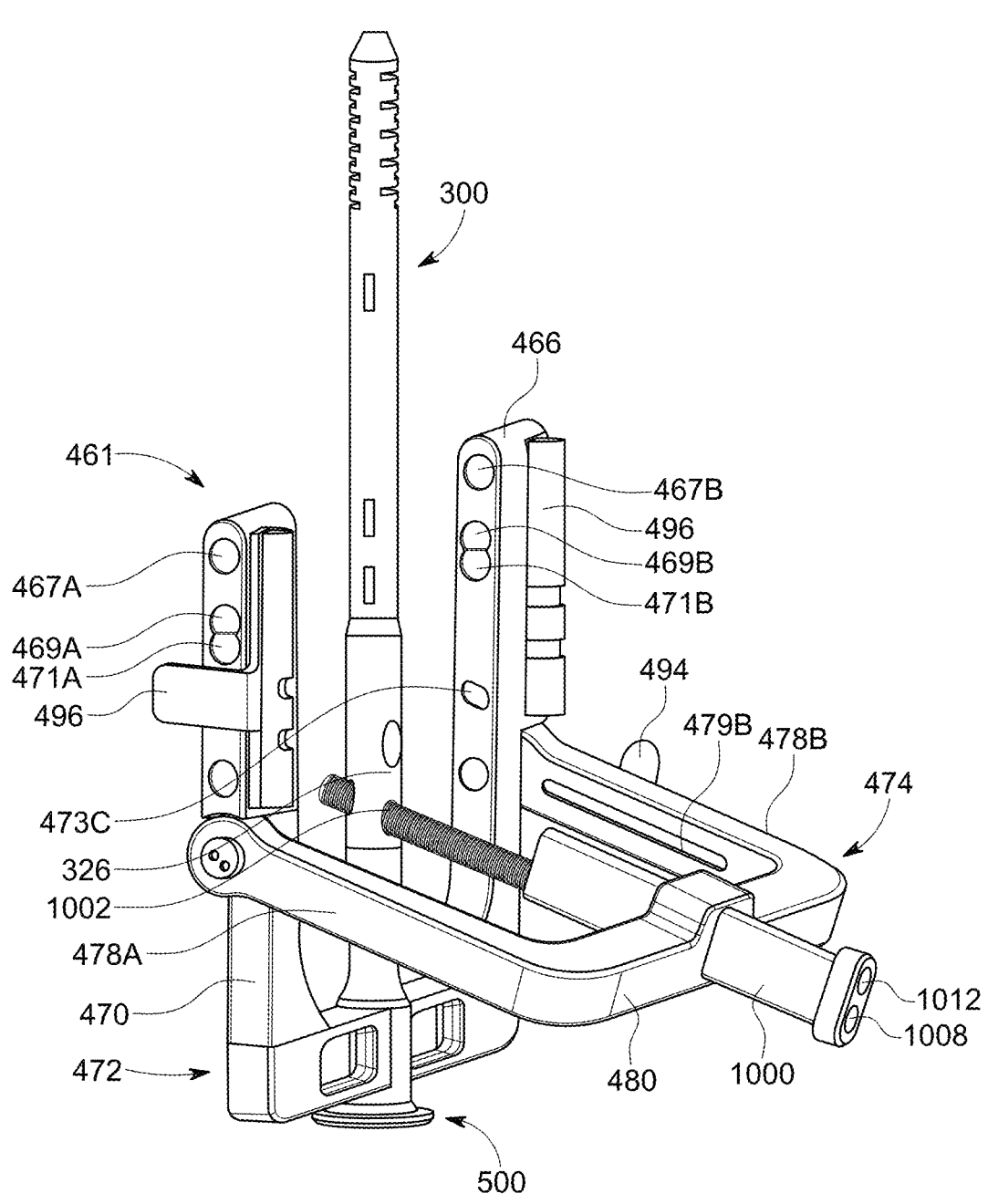
FIG. 55 is a perspective view of a calcaneal screw guide and the implant guide system of FIG. 43A, in accordance with an aspect of the present disclosure.
Figure 56A:
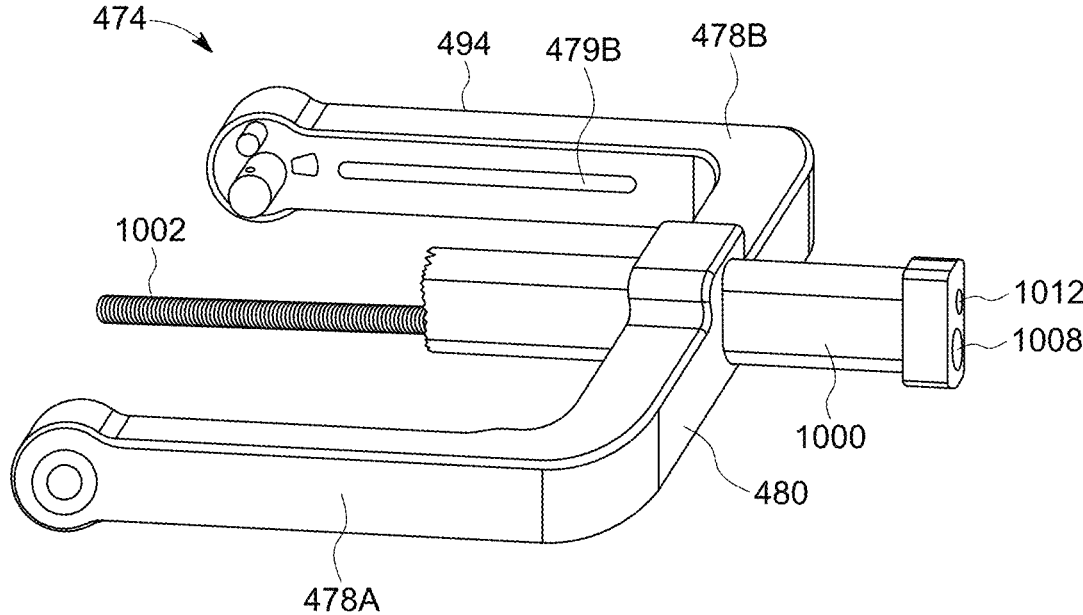
FIG. 56A is a perspective view of a calcaneal screw guide, calcaneal screw and targeting arm of the implant guide system of FIG. 43A, in accordance with an aspect of the present disclosure.
Figure 56B:
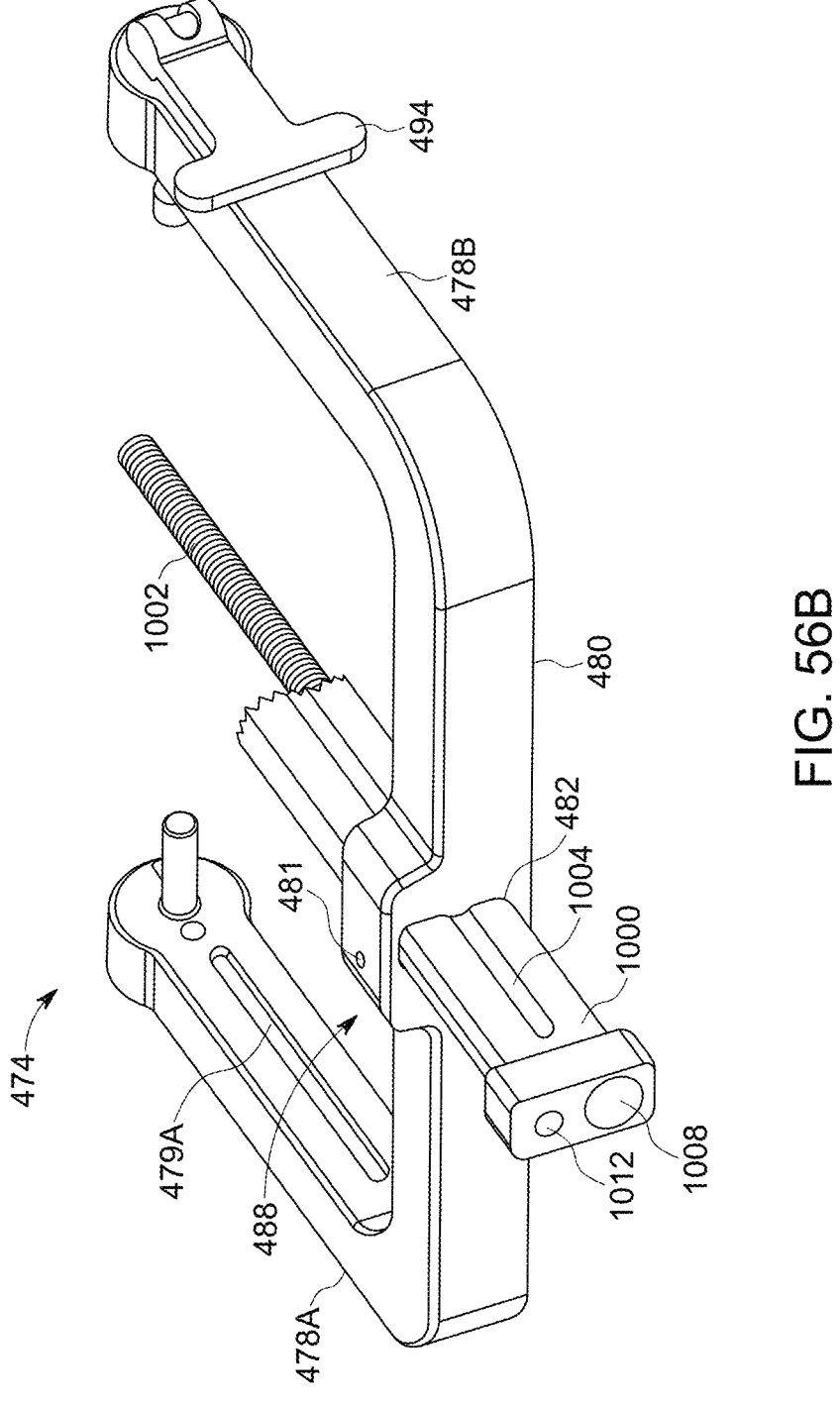
FIG. 56B is a perspective view of a calcaneal screw guide, calcaneal screw and targeting arm of the implant guide system of FIG. 43A, in accordance with an aspect of the present disclosure.
Figure 56C:
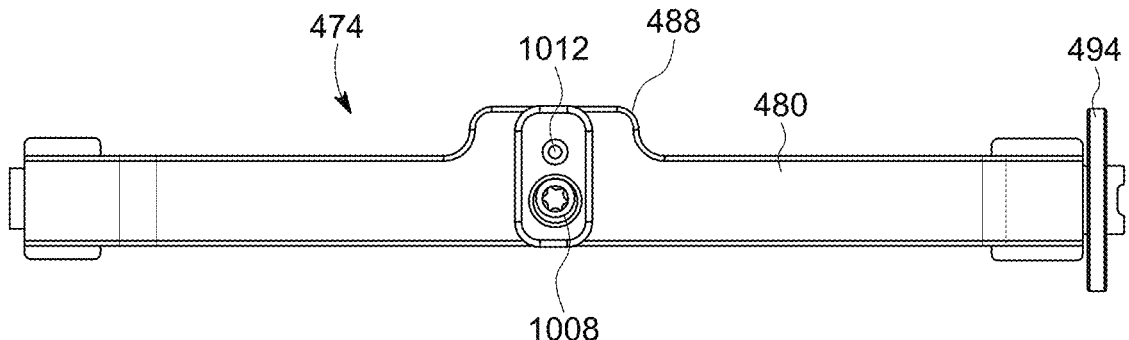
FIG. 56C is a bottom view of a calcaneal screw guide and targeting arm of the implant guide system of FIG. 43A, in accordance with an aspect of the present disclosure.

Referring now to FIGS. 52-53B, once the implant 300 has been inserted into the patient's lower extremity 600, the implant guide device 461 may then be positioned for insertion of the calcaneal screw 1002 (see FIG. 55). According to one embodiment, using fluoroscopy to view the patient's lower extremity 600 may facilitate aligning the targeting arm 474 for a desired positioning of the calcaneal screw 1002 (see FIG. 55). For instance, as shown in FIGS. 53A-53B, viewing the implant guide device 461 using fluoroscopy may facilitate viewing a first inlay 479A if one side support portion 478A and a second inlay 479B of another side support portion 478B of the targeting arm 474 of the implant guide device 461, where the first inlay 479A and the second inlay 479B serve as fluoroscopic markers. FIG. 53A shows, for example, a lateral view of the patient's lower extremity 600 where the first inlay 479A and the second inlay 479B are not aligned. In order to obtain an accurate trajectory representation for inserting the calcaneal screw 1002 (see FIG. 55), a medical professional may position the first inlay 479A and the second inlay 479B to be aligned as shown, for example, in FIG. 53B.

Figure 54:
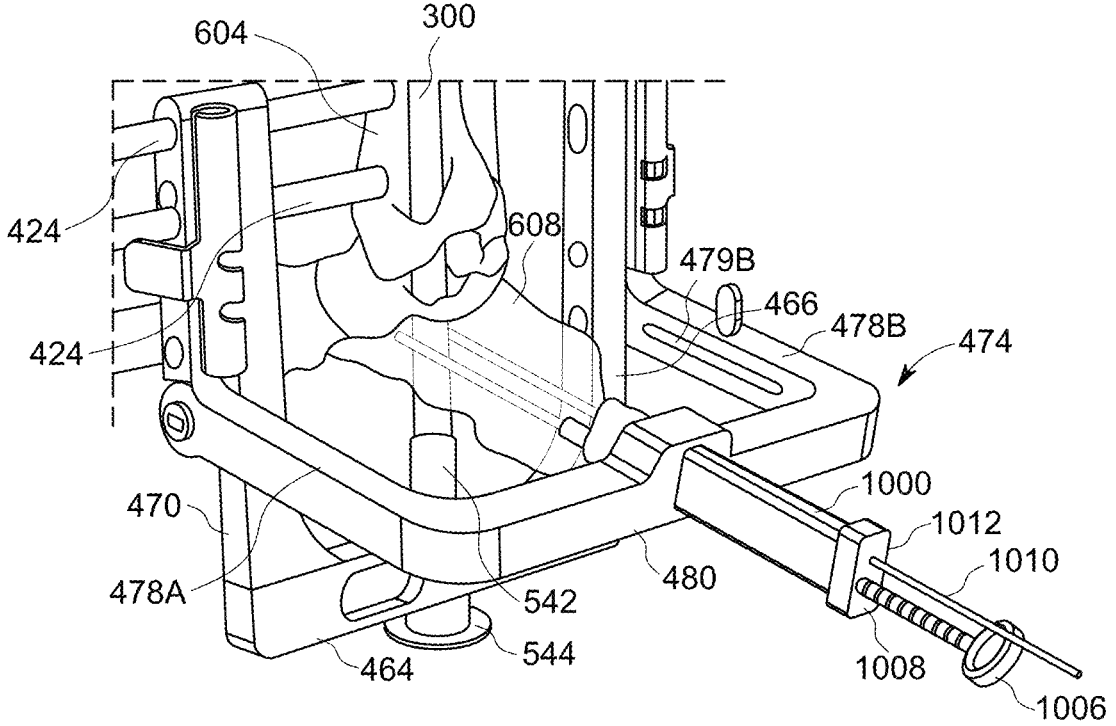
FIG. 54 is a perspective view of the implant guide system of FIG. 43A, a calcaneal screw guide, depth gauge and a pin in relation to a patient's lower extremity, in accordance with an aspect of the present disclosure.

Once the targeting arm 474 is properly aligned, a medical professional may, for example, insert a pin 1010 into the posterior portion of the patient's calcaneus 608 to provide drill stabilization for drilling into the patient's bone, where the pin 1010 passes through a pin aperture 1012 of the calcaneal screw guide 1000 as shown, for instance, in FIG. 54. Once the targeting arm 474 is aligned and stabilized, the medical professional may, for example, drill into the posterior portion of the patient's calcaneus 608 prior to inserting the calcaneal screw 1002 (see FIG. 55). Various methods may be used to determine the depth of the drilled portion of the patient's calcaneus 608. For instance, lateral fluoroscopy of the patient's lower extremity 600 may provide a visual depiction of the depth. Additionally, the depth may, for example, be measured using markings on a depth gauge 1006 that may be inserted through a drill guide aperture 1008 of the calcaneal screw guide 1000 as shown, for instance, in FIG. 54.

Referring now to FIGS. 55-57D, once inserted, the calcaneal screw 1002 may, for example, traverse a fastener hole 326 of the implant 300 (i.e., IM nail) as shown in FIG. 55. To ensure the calcaneal screw 1002 aligns with the fastener hole 326, the calcaneal screw 1002 may be inserted through the drill guide aperture 1008 of the calcaneal screw guide 1000. The calcaneal screw guide 1000 may be retained in position within the targeting arm through hole 482 via a spring 483 inserted into a cavity 481 of the accessory engagement portion 480 of the targeting arm 474, as shown in FIG. 57C. Additionally, the alignment channel 1004 (FIGS. 51-52) of the calcaneal screw guide 1000 may engage with a protrusion 498 in the targeting arm through hole 482.

Figure 58A:
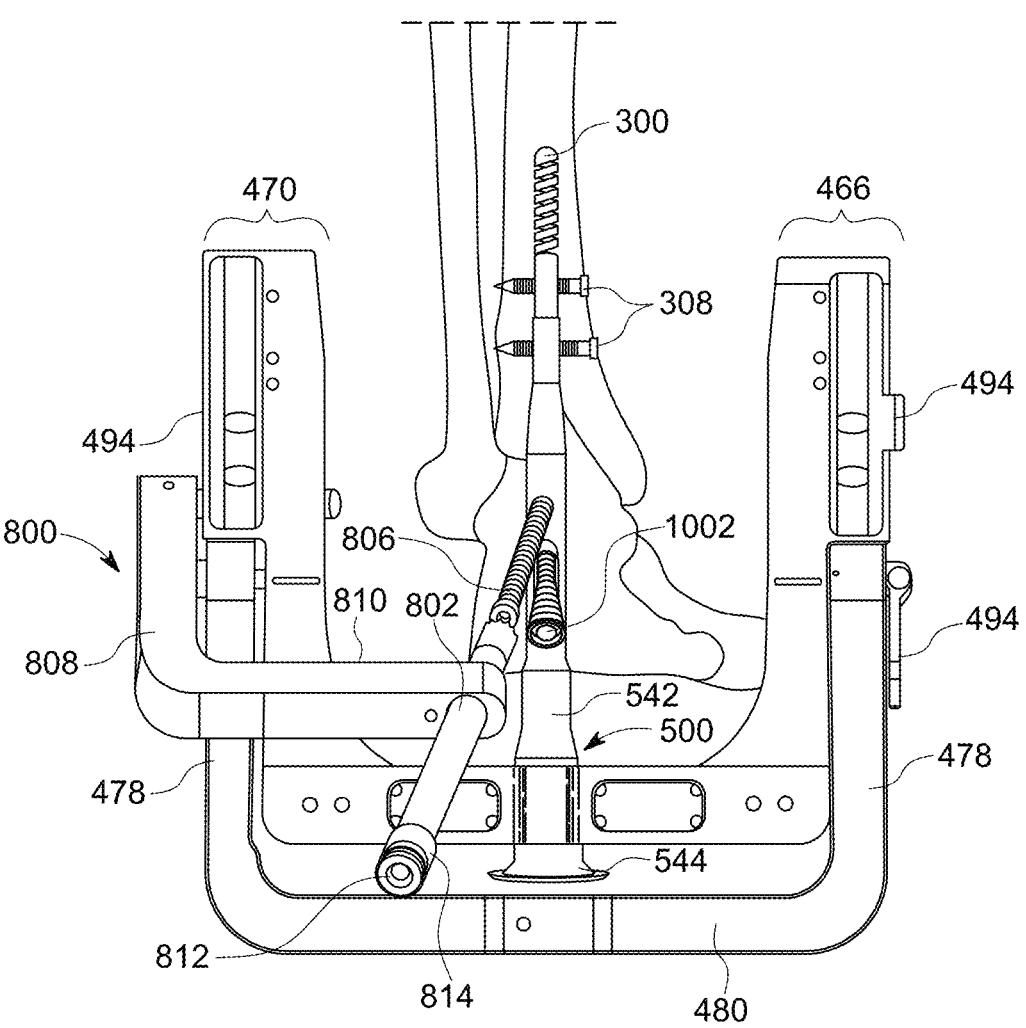
FIG. 58A is a perspective view of the implant guide system of FIG. 43A that includes a single-armed targeting accessory, in accordance with an aspect of the present disclosure.
Figure 58B:
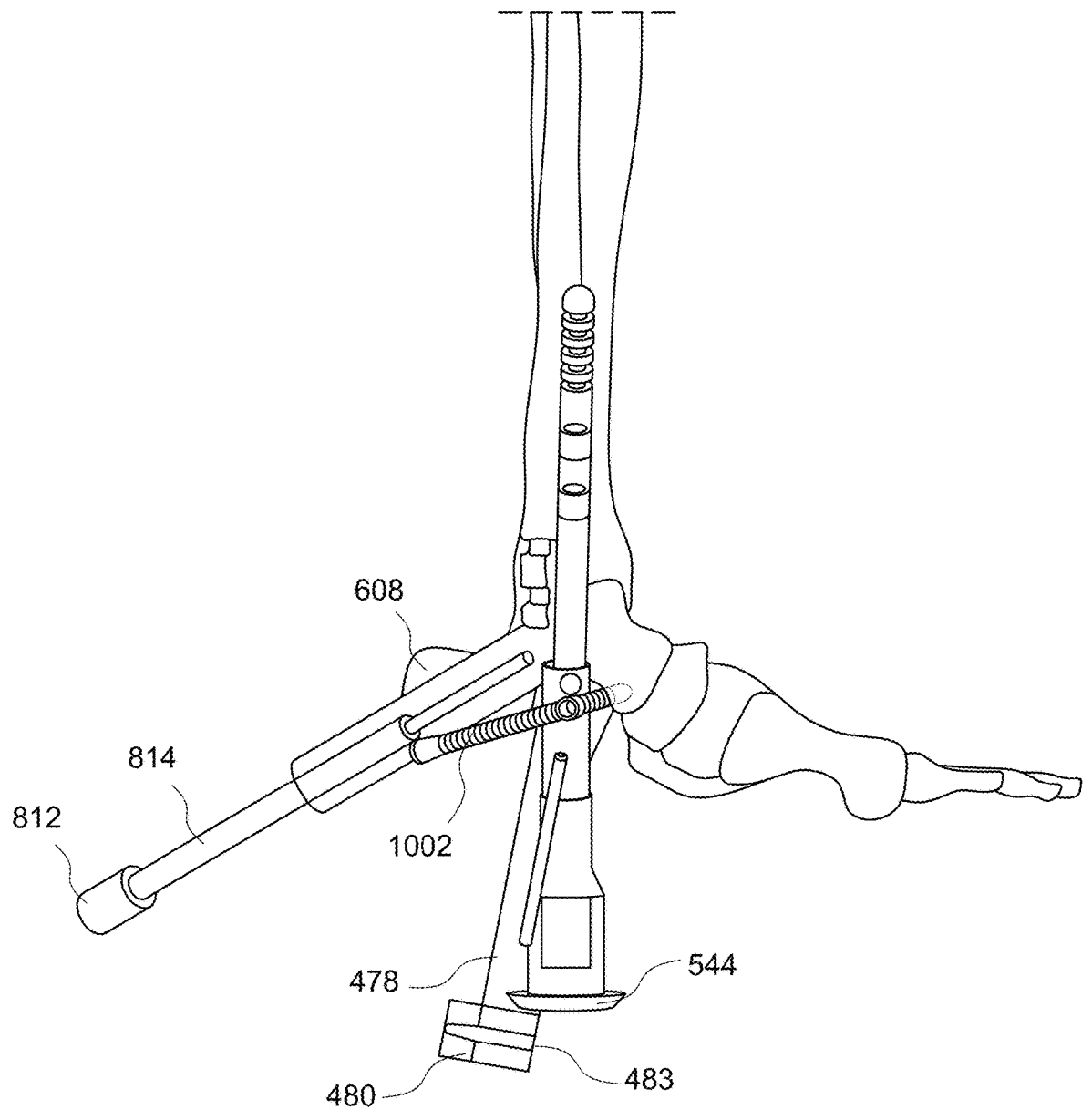
FIG. 58B is a lateral view of the implant guide system of FIG. 43A that includes a single-armed targeting accessory in relation to the patient's lower extremity, in accordance with an aspect of the present disclosure.
Figure 59:
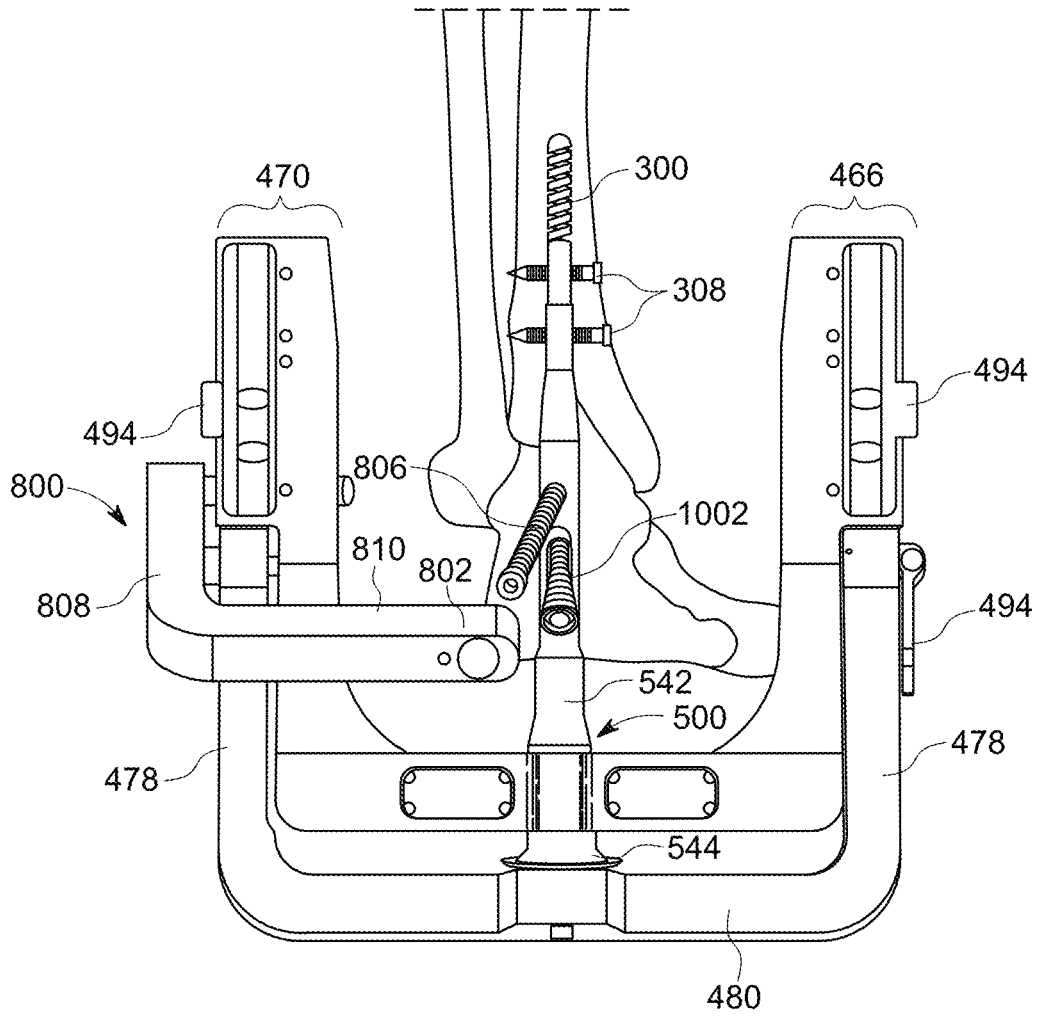
FIG. 59 is a bottom view of the implant guide system of FIG. 43A that includes a single-armed targeting accessory in relation to the patient's lower extremity, in accordance with an aspect of the present disclosure.
Figure 60:
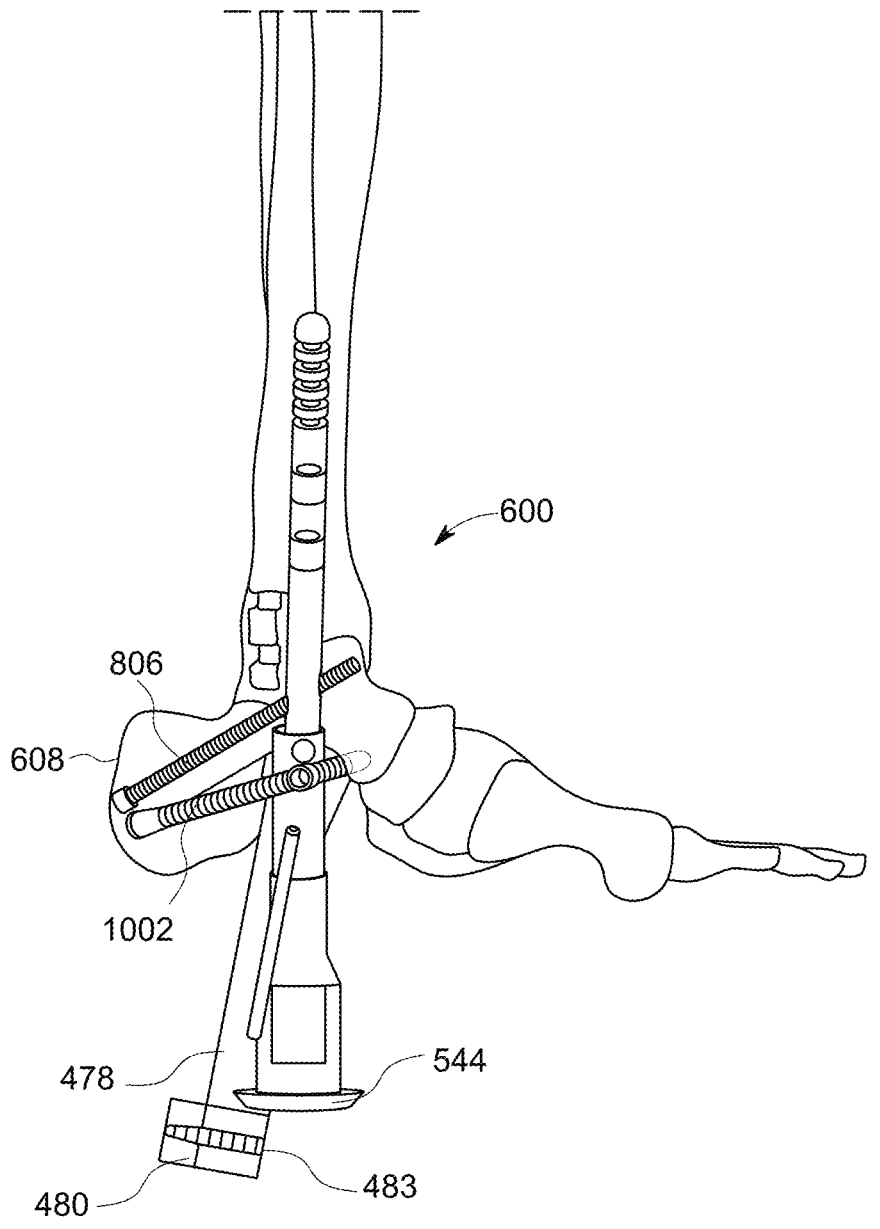
FIG. 60 is a lateral of the implant guide system of FIG. 43A in relation to the patient's lower extremity, in accordance with an aspect of the present disclosure.
Figure 61:
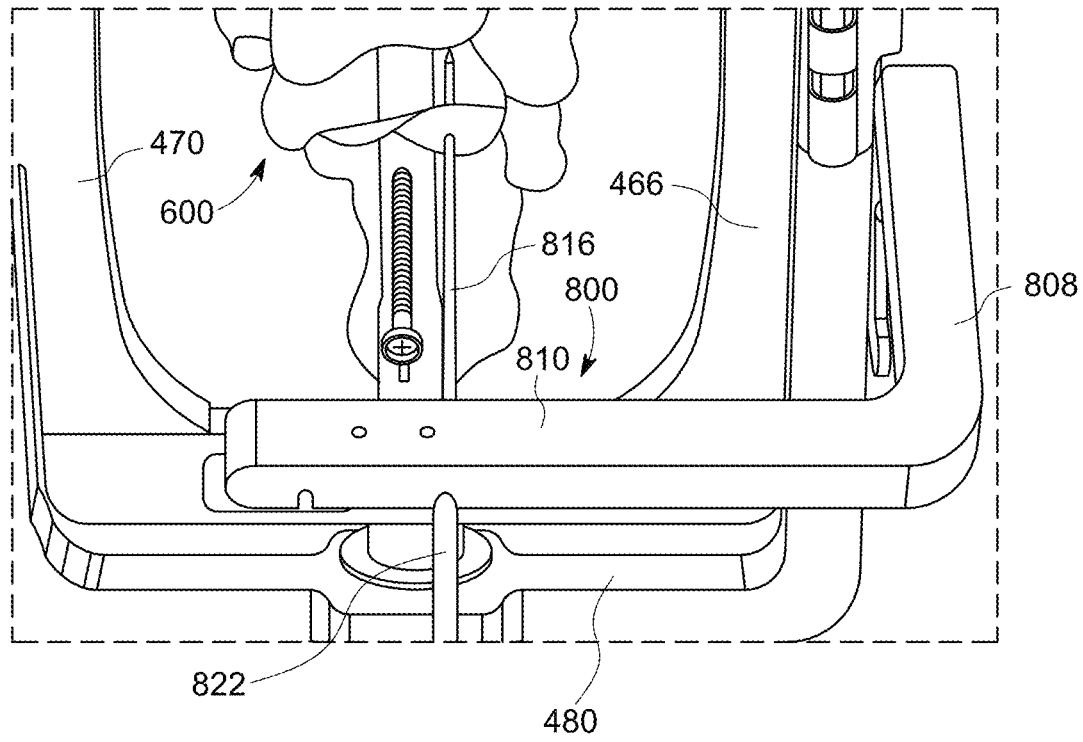
FIG. 61 is a magnified view of a single-armed targeting accessory in relation to the implant guide system of FIG. 43A, in accordance with an aspect of the present disclosure.

As shown in FIG. 55, the first arm 466 and the second arm 470 may include various through holes 467A, 467B, 469A, 469B, 471A, 471B, 473A, 473B traversing at least one of the first arm 466 and the second arm 470 in a medial to lateral direction. The most distal tibial through holes 467A and 467B may be configured or sized and shaped to receive a screw guide 424 (see FIG. 54) to facilitate inserting a screw 308 (see FIGS. 58A, 59) through the implant 300 and into the patient's tibia 604 (see FIG. 54) in order to secure the implant 300. Through holes 469A and 469B may provide proper screw positioning within the implant 300 and the patient's tibia 604 (see FIG. 54) to provide weight bearing post-operative compression, known as dynamization. Alternatively, through holes 471A and 471B may provide proper screw positioning within the implant 300 and the patient's tibia 604 (see FIG. 54), if post-operative dynamization is not desired. In particular, through holes 471A and 471B may provide relatively static support for the implant 300. Through holes 473A and 473B may allow for inserting one or more accessories (i.e., a single-armed targeting accessory 800 (see FIGS. 58A-64)). Optionally, through holes 467A, 467B, 471A, and 471B may also be configured or sized and shaped to receive, for example, an extension accessory 900 (see FIGS. 65A, 65B).

Referring now to FIGS. 58A-60, once the calcaneal screw 1002 is inserted into the patient's calcaneus 608, the implant guide device 461 may, according to one embodiment, be used to insert a subtalar screw 806. The single-armed targeting accessory 800 may be, for example, attached to the second arm 470 of the implant guide device 461 via a targeting arm lock 494. According to one embodiment, the single-armed targeting accessory 800 may include a side support portion 808 and an accessory engagement portion 810. Further, a drill guide 812 may be inserted into a subtalar screw guide 814 and inserted through the targeting accessory through hole 802 of the accessory engagement portion 810 of the single-armed targeting accessory 800. The single-armed targeting accessory 800 may be positioned, for example, at approximately 30° below the traverse plane (i.e., approximately 120°) to provide proper placement of the subtalar screw 806 so that the subtalar screw 806 is angled from an inferior to superior (e.g., 19°-35°) position once inserted. Further, the through hole 802 may be angled so that the subtalar screw 806 is angled (e.g., 16.4°) along the sagittal plane from, for example, left to right, which would angle the subtalar screw in a lateral-posterior to medial anterior position (e.g., 11°-25°).

Figure 62:
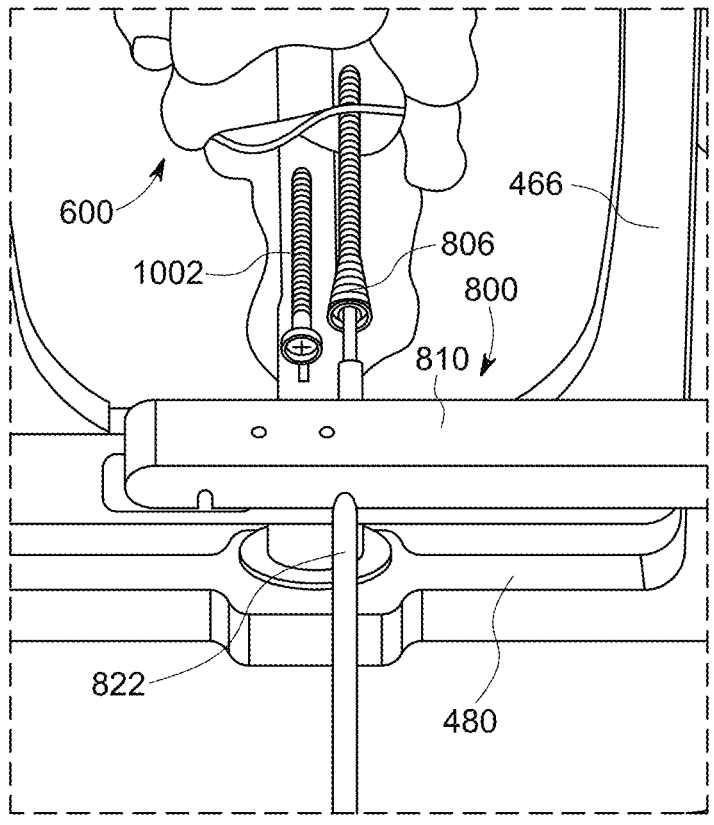
FIG. 62 is a magnified view of a single-armed targeting accessory in relation to the implant guide system of FIG. 43A, in accordance with an aspect of the present disclosure.
Figure 63:
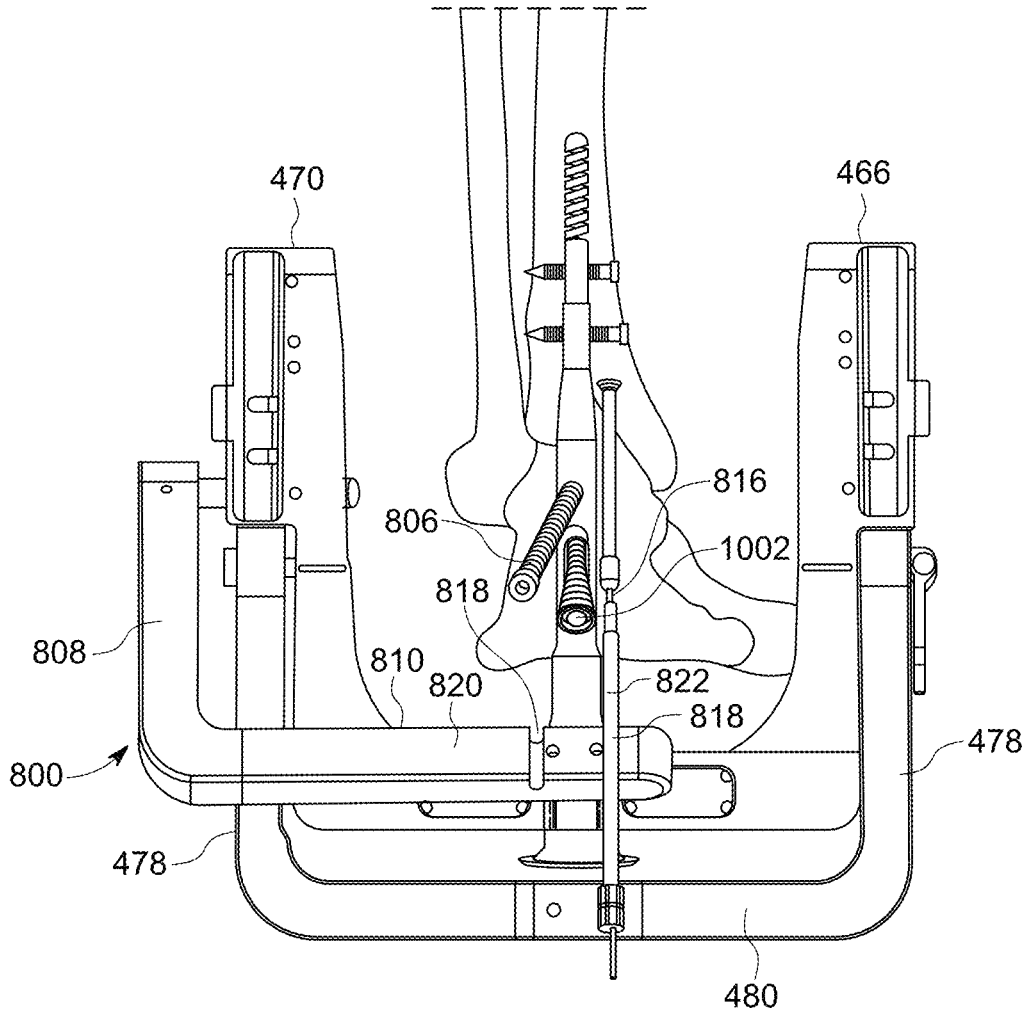
FIG. 63 is a bottom view of an implant guide system of FIG. 43 with a single-armed targeting accessory in relation to a patient's lower extremity, in accordance with an aspect of the present disclosure.
Figure 64:
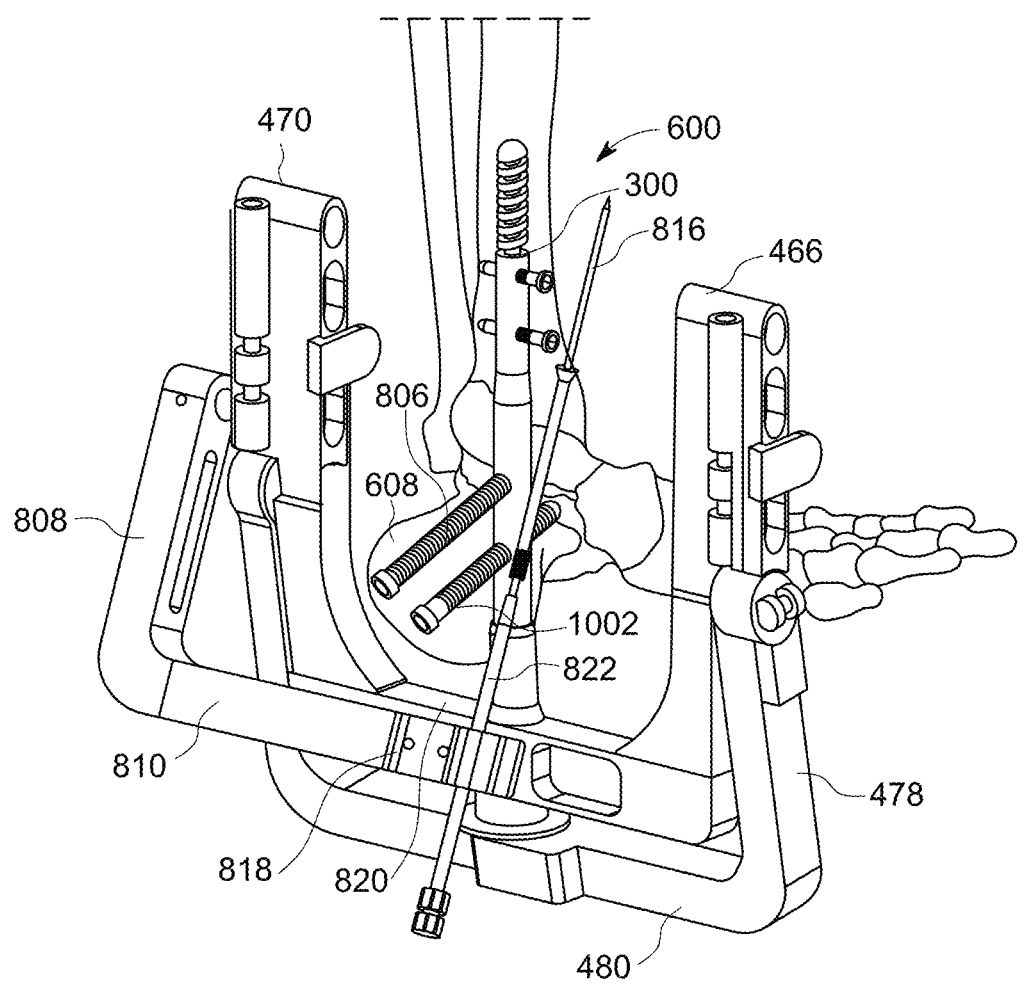
FIG. 64 is a perspective view of an implant guide system of FIG. 43 with a single-armed targeting accessory in relation to a patient's lower extremity, in accordance with an aspect of the present disclosure.

According to another embodiment, as shown in FIGS. 61-64, the single-armed targeting accessory 800, may, for example, be used to insert one or more wires 816 into the patient's lower extremity 600. For instance, if inserting a subtalar screw 806 through the implant 300 is not conducive to patient anatomy, the subtalar screw 806 may be positioned to avoid interference with the implant 300 and calcaneal screw 1002. In particular, wires 816 may facilitate positioning the subtalar screw 806 as shown in FIG. 62. For instance, the single-armed targeting accessory 800 may, for example, include one or more slots 818 traversing the accessory engagement portion 810 of the single-armed targeting accessory 800. The slots 818 may, for example, be grooves traversing a surface 820 of the accessory engagement portion 810 or may be through holes traversing the accessory engagement portion 810. A wire guide 822 may be inserted into a slot 818 of the single-armed targeting accessory 800 and the wire 816 may be inserted through the wire guide 822. Further, a drill may be positioned over the wire 816 to remove portions of the patient's bone prior to inserting the subtalar screw 806. The wire 816 may also be used for other purposes and may be positioned medial or lateral to the implant 300 as shown, for example, in FIG. 63.

Figure 65A:
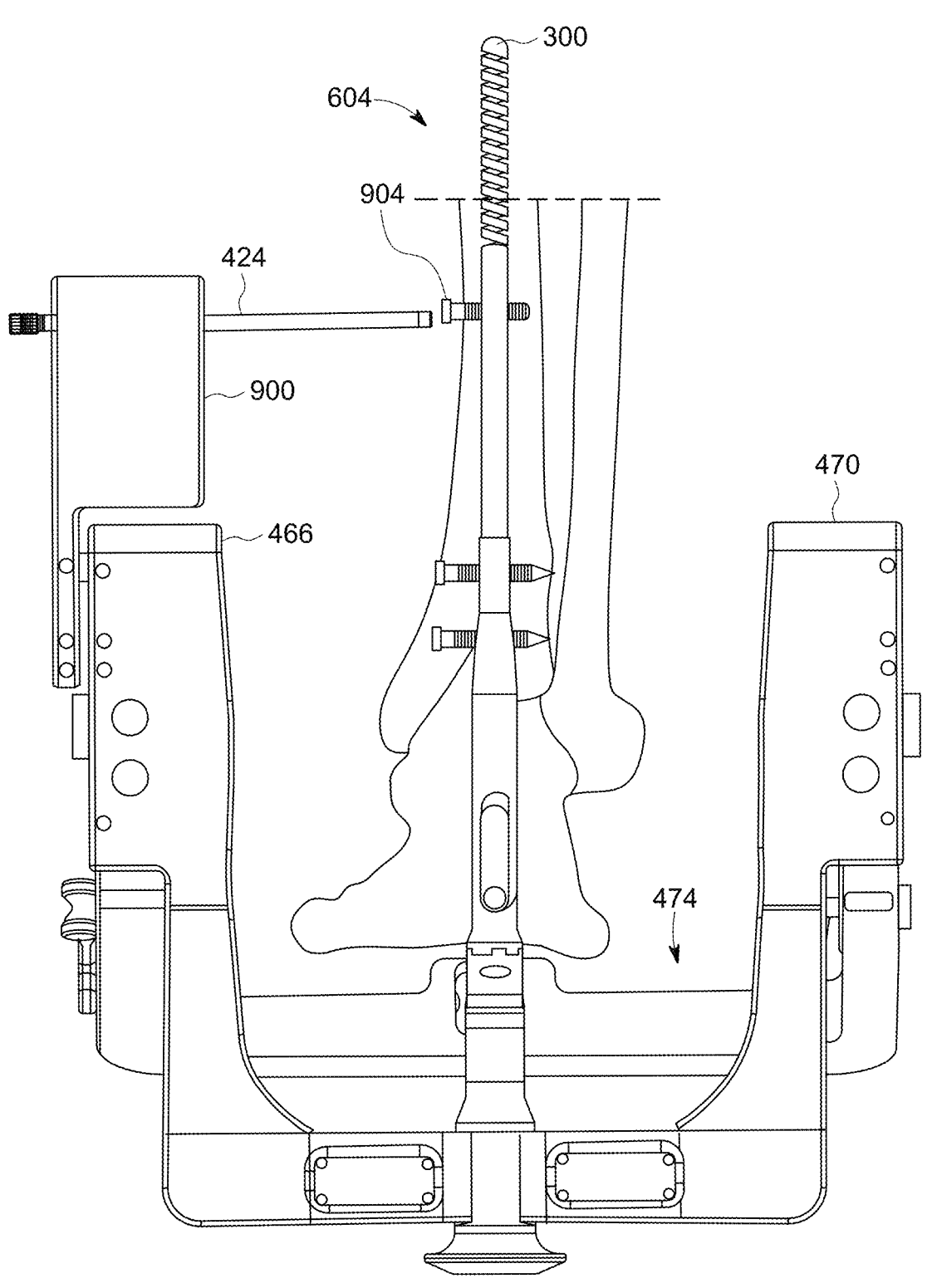
FIG. 65A is a top view of the implant guide system of FIG. 43 that includes an extension accessory, in accordance with an aspect of the present disclosure.
Figure 65B:
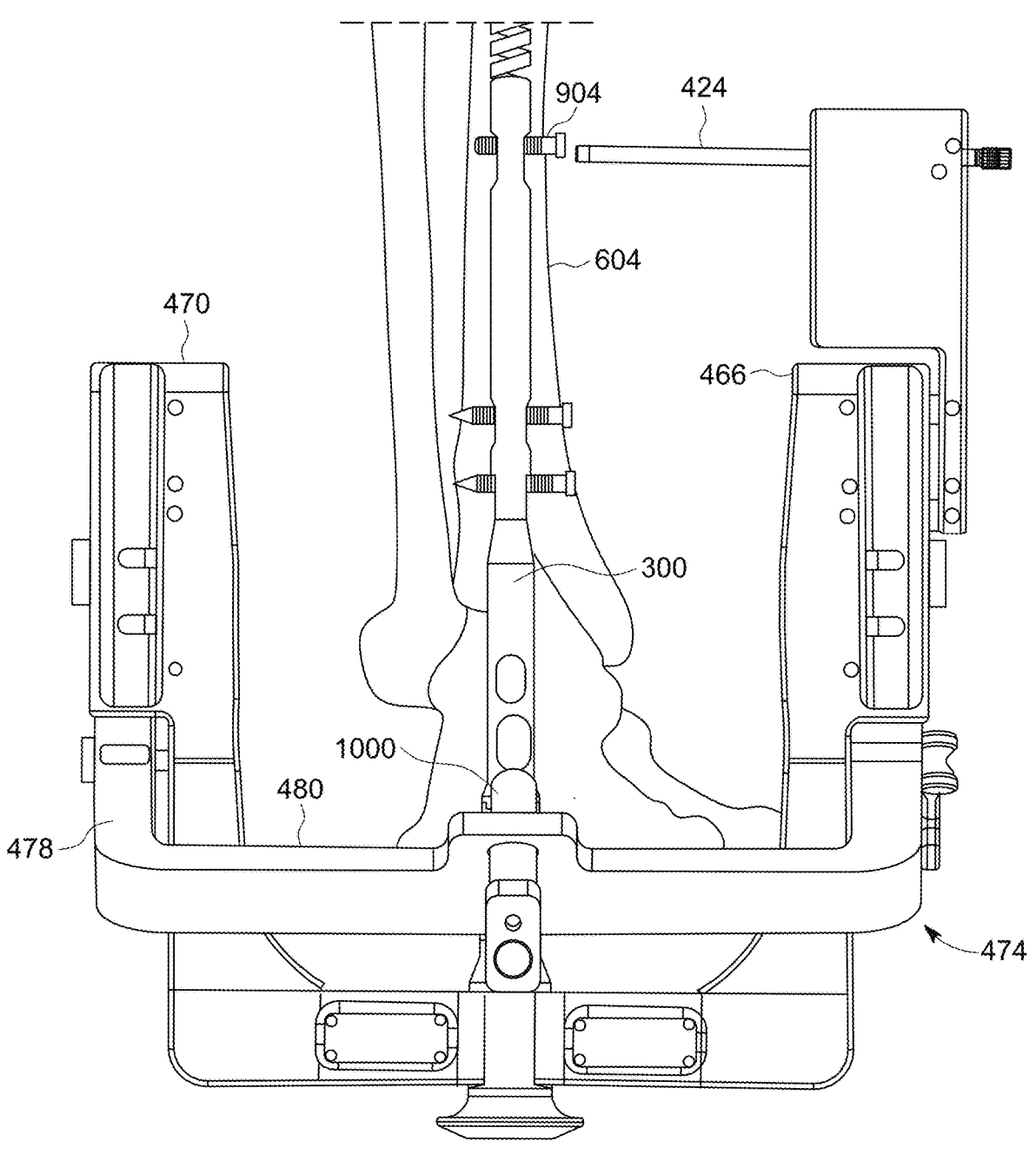
FIG. 65B is a bottom view of the implant guide system of FIG. 43 that includes an extension accessory, in accordance with an aspect of the present disclosure.
Figure 66:
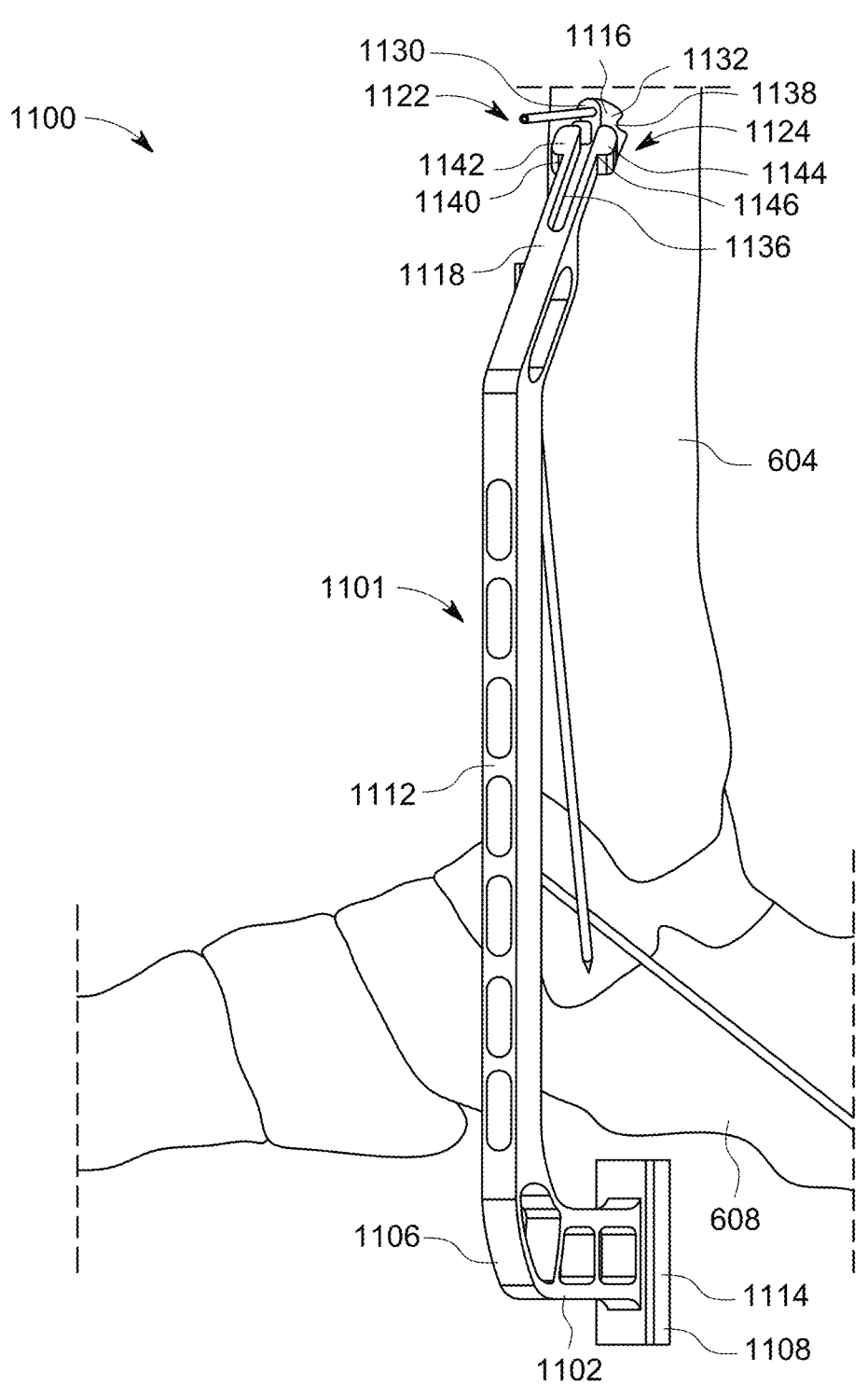
FIG. 66 is a perspective view of a targeting guide assembly of an implant guide system, in accordance with an aspect of the present disclosure.
Figures 67A, 67B:
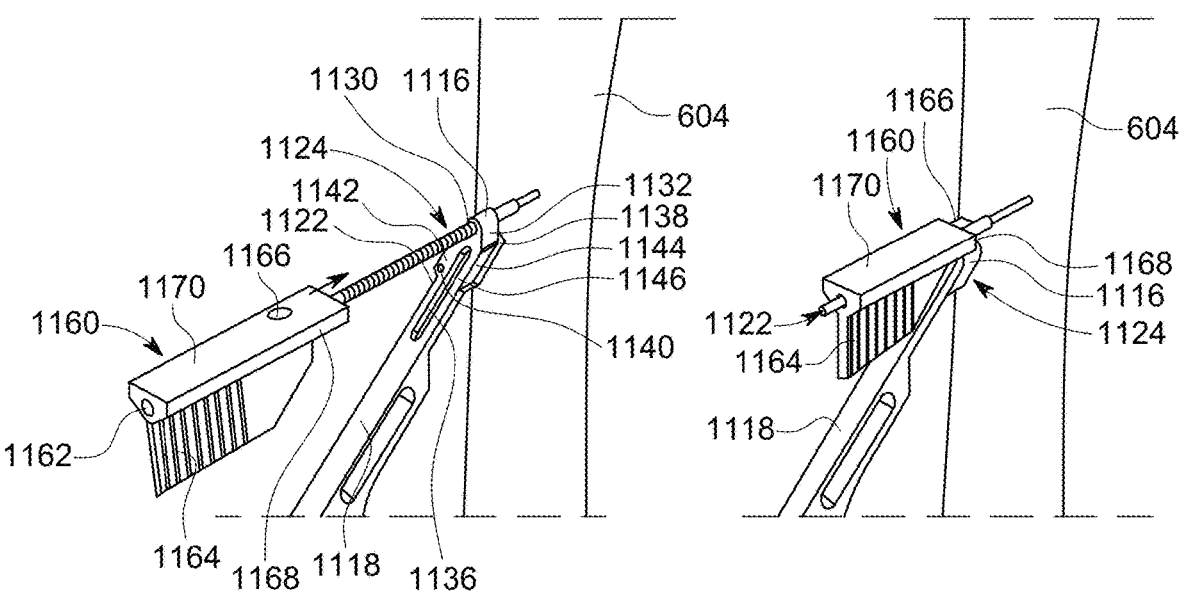
FIG. 67A is a perspective view of an alignment fin in relation to a guide arm of the targeting guide assembly of FIG. 66, in accordance with an aspect of the present disclosure.
FIG. 67B is a perspective view of an alignment fin in relation to a guide arm of the targeting guide assembly of FIG. 66, in accordance with an aspect of the present disclosure.

Referring now to FIGS. 65A-65B, the implant guide device 461 may include, as described in greater detail above and which will not be described again here for brevity sake, an extension accessory 900 configured or sized and shaped to extend at least one of the first arm 466 and the second arm 470 of the implant guide device 461. The extension accessory 900 may facilitate affixing a screw guide 424 for inserting a bone screw 904 into, for example, the patient's tibia 604. The screw guide 424 may retain its positioning in an aperture (not shown) of the extension accessory 900 via, for example, a spring (not shown) inserted within the extension accessory 900.

FIGS. 66-73B, the implant guide system 400 referenced in greater detail above may, according to one embodiment, also include a targeting guide assembly 1100 to facilitate placement of a drill-pin 1180 (see FIG. 69) in the plantar portion of the patient's calcaneus 608. The targeting guide assembly 1100 may be, for example, of the type described in greater detail in U.S. Provisional Application No. 62/805, 777, entitled Threaded Targeting Instruments, Systems and Methods of Use, or may be of the type described in greater detail in U.S. Provisional Application No. 62/464,051, entitled Targeting Instruments, Systems and Methods of Use, which are both hereby incorporated by reference in their entireties. The targeting guide assembly 1100 may include, according to one embodiment, a guide arm 1101, a drill guide tube 1120, a guide pin 1122, an alignment fin 1160, and a drill pin 1180.

As shown in FIGS. 66-70B, the guide arm 1101 includes a body or elongate body 1112 connecting a first end 1114 and a second end 1116. The first end 1114 may, for example, include a first portion 1102 with one or more gaps 1104. A second portion 1106 may include arcuate sides to attach the first portion 1102 to the body 1112, where the first portion 1102 is in a generally perpendicular direction relative to the body 112. The first portion 1102 may also include a coupling portion 1108 with a through hole 1110 that is configured or sized and shaped to receive a drill guide tube 1120. The through hole 1110 may be, for example, larger or smaller than as shown in 66-70B. The through hole 1110 may extend along the first portion 1102 parallel to the body 1112 allowing the drill guide tube 1120 to extend parallel to the body 1112 of the guide arm 1101.

With continued reference to FIGS. 66-73B, the second end 1116 may, for example, include an angled portion 1118. The angled portion 1118 extends in a downward angled direction from the body 1112 to the second end 1116. A housing element 1124 may be positioned at the second end 1116 and may be configured or sized and shaped to receive the guide pin 1122. The housing element 1124 may include a first arm portion 1130 and a second arm portion 1132 separated by a channel 1136. The channel 1136 may extend from an exterior surface of the housing element 1124 into the housing element 1124 and into the angled portion 1118. The housing element 1124 may also include a top opening 1126 and a bottom opening 1128 forming an inner surface or cavity 1134 extending between the top opening 1126 and the bottom opening 1128.

With continued reference to FIGS. 66-73B, the top opening 1126 may be sized to allow for insertion of a spherical member 1156 of the guide pin 1122 into the housing element 1124. The housing element may also include a first protrusion or ear 1140 and a second protrusion or ear 1144, as shown, for example, in FIG. 66. The first protrusion 1140 may extend out from the first arm portion 1130 on a side opposite the channel 1136. The first protrusion 1140 may include a through hole 1142. The through hole 1142 may extend through the first arm 1130, for example, at an angle with respect to an exterior surface of the first protrusion 1140. The second protrusion 1144 may also include a through hole 1146 and the through hole 1146 may extend through the second arm 1132, for example, at an angle with respect to an exterior surface of the second protrusion 1144. The trajectories of the first through hole 1142 and the second through hole 1146 may be positioned, for example, for guide wires inserted into the through holes 1142, 1146 to converge without intersecting. Further, positioned between the first arm portion 1130 and the first protrusion 1140 may be a first groove 1139 configured or sized and shaped to engage a first prong 1166 of the alignment fin 1160, and positioned between the second arm portion 132 and the second protrusion 1144 may be a second groove 1138 configured or sized and shaped to engage a second prong 1168 of the alignment fin 1160. The bottom opening 1128 may be, for example, slightly smaller than the top opening 1126 to capture or retain the guide pin 1122 within the inner cavity 1134 of the housing element 1124. Further, the inner cavity 1134 may intersect with the channel 1136. The inner surface 1134 may be, for example, configured or sized and shaped to allow the guide pin 1122 to pivot, rotate, or move in multiple planes.

With continued reference to FIGS. 66-73B, an alignment fin 1160 may slide over the guide pin 1122 and engage the housing element 1124. Attaching the alignment fin 1160 may, for example, reduce movement of the guide pin 1122 relative to the housing element 1124 and lock the first arm portion 1130 and the second arm portion 1132 to prevent them from splaying open, thereby preventing the guide pin 1122 from disassociating from the guide arm 1101.

With continued reference to FIGS. 66-73B, the guide pin or target pin 1122 may include a shaft 1154, a spherical member 1156, a first end 1148, a second end 1150 opposite the first end 1148, and a cylindrical protrusion 1158. The spherical member or sphere 1156 may be positioned between the first end 1148 and the second end 1150. The guide pin 1122 may, for example, have a smooth outer surface with a tip, point, or sharpened portion 1152 at the first end 1148. The first end 1148 may be threaded; however, it is also contemplated that the first end 1148 may also have a smooth outer surface to facilitate insertion. The tip 1152 may be configured or sized and shaped to allow for the user to insert the guide pin 1122 into a target bone either directly or through the skin. The sphere 1156 may be sized and shaped or configured to be inserted into the housing element 1124, and the sphere 1156 may allow for a full range of pivoting motions, which may, for example, then be fixed into position via the alignment fin 1160. The cylindrical protrusion 1158 may be positioned adjacent to the sphere 1156, and more specifically between the sphere 1156 and the first end 1148. As shown in 66-67B, the guide pin 1122 may be, for example, positioned from a proximal to distal direction through the inner cavity 1134 of the housing element 1124. Once inserted into the target bone, the guide pin 1122 may be secured to establish the target location on the plantar portion of the patient's calcaneus 608.

Figure 68:
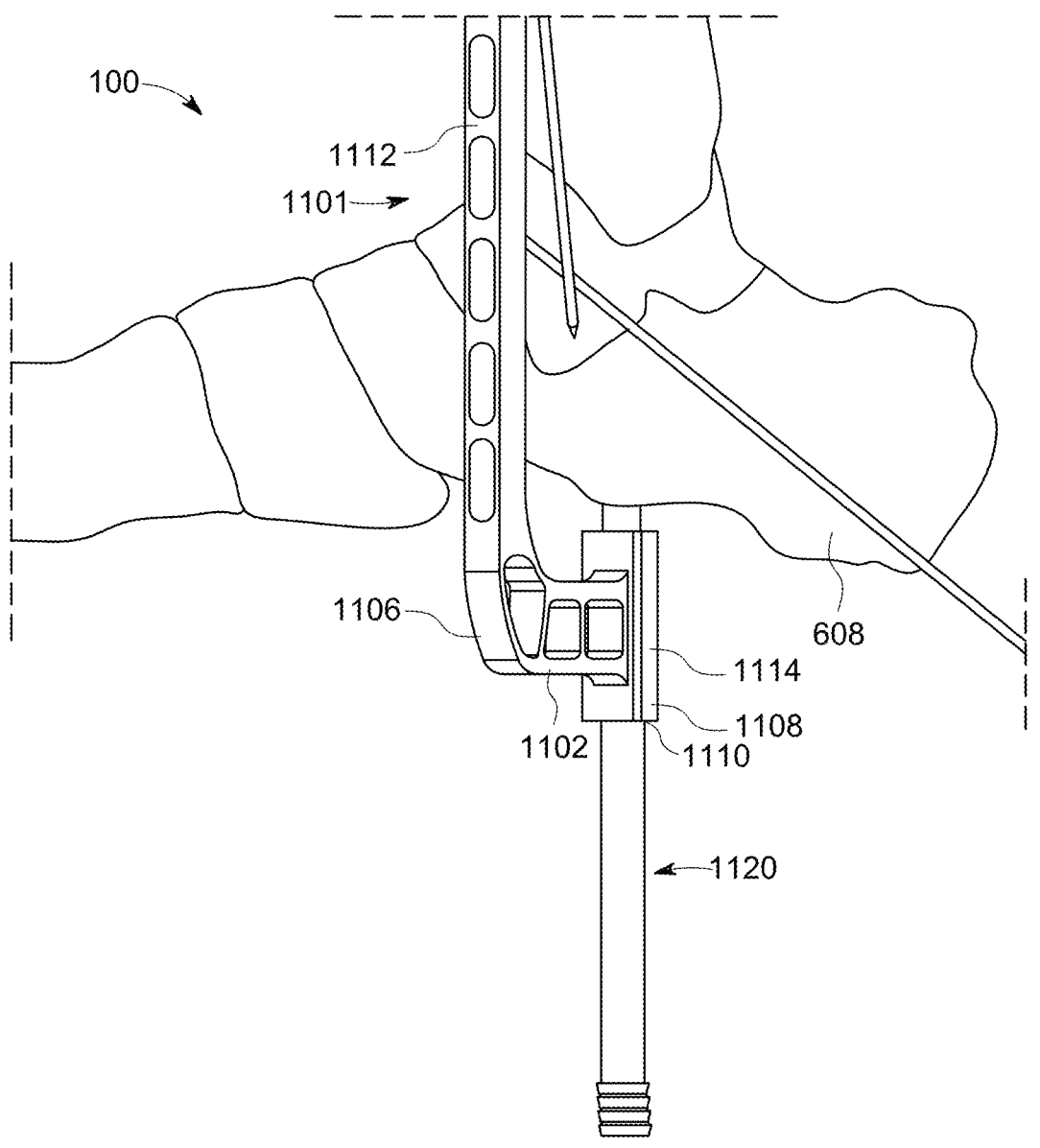
FIG. 68 is a perspective view of a guide arm and drill guide tube of the targeting guide assembly of FIG. 66, in accordance with an aspect of the present disclosure.
Figure 69:
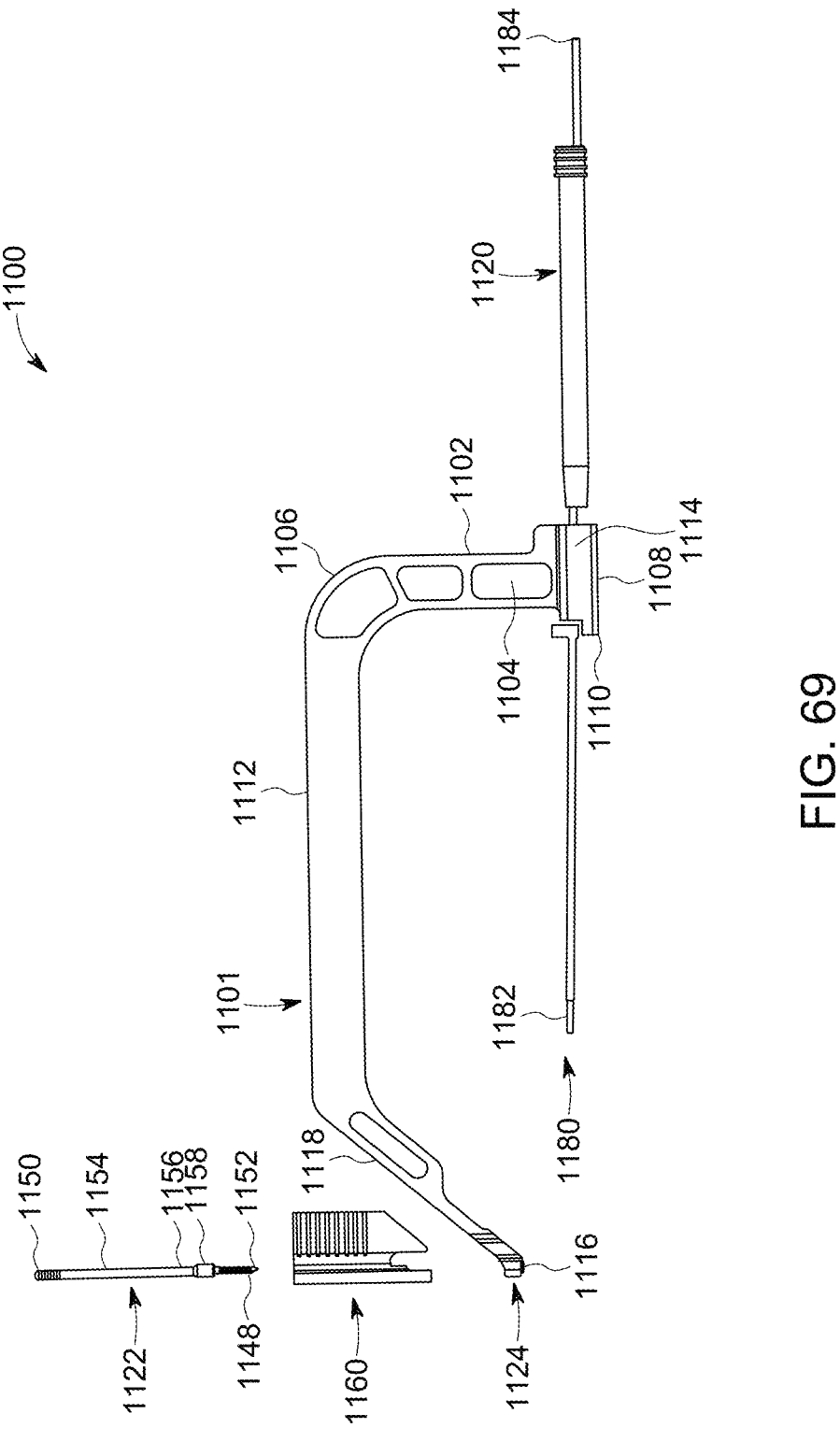
FIG. 69 is a lateral view of a targeting guide assembly of FIG. 66, in accordance with an aspect of the present disclosure.
Figure 70A:
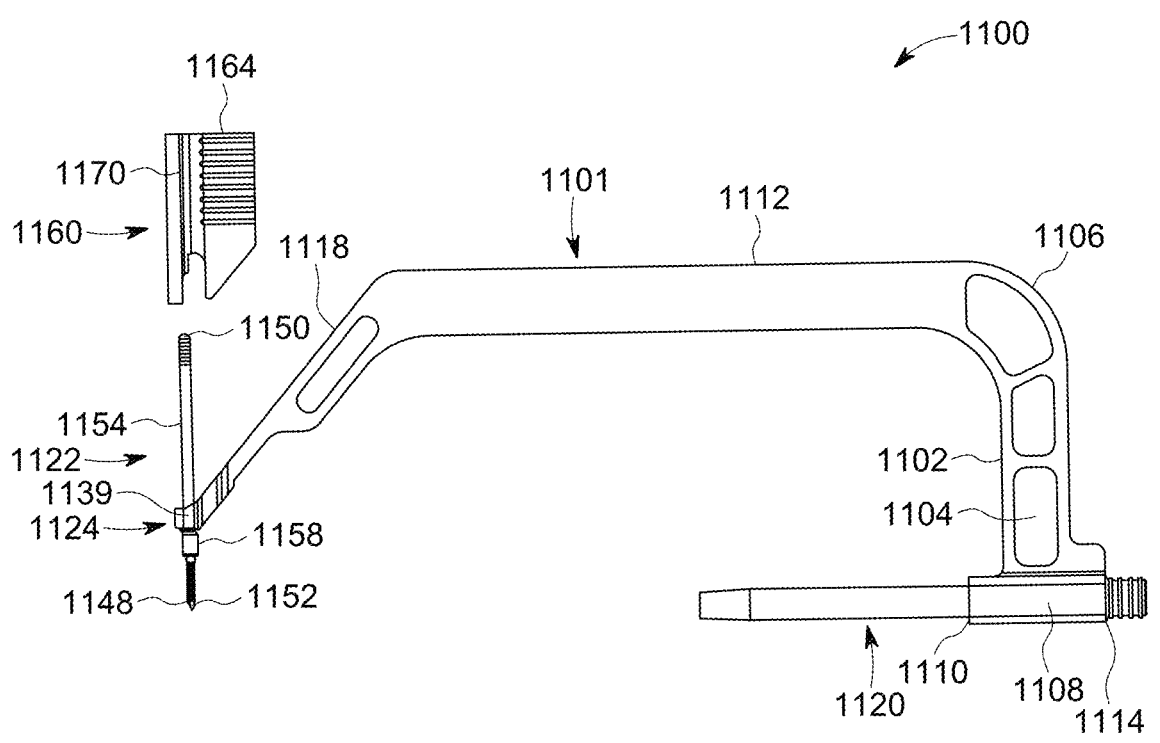
FIG. 70A is a lateral view of a targeting guide assembly of FIG. 66, in accordance with an aspect of the present disclosure.
Figure 70B:
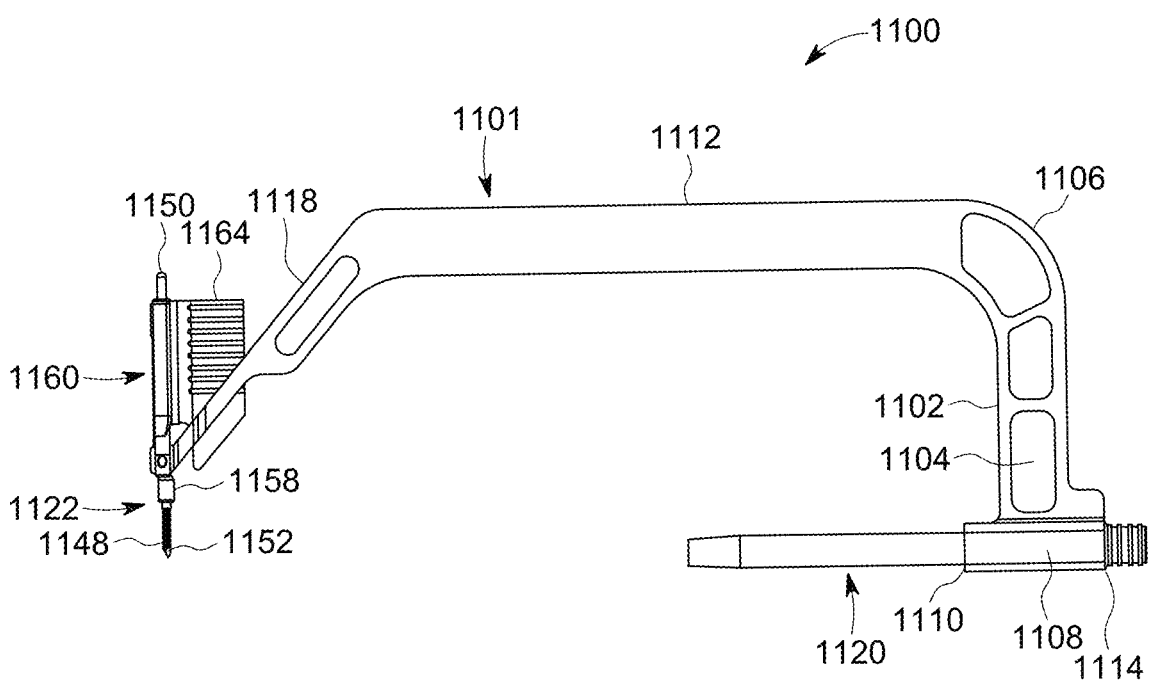
FIG. 70B is a lateral view of a targeting guide assembly of FIG. 66, in accordance with an aspect of the present disclosure.
Figure 71A:
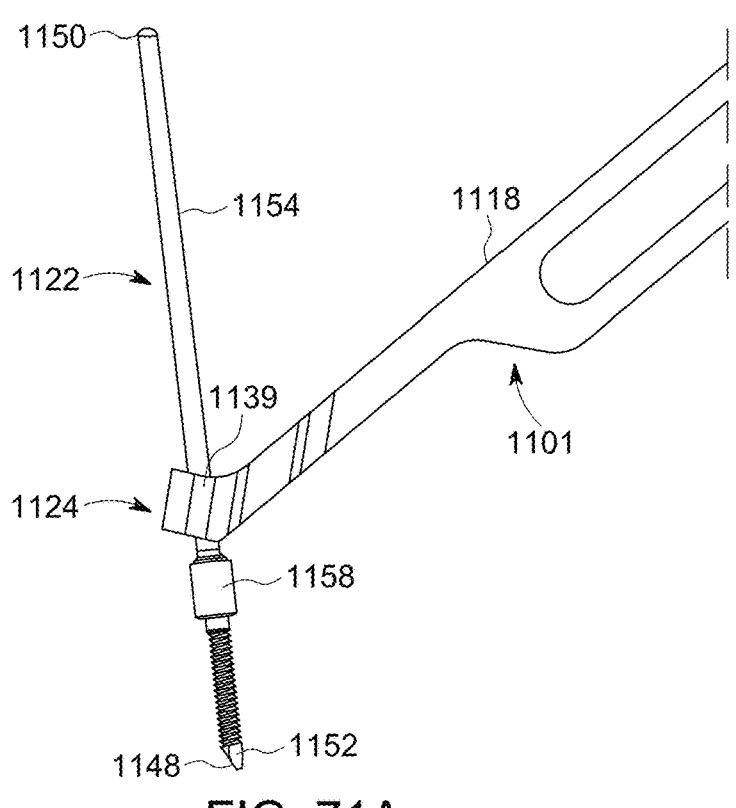
FIG. 71A is a perspective view of a guide pin in relation to a guide arm of the targeting guide assembly of FIG. 66, in accordance with an aspect of the present disclosure.
Figure 71B:
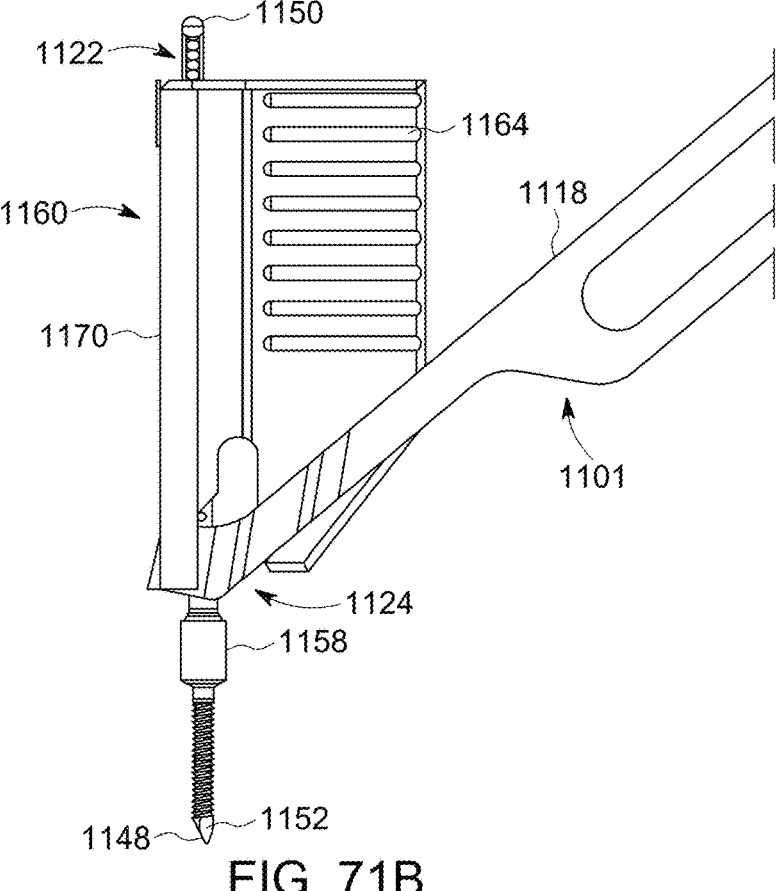
FIG. 71B is a perspective view of a guide pin in relation to a guide arm of the targeting guide assembly of FIG. 66, in accordance with an aspect of the present disclosure.

As shown in FIG. 69, the drill guide tube 1120 and drill pin 1180 may then be inserted through the through hole 1110 of the coupling portion 1108 in order to further establish the target location on the plantar portion of the patient's calcaneus (see FIG. 68). The drill pin 1180 may, for example, include a first end or tip 1182, for insertion into a patient, and a second end 1184 opposite the first end 1182. The drill pin 1180 may be, for example, a guide wire, k-wire, pin or the like elongated pin like structure or member for insertion into the patient's bone. In the depicted embodiment, the drill pin 1180 has a smooth outer surface with a point or sharped tip 1182. The drill pin 1180 may be inserted from a distal to proximal direction through the cannulated opening of the drill guide tube 1120, which may allow for the establishment of a target location at the surgical site.

Figure 72:
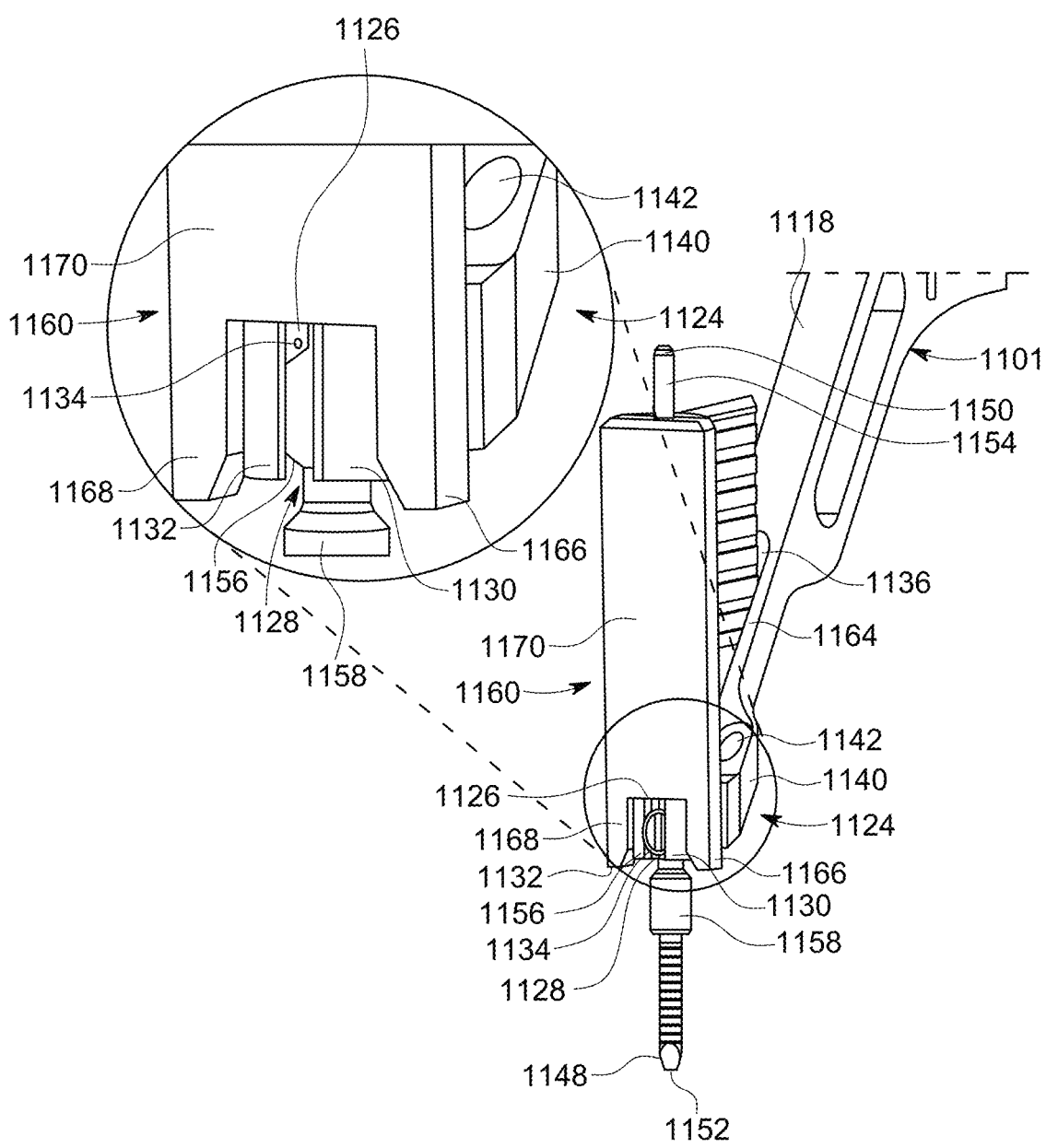
FIG. 72 is a magnified and perspective view of a guide pin in relation to a guide arm of the targeting guide assembly of FIG. 66, in accordance with an aspect of the present disclosure.
Figure 73A:
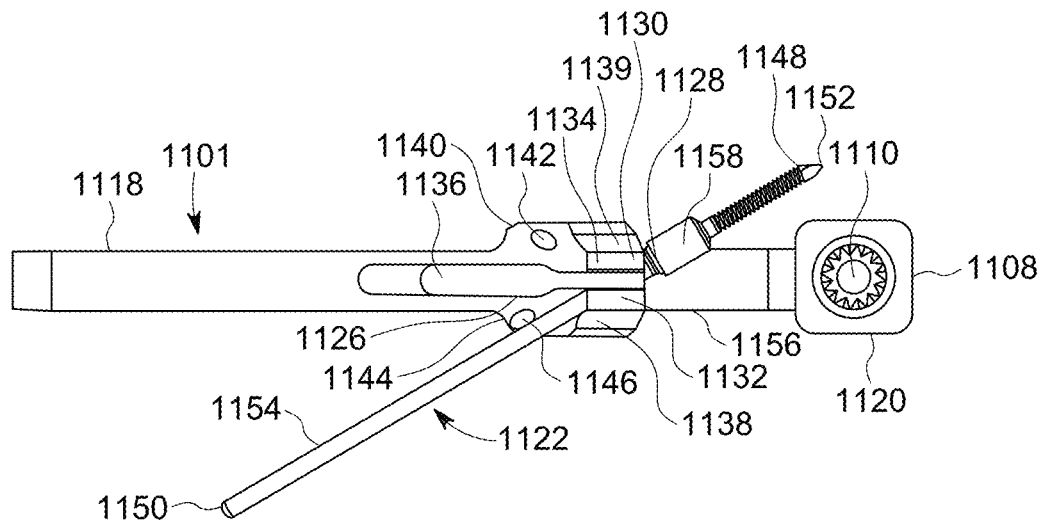
FIG. 73A is a top view of the guide pin and guide arm of the targeting guide assembly of FIG. 66, in accordance with an aspect of the present disclosure.
Figure 73B:
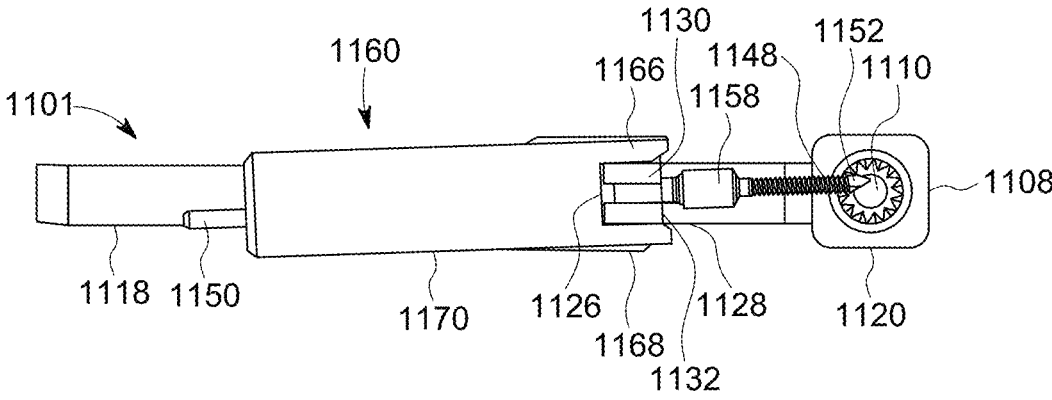
FIG. 73B is a top view of the guide pin, alignment fin, and guide arm of the targeting guide assembly of FIG. 66, in accordance with an aspect of the present disclosure.

As shown in FIGS. 67A, 67B, and 70A-73B, once the guide pin 1122 is inserted into the patient's bone such as, for instance, the patient's tibia 604, the alignment fin 1160 may be inserted over the guide pin 1122 such that the through hole 1162 in the alignment fin 1160 receives the guide pin 1122. Further, the fin body 1164 may be inserted into the channel 1136 of the housing element 1124, and the first prong 1166 and the second prong 1168 of the pin engagement portion 1170 of the alignment fin 1160 may fasten around the outside surface of the first arm 1130 and the second arm 1132 of the housing element 1124 of the guide arm 1101 as shown in FIG. 72. Securing the first prong 1166 and the second prong 1168 of the alignment fin 1160 around the first arm 1130 and the second arm 1132 of the housing element 1124 may, for example, lock the guide pin 1122 into position so that the sphere 1156 may no longer rotate within the inner cavity 1134 of the housing element 1124, as shown in FIGS. 73A and 73B.

Referring now to FIGS. 74A-74H, the alignment fin 1160 may include a pin engagement portion 1170 and a fin body 1164. The pin engagement portion 1170 may, according to one embodiment, include a pentagonal shape having a relatively planar first surface 1172. The pin engagement portion 1170 may, for example, include a second surface 1191 and third surface 1192 that are relatively perpendicular to the first surface 1172. Further, the pin engagement portion 1170 may include a first slanted surface 1193 and a second slanted surface 1194, where the first slanted surface 1193 and the second slanted surface 1194 may converge at the fin body 1164. Positioned between a first face 1200 of the fin body 1164 and the first slanted surface 1193 is a channel 1196 and positioned between the second face 1202 of the fin body 1164 and the second slanted surface 1194 is also a channel 1195.

Figure 74A:
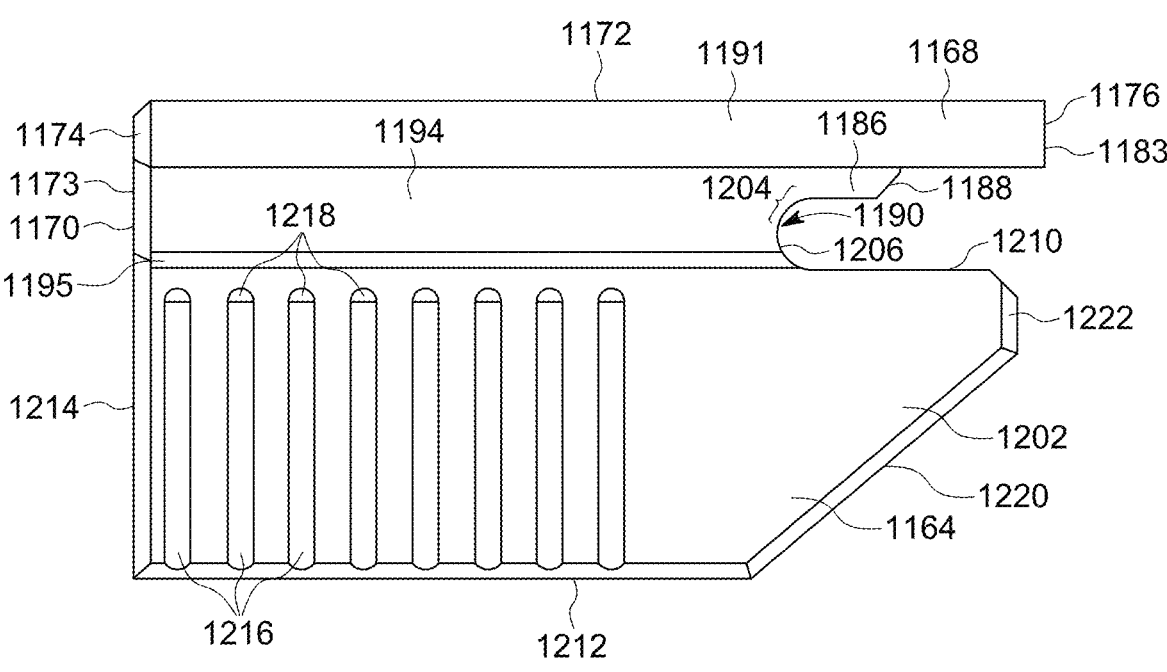
FIG. 74A is a first side view of the alignment fin of the targeting guide assembly of FIG. 66, in accordance with an aspect of the present disclosure.
Figure 74B:
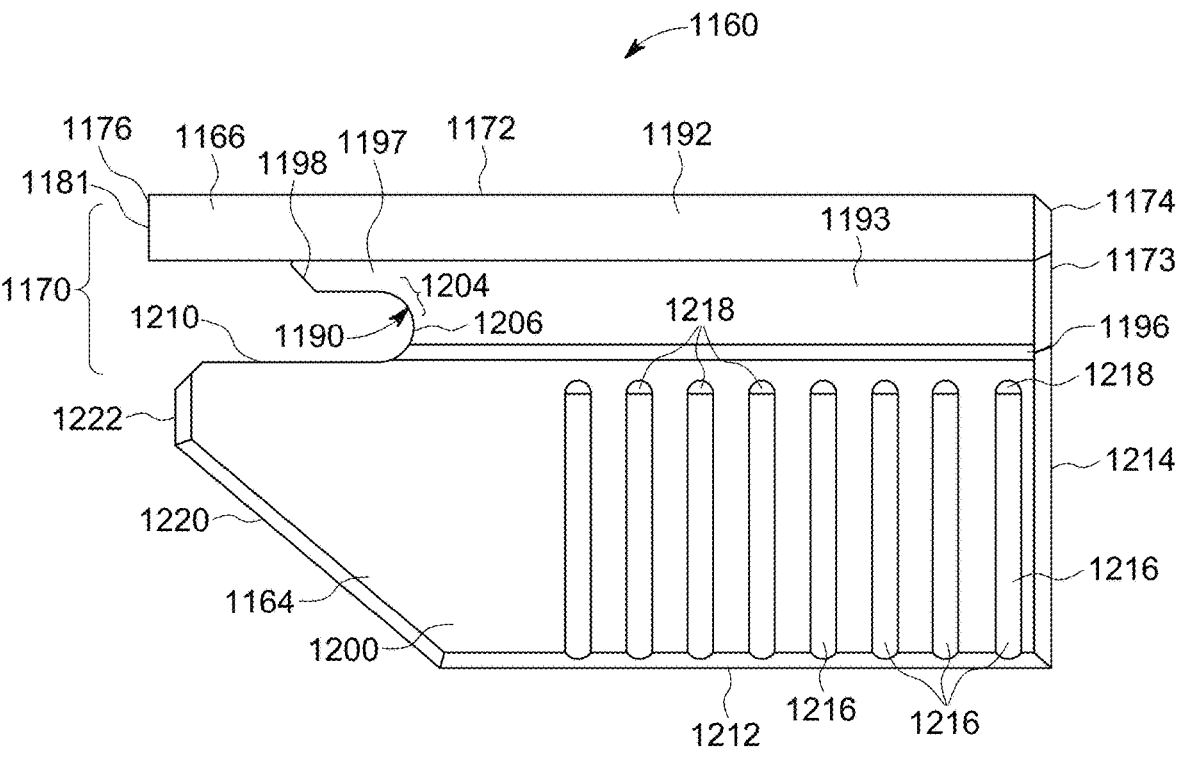
FIG. 74B is a second side view of the alignment fin of the targeting guide assembly of FIG. 66, in accordance with an aspect of the present disclosure.
Figure 74C:
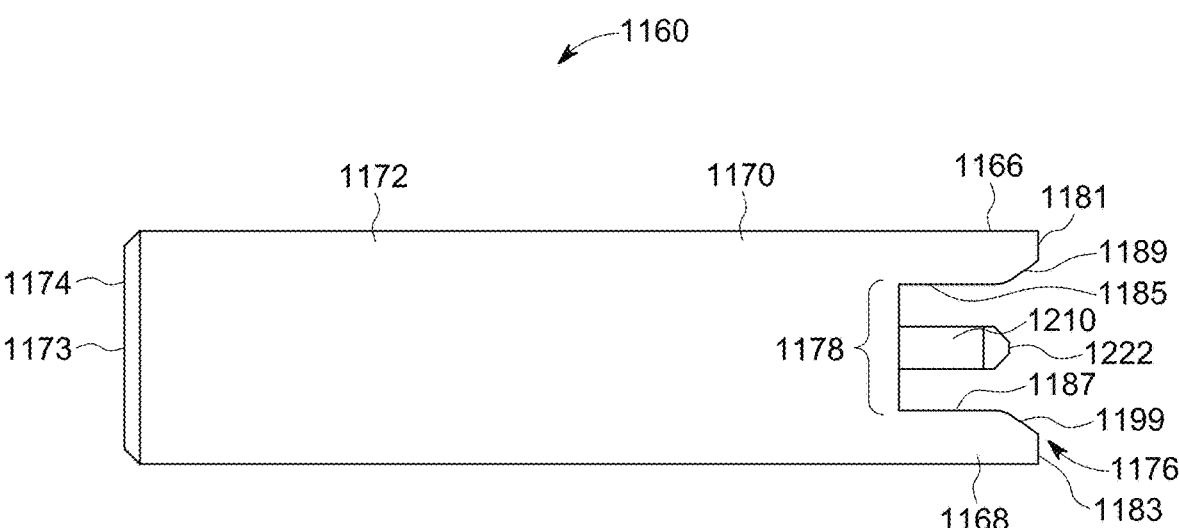
FIG. 74C is a top view of the alignment fin of the targeting guide assembly of FIG. 66, in accordance with an aspect of the present disclosure.
Figure 74D:
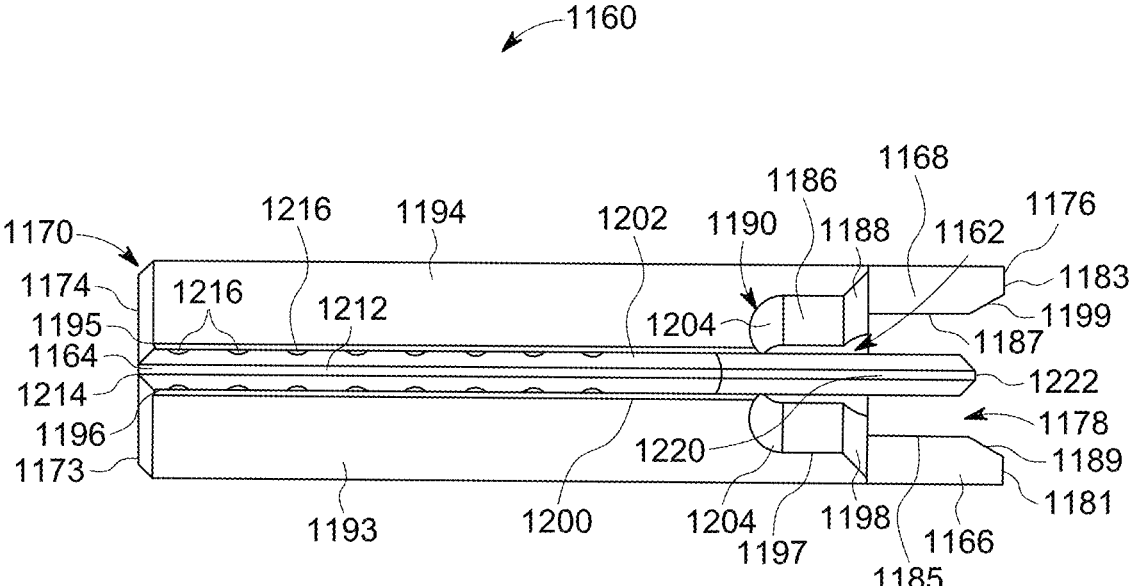
FIG. 74D is a bottom view of the alignment fin of the targeting guide assembly of FIG. 66, in accordance with an aspect of the present disclosure.
Figure 74E:
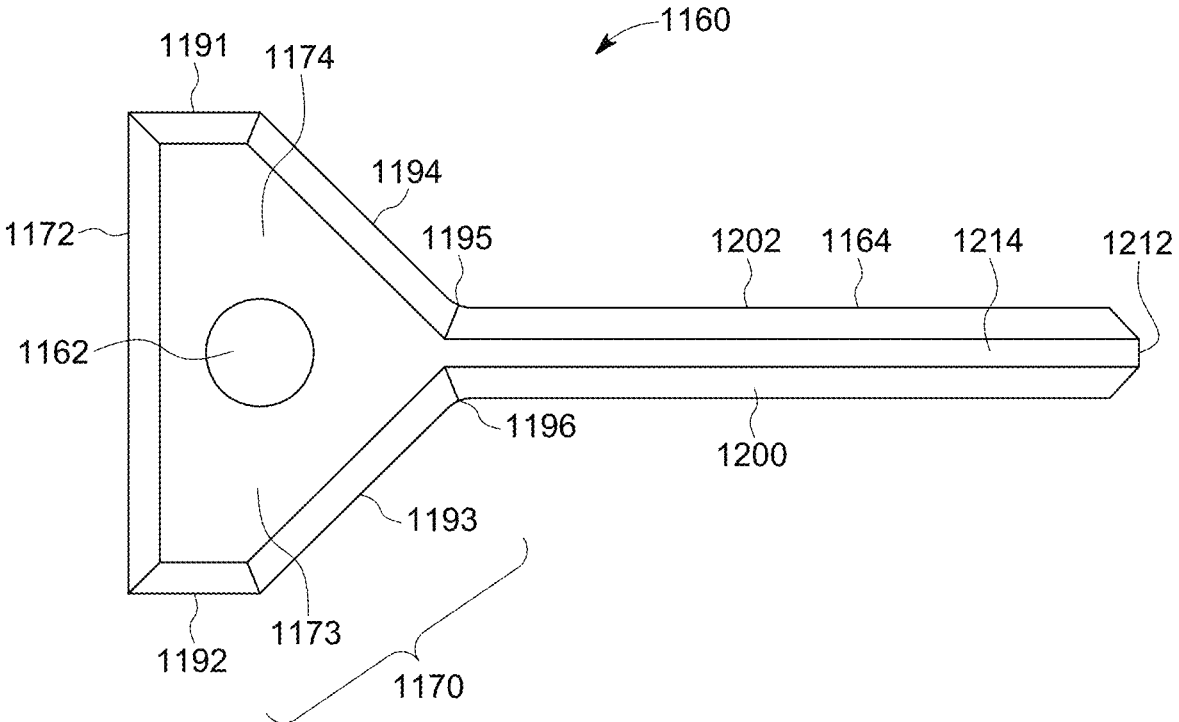
FIG. 74E is a first end view of the alignment fin of the targeting guide assembly of FIG. 66, in accordance with an aspect of the present disclosure.
Figure 74F:
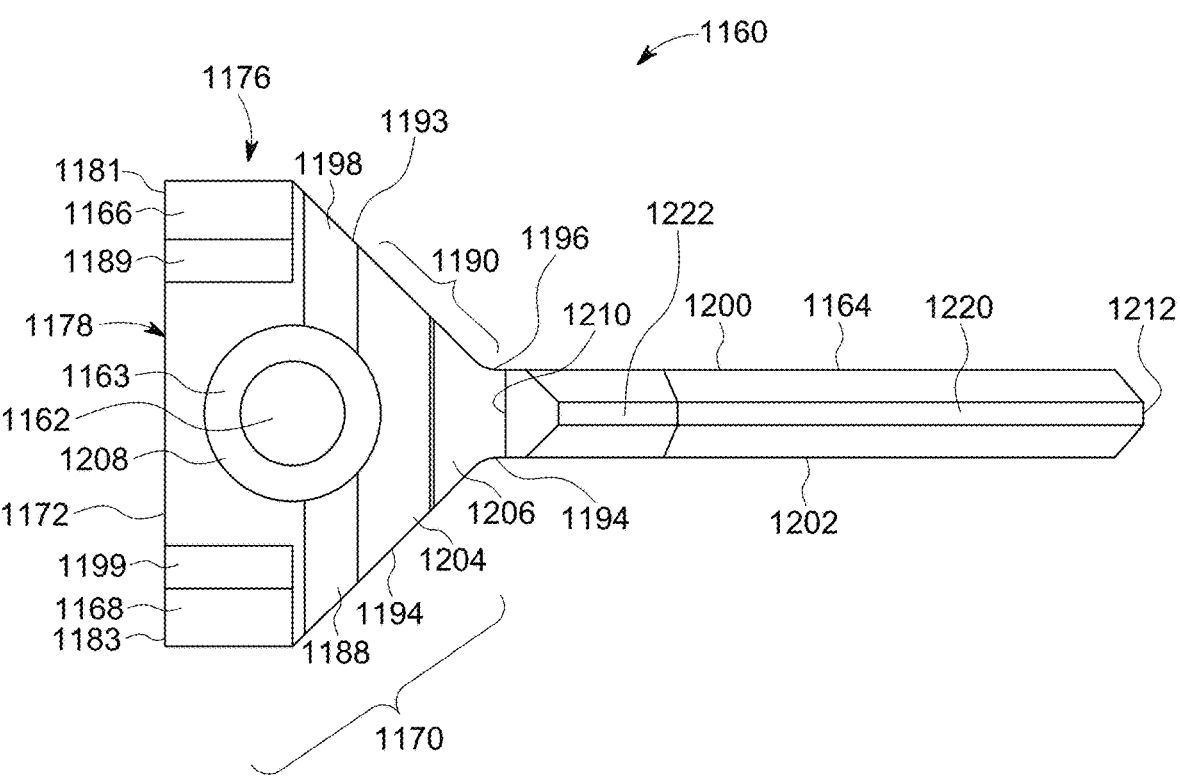
FIG. 74F is a second end view of the alignment fin of the targeting guide assembly of FIG. 66, in accordance with an aspect of the present disclosure.
Figure 74G:
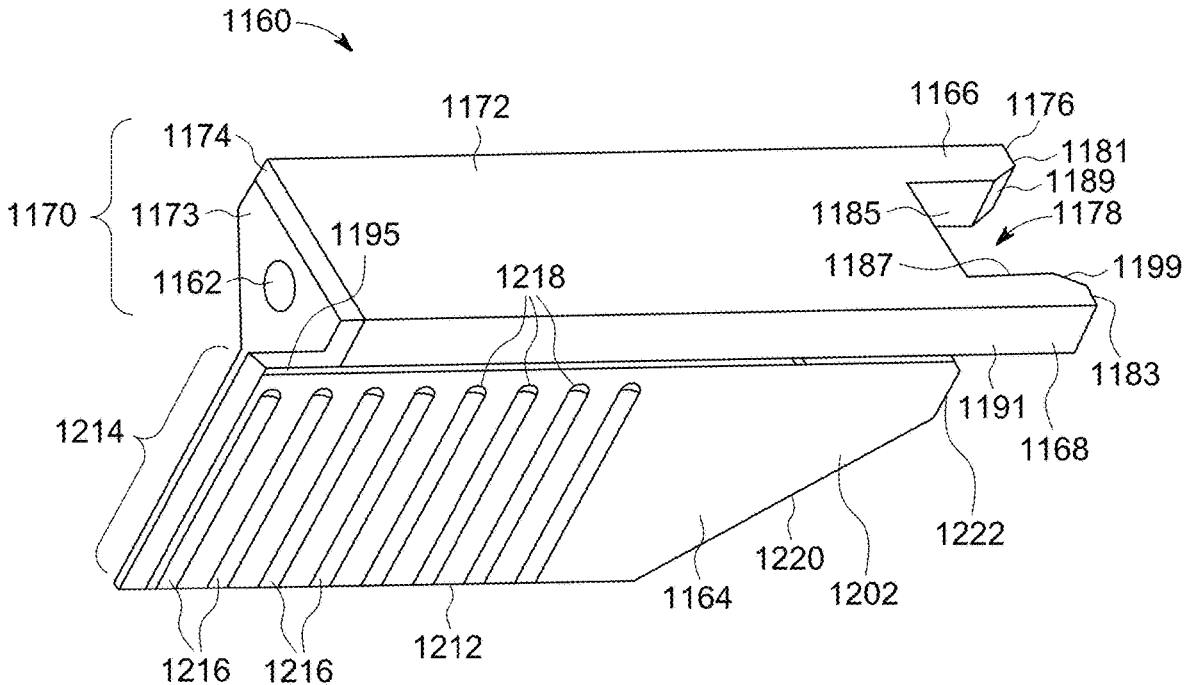
FIG. 74G is a top perspective view of the alignment fin of the targeting guide assembly of FIG. 66, in accordance with an aspect of the present disclosure.
Figure 74H:
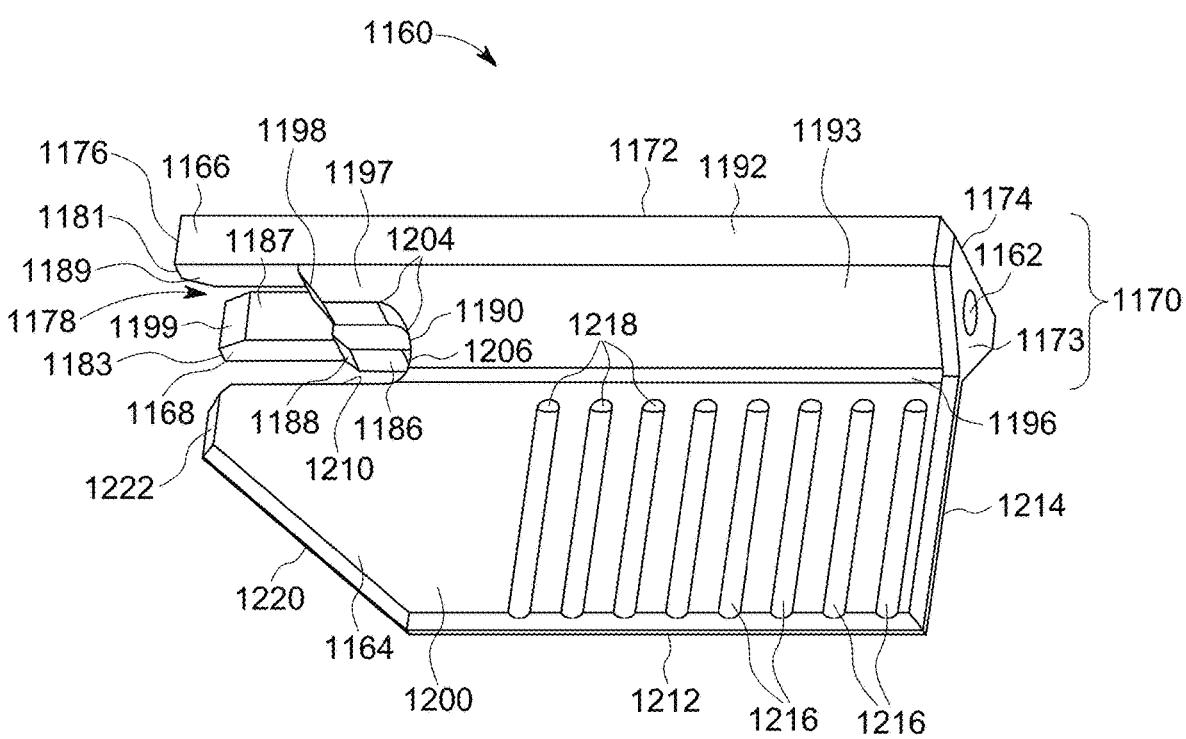
FIG. 74H, is a bottom perspective view of the alignment fin of the targeting guide assembly of FIG. 66, in accordance with an aspect of the present disclosure.

Continuing with FIGS. 74A-74H, the pin engagement portion 1170 may include a first end 1174 having a head 1173 with a through hole 1162 extending from the first end 1174 of the alignment fin 1160 to a second end 1176. Towards the second end 1176 of the pin engagement portion 1170, the through hole 1162 may include a rim 1163 surrounding the through hole 1162. The pin engagement portion 1170 may also include a conduit 1178 positioned between the first prong 1166 and the second prong 1168, where the conduit is configured or sized and shaped to engage the housing element 1124 of the guide arm 1101. The first prong 1166 may include a slanted edge 1189 extending from a first wall 1185 of the conduit 1178 to an end 1181 of the first prong 1166, as shown in FIGS. 74C-74D. Further, the second prong 1168 may also include a slanted edge 1199 extending from a second wall 1187 of the conduit 1178 to an end 1183 of the second prong 1168, as shown in FIGS. 74C-74D.

Continuing with FIGS. 74A-74H, and specifically as shown in FIGS. 74A-74B, the first slanted surface 1193 may include a ledge 1197 having a longitudinally slanted surface 1198 extending from the first prong 1166 to a concavity 1190 toward the second end 1176 of the first slanted surface 1193 of the alignment fin 1160. The second slanted surface 1194 may also include a ledge 1186 having a longitudinally slanted surface 1188 extending from the second prong 1168 to the concavity 1190 (see FIG. 74D). The concavity 1190 may include a first arcuate surface 1204 adjoining ledge 1197 and ledge 1186, where the first arcuate surface 1204 converges with a second arcuate surface 1206 that adjoins an inner surface 1210 of the fin body 1164.

Continuing with FIGS. 74A-74H, the fin body 1164 may include a first face 1200 extending longitudinally from the first end 1174 of the alignment fin 1160 to the second end 1176 and a second face 1202 opposite the first face 1200, the second face 1202 also extending longitudinally from the first end 1174 to the second end 1176. The alignment fin 1160 may also include a spine 1212 extending longitudinally from the first end 1174 to the second end 1176 connecting the first face 1200 to the second face 1202. The head 1173 of the pin engagement portion 1170 may adjoin a ridge 1214 extending from the planar first surface 1172 to the spine 1212 of the fin body 1164, and the spine 1212 may be perpendicular to the ridge 1214. Along the first face 1200 and the second face 1202 may be one or more furrows or depressions 1216 extending crosswise across the surface of the first face 1200 and the second face and parallel to the ridge 1214. Each of the furrows 1216 may extend from the spine 1212 to an inner lip 1218. The fin body 1164 may include a slanted portion 1220 extending longitudinally from the spine 1212 to a projection 1222, the projection 1222 adjoining the inner surface 1210 of the fin body. The projection 1222 may be configured or sized and shaped to engage the channel 1136 of the housing element 1124 of the guide arm 1101.

Figure 83:
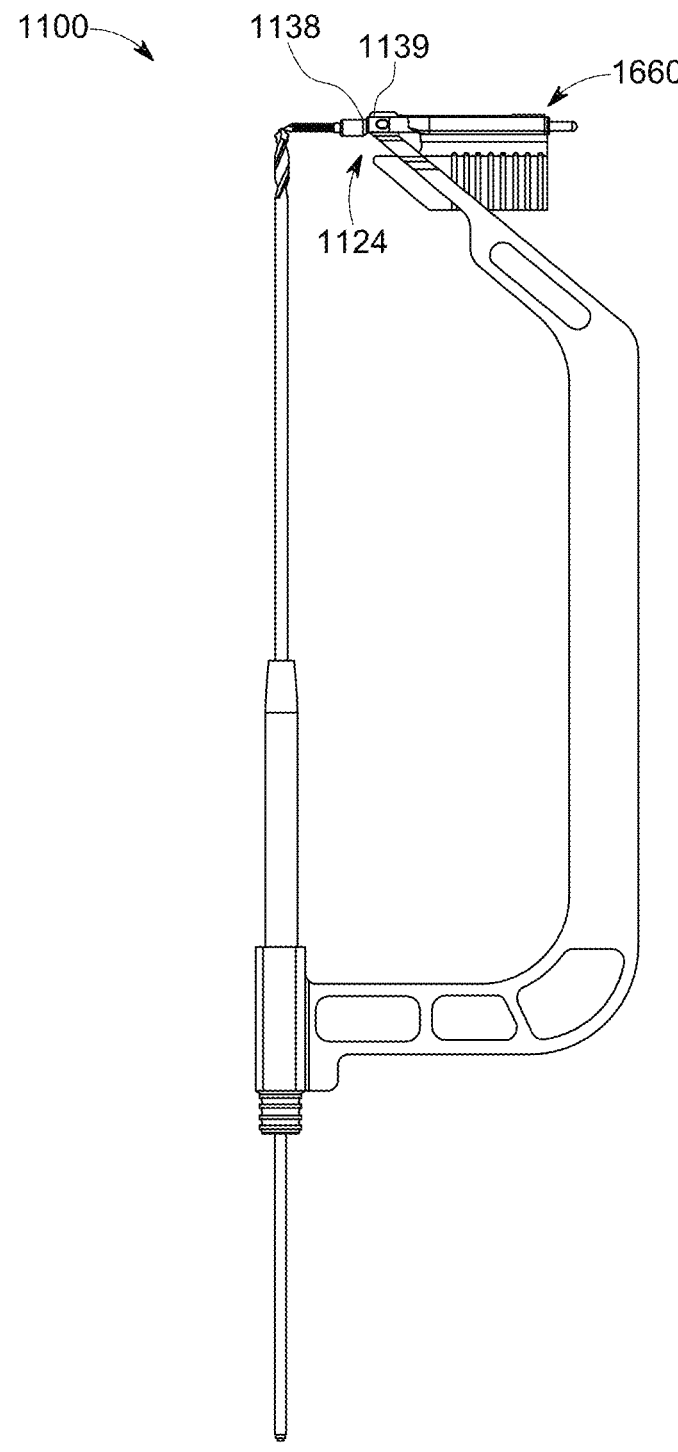
FIG. 83 is a side view of an alternate embodiment of a targeting guide assembly of an implant guide system, in accordance with aspects of the present disclosure.
Figure 84:
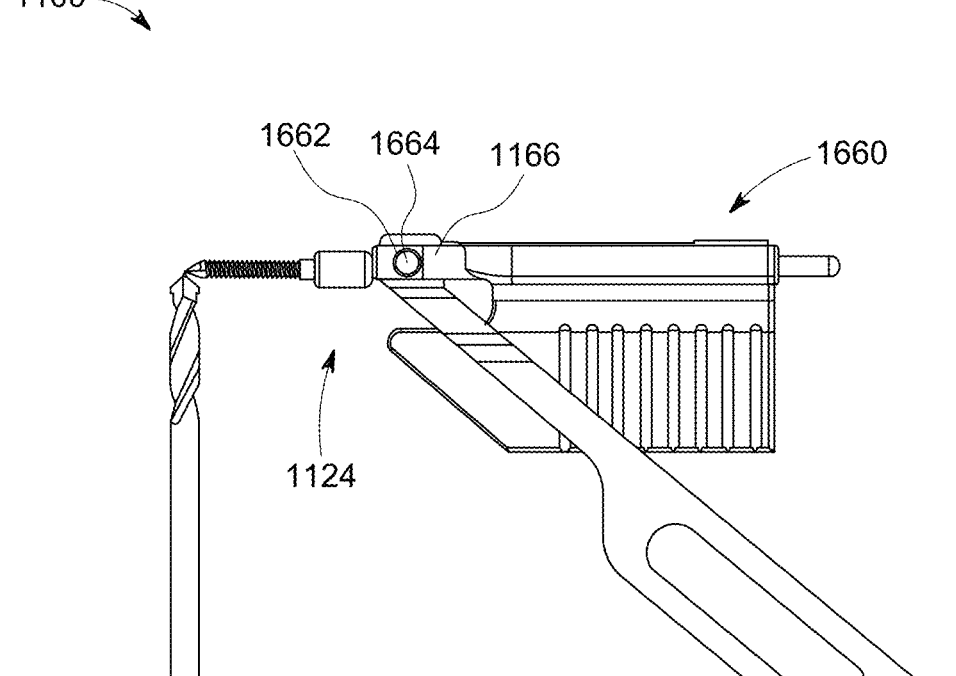
FIG. 84 is a side enlarged view of an alternate embodiment of an alignment fin of the targeting guide assembly of FIG. 83, in accordance with aspects of the present disclosure.

Referring now to FIGS. 83-84, an alternate embodiment of the targeting guide assembly 1100 and components thereof are shown. The targeting guide assembly 1100 as shown in FIGS. 83-84 may include one or more components that are the same as and/or similar to those shown in FIGS. 66 and 68-70B. The targeting guide assembly 1100 of FIGS. 83-84 is shown to include an alignment fin 1660 that is configured to be received by the housing element 1124 in a manner that is the same as or similar to the alignment fin 1160. For example, the alignment fin 1660 is shown to include a first and second prong the same as or similar to the first prong 1166 and the second prong 1168 of the alignment fin 1160, with said first and second prongs configured to engage the first groove 1139 and the second groove 1138 of the housing element 1124. The alignment fin 1660 is shown to include an aperture (e.g., a bore, depression, etc.) 1662 arranged on the first prong 1166, where the aperture 1662 extends laterally through the first prong 1166 thus providing fluid communication therethrough. In some aspects, the aperture 1662 may be configured to accommodate a protrusion 1664 arranged on the housing element 1124 and disposed within the first groove 1139. In some aspects, the aperture 1662 and the protrusion 1664 may collectively form a retention mechanism (e.g., the alignment fin 1660 is retained by, releasably coupled with the housing element 1124). For example, when the alignment fin 1660 engages with the housing element 1124 (e.g., the first prong 1166 and second prong 1168 engage the first groove 1139 and the second groove 1138), the aperture 1662 may receive the protrusion 1664 so as to facilitate retention and/or allow to be releasably coupled from the alignment fin 1660 with the housing element 1124. In some aspects, the aperture 1662 may be arranged on the second prong 1168 with the protrusion arranged within the second groove 1138. Further, in some aspects the housing element 1124 may include multiple protrusions (e.g., a protrusion disposed within both the first groove 1139 and the second groove 1138) with the alignment fin 1660 including multiple apertures (e.g., an aperture disposed on both the first prog 1166 and the second prong 1168). In some aspects, the one or more protrusions 1664 may have a substantially hemispherical geometry with the one or more apertures 1662 having a complimentary cylindrical geometry (e.g., forming a ball detent). In some aspects, the one or more protrusions 1664 may have other geometries for example square, rectangular, hemi-elliptic, etc. with the one or more apertures 1662 having a corresponding geometry. Further, in some aspects the one or more apertures 1662 may have a complimentary geometry to the one or more protrusions 1664. For example, if the one or more protrusions 1664 are hemispherical, the one or more apertures 1662 may be similarly hemispherical and may not extend through the first prong 1166 (and/or the second prong 1668). Further, it should be noted that the alignment fin 1160 and/or the alignment fin 1660 may include a combination of the features shown and described herein (e.g., one or more apertures 1662, one or more protrusions 1664, etc.).

Figure 76:
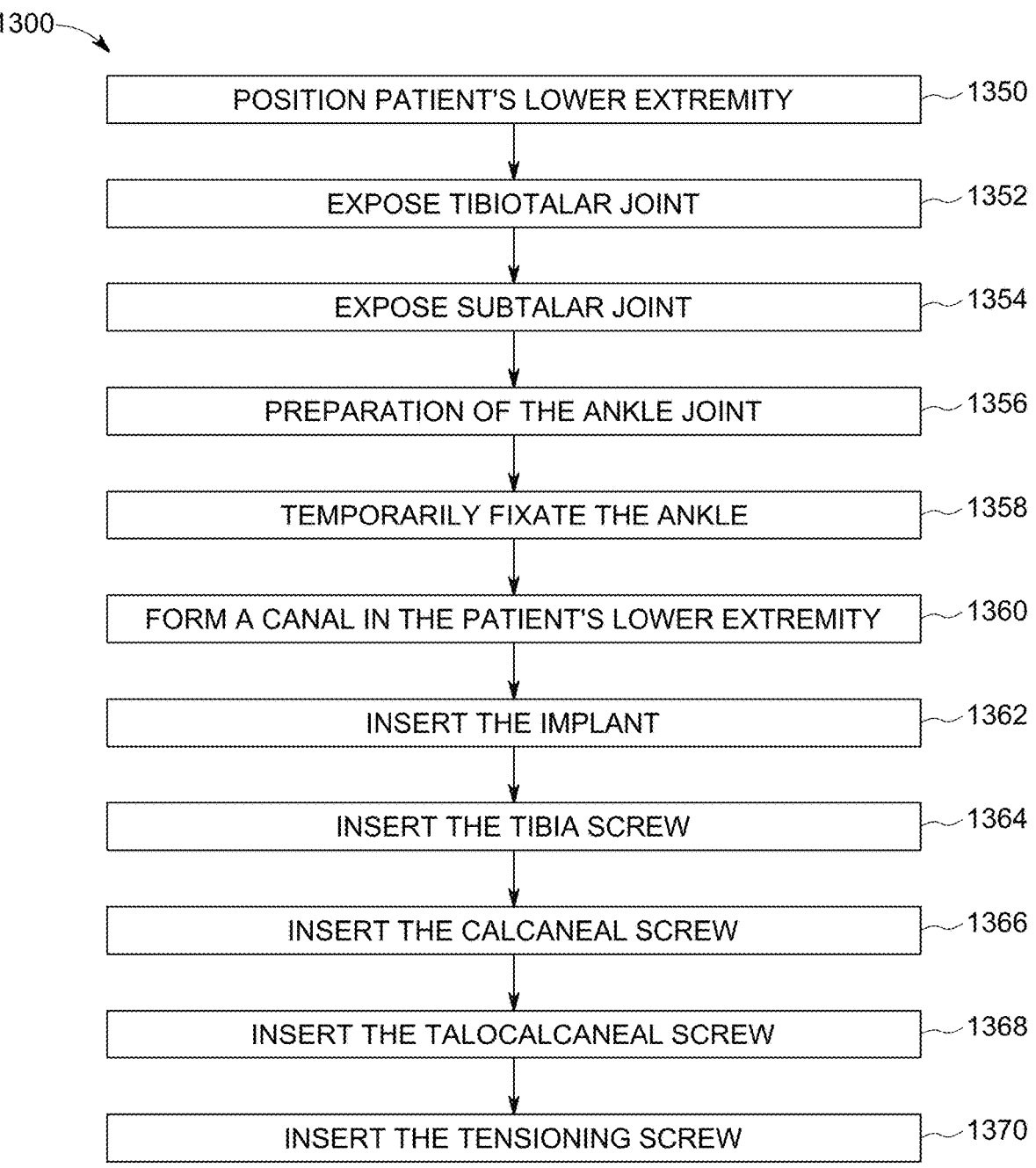
FIG. 76 depicts a second surgical method, in accordance with aspects of the present disclosure.
Figure 78:
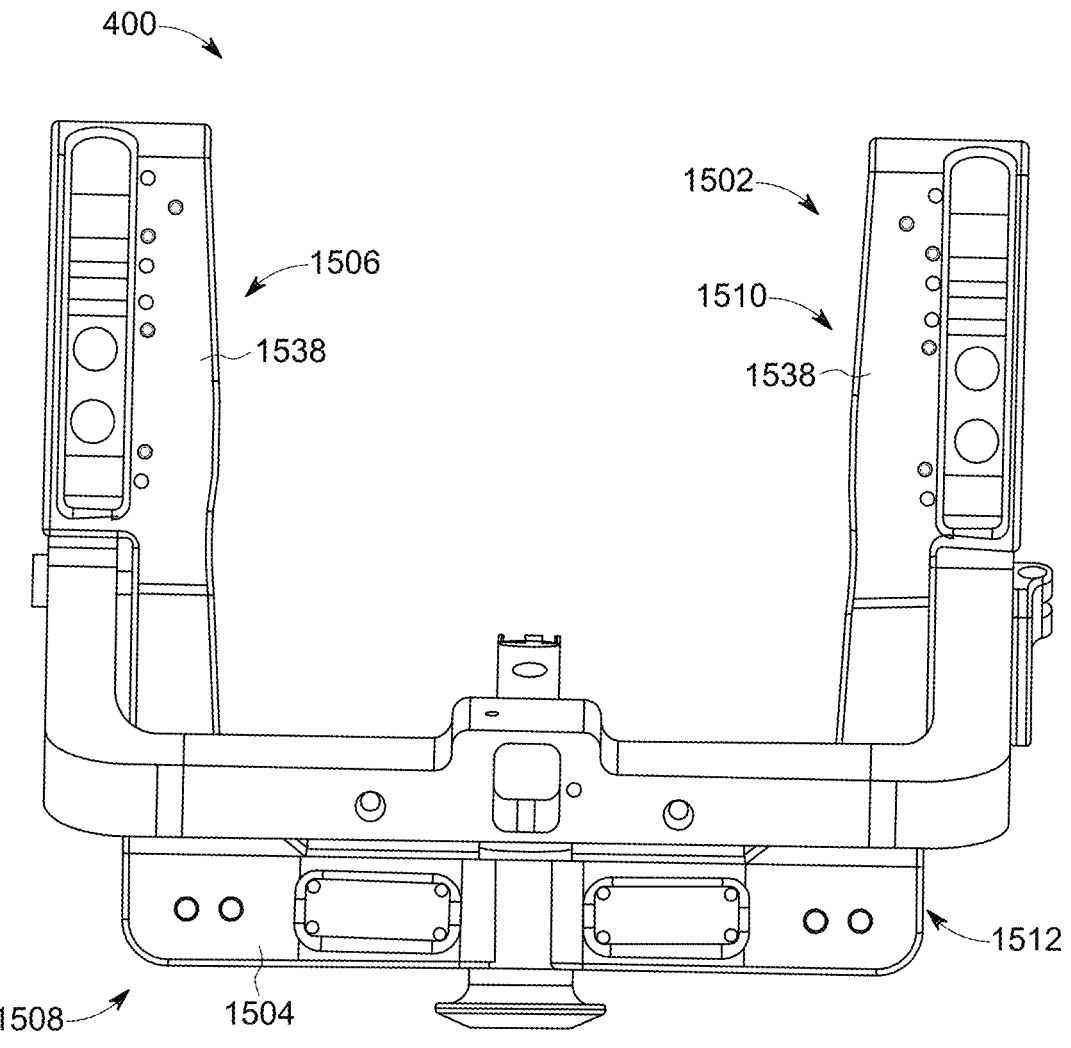
FIG. 78 depicts a front view of an alternate embodiment of an implant guide system, in accordance with aspects of the present disclosure.
Figure 79:
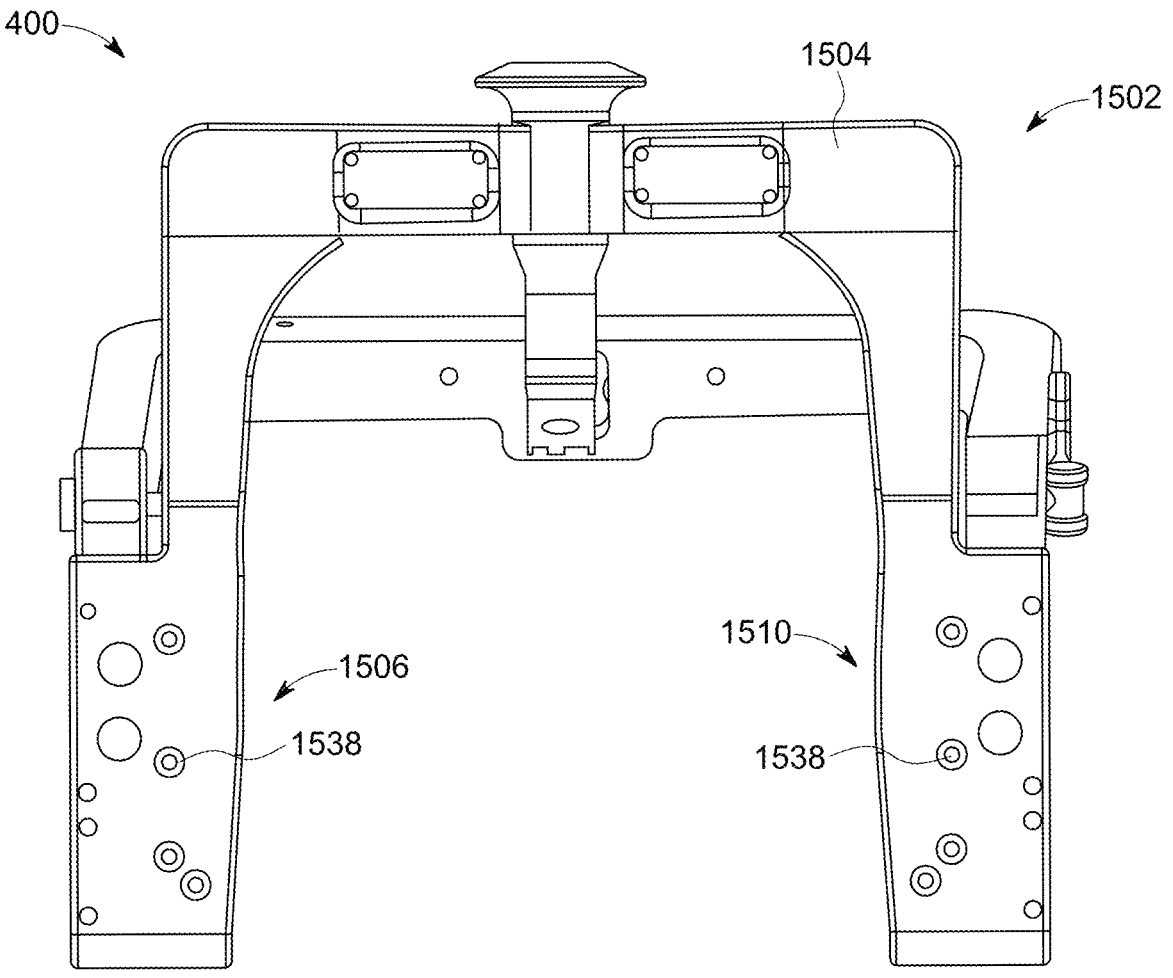
FIG. 79 depicts an inverted, back view of the alternate embodiment of the implant guide system shown in FIG. 78, in accordance with aspects of the present disclosure.
Figure 80:
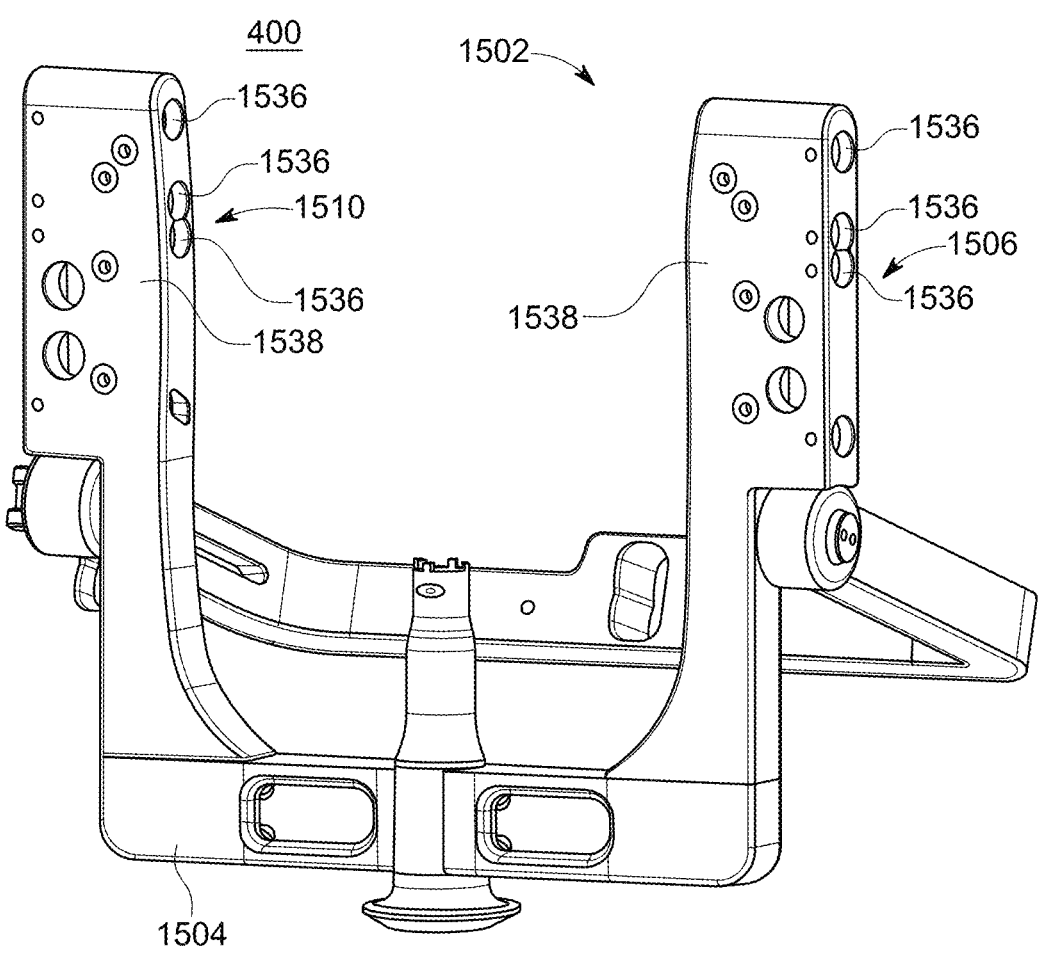
FIG. 80 depicts a back view of the alternate embodiment of the implant guide system shown in FIG. 78, in accordance with aspects of the present disclosure.
Figure 81:
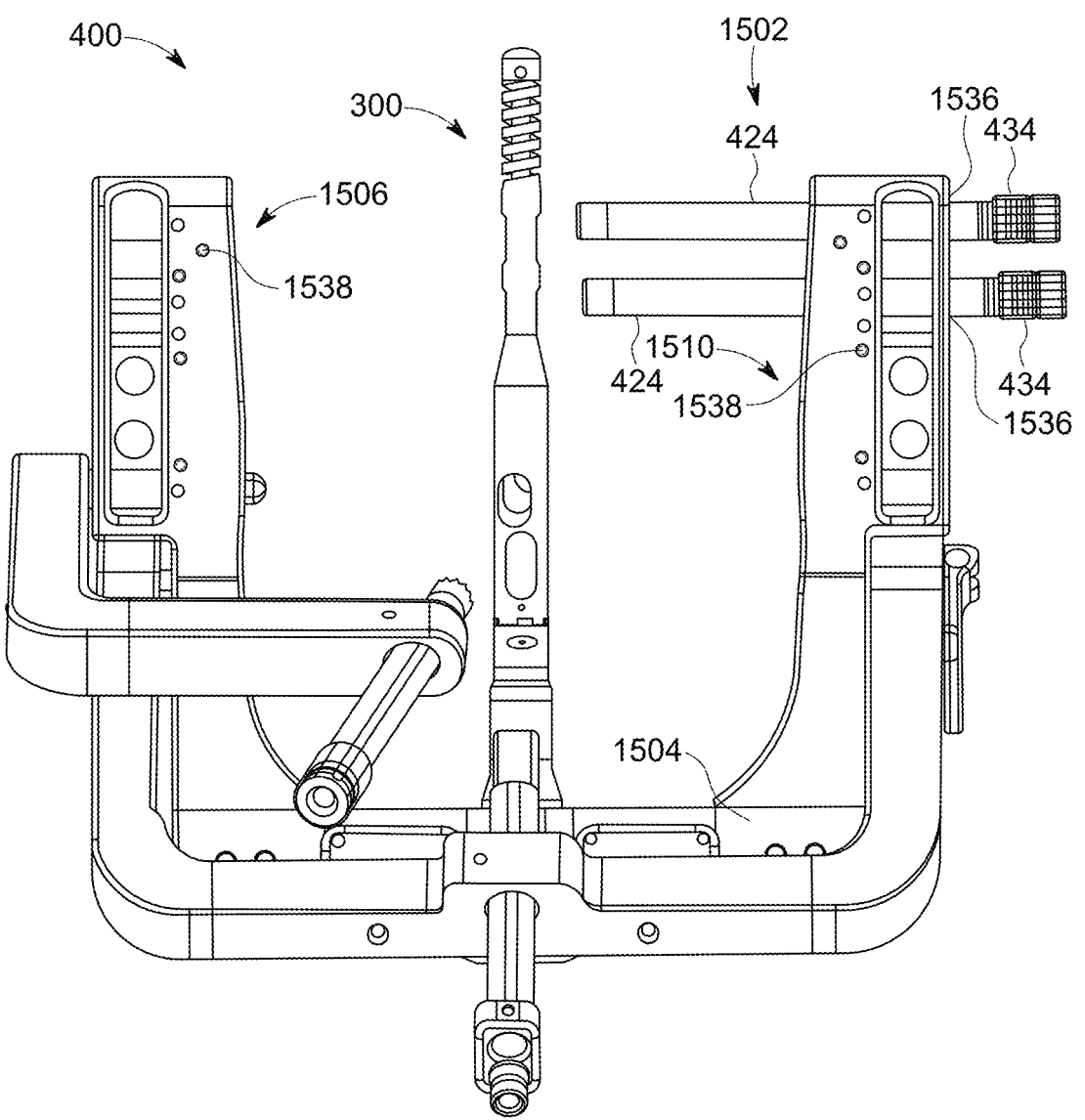
FIG. 81 depicts a front perspective view of the alternate embodiment of the implant guide system shown in FIG. 78, in accordance with aspects of the present disclosure.
Figure 82:
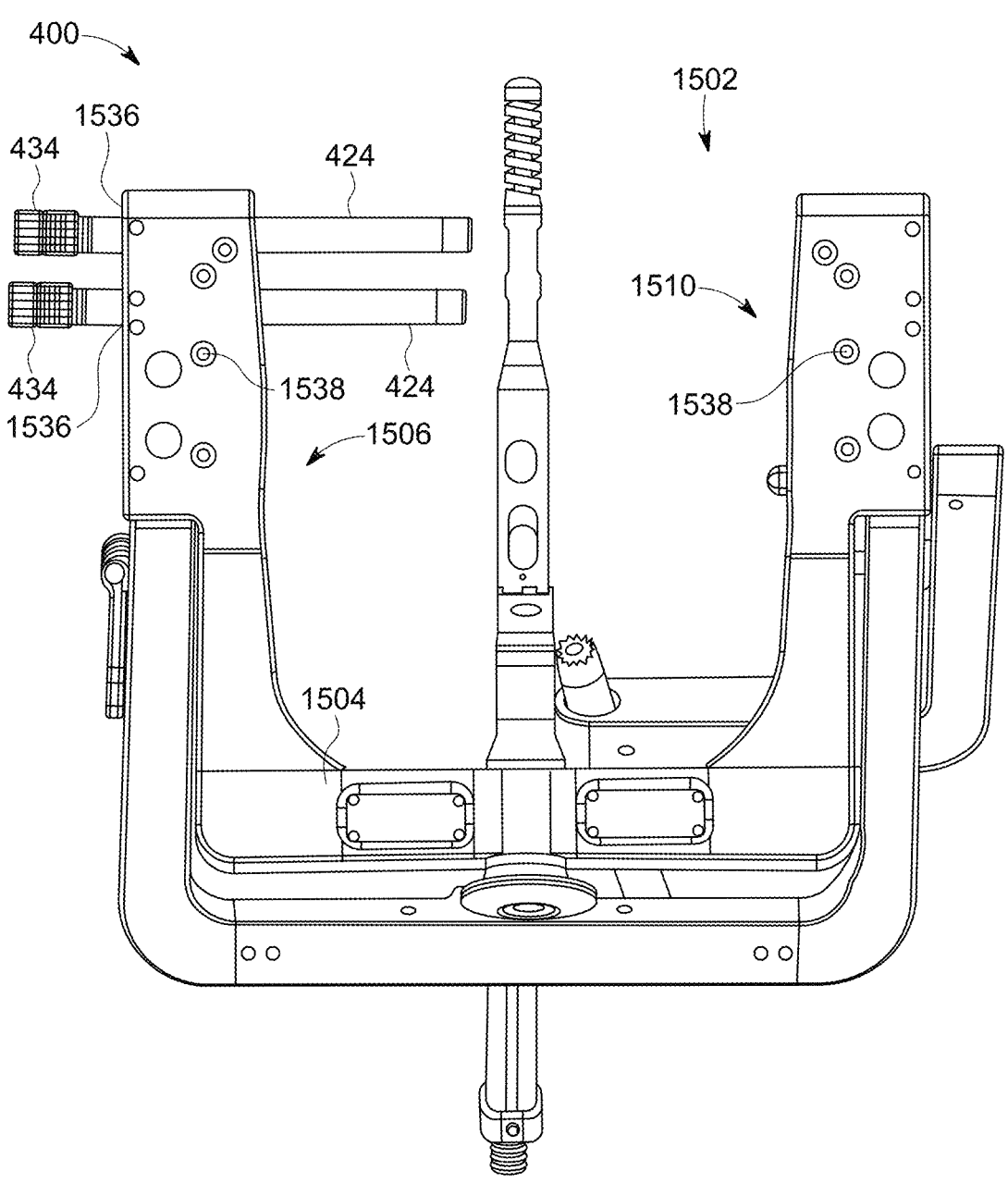
FIG. 82 depicts a back perspective view of the alternate embodiment of the implant guide system shown in FIG. 78, in accordance with aspects of the present disclosure.

Referring now to FIGS. 75-76, a surgical method 1300 is shown. The surgical method 1300 may be, for example, performed to aid in TTC fusions of the ankle complex. The surgical method 1300 may include selecting an implant guide system 1302. The method also includes coupling an implant to a mounting system 1304. The method further includes positioning an implant guide device of the implant guide system for desired implant orientation 1306 in addition to inserting the implant into a lower extremity of a patient using the implant guide system 1308. Further, the method includes inserting at least one screw into the patient's lower extremity and through the implant using the implant guide system 1310. The method also includes releasing the implant inside the lower extremity of the patient by removing the implant guide device and the mounting system 1312. In addition, the method includes closing the patient's incisions 1314.

The surgical method 1300 may also include, for example, positioning a patient's lower extremity in a supine or lateral decubitus position on an operating (e.g., radiolucent) table 1350. The patient's lower extremity, including the entire foot and lower limb, is prepared such that the patient is draped above the knee of the patient, and visualization of the knee and lower limb is present to allow for assessment of lower limb alignment. For example, the distal limbs may be extended over the operating room table approximately 5 cm to 50 cm, and more specifically 20 cm, to provide optimal access to the lower limb. Further, a C-arm may be positioned over the operative site from the contralateral side of the patient's lower extremity.

Still referencing surgical method 1300, the tibiotalar joint may be exposed 1352. For instance, exposure of the tibiotalar joint may include making a longitudinal midline incision over the anterior ankle of the patient, wherein the longitudinal midline incision may begin, for example, at approximately 8 cm to 12 cm and, more specifically 10 cm, proximal to the ankle joint and terminate distal to the talonavicular joint. Further, the incision may, for example, begin approximately 0.5 cm to 1.5 cm, and more specifically 1 cm, lateral to the tibial crest and just lateral to the tibialis anterior tendon, although alternative measurements are also contemplated as would be known or understood by one of ordinary skill in the art. The initial incision should penetrate skin only, but no direct tension should be placed on the skin margins until full-thickness retraction is possible. Further, the superficial peroneal nerve should be identified and retracted laterally. Also, exposure should be continued to the extensor retinaculum. Additionally, the extensor hallucis longus (EHL) tendon should be identified below the retinaculum, and the retinaculum should be divided longitudinally over the extensor hallucis longus tendon. Optimally, the sheath of the tibialis anterior (TA) tendon should remain intact.

Further, exposure of the tibiotalar joint may include retracting the EHL tendon laterally and the TA tendon medially. Also, the neurovascular bundle should be identified and retracted laterally with the EHL tendon. Exposure should continue until the anterior capsule is visualized. An anterior capsulotomy should be performed via a longitudinal incision. The capsule and periosteum should be elevated over the anterior tibia and talus to expose the anterior ankle joint, the tibial plafond, the medial and lateral gutters, and the anterior and dorsal talus. Any osteophytes on the tibia and talus should be removed to allow for exposure to the ankle joint and facilitate entry of instrumentation for cartilage removal.

The surgical method 1300 may also include exposure of the subtalar joint 1354. For instance, an incision may be made over the subtalar joint by starting at the distal aspect of the lateral malleolus extending toward the fourth metatarsal base while stopping at the calcaneocuboid joint. Further exposure may continue through the subcutaneous tissue, with care being taken to identify and retract the anterior branch of the sural nerve. Also, the extensor hallucis brevis muscle may be reflected distally to expose the sinus tarsi and posterior facet of the subtalar joint. Exposure of the subtalar joint 1354 may also include dissection of the fat pad out of the sinus tarsi, with reflection of the tissue dorsally.

The surgical method 1300 may also include preparation of the ankle joint 1356. Preparation of the joint 1356 may include removing cartilage from the ankle joint, as desired. For example, removal of cartilage from the ankle joint may include removing cartilage from the posterior, middle and anterior facets of the subtalar joint based on surgeon preference.

In the surgical method 1300, the ankle may be temporarily fixated 1360. Temporary fixation 1358 may include, for instance, aligning the ankle and subtalar joint. The foot and ankle should be positioned such that the ankle is neutral with respect to dorsiflexion and plantarflexion. Further, the foot may be in 5-10° of external rotation and 5° of hindfoot valgus. Additionally, with the subtalar joint and ankle joint held in this alignment, guide wires, k-wires, or the like may be used to temporarily fix the tibiotalar joint and the subtalar joint in the preferred alignment. The wire across the tibiotalar joint should pass from the anterolateral tibia to the lateral talus, thereby avoiding the anticipated path of the implant.

The surgical method 1300 may also include reaming to form a canal in the patient's lower extremity 1360. For instance, the plantar incision may be determined using lateral and axial views in fluoroscopy. Also, a desired start point may be marked, and an incision may be made over the starting point and care may be taken to bluntly dissect to the plantar surface of the calcaneus. Further, a drill may be used to establish an entry point on the calcaneus. For example, the drill may be used to drill past the distal epiphyseal line in the tibia. Still further, an x-ray template may be utilized to determine a length of the implant, and a ball-tipped guide wire, k-wire or the like, may be inserted from the plantar calcaneus into the distal tibia. Position and length may be confirmed using fluoroscopy. Additionally, a reamer may be used to ream over the ball-tipped k-wire to a desired depth. For instance, the reamer may be used to ream incrementally in 0.5 mm increments, which increase in size until the desired implant diameter is obtained. The ball-tipped k-wire and the reamer may then be removed after obtaining the desired reaming size.

The surgical method 1300 may also include insertion of the implant 1362. For instance, an implant (e.g., IM nail) of a measured size may be retrieved. Once retrieved, an implant engaging portion of a mounting system may be coupled to a distal aspect of the implant. The implant may further be coupled to the implant guide device via insertion of the mounting system and the implant into a portion of the implant guide device. The mounting system may be coupled to the implant by screwing the mounting system clockwise, while connected to the implant, until snug. Coupling of the implant engaging portion and mounting system may be configured or sized and shaped to provide proper orientation of the implant relative to the implant guide device. Further, the implant attached to the implant guide device may be inserted into the reamed canal. For instance, a mallet may be used to tap the mounting system coupled to the implant guide device and the implant in order to insert the implant into the reamed canal. The mallet may be used to tap the mounting system until the implant is fully seated or implanted a desired distance within the patient's lower extremity. Implant size and placement may be confirmed using fluoroscopy. The implant guide device position may be rotated and/or adjusted to provide a desired implant orientation, if necessary.

The surgical method 1300 may also include insertion of a tibia screw 1364. For instance, a 3.8 mm drill guide may be inserted into a through hole of at least one of a first arm and a second arm of the implant guide device. The through hole through which the drill guide may be inserted may be positioned to align with the tibia of the patient's lower extremity. Once the drill guide is inserted, a 3.8 mm drill may be used to drill, via the drill guide, into the tibia. Drilling into the tibia may include measuring a depth of the drill using laser markings associated with the drill guide. Based on the tibia being drilled into, a screw may be inserted into the tibia using a driver, wherein insertion of the screw includes turning the driver in a clockwise direction until the screw is flush with a surface of the tibia. Additional screws may be inserted into the tibia, as necessary, using this same process.

The surgical method 1300 may also include calcaneal screw insertion 1366. For instance, a targeting arm of the implant guide device may be swiveled, relative to at least one of a first arm and a second arm, to its highest (e.g., most proximal) position. Further, a drill guide (e.g., 4.6 mm drill guide) may, for example, be inserted into the targeting arm. Additionally, a drill (e.g., 4.6 mm drill) may be used to drill into the calcaneus while measuring depth of the drill using laser markings. Once the calcaneus has been drilled into, a calcaneal screw may be inserted using a driver engaging a screw guide.

The surgical method 1300 may also include insertion of a talocalcaneal screw 1368. To facilitate insertion of the talocalcaneal screw, the targeting arm of the implant guide device may be swiveled to its most distal position. A single-armed targeting accessory may be inserted into a through hole of the implant guide device and locked into place using a lock of the implant guide device. Further, a drill guide (e.g. 4.6 mm drill guide) may be inserted into a targeting accessory through hole of the single-armed targeting accessory and locked into place using a targeting accessory fastener. A drill (e.g., 4.6 mm drill) may be used to engage the drill guide and drill into the calcaneus and talus while measuring depth using laser markings. Additionally, a driver may be used to insert the talocalcaneal screw into the patient's talus and calcaneus.

The surgical method 1300 may also include removal of the implant guide device. For instance, removal of the implant guide device may include removing the implant guide device by turning the mounting system in a counter-clockwise direction. Further, the implant engaging portion may be removed from the implant by using a driver and turning the driver in a counter-clockwise direction.

The surgical method 1300 may also include insertion of a tensioning screw 1370. For instance, inserting a tensioning screw into the plantar portion of the implant may apply compression across the tibiotalar joint. For example, the tensioning screw may be inserted into the implant using a driver and tightened into position by rotating the driver in a clockwise direction. Applying compression across the tibiotalar joint facilitates proper alignment of the tibiotalar joint, which may be verified using fluoroscopy.

Referring now to FIG. 77, a surgical method 1400 is shown, which may, for example be applied to correct pre-existing deformities. The surgical method 1400 may include positioning a patient 1402. The patient may be positioned 1402 based on various medical professional preferences and may depend on the pathology and/or previous surgical approaches for a particular patient. Patient positioning options may include supine with an ipsilateral bump, lateral decubitus, or prone positions. The medical professional may obtain, for example, a radiolucent table. The medical professional may prepare the patient's lower limb and foot such that the patient is draped above the knee and visualization of the knee and lower limb is present to allow for assessment of lower limb alignment. The distal limbs may extend slightly over the edge of the operating table. A large C-arm may be available for entry over the operative side from the contralateral side.

Continuing with method 1400, the method 1400 may include preparing the tibiotalar joint and the anterior, middle, and posterior facets of the subtalar joint for temporary arthrodesis 1404 according to the medical professional's preferred technique and approach. For instance, this preparation 1304 may include removing cartilage and penetrating the subchondral plate with, for example, a subchondral drill, burrs and/or bone fenestration chisels to promote healing. Optionally, one approach may include aligning the ankle and subtalar joint such that the ankle is neutral with respect to dorsiflexion and plantarflexion. The foot may be, for example, at 5° of hindfoot valgus and 0-5° of calcaneal external rotation equal to the contralateral side. With the subtalar joint and ankle joint held in this alignment, one or more wires, such as a k-wire or the like, may be used to temporarily fixate the tibiotalar joint and the subtalar joint in the preferred alignment. The wire across the tibiotalar joint may, for example, pass from the anterolateral tibia to the lateral talus, which may avoid the anticipated path of the IM nail implant.

Continuing with method 1400, an implant sizer may be used to determine an implant size 1406. For instance, utilizing a true lateral fluoroscopic view, the sizer may be placed along the subtalar and ankle joints along the side of the patient's leg that may be best suited for the positioning. The distal hole of the implant sizer may be aligned within the body of the talus. Further, the plantar calcaneal window may show intended calcaneal screw trajectory and the plantar notch may indicate the termination point of the nail. The appropriate nail length may be determined by measuring the canal length within the tibia via the measurement notches of the implant sizer. In addition to determining nail length, the nail diameter may be estimated using diameter holes in the proximal aspect of the sizer. The holes may be positioned to the projected termination point of the nail, and the approximate nail diameter may be determined by determining which template hole best fills the tibia canal without violating the cortex.

The method 1400 may also include establishing entry point incision 1408. For instance, the targeting guide assembly may facilitate establishing an entry point for incision. According to one embodiment, a plantar incision may be made just distal to the plantar fat pad, slightly lateral to midline, and blunt dissection may be carried down to the plantar calcaneus to avoid disruption of nearby neurovascular bundles. For instance, the guide arm and guide pin may be obtained. The plantar end of the guide arm may be, for example, positioned approximately one finger breadth plantar to the fat pad of the heel, with the proximal end positioned along the medial tibial crest. The entry point of the guide pin may be obtained along the medial tibial crest. The entry point for the guide pin may be marked and a small stab incision may be made in the area of intended guide pin placement. Further, the guide pin may be positioned perpendicular to the tibial crest and parallel to the foot. The guide pin may be driven until, for example, cylindrical protrusion contacts bone. Placement may be confirmed using fluoroscopy to ensure that the tip of the guide pin is centered in the medullary canal. In particular, an oblique fluoroscopic view may be taken down the center of the wire to ensure that the guide pin is centered in the anteromedial crest of the tibia. Further, the drill-pin's trajectory will terminate at the tip of the guide pin and the tip may need to be adjusted according to the patient's anatomy. Further, the guide arm may be snapped into or otherwise attached onto the guide pin. The alignment fin may be inserted over the guide pin and engage the guide arm such that the hole in the alignment fin receives the guide pin and the fin body portion is inserted into the oblong channel or recess of the guide arm near the guide pin, which may allow the first prong and the second prong to grasp the guide pin.

Continuing with the method 1400, the drill-pin may be inserted 1410. For instance, the drill-pin tube or drill guide tube may be positioned through the plantar aspect of the guide arm. The intended drill-pin start point may be confirmed via lateral fluoroscopy, as previously described in greater detail above. The drill pin may be retrieved and, based on establishing the correct start point, driven into the calcaneus, talus, and tibia using anterior-posterior (AP), lateral and calcaneal axial fluoroscopic views during and after the process to ensure that the drill-pin is centered in the calcaneus, tibia, and talus to terminate in the medullary canal of the tibia just proximal to the metaphyseal flair. The alignment fin may then be removed from the guide wire and the guide arm may be removed from the guide wire by detaching the guide arm from the guide wire and sliding the guide arm over the drill-pin with the drill-pin guide to remove the guide arm from the operative field. Further, the guide wire may be removed from the tibia. According to one embodiment, the drill-pin may also be inserted without the guide arm, where the tip of the drill-pin is placed against the plantar calcaneus and lateral fluoroscopic images may be taken to ensure correct distal to proximal placement on the calcaneus. Additionally, upon establishing the correct start point, the drill pin may be driven into the calcaneus, talus and tibia using AP, lateral and calcaneal axial fluoroscopic views during and after the process to ensure that the drill pin is centered in the calcaneus, tibia, and talus to terminate in the medullary canal of the tibia, just proximal to the metaphyseal flare. If angulation of the drill-pin is suitable, but the drill-pin position is too anterior, posterior, medial or lateral, a parallel offset guide may be used. For instance, a central hole of the parallel offset guide may be slid over the initial wire. Further, a second wire may be placed in any of the adjacent holes to allow for the second wire to be placed parallel to the first but offset, for example, approximately 4 mm (center-to-center) in a desired direction.

Continuing with method 1400, the method may include drilling through the plantar surface of the calcaneus and into the tibia 1412. For instance, the drilling 1412 may include extending the plantar incision, if necessary, such that the plantar incision measures, for example, approximately 3-4 cm. The plantar surface of the calcaneus may then be bluntly dissected. The entry tissue protector may then be placed over the drill-pin and positioned within the incision site against the calcaneal cortex. Further, an entry drill may be inserted over the drill-pin, and the drill may be advanced proximally. The drill path trajectory may be confirmed under fluoroscopy at each joint. Drilling 1412 may continue, for example, past the distal epiphyseal line in the tibia. The entry drill and entry tissue protector may then be removed while maintaining the position of the drill-pin.

Continuing with the method 1400, a stepped reamer and tissue protector may be retrieved and inserted over the drill pin. The method 1400 may include reaming to increase the diameter of the portion of the patient's drilled-out bone 1414. For instance, a medical professional may ream proximally until the laser mark on the stepped drill reaches the tissue protector. If resistance is felt when passing larger diameter portions of the stepped reamer through the ankle joint, the reamer may be removed from the foot and bone debris may be cleared from the cutting flutes of the reamer. Lateral fluoroscopy may be used to ensure that the larger diameter contacts metaphyseal bone of the tibia and that the proximal portion of the drill matches the intended countersink of the nail. The drill-pin may be removed once the reaming has been completed. A ball-tipped guide rod may then be placed through the reamed-out bone from the plantar calcaneus and into the distal tibia. If not yet removed, temporary fixation pins may be removed at this time or after placement of the nail. A hammer or mallet may then be used to fully seat the guide rod within the canal. The position and length of the ball-tipped guide rod may be confirmed using fluoroscopy. Further, the flexible reamer shaft may be retrieved, and the desired reamer head may be attached. It may be desirous to begin with the smallest diameter reamer head. Additionally, using the reamer construct, a medical professional may ream over the guide rod to the distal laser marking on the flexible shaft. The reamer head size may be increased as appropriate resistance is appreciated while reaming. The medical professional may ream incrementally with increasing size increments until desired resistance is reached, which may be confirmed using fluoroscopy. Removing the reamer construct during incremental reaming may inadvertently cause partial extraction of the guide rod, and the hammer may be used to prevent extraction of the guide rod. It may be desirous to undersize the nail diameter following desired resistance that may be felt during reaming. The guide rod may then be removed from the tibial canal.

The method 1400 may include preparing the implant guide 1416 for insertion of the nail implant. For instance, the measured nail size may be retrieved and if internal compression is desired, the internal compression screw may be retrieved. The internal compression screw may be attached to a driver and handle. The internal compression screw may be inserted into the plantar end of the nail and turned clockwise until the screw is just visible through a calcaneal window of the nail. The targeting arm lock may be opened to access the plantar end of the targeting arm. Once positioned, the targeting arm lock may be locked, and a mounting screw or mounting bolt may be inserted through the plantar end of the mounting system. A mounting driver may be retrieved. Further, the at least one tab of the mounting system may be aligned with the corresponding recesses in the nail implant. The nail may be mounted by positioning the corresponding anterior/posterior laser marking to the desired position. The mounting system may be secured to the nail by placing the mounting driver through the plantar aspect of the mounting system and nail and turning in a clockwise direction. Additionally, preparing the implant guide 1416 may include inserting the tibial drill guide into the tibial screw guide and turning in a clockwise direction. Further, the locks along the first arm and the second arm may be opened. The implant guide device may include labels for the holes in the first arm and the second arm, which may be used to facilitating identifying a dynamic or static slot (e.g., the slot closer to the base of the implant guide device) that may align with the most distal tibial slot. If immediate post-operative dynamization is desired, the screw/drill guide may be inserted into the dynamic hole. If immediate post-operative dynamization is not desired, the screw/drill guide may be inserted into the static hole. Each tibial screw guide may be inserted into the applicable tibial outrigger holes based on determining whether to have dynamic or static tibial screw placement. The locks may be closed to lock the tibial screw guides in position. Further, the calcaneal drill guide may be inserted into the calcaneal screw guide and turned, for example, in a clockwise direction to tighten the calcaneal drill guide into position. The calcaneal drill/screw guide may be inserted into the targeting arm through hole. Further, the protrusion may ensure that the pin aperture is properly positioned to be on the proximal position of the calcaneal screw guide. To ensure the implant guide will be operational, the medical professional may insert a drill into each screw/drill guide construct, attached to the first arm and the second arm, to ensure that the drill passes through the respective holes in the nail. Further, a drill may be inserted into the calcaneal drill/screw guide construct to ensure the drill passes through the nail at the desired position. Additionally, a single-armed targeting accessory, in particular the subtalar arm, may be retrieved, the locks may be opened, and the subtalar arm may be positioned within the appropriate through hole in the first arm or the second arm. The locks may then be closed to lock the subtalar arm into place, and a drill may be inserted through the subtalar arm to ensure the trajectory of the subtalar screw will be appropriate. All drills may then be removed once the implant guide has been prepared 1416.

The method 1400 may also include inserting the nail implant into the patient 1418. The nail, attached to the mounting system and implant guide device, may be inserted into the reamed canal. For instance, placement of the nail may be, for example, 5 mm past the plantar cortex of the calcaneus to account for compression. The inlays of the targeting arm may serve as fluoroscopic markers to indicate 5 mm proximal to the nail end. Further, proper positioning may include ensuring that the fluoroscopic marker is flush to the plantar surface of the calcaneus. A hammer may be used to tap the strike plate of the mounting system until the nail is fully seated. Confirmation that the selected nail size is appropriate and that the nail is properly placed may be provided using fluoroscopy.

Continuing with the method 1400, the inlays of the targeting arm may provide a visual trajectory using fluoroscopy. For instance, aligning the inlay of one side support with the inlay of the other side support such that they are viewed, via fluoroscopy, as a single line would indicate a true lateral view. The position of the calcaneal screw may be assessed using the inlays as markers. The calcaneal targeting arm may be swiveled into a superior position and the particular angle of the targeting arm may be based on the patient's anatomy and the medical professional's preferential screw trajectory. The position of the calcaneal drill/screw guide construct may be reviewed relative to the orientation of the calcaneus. For instance, the medical professional may palpate the medial edge of the calcaneus and ensure that the calcaneal screw guide is lateral to the medial edge of the calcaneus while not being too far central in order to allow for future placement of the subtalar screw.

Continuing with the method 1400, once the nail and attached mounting system are inserted into the reamed canal and fully seated, a pin (e.g., k-wire) may be inserted into the superior hole of the calcaneal screw guide. An axial position of the projected screw path may be confirmed by taking a fluoroscopic calcaneal axial view. The nail height, size, and placement may also be confirmed using a lateral fluoroscopic view. Once the appropriate calcaneal screw placement is determined, the medical professional may lightly press the calcaneal drill guide against the skin to notate a start point of the drill. An incision (e.g., 1 cm incision) may then be made, and blunt dissection to the bone may be performed. The medical professional may drill into the calcaneus using the drill, with intermediate checking to ensure a proper stop point using lateral fluoroscopy. For example, the intended end point may be at the distal aspect of the calcaneus and centrally located from superior to inferior. Alternatively, depth can be measured using drill markings on the screw guide. The drill guide may then be removed from the screw guide by rotating the drill guide, for example, counterclockwise to disengage. The depth gauge may be inserted into the screw guide to measure the screw length. If a cannulated drilling technique for calcaneal screw insertion is preferred, a k-wire guide may be inserted into the calcaneal drill guide and a k-wire may be inserted into the pin aperture of the calcaneal screw guide. Fluoroscopy may then be used to confirm positioning, and the k-wire length may be measured using a cannulated depth gauge. The calcaneal threaded peg or calcaneal screw may be inserted using a driver. The calcaneal screw length and placement may then be verified using fluoroscopy.

The method 1400 may include inserting one or more tibial screws into the patient 1420. This process 1420 may include locating the most proximal screw/drill guide and gently indenting the skin with the screw guide construct to indicate where to make a small stab incision. Blunt dissection to the bone may then be performed. The medical professional may drill through the drill guide in the medial to lateral direction. Depth may be measured using the drill or a solid depth gauge. The drill guide may then be removed and the appropriately sized screw may be inserted through the screw guide and into the nail using a driver and, for example, turning a handle connected to the driver in a clockwise direction until the laser mark on the driver meets the end of the screw guide or when the head of the screw is snug against the tibia. Screw length and placement may be verified using fluoroscopy. This process 1420 may be repeated for placing other screws into the tibia. If, for instance, the nail is, for example, 250 mm or greater in length, a third tibial threaded peg hole may be included, and a proximal arm guide or extension accessory may be used to insert an additional tibial screw. To attach the extension accessory, the arm of the extension accessory may be inserted into the most proximal through hole of either the first arm or the second arm. The extension accessory may be secured using an extension accessory fastener. The tibial screw insertion process 1420 may be repeated via a through hole of the extension accessory.

Continuing with the method 1400, it may be desired to apply internal compression to the nail. To compress the nail through the internal compression screw, a driver may be inserted into the plantar portion of the nail through the mounting system. The driver may be turned, for example, counter-clockwise until a desired compression is achieved. The internal compression screw may translate proximally to thread into the calcaneal compression slot. According to one embodiment, for every turn there may be, for example, 0.5 mm of compression, and the compression screw may have the ability to travel, for example, 8 mm or approximately 16 turns.

The method 1400 may also include inserting the subtalar screw into the patient 1422. The insertion 1422 may include opening the lock of either the first arm or the second arm and moving the targeting arm inferiorly to align with the inferior aspect, or base, of the implant guide device. The subtalar arm, or single-armed targeting accessory, may be retrieved and positioned within the appropriate right or left through hole of the first arm or the second arm. The respective lock may be closed around the first arm or the second arm to secure the subtalar arm in position. A drill guide may be threaded into the subtalar screw guide and inserted into the subtalar arm. Using the screw guide, an indentation may be made on the skin for an incision. An incision, for example, a stab incision may be made and blunt dissection to the bone may be performed. A medical professional may drill into the calcaneus and talus with the drill, and the subtalar screw length may be measured, for example, using the laser marking on the drill. The drill guide may be removed, and the appropriately sized subtalar screw may be inserted through the bone and the nail using the technique previously described for the calcaneal screw and using the appropriate driver and handle. The screw length and position may be verified under fluoroscopy.

Continuing with the method 1400, if the trajectory of the subtalar screw through the nail is not conducive to patient anatomy, a hindfoot screw may be inserted via another single-armed targeting accessory (i.e., an alternate subtalar screw arm) in order to avoid interference with the nail and calcaneal screw. The alternate subtalar screw arm may be attached to the through hole in the first arm or the second arm and locked into place using the lock. A pin or k-wire guide may be inserted into the desired hole of the alternate subtalar screw arm. Further, according to one embodiment, a headed countersink may be retrieved for the subtalar screw. The countersink may be rotated, for example, clockwise over the wire (e.g., k-wire) to remove adequate bone to seat the screw head. The screw length may be measured using a cannulated depth gauge. If the medical professional is using a headless screw, the screw length may be measured using a cannulated depth gauge prior to using the headless countersink for the headless screw. Further, the medical professional may drill over the wire (e.g., k-wire) using a drill for the headless subtalar screw. The headless subtalar screw may be inserted using a driver, and screw length and placement may be verified using fluoroscopy.

The method 1400 may include removing the implant guide 1424. Once the nail and screw placement have been verified (e.g., using fluoroscopic views) a bolt driver attachment may, for example, be turned counterclockwise until the mounting system and implant guide device are released from the nail. The implant guide device may then be removed from the operative field.

The method 1400 may also include placing an end cap 1426. For instance, an end cap of choice may be retrieved and secured to the posterior end of the nail using a driver. Longer end caps may be selected for nails that are countersunk in the calcaneus.

Finally, the method 1400 includes closing the patient's incision 1428.

Removal of the implant and/or revision of the surgical method, once the implant has been inserted into the patient's lower extremity, may be necessary. For instance, one or more bone screws inserted in the tibia may be located using fluoroscopy. Additionally, a small incision may be made into the patient's lower extremity and a driver may be used to turn the head of the bone screw in a counterclockwise direction until the bone screw is removed. This process may be repeated to remove one or more other bone screws previously inserted into the patient's lower extremity. Also, confirmation that all bone screws have been removed may be performed using fluoroscopy. Further, this confirmation should be performed prior to attempting to remove the implant. Using fluoroscopy, the plantar insertion point of the implant may be located, and a small incision may be made to attach the driver to the tensioning screw coupled to the plantar insertion point of the implant. The driver may be used to turn the tensioning screw in a counterclockwise direction until the tensioning screw is removed. A sliding hammer may be used to engage the implant by inserting and rotating the hammer in a clockwise direction onto the plantar portion of the implant until the sliding hammer is securely coupled to the implant. The sliding hammer may then be pulled distally to the plantar portion of the foot, thereby removing the implant as the sliding hammer is extended away from the plantar portion of the foot. Revision of the surgical method may then be performed.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-74H may be used interchangeably and in alternative combinations as would be modified or altered by one of skill in the art. Further, the steps of the surgical methods associated with the systems of FIGS. 75-77 may be used interchangeably and in alternative combinations as would be modified or altered by one of skill in the art. Accordingly, this detailed description of the currently-preferred embodiments is to be taken as illustrative, as opposed to limiting of the disclosure.

Aspects of the present invention are described herein with reference to flowchart illustrations and/or block diagrams of methods. The flowchart illustrations and/or block diagrams illustrate the functionality and operation of possible implementations of the devices, systems, and methods according to various embodiments of the present invention. In this regard, each block of the flowchart may represent a step, segment, or portion of a process. In some alternative implementations, the functions noted in the blocks may occur out of the order noted in the Figures. For example, two blocks shown in succession may, in fact, be executed substantially concurrently, or the blocks may sometimes be executed in reverse order, depending upon the functionality involved.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements but is not limited to possessing only those one or more steps or elements. Likewise, a step of a method or an element of a device that "comprises," "has," "includes," or "contains" one or more features possesses those one or more features but is not limited to possessing only those one or more features. Furthermore, a device or structure that is configured in a certain way is configured in at least that way but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An implant guide device, comprising:
a base;
a first arm coupled to a first end of the base, wherein the first arm comprises:
  a retention mechanism;
  one or more through holes associated with the retention mechanism, each through hole of the one or more through holes configured to engage an accessory; and
  wherein the accessory facilitates inserting a fastener into a patient's lower extremity;
a second arm coupled to a second end of the base; and
a targeting arm hingedly coupled to the first arm at a first coupling point and the second arm at a second coupling point, wherein a first end of the targeting arm is directly coupled to the first arm, and wherein a second end of the targeting arm is directly coupled to the second arm.

2. The implant guide device of claim 1, wherein the base comprises:
  an aperture configured to receive an implant, wherein the aperture is positioned near a midpoint between the first end and the second end of the base; and
  wherein the implant includes a nail system to be inserted into a patient's lower extremity.

3. The implant guide device of claim 2, wherein the aperture is further configured to receive a portion of a mounting system, the mounting system being coupled to the implant.

4. The implant guide device of claim 1, wherein the targeting arm comprises:
  a lock configured to fixate a position of the targeting arm.

5. The implant guide device of claim 1, wherein the targeting arm comprises:
  one or more inlays configured to provide a visual trajectory of an accessory to be inserted into the implant guide device; and
  wherein the one or more inlays are embedded in a crevice of a side support of the targeting arm.

6. The implant guide device of claim 1, wherein the targeting arm is configured to provide elevated support to a patient's lower extremity.

7. The implant guide device of claim 1, wherein the targeting arm comprises:
  one or more orientation markings; and
  wherein the one or more orientation markings are configured to align with one or more corresponding side support orientation markings, the side support orientation markings being located on at least one of the first arm and the second arm.

8. The implant guide device of claim 1, wherein the first arm extends perpendicularly away from the base, wherein the second arm extends perpendicularly away from the base, and wherein the first arm is positioned parallel to the second arm as the first arm and second arm extend away from the base.

9. An implant guide system, comprising:
an implant guide device, comprising:
  a base;
  a first arm coupled to a first end of the base;
  a second arm coupled to a second end of the base; and
  a targeting arm hingedly coupled to the first arm at a first coupling point and the second arm at a second coupling point, wherein a first end of the targeting arm is directly coupled to the first arm, and wherein a second end of the targeting arm is directly coupled to the second arm, wherein the targeting arm comprises:
  a lock configured to fixate a position of the targeting arm; and
  one or more inlays configured to provide a visual trajectory of an accessory to be inserted into the implant guide device; and
  wherein the one or more inlays are embedded in a crevice of a side support of the targeting arm;
a mounting system traversing an aperture of the base, wherein the aperture is positioned at a midpoint between the first end and the second end of the base; and
an implant coupled to the mounting system.

10. The implant guide system of claim 9, wherein the base comprises:
  the aperture configured to receive the implant; and
  wherein the implant includes a nail system to be inserted into a patient's lower extremity.

11. The implant guide system of claim 10, wherein the aperture is further configured to receive a portion of the mounting system, the mounting system being coupled to the implant.

12. The implant guide system of claim 9, wherein the first arm comprises:
  a lock;
  one or more through holes associated with the lock, wherein each through hole of the one or more through holes are configured to engage an accessory; and
  wherein the accessory facilitates inserting a fastener into a patient's lower extremity.

13. The implant guide system of claim 9, wherein the targeting arm is configured to provide elevated support to a patient's lower extremity.

14. The implant guide system of claim 9, wherein the targeting arm comprises:
  one or more orientation markings; and
  wherein the one or more orientation markings are configured to align with one or more corresponding side support orientation markings, the side support orientation markings being located on at least one of the first arm and the second arm.

15. The implant guide system of claim 9, further comprising:
a targeting guide assembly;
wherein the targeting guide assembly comprises:
  a guide arm;
  a drill guide tube;
  a guide pin;
  an alignment fin; and
  a drill pin.

16. A surgical method, comprising:
selecting an implant guide system, the implant guide system comprising:
  a base;
  a first arm coupled to a first end of the base, wherein the first arm comprises:
    a retention mechanism;
    one or more through holes associated with the retention mechanism, each through hole of the one or more through holes configured to engage an accessory; and
    wherein the accessory facilitates inserting a fastener into a patient's lower extremity;
  a second arm coupled to a second end of the base; and

41 a targeting arm hingedly coupled to the first arm at a
first coupling point and the second arm at a second
coupling point, wherein a first end of the targeting
arm is directly coupled to the first arm, and wherein
a second end of the targeting arm is directly coupled
to the second arm;

coupling an implant to a mounting system of the implant
guide system;

positioning an implant guide device of the implant guide
system for desired implant orientation;

inserting the implant into a lower extremity of a patient
using the implant guide system;

inserting at least one fastener into the patient's lower
extremity and through the implant using the implant
guide system;

releasing the implant inside the lower extremity of the
patient by removing the implant guide device and the
mounting system;

inserting a tensioning fastener onto the implant; and closing the patient's incisions.

17. The surgical method of claim 16, wherein the posi-
tioning an implant guide device of the implant guide system
for desired implant orientation further comprises:
    positioning a patient's lower extremity;
    exposing the patient's tibiotalar joint;
    exposing the patient's subtalar joint;
    preparing the patient's ankle joint; and
    fixating, temporarily, the patient's ankle.

18. The surgical method of claim 17, wherein the inserting
the implant into a lower extremity of a patient using the
implant guide system further comprises:
    forming a canal in the patient's lower extremity; and
    inserting the implant into the canal;

wherein the inserting the at least one fastener into the
patient's lower extremity and through the implant using the
implant guide system further comprises:
    inserting a first fastener into the patient's tibia;
    inserting a second fastener into the patient's calcaneus;
    and
    inserting a third fastener into the patient's talocalcaneal
    joint.

* * * * *